(12) United States Patent
Watterson et al.

(10) Patent No.: US 9,527,819 B2
(45) Date of Patent: Dec. 27, 2016

(54) PYRIDAZINE COMPOUNDS, COMPOSITIONS AND METHODS

(71) Applicants: NORTHWESTERN UNIVERSITY, Evanston, IL (US); UNIVERSITE DE STRASBOURG, Strasbourg (FR); CENTRE NATIONAL DE LA RECHERCHE SCIENTIFIQUE (CNRS), Paris (FR)

(72) Inventors: D. Martin Watterson, Chicago, IL (US); Linda Van Eldik, Chicago, IL (US); Jacques Haiech, Strasbourg (FR); Marcel Hibert, Eschau (FR); Jean-Jacques Bourguignon, Illkirch (FR); Anastasia Velentza, San Diego, CA (US); Wenhui Hu, Guangzhou (CN); Magdalena Zasadzki, Chicago, IL (US)

(73) Assignees: NORTHWESTERN UNIVERSITY, Evanston; UNIVERSITE DE STRASBOURG, Strasbourg (FR); CENTRE NATIONAL DE LA RECHERCHE SCIENTIFIQUE (CNRS), Paris (FR)

( * ) Notice: Subject to any disclaimer, the term of this patent is extended or adjusted under 35 U.S.C. 154(b) by 0 days.

(21) Appl. No.: 14/559,421

(22) Filed: Dec. 3, 2014

(65) Prior Publication Data
US 2015/0175555 A1 Jun. 25, 2015

Related U.S. Application Data

(62) Division of application No. 13/491,986, filed on Jun. 8, 2012, now Pat. No. 8,933,076, which is a division of application No. 11/666,803, filed as application No. PCT/US2005/039541 on Jul. 22, 2008, now Pat. No. 8,367,672.

(60) Provisional application No. 60/624,346, filed on Nov. 2, 2004, provisional application No. 60/723,124, filed on Oct. 3, 2005, provisional application No. 60/723,090, filed on Oct. 3, 2005.

(51) Int. Cl.
| | |
|---|---|
| *C07D 237/20* | (2006.01) |
| *A61K 31/502* | (2006.01) |
| *C07D 403/12* | (2006.01) |
| *C07D 401/04* | (2006.01) |
| *C07D 237/24* | (2006.01) |
| *C07D 237/34* | (2006.01) |
| *C07D 401/12* | (2006.01) |
| *C07D 413/12* | (2006.01) |
| *C07D 413/14* | (2006.01) |
| *C07D 487/04* | (2006.01) |
| *C07H 19/16* | (2006.01) |

(52) U.S. Cl.
CPC .......... *C07D 237/20* (2013.01); *A61K 31/502* (2013.01); *C07D 237/24* (2013.01); *C07D 237/34* (2013.01); *C07D 401/04* (2013.01); *C07D 401/12* (2013.01); *C07D 403/12* (2013.01); *C07D 413/12* (2013.01); *C07D 413/14* (2013.01); *C07D 487/04* (2013.01); *C07H 19/16* (2013.01)

(58) Field of Classification Search
CPC .................................................. C07D 39/417
See application file for complete search history.

(56) References Cited

U.S. PATENT DOCUMENTS

| | | | |
|---|---|---|---|
| 2,857,384 A | 10/1958 | Druey | |
| 3,464,988 A | 9/1969 | Holava | |
| 4,169,158 A | 9/1979 | Laborit | |
| 4,508,720 A | 4/1985 | Kan et al. | |
| 4,654,343 A | 3/1987 | Albright | |
| 4,710,499 A | 12/1987 | Wermuth | |
| 4,721,711 A | 1/1988 | Chambon | |
| 4,977,152 A | 12/1990 | Biziere | |
| 5,045,541 A | 9/1991 | Nakao | |
| 5,461,053 A * | 10/1995 | Boigegrain | .......... C07D 237/04 514/236.5 |
| 5,484,940 A | 1/1996 | Grant | |

(Continued)

FOREIGN PATENT DOCUMENTS

| | | |
|---|---|---|
| EP | 0072726 | 2/1983 |
| EP | 094038 | 11/1983 |

(Continued)

OTHER PUBLICATIONS

Edwards et al., Double-blind comparative study of the antidepressant, unwanted and cardiac effects of minaprine and amitriptylineBritish Journal of Clinical Pharmacology (1996), 42(4), 491-498 CODEN: BCPHBM; ISSN: 0306-5251; English.*
Piao et al., Prevention by minaprine of ischemic neuronal damage and memory impairment in Mongolian gerbils Nippon Shinkei, Seishin Yakurigaku Zasshi (1995), 15(2), 157-63 CODEN: NSSZEW; ISSN: 1340-2544; English.*
Martin et al., Novel arylaminopyridazine-GABA receptor antagonists examined electrophysiologically in Ascaris suum European Journal of Pharmacology (1995), 276(1/2), 9-19 CODEN: EJPHAZ; ISSN: 0014-2999; English.*

(Continued)

*Primary Examiner* — Paul V Ward
(74) *Attorney, Agent, or Firm* — Millen White Zelano and Branigan, PC; John Sopp; Anthony Zelano

(57) ABSTRACT

The invention relates to novel chemical compounds, compositions and methods of making and using the same. In particular, the invention provides pyridazine compounds and/or related heterocyclic derivatives, compositions comprising the same, and methods of making and using pyridazine compounds and/or related heterocyclic derivatives and compositions comprising the same, for modulation of cellular pathways (e.g., signal transduction pathways), for treatment or prevention of inflammatory diseases (e.g., Alzheimer's disease), for research, drug screening, and therapeutic applications.

21 Claims, 46 Drawing Sheets

(56) References Cited

U.S. PATENT DOCUMENTS

| | | | |
|---|---|---|---|
| 6,284,277 B1 * | 9/2001 | Bouloumie | A61K 9/0019 424/450 |
| 7,732,445 B2 | 6/2010 | Watterson | |
| 7,888,357 B2 | 2/2011 | Watterson | |
| 8,088,774 B2 | 1/2012 | Watterson | |
| 2003/0176437 A1 | 9/2003 | Watterson | |
| 2006/0073472 A1 | 4/2006 | Watterson | |
| 2008/0021035 A1 | 1/2008 | Watterson | |
| 2009/0029985 A1 | 1/2009 | Watterson | |
| 2009/0325973 A1 | 12/2009 | Watterson | |
| 2010/0130442 A1 | 5/2010 | Wadgaonkar | |
| 2010/0240668 A1 | 9/2010 | Watterson | |

FOREIGN PATENT DOCUMENTS

| | | |
|---|---|---|
| EP | 0211437 | 2/1987 |
| EP | 0211457 | 2/1987 |
| EP | 0382634 | 8/1990 |
| EP | 0464572 | 1/1992 |
| EP | 0628550 | 12/1994 |
| EP | 1061077 | 12/2000 |
| FR | 2141697 | 1/1973 |
| FR | 2847253 | 5/2004 |
| JP | 59212480 | 12/1984 |
| JP | 63295577 | 12/1988 |
| JP | 4230380 | 8/1992 |
| JP | 2001518908 | 10/2001 |
| JP | 2004510813 | 4/2004 |
| WO | 9846574 | 10/1998 |
| WO | 0222605 | 3/2002 |
| WO | 0230405 | 4/2002 |
| WO | 03018563 | 3/2003 |
| WO | 2004046117 | 6/2004 |
| WO | 2005009976 | 2/2005 |
| WO | 2005061509 | 7/2005 |
| WO | 2005063761 | 7/2005 |
| WO | 2006026135 | 3/2006 |
| WO | 2006050359 | 5/2006 |
| WO | 2006050389 | 5/2006 |
| WO | 2007127375 | 4/2007 |

OTHER PUBLICATIONS

Thomson Innovation, "3-amino-6-aryl-1,2,4-triazolo(4,3-b) pyridazines, their preparation and use," Retrieved from Patent Record View on Sep. 1, 2010; English Abstracts of EP0094038.
Tinsley et al., "Myosin light chain kinase transference induces myosin light chain activation and endothelial hyperpermeability," Am J Physiol Cell Physiol, Oct. 2000, vol. 279, No. 4, pp. 1285-1289.
Translation of Notice of Reasons for Rejections for related Japanese Patent Application No. 2007 539305 dated Apr. 20, 2012.
Translation of office action issued Mar. 22, 2010 in Israeli Application No. 182765.
Translation of office action issued Nov. 27, 2011 in Israeli Application No. 182765.
Translation of Response in related Israeli Patent Application No. 182765 filed Apr. 24, 2012.
Translation of second office action for China Application No. 2005 80037702.6 dated Dec. 2, 2010.
Troy et al., "Beta-amyloid-induced neuronal apoptosis required c-Jun N-terminal kinase activation," J. Neurochem., 2001, vol. 77, pp. 157-164.
Van Eldik et al., "Synthesis and Expression of a Gene Coding for the Calrium-modulated Protein S100B and designed for cassette-based, Site-directed Mutagenesis," J. Biol. Chem., 1988, vol. 263, pp. 7830-7837.
Veber et al., "Molecular 30 properties that influence the oral bioavailability of drug candidates," J. Med. Chem, 2002, vol. 45, pp. 2615-2623.

Verbitsky, M. et al., "Altered hippocampal transcript profile accompanies an age-related spatial memory deficit in mice," 2004, Learning and Memory, vol. 11, pp. 253-260.
Vezzani et al., "Functional role of inflammatory cytokines and anti-inflammatory molecules in seizures and epileptogenesis," Epilepsia, 2002, vol. 43, pp. S30-S35.
Vezzani, A. Epilepsy Currents, vol. 4, No. 2, Feb. 26, 2004, pp. 73-75.
Vezzani, A. et al., "Brain Inflammation in epilepsy: Experimental and clinical evidence," Epilepsia, 2005, vol. 46, pp. 1724-1743.
Vieth et al., "Characteristics physical properties and structural fragments of marketed oral drugs," J. Med. Chem., 2004, vol. 47, pp. 224-232.
Villa et al., J. Het. Chem., 1999, vol. 36(2), pp. 485-492.
Wainwright, M et al., "Carnitine treatment inhibits increases in cerebral carnitine esters and glutamate detected by mass spectrometry following hypoxiaischemia in newborn rats," Stroke 37,2005, pp. 524-530.
Wainwright, M. et al., "Increased susceptibility of S100B transgenic mice to perinatal hypoxia-ischemia," Annals of Neurol., 2004, vol. 56, pp. 61-67.
Watterson, D. M. et al., "Discovery of a new class of synthetic protein kinase inhibitors that suppress selective aspects of glial activation and protect against [J-amyloid induced injury. A foundation for future medicinal chemistry efforts focused on target Alzheimer's Disease progression," Database Caplus XP-002515676, 2003.
Weiss, C. et al., "Spatial learning and memory in aging C57BL/b mice," Neurosci. Res. Comm., 1998, vol. 23, No. 2, pp. 77-92.
Weiss, S. et al., "Anatomic studies of DNA fragmentation in rat brain after systemic kainic acid administration," Neuroscience,74(2): 541-551 (1996).
Wermuth, C. G. et al., Selected Procedures for the Preparation of Pharmaceutically acceptable salts, in Stahl. P. H., Wermuth, C.G. (Ed.) Handbook of Pharmaceutical Salts, Wiley-VCH, pp. 249-264 (2008).
Wikipedia, Isomers, last modified Aug. 16, 2010, http://en.wikipedia.org/wiki/Isomer, downloaded Aug. 24, 2010.
Yamamoto et al., "Development changes in distribution of death-associated protein kinase mRNAs," J Neurosci Res., 1999, vol. 58, pp. 674-683.
Yoshinari et al., "Effects of a dual inhibitor of tumor necrosis factor-alpha and interleukin-1 on lipopolysaccharide-induced lung injury in rats: involvement of the p38 mitogen-activated protein kinase pathway," Crit. Care Med., Mar. 2001, vol. 29, No. 3, pp. 628-634.
Yoshitomi Pharmaceut IND Ltd., "Triazolopyridazine derivative," Patent Abstracts of Japan, Publication Date: Dec. 1, 1988; English Abstract of JP-36-295577.
Zhang, G. et al., "Long-term alterations in glutamate receptor and transporter expression following early-life seizures are associated with increased seizure susceptibility," J. Neurochem., 2004, vol. 88, pp. 91-101.
Zhou et al., "HERG-like K+ Channels in Microglia," J. Gen Physiol, 1998, vol. 111, No. 6, pp. 781-794.
Abdel, M et al., "Synthesis of 3-heterocyclic-5,6-diphenylpyridazines," Egyptian Journal of Pharmaceuticals Sciences, 1998, vol. 38, No. 1-3, pp. 87-93.
Adams et al., "Concise Synthesis of 1H-pyrazin-2-ones and 2-Aminopyrazines," Synlett., 2004, vol. 11, pp. 2031-2033.
Akama et al., "Amyloid Beta-peptide stimulates nitric oxide production in astrocytes through an NFxB-dependent mechanism," PNAS, 1998, vol. 95, pp. 5795-5800.
Australian Office Action (Examiner's first report on patent application No. 2005 302225) dated Apr. 12, 2011, pp. 1-3.
Badger et al., "Pharmacological Profile of SB 203580, a Selective Inhibitor of Cytokine Suppressive Binding Protein/ p38 Kinase, in Animal Models of Arthritis, Bone Resorption, Endotoxin Shock and Immune Funtion," J. Pharmacol Exp. Ther., 279(3):1453-1461, 1996.
Bhagwat et al., "Gene-regulation protein kinases as important anti-inflammatory targets," Drug Disc. Today, 1999, vol. 4, pp. 472-479.

(56) References Cited

OTHER PUBLICATIONS

Bhat et al., "Extracellular Signal-regulated Kinase and p38 Subgroups of Mitogen-Activated Protein Kinases Regulate Nitric Oxide Synthase and Tumor Necrosis Factor-alpha Gene Expression in Endotoxin-Stimulated Primary Gilial Cultures," J. Neurosci., 18(5): 1633-1641 (1988).
Bhattacherjee et al., Zeitschrift fur Kristallographie, 1958, vol. 110, No. 1-6, pp. 472-474.
Blasi et al., "Immortalization of murine microglial cells by a v-raf/v-myc carrying retrovirus," J. Neuroimmunol. vol. 27, pp. 229-237 (1990).
Bluhm, J. Het Chem, 1981, vol. 18, pp. 189-190.
Borsche et al., Justus Liebigs Annalen der Chemie, 1943, vol. 555, 70-77.
Brott et al., "Treatment of acute ischemic stroke," N Engl J Med., Sep. 7, 2000, vol. 343, No. 10, pp. 710-722.
Chambon, J. P. et al., "CM40907: A Structurally novel anticonvulsant in mice, rats, and baboons," The Journal of Pharmacology and experimental therapeutics, Jun. 1985, vol. 233, No. 3, pp. 836-844, Database Medline NLM2989499.
Chen et al., "An Experimental Model of Closed Head Injury in Mice : Pathophysiology, Histopathology, and Cognitive Deficits," J. Neurotrauma, 1996, vol. 13, pp. 557-568.
Chitaley, K. et al., "Antagonism of Rho-Kinase Stimulates Rat Penile Erection Via a Nitric Oxide-Independent Pathway," Nature Medicine, Jan. 2001, vol. 7, No. 1, pp. 119-122.
Communication enclosing European Search Report for related European Patent Application No. 05817588 dated Apr. 4, 2012.
Communication pursuant to Article 94(3) EPC for EP 02796459 dated Sep. 30, 2010.
Communication pursuant to Article 94(3) EPC for EP 02796459.2 dated Feb. 2, 2012.
Communication pursuant to Article 94(3) EPC for EP 05823123.4 dated Jun. 2, 2009.
Communication pursuant to Article 94(3) EPC for EP 05823123.4 dated Dec. 17, 2009.
Communication pursuant to Article 94(3) EPC for EP 07756162 dated Feb. 5, 2010.
Communication pursuant to Article 94(3) EPC for EP 07776351 dated Oct. 9, 2010.
Communication pursuant to Article 94(3) EPC for EP 07776351 a dated Oct. 9, 2009.
Communication pursuant to Article 94(3) EPC for EP 08731122.1 dated Oct. 15, 2010.
Communication pursuant to Article 94(3) EPC for EP07756162 dated Feb. 11, 2009.
Communication pursuant to Article 94(3) EPC for EP-07776351.4 dated Feb. 2, 2012.
Communication pursuant to Article 94(3) for EP 05823123.4 dated Jul. 14, 2010.
Communication pursuant to Rules 70(2) and 70a(2) EPC for related European Patent Application No. 05817588 dated Apr. 23, 2012.
Communication regarding the European Search Report for EP 02796459 dated Oct. 29, 2004.
Communication regarding the Extended European Search Report for EP 05823123 dated Mar. 2, 2009.
Constantino et al., "Synthesis and alsdose reductase inhibitory activitiy of a new series of benzo[h]cinnolinone derivatives," Il Farmaco, 2000, vol. 55, pp. 544-552.
Craft, J. et al., "Enhanced susceptibility of S-100B transgenic mice to neuroinflammation and neuronal dysfunction induced by intracerebroventricular infusion of human Beta-amyloid," GLIA, 2005, vol. 51, pp. 209-216.
D'Ambrosio, R. et al., "Epilepsy after head injury," Curr. Opin. Neurol., 2004, vol. 17, pp. 7431-7735.
Database Beilstein XP-002515678, Feb. 17, 2009.
Database Caplus, Chemical Abstract Service, XP002515676 and J. Mol. Neuroscience, vol. 20, No. 3, pp. 411-423, J (2003).
Database Caplus, Chemical Abstract Service, XP002515675 and JP63 295577 (1988).

Database Caplus, Chemical Abstract Service, XP002525677 and Comptes Rendus Des Seances de L'Academie des Sciences, Serie C: Sciences Chimiques, 1973, vol. 277, No. 8, pp. 319-322.
De Silva et al., "Blockade of p38 Mitogen-activated Protein Kinases Pathway Inhibits Inducibel Nitric-oxide Synthase Expression in Mouse Astrocytes," J. Biol Chem., 272(45): 28373-28380 (1997).
Dogan et al., "Effects of MDL 72527, a Specific Inhibitor of Polyamine Oxidase, on Brain Edema, Ischemic Injury Volume, and Tissue Polyamine Levels in Rats After Temporary Middle Cerebral Artery Occlusion," J. Neurochem., 1999, vol. 72, pp. 765.
Donato, R. et al., "Functional roles of S100 proteins, calcium-binding proteins of the EF-hand type," Biochem Biophys Acta, vol. 1450, pp. 191-231 (1999).
Dos Santos, "Invited review: mechanisms of ventilator-induced lung injury: a perspective," Appl. Physiol, Oct. 2000, vol. 89, No. 4, pp. 1645-1655.
Dragunow M. et al., "Clusterin accumulates in dying neurons following status epilepticus," Mol. Brain. Res., 1005, vol. 32, pp. 279-290 (1995).
Draper, T. L. et al., "Synthesis of Unsymmetrical 3,6-distributed pyridazines. A Palladium-Catalyzed Approach from 3-lodopyridazines," J. Org. Chem., 1995, vol. 60, pp. 748-750.
Du, Y. et al., "Association of an interleukin 1 [alpha] polymorphism with Alzheimer's disease," Neurology, vol. 55, 2000, pp. 480-484.
Dube, C. et al., "Prolonged Febrile Seizures in the immature rat model enhance hippocampal excitability long term," Ann Neurol., 2000, vol. 47, pp. 336-344.
Eddy, S. et al., "Efficient Aromatization of 4,5-Dihydro-3(2H)-Pyridazinones Substituted at 5 Position by Using Anhydrous Copper (II) Chloride," Synthetic Communications, 2000, vol. 30, No. 1, pp. 1-7.
European Search Report for EP 10181297.2 dated Nov. 12, 2010.
Finlayson et al., "Acquired QT interval prolongation and HERG: implications for drug discovery and development," Eur J. Pharmacol., Oct. 2004, vol. 500, No. 1-3, pp. 129-142.
First Examination report for Indian Application No. 1977/KOLNP/2007 dated Jan. 24, 2011.
Frautschy, S. A. et al., "Rodent models of Alzheimer's disease: rat A Beta infusion approaches to amyloid deposits," Neurobiol. Aging., 1996, vol. 17, pp. 311-321.
French, J. et al., "Characteristics of medial temporal lobe epilepsy. I. Results of history and physical examination," Ann Neurol., 1993, vol. 34, pp. 774-780.
Garcia Mera et al., Anales de Quimica, Serie C: Quimica Organica y Bioquimica, 1985, vol. 81, No. 3, pp. 280-283.
Garcia, "Regulation of Endothelial Cell Gap Formation and Barrier Dysfunction: Role of Myosin Light Chain Phosphorylation," J. Cell Physiol, 1995, vol. 163, pp. 510-522.
Griffin et al., "Glial-Neuronal Interactions in Alzheimer's Disease: The Potential Role of a 'Cytokin Cycle' in Disease Progression," Brain Pathol., 1998, vol. 8, pp. 65-72.
Guo, Z. et al., "Head Injury and the risk of AD in the MIRAGE study," Neurology, 2000, vol. 54, pp. 1316-1323.
Hagberg, H. et al., "Effect of inflammation on central nervous system development and vulnerability," Curr. Opin. Neurol., 2005, vol. 18, pp. 117-123.
Hallot, A. et al., "Synthesis and activity of 6-aryl-3-(hydroxypolymethyleneamino) pyridazines in animal models of epilepsy," Journal of Medicinal Chemistry, Mar. 1986, vol. 29, No. 3, pp. 369-375, Database Medline NLM3950916.
Han, B. et al., "Clusterin contributes to caspase-3-independent brain injury following neonatal hypoxia-ischemia," Nature Med., 2001, vol. 7, pp. 338-343.
Hargreaves et al., "A new and sensitive method for measuring thermal nociception in cutaneous hyperalgesia," Pain, 1988, vol. 32, pp. 72-78.
Haut, S. et al., "Susceptibility of immature and adult brains to seizure effects," Lancet Neurol., 2004, vol. 3, pp. 608-617.
Hirohashi et al., "Pharmacological Studies with the Alpha2-Adrenoceptor Antagonist Midaglizole," Arzneim-Forsch./ Drug Res., 1991, vol. 41, pp. 9-18.
Holmes, G. et al., "Effects of seizures on brain development: lessons from the laboratory," Pediatr Neurol., 2005, vol. 33, pp. 1-11.

(56) References Cited

OTHER PUBLICATIONS

Holmes, G. et al., "Seizures in the developing brain: perhaps not so benign after all," Neuron, 1998, vol. 21, pp. 1231-1234.
Huang, Y et al., "Glutamate transporters bring competition to the synapse," Curr. Opin. Neurobiol., 2004, vol. 14, pp. 346-352.
Igarashi et al., "Exogenous Tumor Necrosis Factor-Alpha Mimics Nucleus Pulposus-Induced Neuropathology," Spine, 2000, vol. 25, pp. 2975-2980.
Jensen, F. et al., "NBQX blocks acute and late epileptogenic effects of perinatal hypoxia," Epilepsia, 1995, vol. 36, pp. 966-972.
Koh, S. et al., "Early-life seizures increase susceptibility to seizure-induced brain injury in adulthood," Neurology, 1999, vol. 53, pp. 915-921.
Kulkarni, V., "Structure-activity relationship in pyridazine and phathalazine series of antihypertensive agents by molecular orbital calculations," Indian Juran of Biochemistry & Biophysics, 1975, vol. 12, No. 4, pp. 367-369.
Kumar et al., "Drugs Targeted Against Protein Kinase," Expert Opinion, 2001, vol. 6, No. 2, pp. 303-315.
Lamant, Maurice, "Novel synthesis of 3-phenyl-4-aminocinnolines," Database Caplus XP-002515677, 1973.
Laskowitz et al., "Downregulation of Microglial Activation by Apolopoprotein E and ApoE-Mimetic Peptides," Exp. Neurol. 2001, vol. 167, pp. 74-85.
Letter of McCarthy Tetrault dated May 9, 2012 enclosing Office Action for Mexican Patent Application No. MX/a/2008/013843.
Letty, S. et al., "Differential impairments of spatial memory and social behavior in two models of limbic epilepsy," Epilepsia, 1995, vol. 36, pp. 973-982.
Levition, A. et al., "Brain damage markers in children. Neurobiological and clinical aspects," Acta Paediatrica, 2002, vol. 91, pp. 9-13.
Longa et al., "Reversible Middle Cerebral Artery Occlusion Without Craniectomy in Rats," Stroke, 1989, vol. 30, pp. 84-91.
Loscher, W. et al., "New Horizons in the development of antiepileptic drugs," Epilepsy Res., 2002, vol. 50, pp. 3-16.
Maragakis, N. et al., "Glutamate transporters: animal models t neurologic disease," Neurobiol Dis. 2004, vol. 15, pp. 461-473.
Maroney et al., "CEP-1347 (KT7515), a semisynthetic inhibitor of the mixed lineage kinase family," J. Biol Chem., 2001, vol. 276, No. 27, pp. 25302-25308.
Maroney et al., "CEP-1347 (KT7515), an inhibitor of JNK Activation, Rescues Sympathetic Neurons and Neuronally Differentiated PC 12 Cells from Death Evoked by Three Distinct Insults," J. Neurochem., 2001, vol. 73, pp. 1901-1912.
Matyus, P. et al. "Some aspects of the chemistry of pyrimido[1,2-b]pyridazinones," Journal of Heterocyclic Chemistry, 1988, vol. 25, No. 5, pp. 1535-1542.
Minghetti, L. et al., "Role of Inflammation in neurodegenerative diseases," Curr. Opin. Neurol., 2005, vol. 18, pp. 315-321.
Morris, R. G. M., "Spatial Localization Does Not Require the Presence of Local Cues," Learning and Motivation vol. 12, 1981, pp. 239-260.
Morris, R., "Developments of a Water-Maze Procedure for Studying Spatial Learning in the Rat," Journal of Neuroscience Methods, vol. 11, 1984, pp. 47-60.
Mrak, R. et al., "Glia and cytoknes in progression of neurodogeneration," Neurobiol Aging, 2005, Volo. 26, pp. 349-354.
Nakao, Tatsu et al., "Preparation of triazolopyridazine-containing polyheterocycles as pharmaceuticals," Database Caplus XP-002515675, 1989.
Namura et al., "Intravenous administration of MEK inhibitor U00126 affords brain protection against forebrain Ischemia and focal cerebral ischemia," Proc Natl Acad Sci USA, Sep. 25, 2001, vol. 98, No. 20, pp. 11569-11574, Epub Aug. 14, 2001.
Nelson et al,, "Compound holds promise for neurogenerative disease," Lancet Neurology, 2006, vol. 5, No. 3, p. 210.
Nicolause, BJR, Decision Making in Drug Research, XX XX, Jan. 1, 1983, pp. 173-186.

Nippon Soda Co Ltd., "Pyridazine derivative and herbicide," Patent Abstracts of Japan, Publication Date: Dec. 1, 1984; English Abstract of JP-59 212480.
Non-final Office Action for related U.S. Appl. No. 12/298,623 dated Mar. 31, 2011.
Non-final Office Action for related U.S. Appl. No. 12/298,624 dated Sep. 23, 2011.
Non-final Office Action for related U.S. Appl. No. 12/298,652 dated Jan. 26, 2012.
Non-final Office Action for related U.S. Pat. No. 7,888,357 dated Jun. 26, 2009.
Non-final Office Action for related U.S. Pat. No. 8,063,047 dated Sep. 17, 2010.
Office Action for China Application No. 2007 80023749.6 dated Jun. 22, 2011.
Office Action for CN 200580037702 dated Sep. 4, 2009 with translation.
Office Action for MX/a/2007/005247 dated Aug. 25, 2009 with translation.
Office Action for related Canadian Patent Application No. 2 589 102 dated Feb. 24, 2012.
Office Action for related Japanese Patent Application No. 2007 539297 dated Feb. 9, 2012.
Office Action in related Canadian Patent Application No. 2 589 106 dated Feb. 24, 2012.
Office Action issued on Feb. 24, 2012 in corresponding Canadian Application No. 2 589 106.
Office Action issued on Jan. 24, 2011 in corresponding Indian Patent Application No. 1977/KOLNP/2007, filed Jun. 1, 2007, 10 pages.
Office Action issued on Sep. 26, 2011 in corresponding Mexican Patent Application No. MX/a/2010/005141 filed May 2, 2007, 2 pages.
Office Action regarding POA documents for MX/a/2007/005247 dated Nov. 2, 2005.
Ohno et al., "Differential effects of Alpha-CaMKII mutation on hippocampal learning and changes in intrinsic neuronal excitability," Eur. J. Neurosci., 2006, vol. 23, No. 8, pp. 2235-2240.
Ohno et al., "Trace eyeblink conditioning requires the hippocampus but not autophosphorylation of Alpha-CaMKII in mice," Learning & Memory, 2005, vol. 12, No. 3, pp. 211-215.
Our comments on the Office Action for related Japanese Patent Application No. 2007 539305 dated Apr. 20, 2012.
Parker, J. et al., "Inhibitors of myosin light chain kinase and phosphodiesterase reduce ventilator-induced lung injury," J. Appl. Physiol, Dec. 2000, vol. 89, No. 6, pp. 2241-2248.
Partyka et al., J. Med. Chem., 1971, vol. 14, No. 3, pp. 262-264.
Perry, V et al., "Systemic infections and inflammation affect chronic neurodegeneration," Nat Rev Immunol., 2007, doi: 10.1038/nri 2015.
Petrova et al., "Cyclopentenone prostaglandins suppress activation of microglia: Down-regulation of inducible nitric-oxide synthase by 15-deoxy-$\Delta$12, 14-prostaglandin J2," PNAS, 1999, vol. 96, pp. 4668-4673.
Pirvola, U. et al., "Rescue of Hearing Auditory Hair Cells, and Neurons by CEP-1347/KT7515, an inhibitor of c-Jun N-Terminal Kinase Activation," J. Neurosci., 2000, vol. 20, pp. 43-50.
Prusiner, S. B. et al., "Shattuck Lecture—Neurodegenerative Disease and Prions," New Engl. J. Med., 2001, vol. 344, pp. 1516-1526.
Rao, V. et al., "Antisense Knockdown of the glial glutamate transporter GLT-1 exacerbates hippocampal damage following traumatic injury to rat brain," Eur. J. Neurosci., 2001, vol. 13, pp. 119-128.
Ravizza et al., "Inflammatory response and glia activation in developing rat hippocampus after status epilepticus," Epilepsia, 2005, vol. 46, pp. S113-S117.
Recanatini et al., "QT prolongation through hERG K (+) channel blockade: current knowledge and strategies for the early prediction during drug development," Med Res Rev, Mar. 2005, vol. 25, No. 2, pp. 133-166.
Reply to Communication pursuant to Article 94(3) EPC for EP 02796459 of Sep. 30, 2010 dated Apr. 8, 2009.
Reply to Communication pursuant to Article 94(3) EPC for EP07756162 of Feb. 11, 2009 dated Nov. 19, 2009.

(56) References Cited

OTHER PUBLICATIONS

Reply to Office Action for MX/a/2007/005247 of Aug. 25, 2009 dated Mar. 1, 2010.
Response dated Jan. 23, 2011 to Mar. 22, 2010 office action.
Response in related Australian Patent Application No. 2005 302 225 filed Apr. 11, 2012.
Response to communication pursuant to Article 94(3) E EPC for EP 07776351.4 dated Jul. 20, 2010.
Response to communication pursuant to Article 94(3) EPC for EP 05823123.4 dated Dec. 8, 2009.
Response to communication pursuant to Article 94(3) EPC for EP 05823123.4 dated Jun. 21, 2010.
Response to communication pursuant to Article 94(3) EPC for EP 05823123.4 dated Jan. 10, 2011.
Response to first examination report dated Jan. 20, 2012.
Response to first office action for China Application No. 200580037702.6 Mar. 11, 2011.
Response to Office Action filed Apr. 11, 2012 in corresponding Australian Application No. 2005 30222.5.
Response to office action for china application No. 200780023749.6 dated Jan. 7, 2012.
Rival, Y. et al., "5-HT3 Antagonists derived from aminopyridazine-type muscarinic M1 Agonists," J. Med. Chem., 1998, vol. 41, pp. 311-317.
Rizzi et al., "Glia activation and cytokine increase in rat hippocampus by kainic acid-induced status epilepticus during postnatal development," Neurobiol. Dis., 2003, vol. 14, pp. 494-503.
Roden, "Drug-induced prolongation of the QT interval," N. Engl. J. Med., Mar. 4, 2004, vol. 350, No. 10, pp. 1013-1022.
Rohet, F. et al., "Synthesis and analgesic effects of 3-substituted 4,6-Diarylpyridazine derivatives of the arylpiperazine class," Bioorganic & Medicinal Chemistry, Apr. 1997, vol. 5, No. 4, pp. 655-659.
Rothermundt, M. et al., "S100B in brain damage and neurodegeneration," Mircoscopy Research & Technique, 2003, vol. 60, pp. 614-632.
Sanchez et al., "Decreased glutamate receptor 2 expression and enchanced epileptogenesis in immature rat hippocampus after perinatal hypoxia-induced seizures," J. Neurosci., 2001, vol. 21, pp. 8154-8563.
Sauer, J. et al., "Synthesis of 3,5-distributed pyridazines by regioselective [4+2] Cycloadditions with Ethynytributyltin and Subsequent Replacement of the Organotin Substituent," Tetrahedron, 1998, vol. 54, pp. 4297-4312.
Sayin, U., et al., "Seizures in the developing brain cause adverse long-term effects o spatial learning and anxiety," Epilepsia, 2004, vol. 45, pp. 1539-1548.
Schmid, R. et al., "Effects of neonatal seizures on subsequent seizure-induced brain injury," Neurology, 1999, vol. 53, pp. 1754-1761.
Schmued, L. et al., "Fluoro-Jade B: a high affinity fluorescent marker for the localization of neuronal degeneration," Brain Res., 2000, vol. 874, pp. 123-130.
Schumacher et al., "Death Associated Protein Kinase as a Potential Therapeutic Target," Expert Opin. Ther. Targets, Aug. 2002, vol. 6, No. 4, pp. 497-506.
Selkoe, D. J. et al., "Alzheimer's Disease: Genes, Proteins, and Therapy," Physiol. Rev., 2001, vol. 81, pp. 741-766.
Sotelo, E. et al., "Pyridazines. Part 26, Efficient and regioselective Pd-catalyzed arylation of 4-bromo-6-chromo-6-chloro-3-phenylpyridazine," Synless, 2002, vol. 2, pp. 223-226.
South, M. S. et al., "Synthesis and Reactions of Haloazodienes. A new and General Synthesis of Substituted Pyridazines," J. Org. Chem., 1996, vol. 61, pp. 8921-8934.
Stahl, P. H. et al., Handbook of Medicinal Salts. Properties, selection and use. 2002, Verlag Helvetica Chimica Acta & Wiley-VVH, Weinhem.
Stevens et al., "NHLBI workshop report: endothelial cell phenotypes in heart, lung, and blood diseases," Am J Physiol Cell Physiol, Nov. 2001, vol. 281, No. 5, pp. 1422-1433.
Supplementary European Search Report for EP 02796459 dated Oct. 7, 2004.
Supplementary European Search Report for EP05823123 dated Feb. 18, 2009.
Supplementary European Search Report issued Apr. 4, 2012 and Communication pursuant to Rule 70(2) and 70a(2) EPC in corresponding European Application No. 05817588.6.
Suzuki et al., Heterocycles (2002), 57(4), pp. 723-731.
Tereshko et al., "Crystal structures of the catalytic domain of human protein kinase associated with apoptosis and tumor suppression," Nat Struct Biol., Oct. 2001, vol. 8, No. 10, pp. 899-907.

* cited by examiner

MW01-7-029WH

MW01-7-027B-WH

MW01-3-065SRM

PYRIDAZINE COMPOUNDS, COMPOSITIONS AND METHODS

RELATED APPLICATIONS

This application claims priority benefit from prior U.S. Provisional Application Ser. No. 60/624,346 filed Nov. 2, 2004 and U.S. Provisional Application Ser. Nos. 60/723,124, filed Oct. 3, 2005, and 60/723,090, filed Oct. 3, 2005.

This invention was made with government support under P01 AG021184 and R01 NS047586 awarded by the National Institutes of Health. The government has certain rights in the invention.

FIELD OF INVENTION

The invention relates to novel chemical compounds, compositions and methods of making and using the same. In particular, the invention provides pyridazine compounds and/or related heterocyclic derivatives, compositions comprising the same, and methods of using pyridazine compounds and/or related heterocyclic derivatives and compositions comprising the same, for modulation of cellular pathways (e.g., signal transduction pathways), for treatment or prevention of inflammatory diseases (e.g., Alzheimer's disease), for research, drug screening, and therapeutic applications.

BACKGROUND OF INVENTION

The majority of inflammatory conditions and diseases result from a disruption in the homeostatic balance between beneficial and detrimental responses of the organism. For example, there may be a decrease in the production of trophic molecules that mediate cell survival and other beneficial cellular processes, or there may be an overproduction of pro-inflammatory or other detrimental molecules that mediate toxic cellular responses. Disregulation of signal transduction pathways involving protein kinases are often involved in the generation or progression of these diseases. For example, neuroinflammation is a process that results primarily from an abnormally high or chronic activation of glia (microglia and astrocytes). This overactive state of glia results in increased levels of inflammatory and oxidative stress molecules, which can lead to neuron damage or death. Neuronal damage/death can also induce glial activation, facilitating the propagation of a localized, detrimental cycle of neuroinflammation [7].

The inflammation (e.g., neuroinflammation) cycle has been proposed as a potential therapeutic target in the development of new approaches to treat inflammatory disease (e.g., Alzheimer's disease), However, the efficacy and lexicological profile of compounds that focus only on classical non-steroidal anti-inflammatory drug targets have been disappointing to date, for example, most anti-inflammatory therapeutics are palliative, providing minimal, short-lived, symptomatic relief with limited effects on inflammatory disease (e.g., neuroinflammatory diseases such as Alzheimer's disease) progression. Because the major societal impact from inflammatory diseases (e.g., neuroinflammatory diseases such as Alzheimer's disease) is expected to increase greatly in coming decades, there is an urgent need for anti-inflammatory therapeutics that impact disease progression when administered soon after diagnosis (e.g., diagnosis of cognitive decline), or in a chemo-preventive paradigm as combinations of risk factors with prognostic value are identified. In either therapeutic paradigm, new drugs must have a good therapeutic index, especially in regard to potential toxicology in the elderly.

Despite an overwhelming need, and the presence of well-defined molecular targets, the current anti-inflammatory drug development pipeline is lacking chemically diverse compounds that work within the relevant therapeutic window and treatment paradigm needed for altering disease progression. An area of comparative neglect that fits this therapeutic window is neuroinflammation [1]. Thus, development of new classes of anti-inflammatory compounds that can modulate inflammatory disease-relevant pathways are urgently needed.

SUMMARY OF INVENTION

The present invention relates to novel chemical compounds, compositions and methods of making and using the same. In particular, the present invention provides pyridazine compounds and/or related heterocyclic derivatives, compositions comprising the same, and methods of using pyridazine compounds and/or related heterocyclic derivatives, and compositions comprising the same, for modulation of cellular pathways (e.g., signal transduction pathways), for treatment or prevention of inflammatory diseases (e.g., Alzheimer's disease), for research, drug screening, and therapeutic applications.

The invention provides a method for treating a disease disclosed herein, in particular an inflammatory disease in a subject comprising administering to the subject a pyridazinyl radical pendant with an aryl or substituted aryl, in particular phenyl or substituted phenyl, a heteroaryl or substituted heteroaryl, in particular piperazinyl substituted with pyrimidinyl, or pyridinyl.

In an aspect, the invention provides a method for treating a disease disclosed herein, in particular an inflammatory disease, in a subject comprising administering to the subject a compound of the Formula I, comprising Ia and Ib:

Formula I

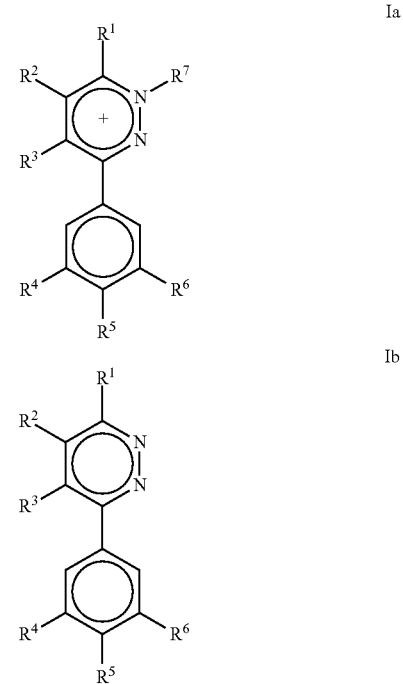

wherein $R^1$, $R^2$, and $R^3$ are independently hydrogen, hydroxyl, alkyl, alkenyl, alkynyl, alkylene, alkenylene, alkoxy, alkenyloxy, cycloalkyl, cycloalkenyl, aryl, aryloxy, arylalkoxy, aroyl, heteroaryl, heterocyclic, acyl, acyloxy, sulfonyl, sulfinyl, sulfenyl, amino, imino, azido, thiol, thioalkyl, thioalkoxy, thioaryl, nitro, ureido, cyano, halo, silyl, silyloxy, silylalkyl, silylthio, =O, =S, carboxyl, carbonyl, carbamoyl, or carboxamide; $R^7$ is hydrogen, hydroxyl, alkyl, alkenyl, alkynyl, alkylene, alkenylene, alkoxy, alkenyloxy, cycloalkyl, cycloalkenyl, aryl, aryloxy, arylalkoxy, aroyl, heteroaryl, heterocyclic, acyl, acyloxy, sulfonyl, sulfinyl, sulfenyl, amino, imino, azido, thiol, thioalkyl, thioalkoxy, thioaryl, nitro, ureido, cyano, halo, silyl, silyloxy, silylalkyl, silylthio, =O, =S, carboxyl, carbonyl, carbamoyl, or carboxaimde or R7 may be absent and there is a double bond between N at position 1 and C at position 6; $R^4$, $R^5$, and $R^6$ are independently hydrogen, alkyl, alkoxy, halo, or nitro; or $R^1$ and $R^2$, $R^1$ and $R^7$, or $R^2$ and $R^3$ may form a heteroaryl or heterocyclic ring; or an isomer or a pharmaceutically acceptable salt thereof.

In an embodiment, $R^1$ is a piperazinyl or substituted piperazinyl, in particular a piperazinyl substituted with a pyrimidinyl of Formula A below.

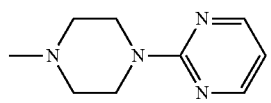

A

Therefore, the invention also provides a method for treating a disease disclosed herein, in particular an inflammatory disease, in a subject comprising administering to the subject a compound of the Formula II:

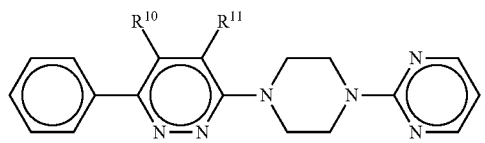

II wherein $R^{10}$ and $R^{11}$ are independently hydrogen, hydroxyl, alkyl, alkenyl, alkynyl, alkylene, alkenylene, alkoxy, alkenyloxy, cycloalkyl, cycloalkenyl, aryl, aryloxy, arylalkoxy, aroyl, heteroaryl, heterocyclic, acyl, acyloxy, sulfonyl, sulfinyl, sulfenyl, amino, imino, azido, thiol, thioalkyl, thioalkoxy, thioaryl, nitro, ureido, cyano, halo, silyl, silyloxy, silylalkyl, silylthio, =O, =S, carboxyl, carbonyl, carbamoyl, or carboxamide; or an isomer or a pharmaceutically acceptable salt thereof In an aspect, the invention provides a method for treating a disease disclosed herein, in particular an inflammatory disease, in a subject comprising administering to the subject a compound of the Formula III:

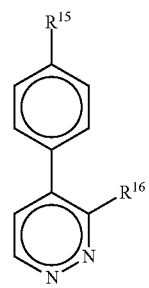

III wherein $R^{15}$ and $R^{16}$ are independently hydrogen, hydroxyl, alkyl, alkenyl, alkynyl, alkylene, alkenylene, alkoxy, alkenyloxy, cycloalkyl, cycloalkenyl, aryl, aryloxy, arylalkoxy, aroyl, heteroaryl, heterocyclic, acyl, acyloxy, sulfonyl, sulfinyl, sulfenyl, amino, imino, azido, thiol, thioalkyl, thioalkoxy, thioaryl, nitro, ureido, cyano, halo, silyl, silyloxy, silylalkyl, silylthio, =O, =S, carboxyl, carbonyl, carbamoyl, or carboxamide; or an isomer or a pharmaceutically acceptable salt thereof.

In another aspect, the invention provides a method for treating a disease disclosed herein, in particular an inflammatory disease, in a subject comprising administering to the subject a compound of the Formula IV:

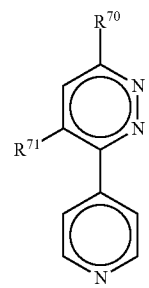

IV wherein $R^{70}$ is substituted or unsubstituted hydrogen, hydroxyl, alkyl, alkenyl, alkynyl, alkylene, alkenylene, alkoxy, alkenyloxy, cycloalkyl, cycloalkenyl, aryl, aryloxy, arylalkoxy, aroyl, heteroaryl, heterocyclic, acyl, acyloxy, sulfonyl, sulfinyl, sulfenyl, amino, imino, azido, thiol, thioalkyl, thioalkoxy, thioaryl, nitro, ureido, cyano, halo, silyl, silyloxy, silylalkyl, silylthio, =O, =S, carboxyl, carbonyl, carbamoyl, or carboxamide, especially heterocyclic, heteroaryl, amino, and substituted amino and $R^{71}$ is aryl or substituted aryl; or an isomer or a pharmaceutically acceptable salt thereof.

In a further aspect, the invention provides a method for treating a disease disclosed herein, in particular an inflammatory disease, in a subject comprising administering to the subject a compound of the Formula V:

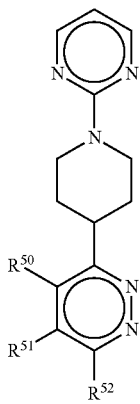

wherein $R^{50}$, $R^{51}$, and $R^{52}$ are independently hydrogen, hydroxyl, alkyl, alkenyl, alkynyl, alkylene, alkenylene, alkoxy, alkenyloxy, cycloalkyl, cycloalkenyl, aryl, aryloxy, arylalkoxy, aroyl, heteroaryl, heterocyclic, acyl, acyloxy, sulfonyl, sulfinyl, sulfenyl, amino, imino, azido, thiol, thioalkyl, thioalkoxy, thioaryl, nitro, ureido, cyano, halo, silyl, silyloxy, silylalkyl, silylthio, =O, =S, carboxyl, carbonyl, carbamoyl, or carboxamide; or an isomer or a pharmaceutically acceptable salt thereof.

In an aspect, a method is provided for treating a disease disclosed herein in a subject comprising administering a compound of the Formula I, II, III, IV, or V as defined herein, with the proviso that compounds depicted in Table 1 are excluded.

The invention relates to a method for treating diseases disclosed herein in a subject comprising administering to the subject a therapeutically effective amount of one or more compound of the Formula I, II, III, IV, or V, or a pharmaceutically acceptable salt thereof, or a composition comprising a compound of the Formula I, II, III, IV, or V and a pharmaceutically acceptable carrier, excipient, or vehicle. In an aspect the invention provides beneficial effects following treatment. The methods of the invention can be used therapeutically or prophylactically in a subject susceptible to or having a genetic predisposition to a disease disclosed herein.

In another aspect of the invention, a method is provided for treating in a subject a disease involving or characterized by inflammation, in particular neuroinflammation, comprising administering to the subject a therapeutically effective amount of a compound of the Formula I, II, III, IV, or V, or a pharmaceutically acceptable salt thereof. In a further aspect, a method is provided for treating in a subject a condition involving inflammation, in particular neuroflammation, comprising administering to the subject a therapeutically effective amount of a composition comprising a compound of the Formula I, II, III, IV, or V and a pharmaceutically acceptable carrier, excipient, or vehicle.

In a further aspect, the invention provides a method involving administering to a subject a therapeutic compound of the Formula I, II, III, IV, or V, or a pharmaceutically acceptable salt thereof, or a composition comprising a compound of the Formula I, II, III, IV, or V, and a pharmaceutically acceptable carrier, excipient, or vehicle which inhibit or reduce neuroinflammation, activation of glia, proinflammatory cytokines, oxidative stress-related enzymes, acute phase proteins and/or components of the complement cascade.

In another aspect, the invention provides a method for treating in a subject a disease associated with neuroinflammation that can be decreased or inhibited with a compound disclosed herein comprising administering to the subject a therapeutically effective amount of a compound of the Formula I, II, III, IV, or V, a pharmaceutically acceptable salt thereof, or a composition comprising a compound of the Formula I, II, III, IV, or V, n particular the compounds depicted in the Figures and Tables, more particularly Table 2, 3, 4 or 5 and derivatives thereof and an isomer or pharmaceutically acceptable carrier, excipient, or vehicle.

Methods of the invention may be used to prevent or inhibit activation of protein kinases, in particular death associated protein kinase (DAPK); reduce or inhibit kinase activity, glial activation, neuronal cell damage, and/or neuronal cell death; inhibit cell signaling molecule production (e.g., IL-1β and TNFα), amelioriate progression of a disease or obtain a less severe stage of a disease in a subject suffering from such disease (e.g., neuroinflammatory disease, in particular a neurodegenerative disease, more particularly Alzheimer's disease); delay the progression of a disease (e.g. neuroinflammatory disease, in particular a neurodegenerative disease, more particularly Alzheimer's disease), increase survival of a subject suffering from a disease (e.g. neuroinflammatory disease, in particular a neurodegenerative disease, more particularly Alzheimer's disease; treat or prevent a neurodegenerative disease, in particular Alzheimer's disease; treat mild cognitive impairment (MCI); reverse or inhibit neuroinflammation, activation of signaling pathways involved in inflammation (e.g., neuroinflammation), cell signaling molecule production, activation of glia or glial activation pathways and responses, proinflammatory cytokines or chemokines (e.g., interleukin (IL) or tumor necrosis factor (TNF), oxidative stress-related responses such as nitric oxide synthase production and nitric oxide accumulation, acute phase proteins, components of the complement cascade, protein kinase activity (e.g., death associated protein kinase activity), neuronal cell damage, and/or neuronal cell death, after the onset of cognitive deficits and Alzheimer's disease neuropathology in a subject; improve memory of a healthy subject or the memory of a subject with age impaired memory; improve memory, especially short-term memory and other mental dysfunction associated, with the aging process; treat a mammal in need of improved memory, wherein the mammal has no diagnosed disease, disorder, infirmity or ailment known to impair or otherwise diminish memory; and/or improve the lifespan of a subject suffering from Alzheimer's disease.

The invention provides a method of preventing a disease disclosed herein in a subject with a genetic predisposition to such disease by administering an effective amount of a compound of the Formula I, II, III, IV, or V, or a pharmaceutically acceptable salt thereof, or a composition comprising a compound of the Formula I, II, III, IV, or V and a pharmaceutically acceptable carrier, excipient, or vehicle.

The invention relates to compounds of the Formula I with the proviso that the compounds depicted in Table 1 are excluded.

The invention relates to compounds of the Formula II with the proviso that the compounds depicted in Table 1 are excluded.

The invention also relates to compounds of the Formula III with the proviso that compounds depicted in Table 1 are excluded.

The invention also relates to compounds of the Formula IV with the proviso that compounds depicted in Table 1 are excluded.

The invention also relates to compounds of the Formula V with the proviso that compounds depicted in Table 1 are excluded.

A compound of the Formula I, II, III, IV, or V may optionally comprise a carrier interacting with one or more radicals in the compound, for example $R^1$, $R^2$, $R^3$, $R^4$, $R^5$, $R^6$ or $R^7$ in Formula I. A carrier may be a polymer, carbohydrate, or peptide, or combinations thereof, and it may be optionally substituted, for example, with one or more alkyl, halo, hydroxyl, halo, or amino.

In accordance with aspects of the invention pyridazine compounds and/or related heterocyclic derivatives thereof (See, e.g., the Figures and Tables herein, in particular Table 2, 3, 4 or 5 or derivatives thereof) are provided for use in research, drug screening, for modulation of cellular pathways (e.g., signal transduction pathways), and for treatment or prevention of inflammatory diseases (e.g., Alzheimer's disease). In some embodiments, the present invention provides new classes of chemical compounds capable of modulating pro-inflammatory and oxidative stress related, cellular signaling pathways (e.g., in activated glial cells). In some embodiments, one or more compounds of the Figures and Tables herein are used to modulate kinase activity alone or in combination with other compounds or therapies. In some embodiments, compounds, and methods of using the compounds, provided by the invention are those depicted in the Figures and Table 2, 3, 4, and/or 5 and derivatives thereof. In some embodiments, the invention provides MW01-3-5-183WH, MWO1-5-188WH, MWO1-2-065LKM, MWO1-2-184WH, MW01-2-189WH and MW01-2-151SRM and methods of synthesizing the same.

In some embodiments, the invention provides MW01-3-5-183WH, MWO1-5-188WH, MWO1-2-065LKM, MWO1-2-184WH, MW01-2-151SRM, MW01-2-189WH, MW01-1-01-L-D07, and/or related heterocyclic derivatives of these compounds and methods of making and using the same for modulating cellular pathways (e.g., signal transduction pathways) for use in research, drug screening, and therapeutic applications.

In an aspect, the invention provides compositions for prevention and/or treatment of a disease disclosed herein. Thus, the invention provides a pharmaceutical composition comprising a compound of the Formula I, II, III, IV, or V, in particular a therapeutically effective amount of a compound of the Formula I, II, III, IV, or V, more particularly a compound depicted in the Figures and Table 2, 3, 4, and/or 5 or derivatives thereof, for treating a disease. More particularly, the invention provides a pharmaceutical composition in a form adapted for administration to a subject to provide therapeutic effects, in particular beneficial effects to treat a disease disclosed herein.

In another aspect, the composition is in a form such that administration to a subject suffering from a disease results in a decrease or reversal of one or more of the following: inflammation (e.g. neuroinflammation), activation of signaling pathways involved in inflammation (e.g., neuroinflammation), cell signaling molecule production, activation of glia or glial activation pathways and responses, proinflammatory cytokines or chemokines (e.g., interleukin (IL) or tumor necrosis factor (TNF), oxidative stress-related responses such as nitric oxide synthase production and nitric oxide accumulation, acute phase proteins, components of the complement cascade, protein kinase activity (e.g., death associated protein kinase activity), cell damage (e.g., neuronal cell damage), and/or cell death (e.g., neuronal cell death). A composition of the invention can be in a form that results in one or more of a decrease or reversal of one or more of the following inflammation (e.g. neuroinflammation), activation of signaling pathways involved in inflammation (e.g., neuroinflammation), cell signaling molecule production, activation of glia or glial activation pathways and responses, proinflammatory cytokines or chemokines (e.g., interleukin (IL) or tumor necrosis factor (TNF), oxidative stress-related, responses such as nitric oxide synthase production and nitric oxide accumulation, acute phase proteins, components of the complement cascade, protein kinase activity (e.g., death associated protein kinase activity), cell damage (e.g., neuronal cell damage), and/or cell death (e.g., neuronal cell death) in a subject.

In an aspect, the invention features a composition comprising a compound of the invention in a therapeutically effective amount for decreasing or reversing of one or more of the following: inflammation (e.g. neuroinflammation), activation of signaling pathways involved in inflammation (e.g., neuroinflammation), cell signaling molecule production, activation of glia or glial activation pathways and responses, proinflammatory cytokines or chemokines (e.g., interleukin (IL) or tumor necrosis factor (TNF), oxidative stress-related responses such as nitric oxide synthase production and nitric oxide accumulation, acute phase proteins, components of the complement cascade, protein kinase activity (e.g., death associated protein kinase activity), cell damage (e.g., neuronal cell damage), and/or cell death (e.g., neuronal cell death) in a subject. The composition can be in a pharmaceutically acceptable carrier, excipient, or vehicle.

Additionally the invention contemplates a method of preparing a stable pharmaceutical composition comprising one or more compound of the Formula I, II, III, IV, or V. After a composition is prepared, it can be placed in an appropriate container and labeled for treatment of an indicated disease. For administration of a composition of the invention, such labeling would include amount, frequency, and method of administration.

In some aspects the invention provides methods to make commercially available pills, tablets, caplets, soft and hard gelatin capsules, lozenges, sachets, cachets, vegicaps, liquid drops, elixirs, suspensions, emulsions, solutions, syrups, aerosols (as a solid or in a liquid medium) suppositories, sterile injectable solutions, and/or sterile packaged powders, which contain a compound of the Formula I, II, III, IV, or V of the invention.

In an aspect, compounds and compositions of the invention may be administered therapeutically or prophylactically to treat a disease disclosed herein. While not wishing to be bound by any particular theory, the compounds and compositions may act to ameliorate the course of a disease using without limitation one or more of the following mechanisms: preventing, reducing and/or inhibiting inflammation (e.g. neuroinflammation), activation of signaling pathways involved in inflammation (e.g., neuroinflammation), cell signaling molecule production, activation of glia or glial activation pathways and responses, proinflammatory cytokines or chemokines (e.g., interleukin (IL) or tumor necrosis factor (TNF), oxidative stress-related responses such as nitric oxide synthase production and nitric oxide accumulation, acute phase proteins, components of the complement cascade, protein kinase activity (e.g., death associated protein kinase activity), cell damage (e.g., neuronal cell damage), and/or cell death (e.g., neuronal cell death).

The invention relates to the use of a composition comprising at least one compound of the Formula I, II, III, IV, or V for the preparation of a medicament for treating a disease disclosed herein. The invention additionally relates to uses of a pharmaceutical composition of the invention in the preparation of medicaments for the prevention and/or treatment of a disease disclosed herein. The medicament may be in a form suitable for consumption by a subject, for example, a pill, tablet, caplet, soft and hard gelatin capsule, lozenge, sachet, cachet, vegicap, liquid drop, elixir, suspension, emulsion, solution, syrup, aerosol (as a solid or in a liquid medium) suppository, sterile injectable solution, and/or sterile packaged powder.

The invention further relates to a kit comprising one or more compound of the Formula I, II, III, IV, or V or a composition comprising a compound of the Formula I, II, III, IV, or V. In an aspect, the invention provides a kit for preventing and/or treating, a disease disclosed herein comprising one or more compound of the Formula I, II, III, IV, or V, a container, and instructions for use. The composition of a kit of the invention can further comprise a pharmaceutically acceptable carrier, excipient, or vehicle.

The compounds of the Formula I, II, III, IV, or V (in particular the compounds depicted in Table 2, 3, 4 and/or 5 or derivatives thereof) provide a structural scaffold on which to base compositions for decreasing or reversing one or more of the following: inflammation (e.g. neuroinflammation), activation of signaling pathways involved in inflammation (e.g., neuroinflammation), cell signaling molecule production, activation of glia or glial activation pathways and responses, proinflammatory cytokines or chemokines (e.g., interleukin (IL) or tumor necrosis factor (TNF), oxidative stress-related responses such as nitric oxide synthase production and nitric oxide accumulation, acute phase proteins, components of the complement cascade, protein kinase activity (e.g., death associated protein kinase activity), cell damage (e.g., neuronal cell damage), and/or cell death (e.g., neuronal cell death), wherein the compound comprise a structure of Formula I, II, III, IV, or V.

Thus, the invention also contemplates libraries or collections of compounds all of which are represented by a compound of the Formula I, II, III, IV, or V, in particular a compound depicted in Table 2, 3, 4, and/or 5 or derivatives thereof. In particular, the invention contemplates a combinatorial library comprising compounds for decreasing or reversing one or more of the following: inflammation (e.g. neuroinflammation), activation of signaling pathways involved in inflammation (e.g., neuroinflammation), cell signaling molecule production, activation of glia or glial activation pathways and responses, proinflammatory cytokines or chemokines (e.g., interleukin (IL) or tumor necrosis factor (TNF), oxidative stress-related responses such as nitric oxide synthase production and nitric oxide accumulation, acute phase proteins, components of the complement cascade, protein kinase activity (e.g., death associated protein kinase activity), cell damage (e.g., neuronal cell damage), and/or cell death (e.g., neuronal cell death), wherein the compound comprise a structure of Formula I, II, III, IV, or V.

These and other aspects, features, and advantages of the present invention should be apparent to those skilled in the art from the following detailed description.

DETAILED DESCRIPTION

Figure 1:
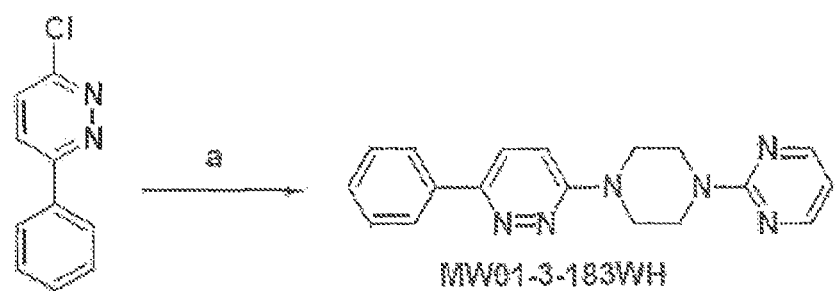
FIG. 1 depicts a synthetic scheme for synthesis of MWO1-3-183WH.

For convenience, certain terms employed in the specification, examples, and appended claims are collected here.

Numerical ranges recited herein by endpoints include all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about." The term "about" means plus or minus 0.1 to 50%, 5-50%, or 10-40%, preferably 10-20%, more preferably 10% or 15%, of the number to which reference is being made. Further, it is to be understood that "a," "an," and "the" include plural referents unless the content clearly dictates otherwise. Thus, for example, reference to a composition comprising "a compound" includes a mixture of two or more compounds.

As used herein the terms "administering" and "administration" refer to a process by which a therapeutically effective amount of a compound or composition contemplated herein is delivered to a subject for prevention and/or treatment purposes. Compositions are administered in accordance with good medical practices taking into account the subject's clinical condition, the site and method of administration, dosage, patient age, sex, body weight, and other factors known to physicians.

As used herein, the term "co-administration" refers to the administration of at least two compounds or agent(s) (e.g., compound of the Formula I, II, III, IV, or V or pyridazines) or therapies to a subject. In some embodiments, the co-administration of two or more agents/therapies is concurrent. In other embodiments, a first agent/therapy is administered prior to a second agent/therapy. Those of skill in the art understand that the Formulations and/or routes of administration of the various agents/therapies used may vary. The appropriate dosage for co-administration can be readily determined by one skilled in the art. In some embodiments, when agents/therapies are co-administered, the respective agents/therapies are administered at lower dosages than appropriate for their administration alone. Thus, co-administration is especially desirable in embodiments where the co-administration of the agents/therapies lowers the requisite dosage of a known potentially harmful (e.g., toxic) agent(s).

The term "treating" refers to reversing, alleviating, or inhibiting the progress of a disease, or one or more symptoms of such disease, to which such term applies. Depending on the condition of the subject, the term also refers to preventing a disease, and includes preventing the onset of a disease, or preventing the symptoms associated with a disease. A treatment may be either performed in an acute or chronic way. The term also refers to reducing the severity of a disease or symptoms associated with such disease prior to affliction with the disease. Such prevention or reduction of the severity of a disease prior to affliction refers to administration of a compound or composition of the present invention to a subject that is not at the time of administration afflicted with the disease. "Preventing" also refers to preventing the recurrence of a disease or of one or more symptoms associated with such disease. "Treatment" and "therapeutically," refer to the act of treating, as "treating" is defined above.

The terms "subject", "individual", or "patient" are used interchangeably herein and refer to an animal preferably a warm-blooded animal such as a mammal. Mammal includes without limitation any members of the Mammalia. In general, the terms refer to a human. The terms also include domestic animals bred for food or as pets, including equines, bovines, sheep, poultry, fish, porcines, canines, felines, and zoo animals, goats, apes (e.g. gorilla or chimpanzee), and rodents such as rats and mice.

In aspects of the invention, the terms refer to organisms to be treated by the methods of the present invention. Such organisms preferably include, but are not limited to, mammals (e.g., murines, simians, equines, bovines, porcines, canines, felines, and the like), and most preferably includes humans. In the context of particular aspects of the invention, the term "subject" generally refers to an individual who will receive or who has received treatment (e.g., administration of a compound of the Formula I, II, III, IV, or V or a pyridazine compound(s), and optionally one or more other agents) for a condition characterized by inflammation, the dysregulation of protein kinase activity, and/or dysregulation of apototic processes.

Typical subjects for treatment include persons afflicted with or suspected of having or being pre-disposed to a disease disclosed herein, or persons susceptible to, suffering from or that have suffered a disease disclosed herein. A subject may or may not have a genetic predisposition for a disease disclosed herein such as Alzheimer's disease. In particular aspects, a subject shows signs of cognitive deficits and Alzheimer's disease neuropathology. In embodiments of the invention the subjects are suspectible to, or suffer from Alzheimer's disease.

As utilized herein, the term "healthy subject" means a subject, in particular a mammal, having no diagnosed disease, disorder, infirmity, or ailment, more particularly a disease, disorder, infirmity or ailment known to impair or otherwise diminish memory.

The term "diagnosed," as used herein, refers to the recognition of a disease by its signs and symptoms (e.g., resistance to conventional therapies), or genetic analysis, pathological analysis, histological analysis, and the like.

As used herein, the term "modulate" refers to the activity of a compound (e.g., a compound of the Formula I, II, III, IV, or V, or a pyridazine compound) to affect (e.g., to promote or retard) an aspect of cellular function, including, but not limited to, cell growth, proliferation, apoptosis, and the like.

A "beneficial effect" refers to an effect of a compound of the invention or composition thereof in certain aspects of the invention, including favorable pharmacological and/or therapeutic effects, and improved biological activity. In aspects of the invention, the beneficial effects include without limitation prevention, reduction, reversal, or inhibition of one or more of the following: inflammation (e.g. neuroinflammation), activation of signaling pathways involved in inflammation (e.g., neuroinflammation), cell signaling molecule production, activation of glia or glial activation pathways and responses, proinflammatory cytokines or chemokines (e.g., interleukin (IL) or tumor necrosis factor (TNF), oxidative stress-related responses such as nitric oxide synthase production and nitric oxide accumulation, acute phase proteins, components of the complement cascade, protein kinase activity (e.g., death associated protein kinase activity), cell damage (e.g., neuronal cell damage), and/or cell death (e.g., neuronal cell death). In some aspects, a beneficial effect is a favourable characteristic of a composition comprising a compound of the Formula I, II, III, IV, or V including without limitation enhanced stability, a longer half life, and/or enhanced uptake and transport across the blood brain barrier.

The beneficial effect can be a statistically significant effect in terms of statistical analysis of an effect of a compound of the formula I, II, III, IV, or V versus the effects without the compound or compound that is not within the scope of the invention. Statistically significant" or "significantly different" effects or levels may represent levels that are higher or lower than a standard. In aspects of the invention, the difference may be 1.5, 2, 3, 4, 5, or 6 times higher or lower compared with the effect obtained without a compound of the Formula I, II, III, IV, or V.

The term "pharmaceutically acceptable carrier, excipient, or vehicle" refers to a medium which does not interfere with the effectiveness or activity of an active ingredient and which is not toxic to the hosts to which it is administered. A carrier, excipient, or vehicle includes diluents, binders, adhesives, lubricants, disintegrates, bulking agents, wetting or emulsifying agents, pH buffering agents, and miscellaneous materials such as absorbants that may be needed in order to prepare a particular composition. Examples of carriers etc. include but are not limited to saline, buffered saline, dextrose, water, glycerol, ethanol, and combinations thereof. The use of such media and agents for an active substance is well known in the art.

The compounds of the Formula I, II, III, IV, or V disclosed herein also include "pharmaceutically acceptable salt(s)". By pharmaceutically acceptable salts is meant those salts which are suitable for use in contact with the tissues of a subject or patient without undue toxicity, irritation, allergic response and the like, and are commensurate with a reasonable benefit/risk ratio. Pharmaceutically acceptable salts are described for example, in S. M. Berge, et al., J. Pharmaceutical Sciences, 1977, 66:1. Examples of salts include MW01-1-01-L-D10, MW01-1-01-L-E02, MW01-1-01-L-E08, MW01-1-03-L-A05, MW01-1-16-L-D09, and MW01-1-17-L-G04.

A compound of the Formula I, II, III, IV, or V can contain one or more asymmetric centers and may give rise to enantiomers, diasteriomers, and other stereoisomeric forms which may be defined in terms of absolute stereochemistry as (R)- or (S)-. Thus, compounds of the Formula I, II, III, IV, or V include all possible diasteriomers and enantiomers as well as their racemic and optically pure forms. Optically active (R)- and (S)-isomers may be prepared using chiral synthons or chiral reagents, or resolved using conventional techniques. When a compound of the Formula I, II, III, IV, or V contains centers of geometric asymmetry, and unless specified otherwise, it is intended that the compounds include both E and A geometric isomers. All tautomeric forms are also included within the scope of a compound of the Formula I, II, III, IV, or V.

A compound of the Formula I, II, III, IV, or V can exist in unsolvated as well as solvated forms with pharmaceutically acceptable solvents such as water, ethanol, and the like. The solvated forms may be considered equivalent to the unsolvated forms for the purposes of the present invention.

"Therapeutically effective amount" relates to the amount or dose of an active compound of the Formula I, II, III, IV, or V or composition comprising the same, that will lead to one or more desired effects, in particular, one or more therapeutic effects, more particularly beneficial effects. A therapeutically effective amount of a substance can vary according to factors such as the disease state, age, sex, and weight of the subject, and the ability of the substance to elicit a desired response in the subject. A dosage regimen may be adjusted to provide the optimum therapeutic response (e.g. sustained beneficial effects). For example, several divided doses may be administered daily or the dose may be proportionally reduced as indicated by the exigencies of the therapeutic situation.

As used herein, the term "pure" in general means better than 95% pure, and "substantially pure" means a compound synthesized such that the compound, as made or as available for consideration into a composition or therapeutic dosage described herein, has only those impurities that can not readily nor reasonably be removed by conventional purification processes.

The term "derivative" of a compound, as used herein, refers to a chemically modified compound wherein the chemical modification takes place either at a functional group of the compound or on the aromatic ring. Non-limiting examples of derivatives of compounds of the Formula I, II, III, IV, or V (e.g., pyridazine derivatives of the present invention) may include N-acetyl, N-methyl, N-hydroxy groups at any of the available nitrogens in the compound.

A "polymer" refers to molecules comprising two or more monomer subunits that may be identical repeating subunits or different repeating subunits. A monomer generally comprises a simple structure, low-molecular weight molecule containing carbon. Polymers may optionally be substituted. Polymers that can be used in the present invention include without limitation vinyl, acryl, styrene, carbohydrate derived polymers, polyethylene glycol (PEG), polyoxyethylene, polymethylene glycol, poly-trimethylene glycols, polyvinylpyrrolidone, polyoxyethylene-polyoxypropylene block polymers, and copolymers, salts, and derivatives thereof. In aspects of the invention, the polymer is poly(2-acrylamido-2-methyl-1-propanesulfonic acid); poly(2-acrylamido-2-methyl,-1-propanesulfonic acid-coacrylonitrile, poly(2-acrylamido-2-methyl-1-propanesulfonic acid-co-styrene), poly(vinylsulfonic acid); poly(sodium 4-styrenesulfonic acid); and sulfates and sulfonates derived therefrom; poly(acrylic acid), poly(methylacrylate), poly(methyl methacrylate), and poly(vinyl alcohol).

A "carbohydrate" as used herein refers to a polyhydroxyaldehyde, or polyhydroxyketone and derivatives thereof. The term includes monosaccharides such as erythrose, arabinose, allose, altrose, glucose, mannose, threose, xylose, gulose, idose, galactose, talose, aldohexose, fructose, ketohexose, ribose, and aldopentose. The term also includes carbohydrates composed of monosaccharide units, including disaccharides, oligosaccharides, or polysaccharides. Examples of disaccharides are sucrose, lactose, and maltose. Oligosaccharides generally contain between 3 and 9 monosaccharide units and polysaccharides contain greater than 10 monosaccharide units. A carbohydrate group may be substituted at one two, three or four positions, other than the position of linkage to a compound of the Formula I, II, III, IV, or V. For example, a carbohydrate may be substituted with one or more alkyl, amino, nitro, halo, thiol, carboxyl, or hydroxyl groups, which are optionally substituted. Illustrative substituted carbohydrates are glucosamine, or galactosamine. In aspects of the invention, the carbohydrate is a sugar, in particular a hexose or pentose and may be an aldose or a ketose. A sugar may be a member of the D or L series and can include amino sugars, deoxy sugars, and their uronic acid derivatives. In embodiments of the invention where the carbohydrate is a hexose, the hexose is glucose, galactose, or mannose, or substituted hexose sugar residues such as an amino sugar residue such as hexosamine, galactosamine, glucosamine, in particular D-glucosamine (2-amino-2-doexy-D-glucose) or D-galactosamine (2-amino-2-deoxy-D-galactose). Illustrative pentose sugars include arabinose, fucose, and ribose.

A sugar residue may be linked to a compound of the Formula I, II, III, IV, or V from a 1,1 linkage, 1,2 linkage, 1,4 linkage, 1,5 linkage, or 1,6 linkage. A linkage may be via an oxygen atom of a compound of the Formula I, II, III, IV, or V. An oxygen atom can be replaced one or more times by —CH$_2$— or —S— groups.

The term "carbohydrate" also includes glycoproteins such as lectins (e.g. concanavalin A, wheat germ agglutinin, peanutagglutinin, seromucoid, and orosomucoid) and glycolipids such as cerebroside and ganglioside.

A "peptide" carrier for use in the practice of the present invention includes one, two, three, four, or five or more amino acids covalently linked through a peptide bond. A peptide can comprise one or more naturally occurring amino acids, and analogs, derivatives, and congeners thereof. A peptide can be modified to increase its stability, bioavailability, solubility, etc. "Peptide analogue" and "peptide derivative" as used herein include molecules which mimic the chemical structure of a peptide and retain the functional properties of the peptide. A carrier for use in the present invention can be an amino acid such as alanine, glycine, proline, methionine, serine, threonine, histidine, asparagine, alanyl-alanyl, prolyl-methionyl, or glycyl-glycyl. A carrier can be a polypeptide such as albumin, antitrypsin, macroglobulin, haptoglobin, caeruloplasm, transferring, α- or β-lipoprotein, β- or γ-globulin or fibrinogen.

Approaches to designing peptide analogues, derivatives and mimetics are known in the art. For example, see Farmer, P. S. in Drug Design (E. J. Ariens, ed.) Academic Press, New York, 1980, vol 10, pp. 119-143; Ball. J. B. and Alewood, P. F. (1990) J Mol. Recognition 3:55; Morgan, B. A. and Gainor, J. A. (1989) Ann. Rep. Med. Chem. 24:243; and Freidinger, R. M. (1989) Trends Pharmacol Sci. 10:270. See also Sawyer, T. K. (1995) "Peptidomimetic Design and Chemical Approaches to Peptide Metabolism" in Taylor, M. D. and Amidon, G. L. (eds.) Peptide-Based Drug Design: Controlling Transport and Metabolism, Chapter 17; Smith, A. B. 3rd, et al. (1995) J. Am. Chem. Soc. 117:11113-11123: Smith, A. B. 3rd, et al. (1994) J. Am. Chem. Soc. 116:9947-9962; and Hirschman, R., et al. (1993) J. Am. Chem. Soc. 115:12550-12568.

A peptide can be attached to a compound of the Formula I, II, III, IV, or V through a functional group on the side chain of certain amino acids (e.g. serine) or other suitable functional groups. A carrier may comprise four or more amino acids with groups attached to three or more of the amino acids through functional groups on side chains. In an aspect, the carrier is one amino acid, in particular a sulfonate derivative of an amino acid, for example cysteic acid.

The term "alkyl", either alone or within other terms such as "thioalkyl" and "arylalkyl", means a monovalent, saturated hydrocarbon radical which may be a straight chain (i.e. linear) or a branched chain. An alkyl radical for use in the present invention generally comprises from about 1 to 20 carbon atoms, particularly from about 1 to 10, 1 to 8 or 1 to 7, more particularly about 1 to 6 carbon atoms, or 3 to 6. Illustrative alkyl radicals include methyl, ethyl, n-propyl, n-butyl, n-pentyl, n-hexyl, isopropyl, isobutyl, isopentyl, amyl, sec-butyl, tert-butyl, tert-pentyl, n-heptyl, n-octyl, n-nonyl, n-decyl, undecyl, n-dodecyl, n-tetradecyl, pentadecyl, n-hexadecyl, heptadecyl, n-octadecyl, nonadecyl, eicosyl, dosyl, n-tetracosyl, and the like, along with branched variations thereof. In certain aspects of the invention an alkyl radical is a $C_1$-$C_6$ lower alkyl comprising or selected from the group consisting of methyl, ethyl, n-propyl, n-butyl, pentyl, n-hexyl, isopropyl, isobutyl, isopentyl, amyl, tributyl, sec-butyl, tert-butyl, tert-pentyl, and n-hexyl. An alkyl radical may be optionally substituted with substituents as defined herein at positions that do not significantly interfere with the preparation of compounds of the Formula I, II, III, IV, or V and do not significantly reduce the efficacy of the compounds. In certain aspects of the invention, an alkyl radical is substituted with one to five substituents including halo, lower alkoxy, lower aliphatic, a substituted lower aliphatic, hydroxy, cyano, nitro, thio, amino, keto, aldehyde, ester, amide, substituted amino, carboxyl, sulfonyl, sulfinyl, sulfenyl, sulfate, sulfoxide, substituted carboxyl, halogenated lower alkyl (e.g. $CF_3$), halogenated lower alkoxy, hydroxycarbonyl, lower alkoxycarbonyl, lower alkylcarbonyloxy, lower alkylcarbonylamino, cycloaliphatic, substituted cycloaliphatic, or aryl (e.g., phenylmethyl (i.e. benzyl)). Substituent on an alkyl group may themselves be substituted.

As used herein in respect to certain aspects of the invention, the term "substituted aliphatic" refers to an alkyl or an alkane possessing less than 10 carbons where at least one of the aliphatic hydrogen atoms has been replaced by a halogen, an amino, a hydroxy, a nitro, a thio, a ketone, an aldehyde, an ester, an amide, a lower aliphatic, a substituted lower aliphatic, or a ring (aryl, substituted aryl, cycloaliphatic, or substituted cycloaliphatic, etc.). Examples of such groups include, but are not limited to, 1-chloroethyl and the like.

As used herein in respect, to certain aspects of the invention, the term "lower-alkyl-substituted-amino" refers to any alkyl unit containing up to and including eight carbon atoms where one of the aliphatic hydrogen atoms is replaced by an amino group. Examples of such include, but are not limited to, ethylamino and the like.

As used herein in respect to certain aspects of the invention, the term "lower-alkyl-substituted-halogen" refers to any alkyl chain containing up to and including eight carbon atoms where one of the aliphatic hydrogen atoms is replaced by a halogen. Examples of such include, but are not limited to, clorethyl and the like.

As used herein, the term "acetylamino" shall mean any primary or secondary amino that is acetylated. Examples of such include, but are not limited to, acetamide and the like.

As used herein the term "alkenyl" refers to an unsaturated, acyclic branched or straight-chain hydrocarbon radical comprising at least one double bond. An alkenyl radical may contain from about 2 to 10 carbon atoms, in particular from about 3 to 8 carbon atoms and more particularly about 3 to 6 carbon atoms. Suitable alkenyl radicals include without limitation ethenyl, propenyl (e.g., prop-1-en-1-yl, prop-1-en-2-yl, prop-2-en-1-yl (allyl), prop-2-en-2-yl), buten-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, hexen-1-yl, 3-hydroxyhexen-1-yl, hepten-1-yl, and octen-1-yl, and the like. An alkenyl radical may be optionally substituted similar to alkyl.

As used herein, the term "alkynyl" refers to an unsaturated, branched or straight-chain hydrocarbon radical comprising one or more triple bonds. An alkynyl radical may contain about 1 to 20, 1 to 15, or 2-10 carbon atoms, particularly about 3 to 8 carbon atoms and more particularly about 3 to 6 carbon atoms. Suitable alkynyl radicals include without limitation ethynyl, such as prop-1-yn-1-yl, prop-2-yn-1-yl, butynyls such as but-1-yn-1-yl, but-1-yn-3-yl, but-3-yn-1-yl, pentynyls such as pentyn-1-yl, pentyn-2-yl, 4-methoxypentyn-2-yl, 3-methylbutyn-1-yl, hexynyls such as hexyn-1-yl, hexyn-2-yl, hexyn-3-yl, and 3,3-dimethylbutyn-1-yl radicals and the like. An alkenyl may be optionally substituted similar to alkyl. The term "cycloalkynyl" refers to cyclic alkynyl groups.

As used herein the term "alkylene" refers to a linear or branched radical having from about 1 to 10 carbon atoms and having attachment points for two or more covalent bonds. Examples of such radicals are methylene, ethylene, propylene, butylene, pentylene, hexylene, ethylidene, methylelhylene, and isopropylidene. When an alkenylene radical is present as a substituent on another radical it is typically considered to be a single substituent rather than a radical formed by two substituents.

As used herein the term "alkenylene" refers to a linear or branched radical having from about 2 to 10 carbon atoms, at least one double bond, and having attachment points for two or more covalent bonds. Examples of alkenylene radicals include 1,1-vinylidene (—CH$_2$═C—), 1,2-vinylidene (—CH═CH—), and 1,4-butadienyl (—CH═CH—CH═CH—).

As used herein the term "halo" refers to a halogen such as fluorine, chlorine, bromine or iodine atoms.

As used herein the term "hydroxyl" or "hydroxy" refers to an —OH group.

As used herein the term "cyano" refers to a carbon radical having three of four covalent bonds shared by a nitrogen atom, in particular —C≡N. A cyano group may be substituted with substituents described herein.

As used herein the term "alkoxy" refers to a linear or branched oxy-containing radical having an alkyl portion of one to about ten carbon atoms, such as a methoxy radical, which may be substituted. In aspects of the invention an alkoxy radical may comprise about 1-10, 1-8 or 1-6 carbon atoms. In embodiments of the invention, an alkoxy radical comprises about 1-6 carbon atoms and includes a $C_1$-$C_6$ alkyl-O-radical wherein $C_1$-$C_6$ alkyl has the meaning set out herein. Examples of alkoxy radicals include without limitation methoxy, ethoxy, propoxy, butoxy, isopropoxy and tert-butoxy alkyls. An "alkoxy" radical may optionally be substituted with one or more substituents disclosed herein including alkyl atoms to provide "alkylalkoxy" radicals; halo atoms, such as fluoro, chloro or bromo, to provide "haloalkoxy" radicals (e.g. fluoromethoxy, chloromethoxy, trifluoromethoxy, difluoromethoxy, trifluoroethoxy, fluoroethoxy, tetrafluoroethoxy, pentafluoroethoxy, and fluoropropox) and "haloalkoxyalkyl" radicals (e.g. fluoromethoxymethyl, chloromethoxyethyl, trifluoromethoxymethyl, difluoromethoxyethyl, and trifluoroethoxymethyl).

As used herein the term "alkenyloxy" refers to linear or branched oxy-containing radicals having an alkenyl portion of about 2 to 10 ten carbon atoms, such as an ethenyloxy or propenyloxy radical. An alkenyloxy radical may be a "lower alkenyloxy" radical having about 2 to 6 carbon atoms. Examples of alkenyloxy radicals include without limitation ethenyloxy, propenyloxy, butenyloxy, and isopropenyloxy alkyls. An "alkenyloxy" radical may be substituted with one or more substituents disclosed herein including halo atoms, such as fluoro, chloro or bromo, to provide "haloalkenyloxy" radicals (e.g. trifluoroethenyloxy, fluoroethenyloxy, difluoroethenyhloxy, and fluoropropenyloxy).

A "carbocyclic" includes radicals derived from a saturated or unsaturated, substituted or unsubstituted 5 to 14 member organic nucleus whose ring forming atoms (other than hydrogen) are solely carbon. Examples of carbocyclic radicals are cycloalkyl, cycloalkenyl, aryl, in particular phenyl, naphthyl, norbornanyl, bicycloheptadienyl, tolulyl, xylenyl, indenyl, stilbenyl, terphenylyl, diphenylethylenyl, phenylcyclohexyl, acenapththylenyl, anthracenyl, biphenyl, bibenzylyl, and related bibenzylyl homologs, octahydronaphthyl, tetrahydronaphthyl, octahydroquinolinyl, dimethoxytetrahydronaphthyl and the like.

As used herein, the term "cycloalkyl" refers to radicals having from about 3 to 15 carbon atoms and containing one, two, three, or four rings wherein such rings may be attached in a pendant manner or may be fused, in particular cyclopropyl, cyclobutyl, cyclopentyl, cyclohexyl, cycloheptyl, cyclooctyl, cyclononyl, adamantyl, and the like. In certain aspects of the invention the cycloalkyl radicals are "lower cycloalkyl" radicals having from about 3 to 8 carbon atoms, in particular cyclopropyl, cyclobutyl, cyclopentyl, cyclohexyl and cycloheptyl. In some aspects of the invention the term "cycloalkyl" embraces radicals where cycloalkyl radicals are fused with aryl radicals or heterocyclyl radicals. A cycloalkyl radical may be optionally substituted with groups as disclosed herein.

As used herein in respect to certain aspects of the invention, the term "cycloaliphatic" refers to a cycloalkane possessing less than 8 carbons or a fused ring system consisting of no more than three fused cycloaliphatic rings. Examples of such include, but are not limited to, decalin and the like.

As used herein in respect to certain aspects of the invention, the term "substituted cycloaliphatic" refers to a cycloalkane possessing less than 8 carbons or a fused ring system consisting of no more than three fused rings, and where at least one of the aliphatic hydrogen atoms has been replaced by a halogen, a nitro, a thio, an amino, a hydroxy, a ketone, an aldehyde, an ester, an amide, a lower aliphatic, a substituted lower aliphatic, or a ring (aryl, substituted aryl, cycloaliphatic, or substituted, cycloaliphatic). Examples of such include, but are not limited to, 1-chlorodecalyl and the like.

A used herein, the term "cycloalkenyl" refers to radicals comprising about 2 to 15 carbon atoms, one or more carbon-carbon double bonds, and one, two, three, or four rings wherein such rings may be attached in a pendant manner or may be fused. In certain aspects of the invention the cycloalkenyl radicals are "lower cycloalkenyl" radicals having three to seven carbon atoms. Examples of cycloalkenyl radicals include without limitation cyclobutenyl, cyclopentenyl, cyclohexenyl and cycloheptenyl. A cycloalkenyl radical may be optionally substituted with groups as disclosed, herein, in particular 1, 2, or 3 substituents which may be the same or different.

As used herein the term "cycloalkoxy" refers to cycloalkyl radicals attached to an oxy radical. Examples of cycloalkoxy radicals include cyclohexoxy and cyclopentoxy. A cycloalkoxy radical may be optionally substituted with groups as disclosed herein.

As used herein, the term "aryl", alone or in combination, refers to a carbocyclic aromatic system containing one, two or three rings wherein such rings may be attached together in a pendant manner or may be fused. The term "fused" means that a second ring is present (i.e, attached or formed) by having two adjacent atoms in common or shared with the first ring. Illustrative "aryl" radicals includes without limitation aromatic radicals such as phenyl, benzyl, naphthyl, indenyl, benzocyclooctenyl, benzocycloheptenyl, pentalenyl, azulenyl, tetrahydronaphthyl, indanyl, biphenyl, acephthylenyl, fluorenyl, phenalenyl, phenanthrenyl, and anthracenyl. An aryl radical may be optionally substituted with groups as disclosed herein, in particular hydroxyl, alkyl, carbonyl, carboxyl, thiol, amino, and/or halo, in particular a substituted aryl includes without limitation arylamine and arylalkyamine.

As used herein in respect to certain aspects of the invention, the term "substituted aryl" refers to an aromatic ring, or fused aromatic ring system consisting of no more than three fused rings at least one of which is aromatic, and where at least one of the hydrogen atoms on a ring carbon has been replaced by a halogen, an amino, a hydroxy, a nitro, a thio, an alkyl, a ketone, an aldehyde, an ester, an amide, a lower aliphatic, a substituted lower aliphatic, or a ring (aryl, substituted aryl, cycloaliphatic, or substituted cycloaliphatic). Examples of such include, but are not limited to, hydroxyphenyl, chlorophenyl and the like.

As used herein, the term "aryloxy" refers to aryl radicals, as defined above, attached to an oxygen atom. Exemplary aryloxy groups include napthyloxy, quinolyloxy, isoquinolizinyloxy, and the like.

As used herein the term "arylalkoxy," refers to an aryl group attached to an alkoxy group. Representative examples of arylalkoxy include, but are not limited to, 2-phenylethoxy, 3-naphth-2-ylpropoxy, and 5-phenylpentyloxy.

As used herein, the term "aroyl" refers to aryl radicals, as defined above, attached to a carbonyl radical as defined herein, including without, limitation benzoyl and toluoyl. An aroyl radical may be optionally substituted with groups as disclosed herein.

As used herein the term "heteroaryl" refers to fully unsaturated heteroatom-containing ring-shaped aromatic radicals having at least one heteroatom selected from carbon, nitrogen, sulfur and oxygen. A heteroaryl radical may contain one, two or three rings and the rings may be attached in a pendant manner or may be fused. Examples of "heteroaryl" radicals, include without limitation, an unsaturated 5 to 6 membered heteromonocyclyl group containing 1 to 4 nitrogen atoms, in particular, pyrrolyl, pyrrolinyl, imidazolyl, pyrazolyl, 2-pyridyl, 3-pyridyl, 4-pyridyl, pyridinyl, pyrimidinyl, pyrazinyl, pyridazinyl, triazolyl, tetrazolyl and the like; an unsaturated condensed heterocyclic group containing 1 to 5 nitrogen atoms, in particular, indolyl, isoindolyl, indolizinyl, indazolyl, quinazolinyl, pteridinyl, quinolizidinyl, phthalazinyl, naphthyridinyl, quinoxalinyl, cinnolinyl, phenanthridinyl, acridinyl, phenanthrolinyl, phenazinyl, carbazolyl, purinyl, benzimidazolyl, quinolyl, isoquinolyl, quinolinyl, isoquinolinyl, indazolyl, benzotriazolyl, tetrazolopyridazinyl and the like; an unsaturated 3 to 6-membered heteromonocyclic group containing an oxygen atom, in particular, 2-furyl, 3-furyl, pyranyl, and the like: an unsaturated 5 to 6-membered heteromonocyclic group containing a sulfur atom, in particular, thienyl, 2-thienyl, 3-thienyl, and the like; unsaturated 5 to 6-membered heteromonocyclic group containing 1 to 2 oxygen atoms and 1 to 3 nitrogen atoms, in particular, furazanyl, benzofurazanyl, oxazolyl, isoxazolyl, and oxadiazolyl; an unsaturated condensed heterocyclic group containing 1 to 2 oxygen atoms and 1 to 3 nitrogen atoms, in particular benzoxazolyl, benzoxadiazolyl and the like; an unsaturated 5 to 6-membered heteromonocyclic group containing 1 to 2 sulfur atoms and 1 to 3 nitrogen atoms, for example, thiazolyl, isothiazolyl, thiadiazolyl and the like; an unsaturated condensed heterocyclic group containing 1 to 2 sulfur atoms and 1 to 3 nitrogen atoms such as benzothiazolyl, benzothiadiazolyl and the like. The term also includes radicals where heterocyclic radicals are fused with aryl radicals, in particular bicyclic radicals such as benzofuranyl, benzothiophenyl, phthalazinyl, chromenyl, xanthenyl, and the like. A heteroaryl radical may be optionally substituted with groups as disclosed herein, for example with an alkyl, amino, halogen, etc., in particular a heteroarylamine.

The term "heterocyclic" refers to saturated and partially saturated heteroatom-containing ring-shaped radicals having at least one heteroatom selected from carbon, nitrogen, sulfur and oxygen. A heterocyclic radical may contain one, two or three rings wherein such rings may be attached in a pendant manner or may be fused. Examplary saturated heterocyclic radicals include without 1 initiation a saturated 3 to 6-membered heteromonocylic group containing 1 to 4 nitrogen atoms [e.g. pyrrolidinyl, imidazolidinyl, piperidinyl, and piperazinyl]; a saturated 3 to 6-membered heteromonocyclic group containing 1 to 2 oxygen atoms and 1 to 3 nitrogen atoms [e.g. morpholinyl; sydnonyl]; and, a saturated 3 to 6-membered heteromonocyclic group containing 1 to 2 sulfur atoms and 1 to 3 nitrogen atoms [e.g., thiazolidinyl] etc. Examples of partially saturated heterocyclyl radicals include without limitation dihydrothiophene, dihydropyranyl, dihydrofuranyl and dihydrothiazolyl. Illustrative heterocyclic radicals include without limitation aziridinyl, azetidinyl, 2-pyrrolinyl, 3-pyrrolinyl, pyrrolidinyl, azepinyl, 1,3-dioxolanyl, 2H-pyranyl, 4H-pyranyl, piperidinyl, 1,4-dioxanyl, morpholinyl, pyrazolinyl, 1,4-dithianyl, thiomorpholinyl, 1,2,3,6-tetrahydropyridinyl, oxiranyl, oxetanyl, tetrahydrofuranyl, tetrahydropyranyl, tetrahydropyridinyl, tetrahydrothiopyranyl, thioxanyl, indolinyl, 2H-pyranyl, 4H-pyranyl, dioxanyl, 1,3-dioxolanyl, pyrazolinyl, dihydropyranyl, dihydrothienyl, dihydrofuranyl, pyrazolidinyl, imidazolinyl, imidazolidinyl, 3H-indolyl, quinuclidinyl, quinolizinyl, and the like.

As used herein in respect to certain aspects of the invention, the term "heterocyclic" refers to a cycloalkane and/or an aryl ring system, possessing less than 8 carbons, or a fused ring system consisting of no more than three fused rings, where at least one of the ring carbon atoms is replaced by oxygen, nitrogen or sulfur. Examples of such include, but are not limited to, morpholino and the like.

As used herein in respect to certain aspects of the invention, the term "substituted heterocyclic" refers to a cycloalkane and/or an aryl ring system, possessing less than 8 carbons, or a fused ring system consisting of no more than three fused rings, where at least one of the ring carbon atoms is replaced by oxygen, nitrogen or sulfur, and where at least one of the aliphatic hydrogen atoms has been replaced by a halogen, hydroxy, a thio, nitro, an amino, a ketone, an aldehyde, an ester, an amide, a lower aliphatic, a substituted lower aliphatic, or a ring (aryl, substituted aryl, cycloaliphatic, or substituted cycloaliphatic). Examples of such include, but are not limited to 2-chloropyranyl.

The foregoing heteroaryl and heterocyclic groups may be C-attached or N-attached (where such is possible).

As used herein the term "sulfonyl", used alone or linked to other terms such as alkylsulfonyl or arylsulfonyl, refers to the divalent radicals —$SO_2^-$. In aspects of the invention a sulfonyl group, the sulfonyl group may be attached to a substituted or unsubstituted hydroxyl, alkyl group, ether group, alkenyl group, alkynyl group, aryl group, cycloalkyl group, cycloalkenyl group, cycloalkynyl group, heterocyclic group, carbohydrate, peptide, or peptide derivative.

The term "sulfinyl", used alone or linked to other terms such as alkylsulfinyl (i.e. —S(O)-alkyl) or arylsulfinyl, refers to the divalent radicals —S(O)—.

As used herein the term "amino", alone or in combination, refers to a radical where a nitrogen atom (N) is bonded to three substituents being any combination of hydrogen, hydroxyl, alkyl, cycloalkyl, alkenyl, alkynyl, aryl, silyl, heterocyclic, or heteroaryl with the general chemical formula —$NR^{21}R^{22}$ where $R^{21}$ and $R^{22}$ can be any combination of hydrogen, hydroxyl, alkyl, cycloalkyl, alkoxy, alkenyl, alkynyl, aryl, carbonyl carboxyl, amino, silyl, heteroaryl, or heterocyclic which may or may not be substituted. Optionally one substituent on the nitrogen atom may be a hydroxyl group (—OH) to provide an amine known as a hydroxylamine. Illustrative examples of amino groups are amino (—$NH_2$), alkylamino, acylamino, cycloamino, acycloalkylamino, arylamino, arylalkylamino, and lower alkylsilylamino, in particular methylamino, ethylamino, dimethylamino, 2-propylamino, butylamino, isobutylamino, cyclopropylamino, benzylamino, allylamino, hydroxylamino, cyclohexylamino, piperidinyl, hydrazinyl, benzylamino, diphenylmethylamino, tritylamino, trimethylsilylamino, and dimethyl-tert-butylsilylamino, which may or may not be substituted.

As used herein the term "thiol" means —SH. A thiol may be substituted with a substituent disclosed herein, in particular alkyl(thioalkyl), aryl(thioaryl), alkoxy(thioalkoxy) or carboxyl.

The term "sulfenyl" used alone or linked to other terms such as alkylsulfenyl, refers to the radical —$SR^{24}$ wherein $R^{24}$ is not hydrogen. In aspects of the invention $R^{24}$ is substituted or unsubstituted alkyl, cycloalkyl, alkenyl, alkynyl aryl, silyl, silylalkyl, heterocyclic, heteroaryl, carbonyl, carbamoyl, alkoxy, or carboxyl.

As used herein, the term "thioalkyl", alone or in combination, refers to a chemical functional group where a sulfur atom (S) is bonded to an alkyl, which may be substituted. Examples of thioalkyl groups are thiomethyl, thioethyl, and thiopropyl. A thioalkyl may be substituted with a substituted or unsubstitute carboxyl, aryl, heterocylic, carbonyl, or heterocyclic.

A thiol may be substituted with a substituted or unsubstituted heteroaryl or heterocyclic, in particular a substituted or unsubstituted saturated 3 to 6-membered heteromonocylic group containing 1 to 4 nitrogen atoms [e.g. pyrrolidinyl, imidazolidinyl, piperidinyl, and piperazinyl] or a saturated 3 to 6-membered heteromonocyclic group containing 1 to 2 oxygen atoms and 1 to 3 nitrogen atoms [e.g. morpholinyl; sydnonyl], especially a substituted morpholinyl or piperidinyl.

As used herein the term, "thioaryl", alone or in combination, refers to a chemical functional group where a sulfur atom (S) is bonded to an aryl group with the general chemical formula —$SR^{25}$ where $R^{25}$ is aryl which may be substituted. Illustrative examples of thioaryl groups and substituted thioaryl groups are thiophenyl, chlorothiophenyl, para-chlorothiophenyl, thiobenzyl, 4-methoxy-thiophenyl, 4-nitro-thiophenyl, and para-nitrothiobenzyl.

As used herein the term "thioalkoxy", alone or in combination, refers to a chemical functional group where a sulfur atom (S) is bonded to an alkoxy group with the general chemical formula —$SR^{30}$ where $R^{30}$ is an alkoxy group which may be substituted. A "thioalkoxy group" may have 1-6 carbon atoms i.e. a —S—(O)—$C_1$-$C_6$ alkyl group wherein $C_1$-$C_6$ alkyl have the meaning as defined above. Illustrative examples of a straight or branched thioalkoxy group or radical having from 1 to 6 carbon atoms, also known as a $C_1$-$C_6$ thioalkoxy, include thiomethoxy and thioethoxy.

As used herein, the term "carbonyl" refers to a carbon radical having two of the four covalent bonds shared with an oxygen atom.

As used herein, the term "carboxyl", alone or in combination, refers to —C(O)O$R^{14}$— or —C(=O)O$R^{14}$ wherein $R^{14}$ is hydrogen, alkyl, alkenyl, alkynyl, cycloalkyl, cycloalkenyl, amino, thiol, aryl, heteroaryl, thioalkyl, thioaryl, thioalkoxy, a heteroaryl, or a heterocyclic, which may optionally be substituted. Examples of carboxyl groups are methoxycarbonyl, butoxycarbonyl, tert.alkoxycarbonyl such as tert.butoxycarbonyl, arylmethyoxycarbonyl having one or two aryl radicals including without limitation phenyl optionally substituted by for example lower alkyl, lower alkoxy, hydroxyl, halo, and/or nitro, such as benzyloxycarbonyl, methoxybenxyloxycarbonyl, diphenylmethoxycarbonyl, 2-bromoethoxycarbonyl, 2-iodoethoxycarbonyltert.butylcarbonyl, 4-nitrobenzyloxycarbonyl, diphenylmethoxycarbonyl, benzhydroxycarbonyl, di-(4-methoxyphenylmethoxycarbonyl, 2-bromoethoxycarbonyl, 2-iodoethoxycarbonyl, 2-trimethylsilylethoxycarbonyl, or 2-triphenylsilylethoxycarbonyl. Additional carboxyl groups in esterified form are silyloxycarbonyl groups including organic silyloxycarbonyl. In aspects of the invention, the carboxyl group may be an alkoxy carbonyl, in particular methoxy carbonyl, ethoxy carbonyl, isopropoxy carbonyl, t-butoxycarbonyl, t-pentyloxycarbonyl, or heptyloxy carbonyl, especially methoxy carbonyl or ethoxy carbonyl.

As used herein, the term "carbamoyl", alone or in combination, refers to amino, monoalkylamino, dialkylamino, monocycloalkylamino, alkylcycloalkylamino, and dicycloalkylamino radicals, attached to one of two unshared bonds in a carbonyl group.

As used herein, the term "carboxamide" refers to the group —CONH—.

As used herein, the term "nitro" means —NO$_2$—.

As used herein, the term "acyl", alone or in combination, means a carbonyl or thiocarbonyl group bonded to a radical selected from, for example, optionally substituted, hydrido, alkyl (e.g. haloalkyl), alkenyl, alkynyl, alkoxy ("acyloxy" including acetyloxy, butyryloxy, iso-valeryloxy, phenylacetyloxy, benzoyloxy, p-methoxybenzoyloxy, and substituted acyloxy such as alkoxyalkyl and haloalkoxy), aryl, halo, heterocyclyl, heteroaryl, sulfinyl (e.g. alkylsulfinylalkyl), sulfonyl (e.g. alkylsulfonylalkyl), cycloalkyl, cycloalkenyl, thioalkyl, thioaryl, amino (e.g alkylamino or dialkylamino), and aralkoxy. Illustrative examples of "acyl" radicals are formyl, acetyl, 2-chloroacetyl, 2-bromacetyl, benzoyl, trifluoroacetyl, phthaloyl, malonyl, nicotinyl, and the like.

As used herein, "ureido" refers to the group "—NHCONH—". A ureido radical includes an alkylureido comprising a ureido substituted with an alkyl, in particular a lower alkyl attached to the terminal nitrogen of the ureido group. Examples of an alkylureido include without limitation N'-methylureido, N'-ethylureido, N'-n-propylureido, N'-i-propylureido and the like. A ureido radical also includes a N',N'-dialkylureido group containing a radical —NHCON where the terminal nitrogen is attached to two optionally substituted radicals including alkyl, aryl, heterocylic, and heteroaryl.

The terms used herein for radicals including "alkyl", "alkoxy", "alkenyl", "alkynyl", "hydroxyl" etc. refer to both unsubstituted and substituted radicals. The term "substituted," as used herein, means that any one or more moiety on a designated atom (e.g., hydrogen) is replaced with a selection from a group disclosed herein, provided that the designated atom's normal valency is not exceeded, and that the substitution results in a stable compound. Combinations of substituents and/or radicals are permissible only if such combinations result in stable compounds. "Stable compound" refers to a compound that is sufficiently robust to survive isolation to a useful degree of purity from a reaction mixture, and formulation into an efficacious therapeutic agent.

A radical in a compound of the Formula I, II, III, IV, or V may be substituted with one or more substituents apparent to a person skilled in the art including without limitation alkyl, alkoxy, alkenyl, alkynyl, alkanoyl, alkylene, alkenylene, hydroxyalkyl, haloalkyl, haloalkylene, haloalkenyl, alkoxy, alkenyloxy, alkenyloxyalkyl, alkoxyalkyl, aryl, alkylaryl, haloalkoxy, haloalkenyloxy, heterocyclic, heteroaryl, sulfonyl, alkylsulfonyl, sulfinyl, sulfonyl, sulfenyl, alkylsulfinyl, aralkyl, heteroaralkyl, cycloalkyl, cycloalkenyl, cycloalkoxy, cycloalkenyloxy, amino, oxy, halo, azido, thio, =O, =S, cyano, hydroxyl, phosphonato, phosphinato, thioalkyl, alkylamino, arylamino, arylsulfonyl, alkylcarbonyl, arylcarbonyl, heteroarylcarbonyl, heteroarylsulfinyl, heteroarylsulfony, heteroarylamino, heteroaryloxy, heteroaryloxyalkyl, arylacetamidoyl, aryloxy, aroyl, aralkanoyl, aralkoxy, aryloxyalkyl, haloaryloxyalkyl, heteroaroyl, heteroaralkanoyl, heteroaralkoxy, heteroaralkoxyalkyl, thioaryl, arylthioalkyl, alkoxyalkyl, and acyl groups. These substituents may themselves be substituted.

A chemical substituent is "pendant" from a radical if it is bound to an atom of the radical. In this context, the substituent can be pending from a carbon atom of a radical, a carbon atom connected to a carbon atom of the radical by a chain extender, or a heteroatom of the radical.

A "disease" that can be treated and/or prevented using a compound, composition, or method of the invention includes a condition associated with or requiring modulation of one or more of inflammation (e.g. neuroinflammation), signaling pathways involved in inflammation (e.g., neuroinflammation), cell signaling molecule production, activation of glia or glial activation pathways and responses, proinflammatory cytokines or chemokines (e.g., interleukin (IL) or tumor necrosis factor (TNF), oxidative stress-related responses such as nitric oxide synthase production and nitric oxide accumulation, acute phase proteins, components of the complement cascade, protein kinase activity (e.g., death associated protein kinase (DAPK) activity), cell damage (e.g., neuronal cell damage), and cell death, (e.g., neuronal cell death). In particular a disease is a dementing disorder, a neurodegenerative disorder, a CNS demyelinating disorder, an autoimmune disorder, or a peripheral inflammatory disease.

A disease may be characterized by an inflammatory process due to the presence of macrophages activated by an amyloidogenic protein or peptide. Thus, a method of the invention may involve inhibiting macrophage activation and/or inhibiting an inflammatory process. A method may comprise decreasing, slowing, ameliorating, or reversing the course or degree of macrophage invasion or inflammation in a patient.

Examples of diseases that can be treated and/or prevented using the compounds, compositions and methods of the invention include Alzheimer's disease and related disorders, presenile and senile forms; amyloid angiopathy; mild cognitive impairment; Alzheimer's disease-related dementia (e.g., vascular dementia or Alzheimer dementia); AIDS related dementia, tauopathies (e.g., argyrophilic grain dementia, corticobasal degeneration, dementia pugilistica, diffuse neurofibrillary tangles with calcification, frontotemporal dementia with parkinsonism, Prion-related disease, Hallervorden-Spatz disease, myotonic dystrophy, Niemann-Pick disease type C, non-Guamanian Motor Neuron disease with neurofibrillary tangles, Pick's disease, postencephalitic parkinsonism, cerebral amyloid angiopathy, progressive subcortical gliosis, progressive supranuclear palsy, subacute sclerosing panencephalitis, and tangle only dementia), alpha-synucleinopathy (e.g., dementia with Lewy bodies, multiple system atrophy with glial cytoplasmic inclusions), multiple system atrophies, Shy-Drager syndrome, spinocerebellar ataxia (e.g., DRPLA or Machado-Joseph Disease); striatonigral degeneration, olivopontocerebellar atrophy, neurodegeneration with brain iron accumulation type I, olfactory dysfunction, and amyotrophic lateral sclerosis); Parkinson's disease (e.g., familial or non-familial); Amyotrophic Lateral Sclerosis; Spastic paraplegia (e.g., associated with defective function of chaperones and/or triple A proteins); Huntington's Disease, spinocerebellar ataxia, Freidrich's Ataxia; cerebrovascular diseases including stroke, hypoxia, ischemia, infarction, intracerebral hemorrhage: traumatic brain injury; Down's syndrome; head trauma with post-traumatic accumulation of amyloid beta peptide; Familial British Dementia; Familial Danish Dementia; Presenile Dementia with Spastic Ataxia; Cerebral Amyloid Angiopathy, British Type; Presenile Dementia With Spastic Ataxia Cerebral Amyloid Angiopathy, Danish Type; Familial encephalopathy with neuroserpin inclusion bodies (FENIB); Amyloid Polyneuropathy (e.g., senile amyloid polyneuropathy or systemic Amyloidosis); Inclusion Body myositis due to amyloid beta peptide; Familial and Finnish Type Amyloidosis; Systemic amyloidosis associated with multiple myeloma; Familial Mediterranean Fever; multiple sclerosis, optic neuritis; Guillain-Barre Syndrome; chronic inflammatory demyelinating polyneuropathy; chronic infections and inflammations; acute disseminated encephalomyelitis (ADEM); autoimmune inner ear disease (AIED); diabetes; myocardial ischemia and other cardiovascular disorders; pancreatitis; gout; inflammatory bowel disease; ulcerative colitis, Crohn's disease, rheumatoid arthritis, osteoarthritis: artheriosclerosis, inflammatory aortic aneurysm; asthma; adult respiratory distress syndrome; restenosis; ischemia/reperfusion injury; glomerulonephritis; sacoidosis cancer: restenosis; rheumatic fever; systemic lupus erythematosus; Reiter's syndrome; psoriatic arthritis; ankylosing spondylitis; coxarthritis; pelvic inflammatory disease: osteomyelitis; adhesive capsulitis; oligoarthritis; periarthritis; polyarthritis; psoriasis: Still's disease; synovitis; inflammatory dermatosis; and, wound healing.

In aspects of the invention, a compound, composition, or method disclosed herein may be utilized to prevent and/or treat a disease involving neuroinflammation (i.e., neuroinflammatory disease). Neuroinflammation is a characteristic feature of disease pathology and progression in a diverse array of neurodegenerative disorders that are increasing in their societal impact (for a recent review, see, e.g., Prusiner, S. B. (2001) New Engl. J. Med. 344, 1516-1526). These neuroinflammation-related disorders include Alzheimer's disease (AD), amyotrophic lateral sclerosis, autoimmune disorders, priori diseases, stroke and traumatic brain injury. Neuroinflammation is brought about by glial cell (e.g., astrocytes and microglia) activation, which normally serves a beneficial role as part of an organism's homeostatic response to injury or developmental change. However, disregulation of this process through chronic or excessive activation of glia contributes to the disease process through the increased production of proinflammatory cytokines and chemokines, oxidative stress-related enzymes, acute phase proteins, and various components of the complement cascades. (See, e.g., Akiyama et al., (2000) Neurobiol. Aging 21, 383-421). The direct linkage of glial activation to pathology that is a hallmark of disease underscores the importance of understanding the signal transduction pathways that mediate these critical glial cellular responses and the discovery of cell permeable ligands that can modulate these disease relevant pathways.

For Alzheimer's disease (AD) in particular, the deposition of β-amyloid (Aβ) and neurofibrillary tangles are associated with glial activation, neuronal loss and cognitive decline. On a molecular level, Alzheimer's disease is characterized by; increased expression of nitric oxide synthase (NOS) in glial cells surrounding amyloid plaques; neuropathological evidence of peroxynitrite-mediated neuronal damage; and nitric oxide (NO) overproduction involved in Aβ-induced brain dysfunction. NOSH (iNOS) is induced as part of the glial activation response and is an oxidative stress-related enzyme that generates NO. When NO is present in high levels along with superoxide, the highly reactive NO-derived molecule peroxynitrite is generated, leading to neuronal cell death. The pro-inflammatory cytokine IL-1β is also overexpressed in activated glia in AD brain and polymorphisms in IL-1β genes are associated with an increased risk of early onset sporadic AD (See, e.g., Du et al, (2000) Neurology 55, 480-483). IL-1β can also influence amyloid plaque development and is involved in additional glial inflammatory and neuronal dysfunction responses (See, e.g., Griffin, et al., (1998) Brain Pathol. 8, 65-72; and Sheng, et al, (1996) Neurobiol, Aging 17, 761-766). Therefore, because glial activation and specific glial products are associated with neurodegenerative disorders (e.g., Alzheimer's disease), the compounds and compositions disclosed herein that are capable of modulating cell signaling pathways (e.g., glial activation pathways) will have particular application in the treatment and prevention of inflammatory disease.

In aspects of the invention, a compound, composition, or method disclosed herein may be utilized to prevent and/or treat a disease involving disregulation of protein kinase signaling. Disregulation of protein kinase signaling often accompanies disregulation of cell signaling pathways (e.g., glial cell activation pathways). Protein kinases are a large family of proteins that play a central role in regulating a number of cellular functions including cell growth, differentiation and death. There are thought to be more than 500 protein kinases and 130 protein phosphatases exerting tight control on protein phosphorylation. Each protein kinase transfers the γ-phosphate of ATP to a specific residue(s) of a protein substrate. Protein kinases can be further categorized as tyrosine, serine/threonine or dual specific based on acceptor residue. Examples of serine/threonine kinases include MAP kinase, MAPK kinase (MEK), Akt/PKB, Jun kinase (INK), CDKs, protein kinase A (PRA), protein kinase C (PKC), and calmodulin (CaM)-dependent kinases (CaMKs). Disregulated protein kinase activity (e.g., hyper- or hypo-active) leads to abnormal protein phosphorylation, underlying a great number of diseases including diabetes, rheumatoid arthritis, inflammation, hypertension, and proliferative diseases such as cancer. Therefore, because aberrant kinase activity is associated with inflammatory disease (e.g., neurodegenerative disorders like Alzheimer's disease), the compounds and compositions that are disclosed herein that are capable of modulating kinases involved in cell signaling pathways will have particular application for treatment and prevention of inflammatory disease.

Compounds

The invention provides an isolated and pure, in particular, substantially pure, compound of the Formula I wherein $R^1$, $R^2$, and $R^3$ are independently hydrogen, hydroxyl, alkyl, alkenyl, alkynyl, alkylene, alkenylene, alkoxy, alkenyloxy, cycloalkyl, cycloalkenyl, aryl, aryloxy, arylalkoxy, aroyl, heteroaryl, heterocyclic, acyl, acyloxy, sulfonyl, sulfinyl, sulfenyl, amino, imino, azido, thiol, thioalkyl, thioalkoxy, thioaryl, nitro, ureido, cyano, halo, silyl, silyloxy, silylalkyl, silylthio, =O, =S, carboxyl, carbonyl, carbamoyl, or carboxamide; or $R^7$ is hydrogen, hydroxyl, alkyl, alkenyl, alkynyl, alkylene, alkenylene, alkoxy, alkenyloxy, cycloalkyl, cycloalkenyl, aryl, aryloxy, arylalkoxy, aroyl, heteroaryl, heterocyclic, acyl, acyloxy, sulfonyl, sulfinyl, sulfenyl, amino, imino, azido, thiol, thioalkyl, thioalkoxy, thioaryl, nitro, ureido, cyano, halo, silyl, silyloxy, silylalkyl, silylthio, =O, =S, carboxyl, carbonyl, carbamoyl, or carboxamide: $R^4$, $R^5$, and $R^6$ are independently hydrogen, alkyl, alkoxy, halo, or nitro or $R^7$ may be absent with a double bond between N at position 1 and C at position 6; or $R^1$ and $R^2$, $R^1$ and $R^7$, or $R^2$ and $R^3$ may form a heteroaryl or heterocyclic ring; or an isomer or a pharmaceutically acceptable salt thereof.

In some aspects, one or more of the following compounds do not fall within the scope of the present invention:

In some aspects, one or more of the following compounds do not fall within the scope of the present invention:

a) a compound wherein when $R^1$ is =O, $R^3$ is —COOCH$_3$, CH=CHCOOCH$_3$,      —CH=CHC(=O)-phenyl, —CH=CH(C(=O)OCH$_3$)$_2$, —S-phenyl, —CH=CH(COCH$_3$)(COOCH$_3$), CH=CH(COOCH$_2$CH$_3$)$_2$, -phenyl-COOCH$_3$, —CH=CHCO-phenyl, —CH$_2$CH(Cl)(CH$_2$OH), -methylphenyl, R$^7$ is hydrogen or —CH$_2$OCH$_3$, and R$^1$, R$^2$, R$^4$, R$^5$ and R$^6$ are hydrogen;

b) a compound wherein when R$^1$ is =O, R$^2$ is cyano, R$^3$ is —C(=O)OCH$_3$, and R$_3$, R$^4$, R$^5$, and R$^6$ are hydrogen;

c) a compound wherein when R$^1$ is =O, R$^2$ is -methylthiophene or benzyl, R$^3$, R$^4$, R$^5$, R$^6$, and R$^7$ are hydrogen;

d) a compound wherein when R$^1$ is =O, R$^2$ is methyl, R$^5$ is hydrogen, hydroxyl, chloro, or bromo, R$^7$ is hydrogen or ethylmorpholinyl, and R$^3$, R$^4$, and R$^6$ are hydrogen;

e) a compound wherein when R$^2$ is methyl, R$^5$ is chloro, bromo, or hydrogen, R$^7$ is hydrogen or —CH$_2$CH$_2$-morpholinyl, and R$^1$, R$^3$, R$^4$, and R$^6$ are hydrogen;

f) a compound wherein when R$^1$ is piperazinyl, piperazinyl substituted with pyridinyl, phenyl, or methyl, R$^2$ is hydrogen or methyl, and R$^3$, R$^4$, R$^5$, and R$^6$ are hydrogen;

g) a compound wherein when R$^1$ is chloro or bromo, R$^2$ is C$_1$-C$_3$ alkyl, phenyl, amino, benzyl, morpholinyl, chloro, —C(=O)NH$_2$, —NH$_2$, C$_1$-C$_3$ alkylphenyl, —CH(CH$_3$)$_2$, —CH$_2$CH(CH$_3$)$_2$, -benzylchloro, and R$^3$, R$^4$, R$^5$, and R$^6$ are hydrogen;

h) a compound wherein when R$^1$ is chloro or bromo, R$^3$ is hydroxyl, chloro, bromo, C$_1$-C$_3$ alkyl, phenyl, or —N(CH$_3$)$_2$, and R$^3$, R$^4$, R$^5$ and R$^6$ are hydrogen;

i) a compound wherein when R$^1$ is chloro, R$^2$ is methyl, R$^5$ is hydroxyl, and R$^3$, R$^4$, and R$^6$ are hydrogen;

j) a compound wherein when R$^1$ is chloro, R$^2$, R$^3$, R$^4$, R$^5$ and R$^6$ are hydrogen;

k) a compound wherein when R$^1$ is hydroxyl, R$^2$ is C$_1$-C$_4$ alkyl, and R$^3$, R$^4$, R$^5$ and R$^6$ are hydrogen:

l) a compound wherein, when R$^1$ is —C$_1$-C$_4$ alkoxy, or C$_1$-C$_4$ alkoxy substituted with —N(CH$_3$)$_2$, morpholinyl, or piperidinyl substituted with benzyl, R$^2$ is hydrogen or methyl, R$^3$, R$^4$, R$^5$ and R$^6$ are hydrogen, R$^7$ is absent, hydrogen, or methyl;

m) a compound wherein when R$^1$ is —SH, —SCH$_3$, or —SCH$_2$C(=O)CH$_3$, R$^2$ is hydrogen or methyl, and R$^3$, R$^4$, R$^5$ and R$^6$ are hydrogen;

n) a compound wherein when R$^1$ is =S, R$^2$ is hydrogen or methyl, R$^7$ is methyl or benzyl, and R$^3$, R$^4$, and R$^6$ are hydrogen;

o) a compound wherein when R$^1$ is =S, R$^2$ is methyl and R$^5$ is chloro or R$^7$ is methyl, and R$^3$, R$^4$, and R$^6$ are hydrogen;

p) a compound wherein when R$^1$ is hydroxyl, R$^2$ is hydrogen, methyl, or butyl, and R$^3$, R$^4$, R$^5$ and R$^6$ are hydrogen;

q) a compound wherein when R$^1$ is methoxy, R$^2$, R$^3$, R$^4$, R$^5$ and R$^6$ are hydrogen;

r) a compound wherein when R$^1$ is C$_1$-C$_2$ alkoxy or C$_1$-C$_4$ alkoxy substituted with morpholinyl, —N(CH$_3$)$_2$, or piperidinyl substituted with benzyl, R$^2$ is methyl, and R$^3$, R$^4$, R$^5$ and R$^6$ are hydrogen;

s) a compound wherein R$^2$, R$^3$, R$^4$, R$^5$ and R$^6$ are hydrogen;

t) a compound wherein R$^1$ is cyano or cyano substituted with —C(OCH$_2$CH$_3$)$_2$, —CH(OH)(CH$_3$), —Si(CH$_2$CH$_3$)$_2$, cyclohexol, —CH$_2$O-trimethyldiphenylsilyl or cyclohexyl substituted with hydroxyl, and R$^3$, R$^4$, R$^5$ and R$^6$ are hydrogen;

u) a compound wherein R$^1$ is cyano substituted with —CH(OH)(CH$_3$)$_2$, —Si(CH$_2$CH$_3$)$_2$, morpholinyl, trimethyldiphenylsilyl, or —CH(OCH$_2$CH$_3$)$_2$, R$^2$ is methyl, and R$^3$, R$^4$, R$^5$ and R$^6$ are hydrogen;

v) a compound wherein R$^7$ is oxy, and R$^2$ is hydrogen or methyl, and R$^3$, R$^4$, R$^5$ and R$^6$ are hydrogen;

w) a compound wherein R$^1$ is methyl, and R$^2$, R$^3$, R$^4$, R$^5$ and R$^6$ are hydrogen;

x) a compound wherein R$^2$ is methyl, and R$^1$, R$^3$, R$^4$, R$^5$ and R$^6$ are hydrogen;

y) a compound wherein R$^1$ is methoxycarbonyl, R$^3$ is hydrogen, and R$^2$, R$^4$, R$^5$ and R$^6$ are hydrogen;

z) a compound wherein R$^1$ is —NH$_2$, R$^2$ is methyl, chlorophenyl, methoxyphenyl, ethylphenyl, ethylmethoxyphenyl, propylphenyl, or —CH(CH$_3$)$_2$, R$^4$, R$^5$ and R$^6$ are hydrogen, and R$^7$ is absent or —CH$_2$CH$_2$CH$_2$COOH;

aa) a compound wherein R$^1$ is =OR$^{80}$ wherein R$^{80}$ is ethylmorpholinyl or —CH$_2$CH$_2$N(CH$_3$)$_2$ and R$^2$, R$^3$, R$^4$, R$^5$ and R$^6$ are hydrogen;

bb) a compound wherein R$^1$ is —NH$_2$, R$^3$ is —NH$_2$, and R$^3$, R$^4$, R$^5$ and R$^6$ are hydrogen;

cc) a compound wherein R$^1$ is —NH$_2$, R$^5$ and R$^6$ are methoxy, and R$^3$ and R$^4$ are hydrogen;

dd) a compound wherein R$^1$ is —NH$_2$, R$^5$ is methyl and R$^4$, R$^5$ and R$^6$ are hydrogen;

ee) a compound wherein R$^1$ is —NH$_2$, R$^5$ is chloro, and R$^3$, R$^4$ and R$^6$ are hydrogen;

ff) a compound wherein R$^1$ is —NH-chlorophenyl, and R$^2$ and R$^3$ form a phenyl group, and R$^4$, R$^5$ and R$^6$ are hydrogen;

gg) a compound wherein R$^1$ is —NH$_2$, R$^4$ and R$^5$ is methoxy, and R$^2$, R$^3$ and R$^6$ are hydrogen;

hh) a compound wherein R$^1$ is —NH$_2$, R$^2$ is ethylmethoxyphenyl, R$^7$ is carboxyethyl or carboxypropyl, and R$^3$, R$^4$ and R$^6$ are hydrogen;

ii) a compound wherein R$^1$ is —NHR$^{22}$ wherein R$^{22}$ is ethylmorpholinyl, ethylmorpholinyl substituted with =O, —CH$_2$CH$_2$OCH$_3$, —CH$_2$CH$_2$CH$_2$CH$_2$CH$_2$CH$_2$CH$_2$CH$_3$, —CH$_2$CH$_2$CH$_2$CH$_2$OH, —CH$_2$CH$_2$OH, or —CH$_2$CH$_2$OCH$_3$, R$^2$ is hydrogen, methyl ethyl, —CHO, —CH$_2$OH, —COOH, chloro, —CH$_2$CH$_2$NH$_2$, —NO$_2$, —C≡N, —C(=O)OCH$_2$CH$_3$, or —C(=O)NH$_2$, and R$^3$, R$^4$, R$^5$ and R$^6$ are hydrogen;

jj) a compound wherein R$^1$ is —NHR$^{22}$ wherein R$^{22}$ is ethanol, methylpiperidinylbenzyl, ethylpiperidinyl, ethylpiperldinylbenzyl, or butylpiperidinylbenzyl, R$^2$ is hydrogen, methyl, or —C(CH$_3$)$_2$, and R$^3$, R$^4$, R$^5$ and R$^6$ are hydrogen;

kk) a compound, wherein R$^1$ is —NHR$^{22}$ wherein R$^{22}$ is hydrogen, and R$^3$, R$^4$, R$^5$ and R$^6$ are hydrogen;

ll) a compound wherein R$^1$ is —NHR$^{22}$ wherein R$^{22}$ is —CH$_2$CH$_2$N(CH$_2$CH$_3$)$_2$ or ethylmorpholinyl, R$^3$ is ethyl, and R$^4$, R$^5$ and R$^6$ are hydrogen;

mm) a compound wherein R$^1$ is —NHNH$_2$, R$^3$ is hydrogen, alkyl, or phenyl, and R$^3$, R$^4$, R$^5$ and R$^6$ are hydrogen;

nn) a compound wherein R$^1$ is —NHR$^{22}$ wherein R$^{22}$ is NH$_2$, —CH$_2$CH$_2$OH, CH$_2$CH(OH)(CH$_3$), ethylmorpholinyl, ethylmorpholinyl substituted with =O, ethylphenyl, —CH$_2$CH$_2$NHCH$_3$, —CH$_2$CH$_2$N(—CH$_2$CH$_2$CH$_3$)$_2$, ethylpiperidinyl, or ethylpiperidinylbenzyl, R$^2$ is methyl, and R$^3$, R$^4$, R$^5$ and R$^6$ are hydrogen;

oo) a compound wherein R$^1$ is morpholinyl, R$^2$ is —C(F)$_3$, —C(=O), —CH$_2$OH, —C(=O)H, —COOH, chloro, —NO$_2$, or cyano, and R$^3$, R$^4$, R$^5$ and R$^6$ are hydrogen;

pp) a compound wherein R$^1$ is —NHR$^{22}$ wherein R$^{22}$ is heptyl, phenyl, benzyl, or ethylphenyl, R$^2$ is hydrogen, methyl, or chlorophenyl, R$^4$, R$^5$ and R$^6$ are hydrogen;

qq) a compound wherein R$^1$ is —NR$^{21}$ wherein R$^{21}$ is phenyl and R$^2$, R$^3$, R$^4$, R$^5$ and R$^6$ are hydrogen;

rr) a compound wherein R$^1$ is morpholinyl and R$^2$, R$^3$, R$^4$, R$^5$ and R$^6$ are hydrogen;

ss) a compound wherein R$^1$ is methylpiperazinyl and R$^2$, R$^3$, R$^4$, R$^5$ and R$^6$ are hydrogen;

tt) a compound wherein $R^1$ is —NHCH$_2$CH$_2$OH or NHCH$_2$CH$_2$OCH$_3$, $R^2$ is phenyl and $R^3$, $R^4$, $R^5$ and $R^6$ are hydrogen;

uu) a compound wherein $R^1$ is —NHR$^{22}$ wherein $R^{22}$ is ethylamino, butylamino, ethylaminomethyl, and $R^2$ is hydrogen, methyl, or —C(=O)NHR$^2$, and $R^3$, $R^4$, $R^5$ and $R^6$ are hydrogen;

vv) a compound wherein $R^1$ is —NHR$^{22}$ wherein $R^2$ is ethylpiperidinyl, methylpiperidinylbenzyl, piperidinylbenzyl, ethylpiperidinylbenzyl, methylpyrrolidinylmethyl, ethylpiperazinylbenzyl, —CH$_2$C(=O)-piperazinylbenzyl, —C(=O)-methylnaphthyl, —CH$_2$CH$_2$CH$_2$CH$_2$CH$_2$N(CH$_3$)(C$_7$H$_7$), —CH$_2$C(=O)-piperidinylbenzyl, —C(=O)-methylpiperidinylbenzyl, or —CH(CH$_3$)$_2$, and $R^3$, $R^4$, $R^5$ and $R^6$ are hydrogen;

ww) a compound wherein $R^1$ is —CHCH$_2$CH$_2$-isoquinolinyl, —NHCH$_2$CH$_2$N(CH$_2$CH$_2$CH$_3$)$_2$, propyl substituted with piperidinyl fused to phenyl, —NHCH$_2$CH$_2$, or —NHCH$_2$CH$_2$CH$_2$CH$_2$ substituted with a piperidinyl fused to two adjacent carbon atoms of a phenyl moiety;

xx) a compound wherein $R^1$ is —NH substituted with two pyrrolidinyl groups; $R^3$ is methyl, and $R^2$, $R^4$, $R^5$ and $R^6$ are hydrogen:

yy) a compound wherein $R^1$ is —COOCH$_3$, $R^3$ is methyl, and $R^3$, $R^4$, $R^5$ and $R^6$ are hydrogen;

zz) a compound wherein $R^1$ is hydrogen, $R^2$ is methyl, $R^7$ is oxygen;

aaa) a compound wherein $R^7$ is methyl or oxygen, and $R^1$, $R^2$, $R^4$, $R^5$ and $R^6$ are hydrogen;

bbb) a compound wherein $R^1$ is —NHCH$_2$CH$_2$N(CH$_2$CH$_3$)$_2$, $R^3$ is ethyl, and $R^2$, $R^4$, $R^5$ and $R^6$ are hydrogen; and ccc) a compound wherein $R^1$ is —NHCH$_2$CH(OH)(CH$_3$) or —NHCH$_2$CH$_2$NHCH$_2$CH$_2$OH, $R^2$ methyl, and $R^3$, $R^4$, $R^5$ and $R^6$ are hydrogen.

In an aspect, a compound of the Formula I is provided wherein: (a) $R^1$ is optionally substituted halo, hydroxyl, alkyl, alkenyl, alkoxy, cyano, amino, cycloalkyl, -sulfonyl, sulfinyl, sulfenyl, thioaryl, thioalkyl, carbonyl, silyl, piperazinyl, piperidinyl, pyrrolidinyl, morpholinyl, —SR$^{24}$ wherein R$^{24}$ is optionally substituted alkyl, carbonyl, carboxyl, carbamoyl, aryl, heterocylic, or heteroaryl; (b) $R^2$ is optionally substituted halo, hydroxyl, alkyl, alkenyl, alkoxy, carbonyl, carboxyl, phenyl, benzyl, amino, aryl, cyano, —COH, piperazinyl, alcohol, piperidinyl, morpholinyl, or naphthyl; (c) $R^3$ is hydrogen, halo, hydroxyl, alkyl, alkenyl, alkoxy, phenyl, piperazinyl, piperidinyl, pyrrolidinyl, morpholinyl, thiol, sulfenyl, sulfonyl, sulfinyl, or nitro; (d) $R^4$ is hydrogen, halo, or nitro (e) $R^5$ is hydrogen, halo, alkoxy, or amido: (f) $R^7$ is hydrogen halo, hydroxyl, alkyl, alkenyl, alkoxy, carboxy, morpholino; imidazolyl; piperazinyl, piperidinyl, pyrrolidinyl, morpholinyl or $R^7$ is absent and there is a double bond between N at position 1 and C at position 6; and/or (g) $R^1$ and $R^2$, $R^1$ and $R^7$ or $R^2$ and $R^3$ may form a heteroaryl or heterocyclic ring.

In another aspect of the invention a compound of the Formula I is provided wherein $R^1$ is Cl or Br, —NH$_2$, alkyl, —CN, =S, silyl, sulfonyl, thioalkyl, thioaryl, piperazinyl, piperazinyl, piperidinyl, piperidinyl, morpholinyl, pyrrolidinyl, pyrrolyl, or pyrrolidinyl, which may be optionally substituted with halo, =O, alkoxy, alkenyl, alkyl, substituted alkyl, —CN, —SR$^{24}$ wherein R$^{24}$ is optionally substituted methyl, ethyl, phenyl, heterocyclic, or heteroaryl, or —CO substituted with phenyl or substituted phenyl.

In another aspect of the invention a compound of the Formula I is provided wherein $R^2$ is carbonyl, piperazinyl, morpholinyl, sulfonyl, sulfinyl, sulfenyl, or phenyl, —CN, —COH, CH$_2$OH, —OCH$_2$CH$_3$, or alkyl which may be optionally substituted with alkyl, alkoxy, amino, halo, phenyl, substituted phenyl, benzyl, hydroxyl, amino, piperidinyl, or morpholinyl.

In another aspect of the invention a compound of the Formula I is provided wherein $R^3$ is piperazinyl; substituted piperzinyl; alkyl which may optionally be substituted with amino; phenyl; substituted phenyl; amino which may be optionally substituted with alkyl or alkylamine (e.g., NHCOOC(CH$_3$)$_3$), carboxyl, or substituted carboxyl; hydroxyl; or nitro.

In another aspect of the invention a compound of the Formula I is provided wherein $R^4$ is nitro or hydrogen.

In another aspect of the invention a compound, of the Formula I is provided wherein $R^5$ is hydrogen, halo, —OCH$_2$CH$_2$CH$_2$NHCOOC(CH$_3$)$_3$, or —OCH$_3$.

In another aspect of the invention a compound of the Formula I is provided wherein $R^7$ is alkyl, morpholinyl, benzyl, imidazolyl, —CH$_2$COOCH$_2$CH$_3$, CH$_2$C=COOCH$_2$CH$_3$, CH$_2$CH$_2$CH$_2$SO$_2$OH, CH$_2$CH$_2$CH$_2$SO$_3^-$, CH$_2$CH$_2$CH$_2$CH$_2$PO(OH)$_2$, or CH$_2$CH$_2$CH$_2$PO(OH)$_2$.

In another aspect of the invention a compound of the Formula I is provided wherein $R^7$ is absent and there is a double bond between N at position 1 and C at position 6.

In a further aspect, a compound of the Formula I is provided wherein $R^1$, $R^2$, $R^3$, and $R^7$ are independently substituted aliphatic, lower alkyl substituted amino, lower alkyl substituted halogen, cycloaliphatic, or substituted cycloaliphatic.

In a still further aspect the invention a compound of the Formula I is provided wherein $R^1$ is a piperazinyl which may be substituted (e.g., with a pyrimidinyl moiety); halo; amino which may be substituted; cyano; —SR$^{24}$ wherein R$^{24}$ is alkyl or aryl (e.g. phenyl) which may be substituted (e.g., halo); substituted alkyl [e.g., alkyl substituted with halogen, such as CH(Br)$_2$]; morpholinyl; pyrrolyl which may be substituted; hydroxyl: —OR$^{35}$ wherein R$^{35}$ is alkyl; —C=CHR$^{36}$ wherein R$^{36}$ is alkyl; or pyrrolidinyl.

In a still further aspect the invention a compound of the Formula I is provided wherein $R^2$ is hydrogen; morpholinyl; piperazinyl which may be substituted (e.g., with a pyrimidinyl moiety); phenyl; alkyl; alkoxy (e.g. CH(OCH$_3$)$_2$); substituted alkyl; substituted aryl (e.g., phenyl); cyano; or hydroxyl.

In a still further aspect the invention a compound of the Formula I is provided wherein $R^3$ is hydrogen; hydroxyl; alkyl which may be substituted (e.g., halo); amino which may be substituted; —COR$^{37}$ wherein R$^{37}$ is hydrogen, hydroxyl, alkoxy (e.g. —OCH$_3$); or, aryl (e.g. phenyl) which may be substituted (e.g., alkyl).

In a still further aspect the invention a compound of the Formula I is provided wherein $R^4$ is hydrogen or halo; $R^5$ is hydrogen or halo; $R^6$ is hydrogen or halo.

In a still further aspect the invention a compound of the Formula I is provided wherein $R^7$ is hydrogen; alkyl which may be substituted (e.g. with phenyl); —CH$_2$CH$_2$COOR$^{38}$ wherein R$^{38}$ is alkyl, —CH$_2$C=COOR$^{38}$ wherein R$^{38}$ is alkyl, CH$_2$CH$_2$CH$_2$S(O)$_2$OH, morpholinyl, benzyl, imidazolyl, or [CH$_2$]$_n$PO(OH)$_2$ wherein n is 1 to 6, in particular 3 or 4.

In a still further aspect the invention a compound of the Formula I is provided wherein $R^1$ and $R^2$ form a piperidinyl ring which may optionally be substituted with a carboxyl.

In a still further aspect the invention a compound of the Formula I is provided wherein $R^1$ and $R^7$ form a pyrimidinyl ring which may optionally be substituted with alkyl, aryl, halo, or hydroxyl.

In a particular aspect $R^1$ is —$NR^{21}R^{22}$ wherein $R^{21}$ is hydrogen, and $R^{22}$ is hydrogen, alkyl, carbonyl, aryl, amino, cycloalkane, heterocylic, or heteroaryl which may be substituted. In embodiments $R^{22}$ may comprise or be selected from the group consisting of hydrogen, $C_1$-$C_6$ alkyl (e.g. methyl or ethyl) which may be substituted with optionally substituted hydroxyl, alkyl, amino, carbonyl, carboxyl, morpholinyl, isoquinolinyl, or an amino which may be substituted with one or more of optionally substituted alkyl, benzyl, carboxyl, alcohol group, heteroaryl or heterocyclic, a propanol group, phenyl which may be optionally substituted with halo, benzyl which may be substituted with alkoxy, cyclohexyl, piperidinyl which may be substituted with optionally substituted phenyl, pyrrolidinyl or pyrrolidinylalkyl which may be substituted with alkyl, —$COOR^{40}$ wherein $R^{40}$ is alkyl which may be substituted, or $[CH_2]_m$-piperidinyl wherein m is 1 to 4, in particular 1 to 3 and the piperidinyl is optionally substituted with optionally substituted alkyl, phenyl or benzyl.

In embodiments, $R^{22}$ is —$R^{60}R^{61}$ wherein $R^{60}$ is —NH $[CH_2]_w$NH wherein w is 1 to 4, in particular 2 or 3, and $R^{51}$ is piperazinyl substituted with pyrimidinyl which may be substituted, in particular substituted with alkyl.

In embodiments, $R^{22}$ is —$R^{62}R^{63}$ wherein $R^{62}$ is —$[CH_2]_wN(CH_3)$ wherein w is 1 to 4, in particular 2 or 3, and $R^{63}$ is piperazinyl substituted with pyrimidinyl which may be substituted, in particular substituted with alkyl.

In an aspect of the invention, a compound of the Formula I is provided wherein $R^1$ is halo especially chloro or bromo, $R^2$ is alkyl which may be substituted, in particular substituted with alkoxy (e.g., methoxy, dimethoxy), substituted aryl which may be substituted with alkyl, alkoxy, (e.g., benzyl, methoxy phenyl), halo (e.g. bromo or chloro), or carbonyl, a substituted or unsubstituted saturated 3 to 6-membered heteromonocylic group containing 1 to 4 nitrogen atoms [e.g., piperidinyl, and piperazinyl] or a saturated 3 to 6-membered heteromonocyclic group containing 1 to 2 oxygen atoms and 1 to 3 nitrogen atoms [e.g. morpholinyl; sydnonyl], in particular a substituted morpholinyl, piperazinyl, or piperazinyl substituted with a heteroaryl in particular an unsaturated 5 to 6 membered heteromonocyclyl group containing 1 to 4 nitrogen atoms, in particular, pyrrolyl, pyrrolinyl, imidazolyl, pyrazolyl, 2-pyridyl, 3-pyridyl, 4-pyridyl, pyridinyl, pyrimidinyl, pyrazinyl, or pyridazinyl, especially pyrimidinyl, and optionally $R^3$, $R^4$, $R^5$, $R^6$, and $R^7$ are hydrogen.

In another aspect of the invention, a compound of the Formula I is provided wherein $R^1$ is halo especially chloro or bromo, and $R^3$ is a substituted or unsubstituted saturated 3 to 6-membered heteromonocylic group containing 1 to 4 nitrogen atoms [e.g., piperidinyl, and piperazinyl] or a saturated 3 to 6-membered heteromonocyclic group containing 1 to 2 oxygen atoms and 1 to 3 nitrogen atoms [e.g. morpholinyl; sydnonyl], in particular a substituted morpholinyl, piperazinyl, or piperazinyl substituted with alkyl or a heteroaryl in particular an unsaturated 5 to 6 membered heteromonocyclyl group containing 1 to 4 nitrogen atoms, in particular, pyrrolyl, pyrrolinyl, imidazolyl, pyrazolyl, 2-pyridyl, 3-pyridyl, 4-pyridyl, pyridinyl, pyrimidinyl, pyrazinyl, or pyridazinyl, especially pyrimidinyl, or $R^2$ is a substituted amino, in particular amino substituted with alkyl or substituted alkyl, in particular alkyl substituted with alkoxy carbony, and optionally $R^2$, $R^4$, $R^5$, $R^6$, and $R^7$ are hydrogen.

In further aspect $R^1$ is halo, especially bromo or chloro, and $R^2$ and $R^3$ form an unsaturated ring, in particular phenyl, $R^5$ is a heteroaryl, in particular a substituted or unsubstituted unsaturated 5 to 6 membered heteromonocyclyl group containing 1 to 4 nitrogen atoms, in particular, pyrrolyl, pyrrolinyl, imidazolyl, pyrazolyl, especially imidazolyl, and optionally $R^4$, $R^6$ and $R^7$ are hydrogen.

In a further aspect, $R^1$ is halo, especially bromo or chloro, and $R^4$ is nitro, and optionally $R^2$, $R^3$, $R^5$, $R^6$, and $R^7$ are hydrogen.

In a further aspect, the invention provides a compound of the Formula I wherein $R^1$ is a thiol substituted with alkyl (thioalkyl); substituted alkyl, in particular alkyl substituted with a substituted or unsubstituted saturated 3 to 6-membered heteromonocylic group containing 1 to 4 nitrogen atoms [e.g. pyrrolidinyl, imidazolidinyl, piperidinyl, and piperazinyl] or a saturated 3 to 6-membered heteromonocyclic group containing 1 to 2 oxygen atoms and 1 to 3 nitrogen atoms [e.g. morpholinyl; sydnonyl], especially a substituted morpholinyl or piperidinyl; aryl; substituted aryl; carboxyl which may be substituted with substituted or unsubstituted aryl; optionally $R^2$ is alkyl, in particular lower alkyl; optionally $R^3$ is alkyl, in particular lower alkyl or nitro; optionally $R^5$ is alkoxy; optionally $R^7$ is alkyl; and optionally $R^4$, $R^5$, and $R^6$, are hydrogen.

In a further aspect of the invention, a compound of the Formula I is provided wherein $R^1$ is =S, and optionally $R^2$ is alkyl, in particular lower alkyl, $R^5$ is alkoxy, and $R^3$, $R^4$, $R^6$ and $R^7$ are hydrogen.

In a further aspect of the invention, a compound of the Formula I is provided wherein $R^1$ is sulfonyl which may be substituted with substituted or unsubstituted aryl, in particular substituted phenyl, and optionally $R^2$ is alkyl and $R^3$, $R^4$, $R^5$, $R^6$, and $R^7$ are hydrogen.

In a further aspect of the invention, a compound of the Formula I is provided wherein $R^1$ is substituted or unsubstituted alkyl or alkynyl, in particular alkyl substituted with aryl, substituted aryl, halo, cyano, or alkynyl substituted with alkyl; and optionally $R^2$ is alkyl, $R^7$ is alkyl, and $R^3$, $R^4$, $R^5$ and $R^6$ are hydrogen.

In a further aspect of the invention, a compound of the Formula I is provided wherein $R^1$ is cyano and $R^2$ is aryl or alkyl, and optionally $R^3$, $R^4$, $R^5$, $R^6$, and $R^7$ are hydrogen.

In a further aspect of the invention, a compound of the Formula I is provided wherein one or both of $R^1$ and $R^2$ are a saturated 3 to 6-membered heteromonocyclic group containing 1 to 2 oxygen atoms and 1 to 3 nitrogen atoms [e.g. morpholinyl; sydnonyl], especially a substituted morpholinyl, and optionally $R^3$, $R^4$, $R^5$, $R^6$, and $R^7$ are hydrogen.

In a further aspect of the invention, a compound of the Formula I is provided wherein $R^1$ is a saturated 3 to 6-membered heteromonocylic group containing 1 to 4 nitrogen atoms [e.g. pyrrolidinyl], which may be substituted with substituted or unsubstituted carboxyl; $R^2$ is alkyl or halo, and optionally $R^3$, $R^4$, $R^5$, $R^6$, and $R^7$ are hydrogen.

In a further aspect of the invention, a compound of the Formula I is provided wherein $R^1$ is hydroxyl; $R^2$ is alkyl or substituted alkyl or $R^3$ is a saturated 3 to 6-membered heteromonocylic group containing 1 to 4 nitrogen atoms [e.g. piperidinyl, and piperazinyl] which may optionally be substituted with a heteroaryl [e.g., pyrimidinyl], and the other of $R^2$ or $R^3$ is hydrogen, and optionally $R^4$, $R^5$, $R^6$, and $R^7$ are hydrogen.

In a further aspect of the invention, a compound of the Formula I is provided wherein $R^1$ is a saturated 3 to 6-membered heteromonocylic group containing 1 to 4 nitrogen atoms [e.g., piperidinyl and piperazinyl] which may be substituted with carboxyl or carboxyl substituted with alkyl or alkoxy or with purinyl or substituted purinyl; $R^2$ is alkyl or substituted alkyl, in particular alkylaryl, and optionally $R^3$, $R^4$, $R^5$, $R^6$, and $R^7$ are hydrogen.

In a further aspect of the invention, a compound of the Formula I is provided wherein $R^1$ is =O, and $R^2$ is alkyl, alkylaryl, cyano, alkoxy, or substituted alkoxy, and optionally $R^3$, $R^4$, $R^5$, $R^6$, and $R^7$ are hydrogen.

In a further aspect of the invention, a compound of the Formula I is provided wherein $R^1$ is alkoxy, $R^2$ is alkyl, substituted alkyl, or alkoxy, and optionally $R^3$, $R^4$, $R^5$, $R^6$, and $R^7$ are hydrogen.

In a further aspect of the invention, a compound of the Formula I is provided wherein $R^1$ and $R^2$ form a heterocyclic, in particular a saturated 3 to 6-membered heteromonocylic group containing 1 to 4 nitrogen atoms, in particular a 6-membered ring comprising 1 or 2 nitrogen atoms [e.g., piperidinyl and piperazinyl] which may be substituted for example with alkyl, halo, carboxyl, or alkoxy carbonyl, and optionally $R^3$, $R^4$, $R^5$, $R^6$, and $R^7$ are hydrogen.

In a further aspect of the invention, a compound of the Formula I is provided wherein $R^1$ and $R^7$ form a heteroaryl, in particular an unsaturated 5 to 6 membered heteromonocyclyl group containing 1 to 4 nitrogen atoms, in particular, pyrrolyl, pyrrolinyl, imidazolyl, pyrazolyl, 2-pyridyl, 3-pyridyl, 4-pyridyl, pyridinyl, pyrimidinyl, pyrazinyl, or pyridazinyl, $R^2$ is hydrogen or alkyl, and $R^3$, $R^4$, $R^5$, $R^6$, and $R^7$ are hydrogen.

In a further aspect of the invention, a compound of the Formula I is provided wherein $R^1$ is silyl which may be substituted, in particular substituted with alkyl $R^2$ is alkyl, and $R^3$, $R^4$, $R^5$, $R^6$, and $R^7$ are hydrogen.

In an embodiment, $R^1$ is a piperazinyl or substituted piperazinyl, in particular a piperazinyl substituted with a pyrimidinyl of the Formula II below.

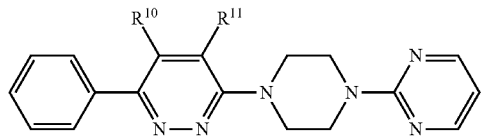

Thus, the invention also provides an isolated and pure, in particular, substantially pure, compound of the Formula II wherein one or both of $R^{10}$ and $R^{11}$ are independently substituted or unsubstituted hydrogen, hydroxyl, alkyl, alkenyl, alkynyl, alkylene, alkenylene, alkoxy, alkenyloxy, cycloalkyl, cycloalkenyl, aryl, aryloxy, arylalkoxy, aroyl, heteroaryl, heterocyclic, acyl, acyloxy, sulfonyl, sulfinyl, sulfenyl, amino, imino, azido, thiol, thioalkyl, thioalkoxy, thioaryl, nitro, ureido, cyano, halo, silyl, silyalkyl, silyloxy, silylthio, =O, =S, carboxyl, carbonyl, or carbamoyl, or an isomer or a pharmaceutically acceptable salt thereof.

In an aspect of the compound of the Formula II is provided wherein $R^{10}$ is hydrogen; hydroxyl; alkyl; aryl [e.g. phenyl which is optionally substituted (e.g., halide)]; piperazinyl which may be substituted (e.g. substituted with a pyrimidinyl); —$NR^{55}R^{56}$ wherein $R^{55}$ is hydrogen or alkyl, and $R^{56}$ is phenyl which may be substituted or alkyl which may be substituted (e.g. amino, in particular —$CH_2CH_2NH_2$; $CH_2CH_2NHCOOC(CH_3)_3$); morpholinyl which may be substituted; or —$SR^{25}$ wherein $R^{25}$ is phenyl which may be substituted; and $R^{11}$ is hydrogen, or aryl (e.g. phenyl) which may be substituted.

In a particular aspect of the invention a compound of the Formula II is provided wherein $R^{10}$ is hydrogen, halo, optionally substituted hydroxyl, alkyl, pyridinyl, phenyl, benzyl, piperazinyl, amino, morpholinyl, or —$SR^{24}$ wherein $R^{24}$ is alkyl or aryl. In an embodiment, $R^{10}$ is —$NH[CH_2]_mNR^{60}R^{61}$ wherein m is 1 to 6, in particular 2 to 4, $R^{60}$ is hydrogen, $R^{61}$ is a carboxyl, in particular —COOC$(CH_3)_3$.

In an aspect of the invention a compound of the Formula II is provided wherein $R^{11}$ is hydrogen, halo, optionally substituted alkyl, pyridinyl, piperidinyl, morpholinyl, piperazinyl, or phenyl.

In another aspect, of the invention a compound of the Formula II is provided wherein both of $R^{10}$ and $R^{11}$ are not hydrogen.

In particular embodiments of the invention one or more of $R^{10}$ and $R^{11}$ are alkyl, in particular $C_1$-$C_6$ alkyl and the other of $R^{10}$ and $R^{11}$ is hydrogen.

In particular embodiments of the invention one or more of $R^{10}$ and $R^{11}$ are aryl in particular phenyl or benzyl and the other of $R^{10}$ and $R^{11}$ is hydrogen.

In particular embodiments of the invention a compound of the Formula II is a compound in Table 3, more particularly MW01-2-065LKM, MW01-2-069SRM, MW01-2-151SRM, MW01-5-188WH, MW01-6-127WH, MW01-6-189WH, MW01-7-107WH, and derivatives thereof.

The invention also provides an isolated and pure, in particular, substantially pure, compound of the Formula III wherein $R^{15}$ and $R^{16}$ are independently substituted or unsubstituted hydrogen, hydroxyl, alkyl, alkenyl, alkynyl, alkylene, alkenylene, alkoxy, alkenyloxy, cycloalkyl, cycloalkenyl, aryl, aryloxy, arylalkoxy, aroyl, heteroaryl, heterocyclic, acyl, acyloxy, sulfonyl, sulfinyl, sulfenyl, amino, imino, azido, thiol, thioalkyl, thioalkoxy, thioaryl, nitro, ureido, cyano, halo, silyl, silyloxy, silylthio, =O, =S, carboxyl, carbonyl, or carbamoyl, or an isomer or pharmaceutically acceptable salt thereof.

The invention also provides an isolated and pure, in particular, substantially pure, compound, of the Formula IV wherein $R^{70}$ and $R^{71}$ are independently substituted or unsubstituted hydrogen, hydroxyl, alkyl, alkenyl, alkynyl, alkylene, alkenylene, alkoxy, alkenyloxy, cycloalkyl, cycloalkenyl, aryl, aryloxy, arylalkoxy, aroyl, heteroaryl, heterocyclic, acyl, acyloxy, sulfonyl, sulfinyl, sulfenyl, amino, imino, azido, thiol, thioalkyl, thioalkoxy, thioaryl, nitro, ureido, cyano, halo, silyl, silyloxy, silylthio, =O, =S, carboxyl, carbonyl, or carbamoyl, or an isomer or pharmaceutically acceptable salt thereof.

In an aspect, the invention relates to a compound of the Formula IV wherein $R^{70}$ is a heterocylic, in particular a saturated 3 to 6-membered heteromonocylic group containing 1 to 4 nitrogen atoms more particularly, pyrrolidinyl, imidazolidinyl, piperidinyl, and piperazinyl, especially piperazinyl or piperidinyl, which may be substituted with alkyl especially methyl, dimethyl, cycloalkyl especially cyclohexyl, aryl especially phenyl, a substituted or unsubstituted unsaturated condensed heterocyclic group containing 1 to 5 nitrogen atoms, in particular, indolyl, isoindolyl, indolizinyl, indazolyl, quinazolinyl, pteridinyl, quinolizidinyl, phthalazinyl, naphthyridinyl, quinoxalinyl, cinnolinyl, phenanthridinyl, acridinyl, phenanthrolinyl, phenazinyl, carbazolyl, purinyl, benzimidazolyl, quinolyl, isoquinolyl, quinolinyl, isoquinolinyl, or indazolyl, especially benzimidazolyl substituted with oxy.

The invention also relates to a compound of the Formula IV wherein $R^{70}$ is amino or substituted amino, and optionally $R^{71}$ is aryl, in particular phenyl. In an aspect $R^{70}$ is —N—$R^{22}$ wherein $R^{21}$ is hydrogen or alkyl, in particular $C_1$-$C_6$ alkyl, more particularly methyl or dimethyl, or —N—$R^{21}R^{22}$ wherein $R^{21}$ is hydrogen or alkyl, in particular $C_1$-$C_6$ alkyl, more particularly methyl and $R^{22}$ is alkyl substituted with amino or substituted amino, heterocyclic, substituted heterocylic, or cycloalkyl. In an embodiment, $R^{70}$ is —N—$R^{21}R^{22}$ wherein $R^{21}$ is hydrogen or alkyl, in particular $C_1$-$C_6$ alkyl, more particularly methyl and $R^{22}$ is $C_1$-$C_6$ alkyl, especially methyl or ethyl substituted with a cycloalkyl especially cyclopropyl, a heterocyclic especially piperidinyl, pyrrolidinyl, or morpholinyl which may be substituted in particular substituted with aryl, especially benzyl.

A compound of the Formula IV may comprise structure 124, 125, 126, 127, 128, 129, 130, 131, 132, 133, 134, 135, 136, 137, 138, or 139 in Table 5 or derivatives thereof.

The invention also provides an isolated and pure, in particular, substantially pure, compound of the Formula V wherein $R^{50}$ and $R^{51}$ are independently substituted or unsubstituted hydrogen, hydroxyl, alkyl, alkenyl, alkynyl, alkylene, alkenylene, alkoxy, alkenyloxy, cycloalkyl, cycloalkenyl, aryl, aryloxy, arylalkoxy, aroyl, heteroaryl, heterocyclic, acyl, acyloxy, sulfonyl, sulfinyl, sulfenyl, amino, imino, azido, thiol, thioalkyl, thioalkoxy, thioaryl, nitro, ureido, cyano, halo, silyl, silyloxy, silylthio, =O, =S, carboxyl, carbonyl, or carbamoyl, or an isomer or pharmaceutically acceptable salt thereof.

The invention relates to a compound of the Formula V wherein $R^{50}$ is substituted or unsubstituted hydrogen, alkyl, aryl, or heterocyclic; $R^{51}$ is substituted or unsubstituted hydrogen or alkyl, and $R^{52}$ is substituted or unsubstituted hydrogen, alkyl, cycloalkyl, heteroaryl or halo. In an aspect, the invention relates to a compound of the Formula V wherein $R^{50}$ is hydrogen, $C_1$-$C_6$ alkyl which may be substituted with alkyl, especially methyl or trimethyl, phenyl, or a 3 to 6-membered heteromonocylic group containing 1 to 4 nitrogen atoms more particularly, piperidinyl or morpholinyl, $R^{51}$ is hydrogen or alkyl especially methyl, and $R^{52}$ is hydrogen, alkyl especially methyl, dimethyl, ethyl, or propyl, cyclohexyl, chloro, or an unsaturated 5 to 6 membered heteromonocyclyl group containing 1 to 4 nitrogen atoms, in particular, pyrrolyl, pyrrolinyl, imidazolyl, pyrazolyl, 2-pyridyl, 3-pyridyl, 4-pyridyl, pyridinyl, pyrimidinyl, pyrazinyl, or pyridazinyl, especially pyridinyl. In an embodiment, $R^{50}$ is aryl, $R^{51}$ is hydrogen, and $R^{52}$ is $C_1$-$C_6$ alkyl.

A compound of the Formula V may comprise compound MW01-7-057WH, or structure 32, 34, 36, 38, 39, 40, 41, 42, 43, 44, 46, 47, 48, 49, 63, 69, 70, 71, 75, 76, 77, 78, 79, 80, 81, and 82 in Table 5 or derivatives thereof.

In some embodiments, the present invention, provides novel organic compounds, and/or heterocyclic derivatives thereof, depicted in Tables 2, 3, 4 or 5.

Derivative groups that may be used to modify the compounds of the Formula I, II, III, IV, or V can be found in U.S. Patent Application No. 20030176437 (herein incorporated by reference in its entirety for all purposes).

A compound of the Formula I, II, III, IV, or V may be in the form of a prodrug that is converted in vivo to an active compound. For example, in a compound of the Formula I one or more of $R^1$, $R^2$, R3, $R^4$, $R^5$, $R^6$, and $R^7$ may comprise a cleavable group that is cleaved after administration to a subject to provide an active (e.g., therapeutically active) compound, or an intermediate compound that subsequently yields the active compound. A cleavable group can be an ester that is removed either enzymatically or non-enzymatically.

A compound of the Formula I, II, III, IV, or V may comprise a carrier, such as one or more of a polymer, carbohydrate, peptide or derivative thereof, which may be directly or indirectly covalently attached to the compound. A carrier may be substituted with substituents described herein including without limitation one or more alkyl, amino, nitro, halogen, thiol, thioalkyl, sulfate, sulfonyl, sulfinyl, sulfoxide, hydroxyl groups. In aspects of the invention the carrier is an amino acid including alanine, glycine, praline, methionine, serine, threonine, asparagine, alanyl-alanyl, prolyl-methionyl, or glycyl-glycyl. A carrier can also include a molecule that targets a compound of the Formula I, II, III, IV, or V to a particular tissue or organ. Thus, a carrier may facilitate or enhance transport of a compound of the Formula I, II, III, IV or V to the brain.

Process

Compounds of the Formula I, II, III, IV, or V can be prepared using reactions and methods generally known to the person of ordinary skill in the art, having regard to that knowledge and the disclosure of this application including the Examples. The reactions are performed in a solvent appropriate to the reagents and materials used and suitable for the reactions being effected. It will be understood by those skilled in the art of organic synthesis that the functionality present on the compounds should be consistent with the proposed reaction steps. This will sometimes require modification of the order of the synthetic steps or selection of one particular process scheme over another in order to obtain a desired compound of the invention. It will also be recognized that another major consideration in the development of a synthetic route is the selection of the protecting group used for protection of the reactive functional groups present in the compounds described in this invention. An authoritative account describing the many alternatives to the skilled artisan is Greene and Wuts (Protective Groups In Organic Synthesis, Wiley and Sons, 1991).

The starting materials and reagents used in preparing compounds or the invention are either available from commercial suppliers or are prepared by methods well known to a person of ordinary skill in the art, following procedures described in such references as Fieser and Fieser's *Reagents for Organic Synthesis*, vols. 1-17, John Wiley and Sons, New York, N.Y., 1991; *Rodd's Chemistry of Carbon Compounds*, vols. 1-5 and supps., Elsevier Science Publishers, 1989; Organic Reactions, vols. 1-40, John Wiley and Sons, New York, N.Y., 1991; March J.: *Advanced Organic Chemistry*, 4th ed., John Wiley and Sons, New York, N.Y.; and Larock: *Comprehensive Organic Transformations*, VCH Publishers, New York, 1989.

The starting materials, intermediates, and compounds of the Formula I, II, III, IV, or V may be isolated and purified using conventional techniques, such as precipitation, filtration, distillation, crystallization, chromatography, and the like. The compounds of the Formula I, II, III, IV, or V may be characterized using conventional methods, including physical constants and spectroscopic methods, in particular HPLC.

The compounds of the Formula I, II, III, IV, or V which are basic in nature can form a wide variety of different salts with various inorganic and organic acids. In practice is it desirable to first isolate a compound of the Formula I, II, III, IV, or V from the reaction mixture as a pharmaceutically unacceptable salt and then convert the latter to the free base compound by treatment with an alkaline reagent and subsequently convert the free base to a pharmaceutically acceptable acid addition salt. The acid addition salts of the base compounds of the Formula I, II, III, IV, or V are readily prepared by treating the base compound with a substantially equivalent amount of the chosen mineral or organic acid in an aqueous solvent medium or in a suitable organic solvent such as methanol or ethanol. Upon careful evaporation of the solvent, the desired solid salt is obtained.

Compounds of the Formula I, II, III, IV, or V which are acidic in nature are capable of forming base salts with various pharmacologically acceptable cations. These salts may be prepared by conventional techniques by treating the corresponding acidic compounds with an aqueous solution containing the desired pharmacologically acceptable cations and then evaporating the resulting solution to dryness, preferably under reduced pressure. Alternatively, they may be prepared by mixing lower alkanolic solutions of the acidic compounds and the desired alkali metal alkoxide together and then evaporating the resulting solution to dryness in the same manner as before. In either case, stoichiometric quantities of reagents are typically employed to ensure completeness of reaction and maximum product yields.

In particular aspects, the present invention provides methods of making the compounds disclosed herein, comprising the steps provided (See, e.g., the Figures and Materials and Methods). Broad Process Description for Pyr PCT Application In an aspect, the invention provides a process for preparing a compound of the formula II wherein R11 is hydrogen and R10 is an unsaturated 5 to 6 membered heteromonocyclyl group containing 1 to 4 nitrogen atoms, in particular, pyrrolyl, pyrrolinyl, imidazolyl, pyrazolyl, 2-pyridyl, 3-pyridyl, 4-pyridyl, pyridinyl, pyrimidinyl, pyrazinyl, pyridazinyl, triazolyl, or tetrazolyl, more particularly pyridinyl, which comprises reacting a compound of the formula II wherein R10 is halo, in particular chloro, and R11 is hydrogen, with boronic acid substituted with an unsaturated 5 to 6 membered heteromonocyclyl group containing 1 to 4 nitrogen atoms, in particular, pyrrolyl, pyrrolinyl, imidazolyl, pyrazolyl, 2-pyridyl, 3-pyridyl, 4-pyridyl, pyridinyl, pyrimidinyl, pyrazinyl, pyridazinyl, triazolyl, or tetrazolyl, more particularly pyridinyl, under suitable conditions to prepare a compound of the formula II wherein R11 is hydrogen and R10 is an unsaturated 5 to 6 membered heteromonocyclyl group containing 1 to 4 nitrogen atoms, in particular, pyrrolyl, pyrrolinyl, imidazolyl, pyrazolyl, 2-pyridyl, 3-pyridyl, 4-pyridyl, pyridinyl, pyrimidinyl, pyrazinyl, pyridazinyl, triazolyl, or tetrazolyl, more particularly pyridinyl. In an embodiment, R10 is phenyl substituted with halo.

In another aspect, the invention provides a process for preparing a compound of the formula II wherein R11 is hydrogen, and R10 is a substituted aryl which comprises reacting a compound of the formula II wherein R10 is halo, in particular chloro, and R11 is hydrogen, with a substituted aryl boronic acid under suitable conditions to prepare a compound of the formula II wherein R11 is hydrogen and R10 is a substituted aryl. In an embodiment, R10 is phenyl substituted with halo.

In another aspect, the invention provides a process for preparing a compound of the formula II wherein R10 is hydrogen and R11 is alkyl which comprises reacting a compound of the formula II wherein R11 is halo, in particular chloro, and R10 is hydrogen, with an alkyl boronic acid under suitable conditions to prepare a compound of the formula II wherein R10 is hydrogen and R11 is alkyl. In an embodiment, R11 is lower alkyl, in particular methyl or ethyl, and a compound of the formula II wherein R11 is chloro is reacted with lower alkyl boronic acid, in particular methyl or ethyl boronic acid under suitable conditions.

In another aspect, the invention provides a process for preparing a compound of the formula II wherein R10 is hydrogen and R11 is an alkyl which comprises reacting a pyridazine substituted at the C3 position with halo (e.g., chloro), at the C4 position with alkyl, and at the 6 position with phenyl, with 2-(piperidin-4-yloxy)pyrimidine under suitable conditions to prepare a compound of the formula II wherein R10 is hydrogen and R11 is an alkyl. In an embodiment, R11 is methyl or ethyl.

In another aspect, the invention provides a process for preparing a compound of the formula II wherein R10 is hydrogen and R11 is aryl which comprises reacting a compound of the formula II wherein R10 is hydrogen and R11 is halo (e.g., chloro), with pyridazine substituted at the C3 position with halo (e.g., chloro), at the C4 position with aryl, and at the 6 position with phenyl, with 2-(piperidin-4-yloxy)pyrimidine under suitable conditions to prepare a compound of the formula II wherein R10 is hydrogen and R11 is aryl. In an embodiment, R11 is phenyl.

In another aspect, the invention provides a process for preparing a compound of the formula II wherein R10 is hydrogen and R11 is an unsaturated 5 to 6 membered heteromonocyclyl group containing 1 to 4 nitrogen atoms, in particular, pyrrolyl, pyrrolinyl, imidazolyl, pyrazolyl, 2-pyridyl, 3-pyridyl, 4-pyridyl, pyridinyl, pyrimidinyl, pyrazinyl, pyridazinyl, triazolyl, or tetrazolyl, more particularly pyridinyl which comprises reacting a compound of the formula II wherein R11 is halo, in particular chloro, and R10 is hydrogen, with a boronic acid substituted with an unsaturated 5 to 6 membered heteromonocyclyl group containing 1 to 4 nitrogen atoms, in particular, pyrrolyl, pyrrolinyl, imidazolyl, pyrazolyl, 2-pyridyl, 3-pyridyl, 4-pyridyl, pyridinyl, pyrimidinyl, pyrazinyl, pyridazinyl, triazolyl, or tetrazolyl, more particularly pyridinyl, under suitable conditions to prepare a compound, of the formula II wherein R10 is hydrogen and R11 is an unsaturated 5 to 6 membered heteromonocyclyl group containing 1 to 4 nitrogen atoms, in particular, pyrrolyl, pyrrolinyl, imidazolyl, pyrazolyl, 2-pyridyl, 3-pyridyl, 4-pyridyl, pyridinyl, pyrimidinyl, pyrazinyl, pyridazinyl, triazolyl, or tetrazolyl, more particularly pyridinyl.

In an embodiment, the invention provides a process for preparing a compound of the formula II wherein R10 is hydrogen and R11 is pyridinyl which comprises reacting a compound of the formula II wherein R11 is halo, in particular chloro, and R10 is hydrogen, with a pyridinyl boronic acid under suitable conditions to prepare a compound of the formula II wherein R10 is hydrogen and R11 is pyridinyl.

In another aspect, the invention provides a process for preparing a compound of the formula II wherein R10 is hydrogen and R11 is an unsaturated 5 to 6 membered heteromonocyclyl group containing 1 to 4 nitrogen atoms, in particular, pyrrolyl, pyrrolinyl, imidazolyl, pyrazolyl, 2-pyridyl, 3-pyridyl, 4-pyridyl, pyridinyl, pyrimidinyl, pyrazinyl, pyridazinyl, triazolyl, or tetrazolyl, more particularly pyridinyl which comprises reacting a pyridazine substituted at the C3 position with halo, at the C4 position with an unsaturated 5 to 6 membered heteromonocyclyl group containing 1 to 4 nitrogen atoms, in particular, pyrrolyl, pyrrolinyl, imidazolyl, pyrazolyl, 2-pyridyl, 3-pyridyl, 4-pyridyl, pyridinyl, pyrimidinyl, pyrazinyl, pyridazinyl, triazolyl, or tetrazolyl, more particularly pyridinyl, and at the 6 position with phenyl, with 2-(piperidin-4-yloxy)pyrimidine under suitable conditions to prepare a compound of the formula II wherein R10 is hydrogen and R11 is an unsaturated 5 to 6 membered heteromonocyclyl group containing 1 to 4 nitrogen atoms, in particular, pyrrolyl, pyrrolinyl, imidazolyl, pyrazolyl, 2-pyridyl, 3-pyridyl, 4-pyridyl, pyridinyl, pyrimidinyl, pyrazinyl, pyridazinyl, triazolyl, or tetrazolyl, more particularly pyridinyl.

In an embodiment, the invention provides a process for preparing a compound of the formula II wherein R10 is hydrogen and R11 is pyridinyl which comprises reacting a pyridazine substituted at the C3 position with halo, at the C4 position with pyridinyl, and at the 6 position with phenyl, with 2-(piperidin-4-yloxy)pyrimidine under suitable conditions to prepare a compound of the formula II wherein R10 is hydrogen and R11 is pyridinyl.

In another aspect, the invention provides a process for preparing a compound of the formula II wherein R10 is hydrogen and R11 is piperidinyl or substituted piperidinyl which comprises reacting a compound of the formula II wherein R11 is halo, in particular chloro, and R10 is hydrogen with piperazinyl or substituted piperazinyl under suitable conditions to prepare a compound of the formula II wherein R10 is hydrogen and R11 is piperidinyl or substituted piperidinyl.

In another aspect, the invention provides a process for preparing a compound of the formula I wherein R1 is piperazinyl or piperazinyl substituted with alkyl, aryl, or cycloalkyl, R2 is aryl, R3, R4, R5 and R6 are hydrogen and R7 is absent, which comprises reacting a pyridazine substituted at the C3 position with halo, at the C4 position with aryl with a piperazinyl or piperazinyl substituted with alkyl, aryl, or cycloalkyl, under suitable conditions to prepare a compound of the formula I wherein R1 is piperazinyl or piperazinyl substituted with alkyl, aryl, or cycloalkyl, R2 is aryl, R3, R4, R5 and R6 are hydrogen and R7 is absent.

In another aspect, the invention provides a process for preparing a compound of the formula I wherein R1 is piperazinyl or piperazinyl substituted with alkyl, aryl, or cycloalkyl, R2 is an unsaturated 5 to 6 membered heteromonocyclyl group containing 1 to 4 nitrogen atoms, in particular, pyrrolyl, pyrrolinyl, imidazolyl, pyrazolyl, 2-pyridyl, 3-pyridyl, 4-pyridyl, pyridinyl, pyrimidinyl, pyrazinyl, pyridazinyl, triazolyl, or tetrazolyl, more particularly pyridinyl, R3, R4, R5 and R6 are hydrogen and R7 is absent, which comprises reacting a pyridazine substituted at the C3 position with halo, at the C4 position with an unsaturated 5 to 6 membered heteromonocyclyl group containing 1 to 4 nitrogen atoms, in particular, pyrrolyl, pyrrolinyl, imidazolyl, pyrazolyl, 2-pyridyl, 3-pyridyl, 4-pyridyl, pyridinyl, pyrimidinyl, pyrazinyl, pyridazinyl, triazolyl, or tetrazolyl, more particularly pyridinyl, with piperazinyl or piperazinyl substituted with alkyl, aryl, or cycloalkyl under suitable conditions to prepare a compound of the formula I wherein R1 is piperazinyl or piperazinyl substituted with alkyl, aryl, or cycloalkyl, R2 is an unsaturated 5 to 6 membered heteromonocyclyl group containing 1 to 4 nitrogen atoms, in particular, pyrrolyl, pyrrolinyl, imidazolyl, pyrazolyl, 2-pyridyl, 3-pyridyl, 4-pyridyl, pyridinyl, pyrimidinyl, pyrazinyl, pyridazinyl, triazolyl, or tetrazolyl, more particularly pyridinyl, R3, R4, R5 and R6 are hydrogen and R7 is absent.

In another aspect, the invention provides a process for preparing a compound of the formula I wherein R1 is substituted amino in particular amino substituted with substituted morpholinyl, in particular morpholinoethyl, R2 is aryl or an unsaturated 5 to 6 membered heteromonocyclyl group containing 1 to 4 nitrogen atoms, in particular, pyrrolyl, pyrrolinyl, imidazolyl, pyrazolyl, 2-pyridyl, 3-pyridyl, 4-pyridyl, pyridinyl, pyrimidinyl, pyrazinyl, pyridazinyl, triazolyl, or tetrazolyl, in particular pyridinyl, R3, R4, R5 and R6 are hydrogen and R7 is absent, which comprises reacting a pyridazine substituted at the C3 position with halo, at the C4 position with aryl or an unsaturated 5 to 6 membered heteromonocyclyl group containing 1 to 4 nitrogen atoms, in particular, pyrrolyl, pyrrolinyl, imidazolyl, pyrazolyl, 2-pyridyl, 3-pyridyl, 4-pyridyl, pyridinyl, pyrimidinyl, pyrazinyl, pyridazinyl, triazolyl, or tetrazolyl, more particularly pyridinyl, with substituted amino in particular amino substituted with substituted morpholinyl, in particular morpholinoethyl, under suitable conditions to prepare a compound of the formula I wherein R1 is substituted amino in particular amino substituted with substituted morpholinyl, R2 is aryl, R3, R4, R5 and R6 are hydrogen and R7 is absent.

In another aspect, the invention provides a process for preparing a compound of the formula V wherein R50 is aryl, R51 is hydrogen, and R52 is alkyl comprising reacting a pyridazine substituted at position C3 with halo, at position C4 with aryl and position 6 with alkyl with 1-(2-pyrimidyl) piperazine under suitable conditions to prepare a compound of the formula V wherein R50 is aryl, R51 is hydrogen, and R52 is alkyl.

In another aspect, the invention provides a process for preparing a compound of the formula I wherein R1 is substituted amino, R2 is an unsaturated 5 to 6 membered heteromonocyclyl group containing 1 to 4 nitrogen atoms, in particular, pyrrolyl, pyrrolinyl, imidazolyl, pyrazolyl, 2-pyridyl, 3-pyridyl, 4-pyridyl, pyridinyl, pyrimidinyl, pyrazinyl, pyridazinyl, triazolyl, or tetrazolyl, in particular pyridinyl, R3, R4, R5 and R6 are hydrogen and R7 is absent comprising reacting a pyridazine substituted at the C3 position with halo, at the C4 position with an unsaturated 5 to 6 membered heteromonocyclyl group containing 1 to 4 nitrogen atoms, in particular, pyrrolyl, pyrrolinyl, imidazolyl, pyrazolyl, 2-pyridyl, 3-pyridyl, 4-pyridyl, pyridinyl, pyrimidinyl, pyrazinyl, pyridazinyl, triazolyl, or tetrazolyl, in particular pyridinyl, and at the C6 position phenyl, and a substituted amino under suitable conditions to prepare a compound of the formula I wherein R1 is substituted amino, R2 is an unsaturated 5 to 6 membered heteromonocyclyl group containing 1 to 4 nitrogen atoms, in particular, pyrrolyl, pyrrolinyl, imidazolyl, pyrazolyl, 2-pyridyl, 3-pyridyl, 4-pyridyl, pyridinyl, pyrimidinyl, pyrazinyl, pyridazinyl, triazolyl, or tetrazolyl, in particular pyridinyl, R3, R4, R5 and R6 are hydrogen and R7 is absent.

In the preparation of compounds of the Formula II, a key precursor (See, e.g., FIG. 1) that may be utilized was obtained commercially and used directly for the synthesis of the illustrated compound MW01-3-183WH without further purification. Compounds may be synthesized with yields of 81-96%. All purified compounds may be characterized by HPLC, mass spectrometry and NMR in order to confirm syntheses. In FIG. 1, a synthetic scheme is shown, for synthesis of MWO1-3-183WH with unconstrained aromatic ring at position 6 and no modification at position 5. Reagent and condition; (a) 1-BuOH, $NH_4Cl$, 2-(piperazin-1-yl)pyrimidine.

Thus, in an aspect, the invention provides a method for preparing a compound of the Formula II wherein a substituted 6-phenylpyridazine is reacted with 2-(piperazin-1yl) pyridmidine to produce a compound of the Formula II wherein $R^{10}$ and $R^{11}$ are hydrogen. A compound of the formula II wherein R10 and R11 are hydrogen can be reacted under suitable conditions and with suitable reagents to introduce the radicals $R^{10}$ and $R^{11}$ which are independently hydrogen, hydroxyl, alkyl, alkenyl, alkynyl, alkylene, alkenylene, alkoxy, alkenyloxy, cycloalkyl, cycloalkenyl, aryl, aryloxy, arylalkoxy, aroyl, heteroaryl, heterocyclic, acyl, acyloxy, sulfonyl, sulfinyl, sulfenyl, amino, imino, azido, thiol, thioalkyl, thioalkoxy, thioaryl, nitro, ureido, cyano, halo, silyl, silyloxy, silylalkyl, silylthio, =O, =S, carboxyl, carbonyl, carbamoyl, or carboxamide Therapeutic efficacy and toxicity of compounds, compositions and methods of the invention may be determined by standard pharmaceutical procedures in cell cultures or with experimental animals such as by calculating a statistical parameter such as the $ED_{50}$ (the dose that is therapeutically effective in 50% of the population) or $LD_{50}$ (the dose lethal to 50% of the population) statistics. The therapeutic index is the dose ratio of therapeutic to toxic effects and it can be expressed as the $ED_{50}/LD_{50}$ ratio. Pharmaceutical compositions which exhibit large therapeutic indices are preferred. By way of example, one or more of the therapeutic effects, in particular beneficial effects disclosed, herein, can be demonstrated in a subject or disease model, for example, a TgCRND8 mouse with symptoms of Alzheimer's disease.

Biological investigations were done with compounds disclosed herein that were >95% homogenous as determined by HPLC/MS analysis. As part of a hierarchal, cell-based screening protocol, the compounds were screened for their ability to block IL-1β and TNFα production by BV-2 mouse microglial cells stimulated with LPS. The data for MW01-3-183WH is shown, in FIG. 2. Derivative groups that may be used to modify the compounds of the present invention can be found in U.S. Patent Application No. 20030176437 (herein incorporated by reference in its entirety for all purposes).

The compounds disclosed herein can be tested for liver toxicity which is an important initial consideration for orally administered compounds since the liver is the major site of initial drug metabolism and is critical to overall metabolism and homeostasis of an animal. An example of an in vivo liver toxicity test in animals is illustrated in Example 2. Compounds disclosed herein may also be tested for cardiac safety by testing for hERG channel inhibition, for example using the method illustrated in Example 3.

Compositions and Kits

A compound of the Formula I, II, III, IV, or V of the invention may be formulated into a pharmaceutical composition for administration to a subject. Pharmaceutical compositions of the present invention or fractions thereof comprise suitable pharmaceutically acceptable carriers, excipients, and vehicles selected based on the intended form of administration, and consistent with conventional pharmaceutical practices. Suitable pharmaceutical carriers, excipients, and vehicles are described in the standard text, Remington's Pharmaceutical Sciences, Mack Publishing Company (Remington's Pharmaceutical Sciences, Mack Publishing Company, Easton, Pa., USA 1985). By way of example for oral administration in the form of a capsule or tablet, the active components can be combined with an oral, non-toxic pharmaceutically acceptable inert carrier such as lactose, starch, sucrose, methyl cellulose, magnesium stearate, glucose, calcium sulfate, dicalcium phosphate, mannitol, sorbital, and the like. For oral administration in a liquid form, the drug components may be combined with any oral, non-toxic, pharmaceutically acceptable inert carrier such as ethanol, glycerol, water, and the like. Suitable binders (e.g. gelatin, starch, corn sweeteners, natural sugars including glucose; natural and synthetic gums, and waxes), lubricants (e.g. sodium oleate, sodium stearate, magnesium, stearate, sodium benzoate, sodium acetate, and sodium chloride), disintegrating agents (e.g. starch, methyl cellulose, agar, bentonite, and xanthan gum), flavoring agents, and coloring agents may also be combined in the compositions or components thereof. Compositions as described herein can further comprise wetting or emulsifying agents, or pH buffering agents.

A composition of the invention can be a liquid solution, suspension, emulsion, tablet, pill, capsule, sustained release formulation, or powder. The compositions can be formulated as a suppository, with traditional binders and carriers such as triglycerides. Oral formulations can include standard carriers such as pharmaceutical grades of mannitol, lactose, starch, magnesium stearate, sodium saccharine, cellulose, magnesium carbonate, etc. Various delivery systems are known and can be used to administer a composition of the invention, e.g. encapsulation in liposomes, microparticles, microcapsules, and the like.

Formulations for parenteral administration may include aqueous solutions, syrups, aqueous or oil suspensions and emulsions with edible oil such as cottonseed oil, coconut oil or peanut oil. Dispersing or suspending agents dial can be used for aqueous suspensions include synthetic or natural gums, such as tragacanth, alginate, acacia, dextran, sodium carboxymethylcellulose, gelatin, methylcellulose, and polyvinylpyrrolidone.

Compositions for parenteral administration may include sterile aqueous or non-aqueous solvents, such as water, isotonic saline, isotonic glucose solution, buffer solution, or other solvents conveniently used for parenteral administration of therapeutically active agents. A composition intended for parenteral administration may also include conventional additives such as stabilizers, buffers, or preservatives, e.g. antioxidants such as methylhydroxybenzoate or similar additives.

Compositions of the invention can be formulated as pharmaceutically acceptable salts as described herein.

A composition of the invention may be sterilized by, for example, filtration through a bacteria retaining filter, addition of sterilizing agents to the composition, irradiation of the composition, or heating the composition. Alternatively, the compounds or compositions of the present invention may be provided as sterile solid preparations e.g. lyophilized powder, which are readily dissolved in sterile solvent immediately prior to use.

After pharmaceutical compositions have been prepared, they can be placed in an appropriate container and labeled for treatment of an indicated condition. For administration of a composition of the invention, such labeling would include amount, frequency, and method of administration.

The invention also provides a pharmaceutical pack or kit comprising one or more containers filled with one or more of the ingredients of a pharmaceutical composition of the invention to provide a beneficial effect, in particular a sustained beneficial effect. Associated with such container(s) can be various written materials such as instructions for use, or a notice in the form prescribed by a governmental agency regulating the labeling, manufacture, use or sale of pharmaceuticals or biological products, which notice reflects approval by the agency of manufacture, use, or sale for human administration.

The invention also provides a kit comprising a compound or a pharmaceutical composition of the invention. The kit can be a package which houses a container which contains a composition of the invention and also houses instructions for administering the composition to a subject.

Applications

The invention contemplates the use of compounds of the Formula I, II, III, IV, or V and compositions comprising the same for treating a disease disclosed herein, in particular preventing, and/or ameliorating disease severity, disease symptoms, and/or periodicity of recurrence of a disease disclosed herein. The invention also contemplates treating in mammals, diseases using the compounds, compositions or treatments of the invention. The present invention in embodiments may provide a composition comprising a compound that provides beneficial effects including greater solubility, stability, efficacy, potency, and/or utility, in particular greater solubility and stability.

Novel compounds and methods for new therapeutic interventions are needed for many areas of medicine and disease treatment. For example, chronic and acute inflammatory conditions form the basis for diseases affecting all organ systems including, but not limited to, asthma, acute inflammatory diseases, vascular inflammatory disease, chronic inflammation, atherosclerosis, angiopathy, myocarditis, nephritis, Crohn's disease, arthritis, type I and II diabetes and associated vascular pathologies. The incidence of these inflammatory conditions is on the rise and the expense is large. For example, for just one form of inflammatory disease, Alzheimer's disease, the direct costs (such as medications, doctors' fees, and nursing home care) and indirect costs (loss of productivity of those suffering Alzheimer's disease and loss of productivity of those caring for these individuals) are estimated to exceed one-hundred billion dollars per year.

With reference to the following examples and related discussions, the present invention provides various methods relating to the modulation of inflammation, glial activation or phosphorylation pathways and/or new therapeutic routes relating thereto. As illustrated more fully elsewhere herein, such methods include but are not limited to use of the compounds and compositions of this invention, preferably in a dose dependent fashion, to selectively inhibit protein kinase activity, glial activation response, oxidative stress-related responses such as nitric oxide synthase production and nitric oxide accumulation, cellular apoptosis and/or death associated protein kinase activity, and/or proinflammatory cytokine responses such as interleukin or tumor necrosis factor production. Such methods can include the preparation and/or formulation of a composition with subsequent administration and/or delivery to activated glial cells, tissue, culture or a related physiological system or medium, such administration/delivery in a dose or at a compositional concentration sufficient to effect the desired regulation and/or inhibition, without substantially inhibiting other desired endogenous anti-inflammatory responses.

In an aspect, the present invention relates to the inhibition of neuronal cell death. Selective neuronal cell death is a characteristic feature of the pathology of a number of neurodegenerative diseases, including Alzheimer's disease (AD), and traumatic brain injury, and stroke. Selected compounds and compositions of the present invention may be used to reduce or inhibit Aβ-induced neuronal cell death and in particular to reduce or inhibit calmodulin regulated protein kineses, such as death associated protein kinase (DAPK).

In some embodiments, the present invention provides methods of inhibiting cell signaling molecule production (e.g., IL-1β and TNFα), comprising administering compositions comprising one or more of the compounds of the Formula I, II, III, IV, or V, in particular one or more compounds depicted in the Figures and Tables herein, in particular the compounds depicted in Tables 2, 3, 4, or 5, or derivatives of these compounds.

The present invention also provides compounds (e.g., compounds listed in the Figures and Tables for use in 1) lowering amounts of proinflammatory cytokines (e.g., TNFa or IL-1p) and/or 2) maintaining normal levels of postsynaptic proteins (e.g., PSD-95). In some embodiments, the reduction of pro-inflammatory cytokines reduces cytokines to levels found in a normal, healthy individual. In some embodiments, the compounds are provided to an individual displaying characteristics of an inflammatory disease (e.g., Alzheimer's disease), such that treatment with the compounds reduces aberrantly high pro-inflammatory cytokine production caused by the disease (e.g., Aβ-induced increase in pro-inflammatory cytokines).

In another aspect, selected compounds and compositions of the invention may be used to modulate cytokine-mediated neuronal cell death, in particular modulate cytokine-induced generation of NO, TNFα signaling through the Fas/TNFR family of death receptors, and/or DAPK, in Alzheimer's disease and other neurodegenerative disorders, and brain injury, and stroke. The evidence for the involvement of pro-inflammatory cytokines and NO in neuronal cell death has been reviewed in Akiyama, H., et al, (2000) Neurobiol. Agir g 21, 383-421; Prusiner, S. B. (2001) New Engl. J. Med. 344, 15 16-1526), cytokine-induced neuronal death could involve DAPK.

In part, the present invention also relates to the inhibition of cell death or tissue loss and cell activation in addition to brain glia and neurons. For example, cell activation and tissue damage is a characteristic of other diseases such as acute lung injury (ALI). ALI due to sepsis, trauma or mechanical ventilation is associated with high mortality and morbidity, yet there are few effective therapies for the treatment of ALL ALI is common during sepsis, which itself has an annual mortality equal to acute myocardial infarction. Endothelial cell (EC) dysfunction and activation has been implicated in the in vivo responses linked to ALI, and EC protein kineses, such as myosin light chain kinase (MLCK), have been shown to be critical to EC barrier function and activation. Similarly, the response of the heart to stress and acute injury results in acute and chronic injuries in which protein phosphorylation regulated pathways and cell activation has been linked to cell death and tissue damage. MLCK and related enzymes such as Rho kinase have been implicated in these processes and may be targets for new therapeutics. Accordingly, compounds of the Formula I, II, III, IV, or V can be used to reduce injury from hypoxia-ischemia, acute lung injury and/or endothelial cell dysfunction in lung or vascular tissue.

In another aspect of the invention, a method is provided for treating in a subject a disease involving or characterized by inflammation, in particular neuroinflammation, comprising administering to the subject a therapeutically effective amount of a compound of the Formula I, II, III, IV, or V, or a pharmaceutically acceptable salt thereof. In a further aspect, a method is provided for treating in a subject a condition involving inflammation, in particular neuroflammation, comprising administering to the subject a therapeutically effective amount of a composition comprising a compound of the Formula I, II, III, IV, or V and a pharmaceutically acceptable carrier, excipient, or vehicle.

In a further aspect, the invention provides a method involving administering to a subject a therapeutic compound of the Formula I, II, III, IV, or V, or a pharmaceutically acceptable salt thereof, or a composition comprising a compound of the Formula I, II, III, IV, or V, and a pharmaceutically acceptable carrier, excipient, or vehicle which inhibit or reduce neuroflammation, activation of glia, proimflammatory cytokines, oxidative stress-related enzymes, acute phase proteins and/or components of the complement cascade.

In another aspect, the invention provides a method for treating in a subject a disease associated with neuroinflammation that can be decreased or inhibited with a compound disclosed herein comprising administering to the subject a therapeutically effective amount of a compound of the Formula I, II, III, IV, or V, a pharmaceutically acceptable salt thereof, or a composition comprising a compound of the Formula I, II, III, IV, or V and a pharmaceutically acceptable carrier, excipient, or vehicle.

In another aspect, the invention provides a method for preventing or inhibiting activation of protein kinases, in particular DAPK, in a subject comprising administering a therapeutically effective amount of a compound of the Formula I, II, III, IV, or V a pharmaceutically acceptable salt thereof, or a composition comprising a compound of the Formula I, II, III, IV, or V and a pharmaceutically acceptable carrier, excipient, or vehicle.

In a further aspect, the invention provides a method for reducing or inhibiting kinase activity, glial activation, neuronal cell damage, and/or neuronal cell death in a subject comprising administering to the subject a therapeutically effective amount of a compound of the Formula I, II, III, IV, or V a pharmaceutically acceptable salt thereof, or a composition comprising a compound of the Formula I, II, III, IV, or V and a pharmaceutically acceptable carrier, excipient, or vehicle.

In some embodiments, the invention provides methods of inhibiting cell signaling molecule production (e.g., IL-1β and TNFα), comprising administering compositions comprising one or more compounds of the Formula I, II, III, IV, or V, in particular the compounds depicted in the Figures and Tables, more particularly Table 2, 3, 4 or 5, or derivatives of these compounds. In some embodiments, one or more of the compounds, in particular the compounds depicted in the Figures and Tables, more particularly Table 2, 3, 4 or 5 or derivatives of these compounds, are co-administered with other recognized therapeutics to treat inflammatory disease (e.g., neuroinflammatory disease, in particular Alzheimer's disease). In some embodiments, the invention provides compounds (e.g., compounds listed in the Figures and Tables) for use in 1) lowering amounts of pro-inflammatory cytokines (e.g., TNFα or IL-1β) and/or 2) maintaining normal levels of postsynaptic proteins (e.g., PSD-95) for research, drug screening, or therapeutic purposes. In some embodiments, the reduction of pro-inflammatory cytokines reduces cytokines to levels found in a normal, healthy individual. In some embodiments, the compounds are provided to an individual displaying characteristics of an inflammatory disease (e.g., neuroinflammatory disease, in particular Alzheimer's disease), such that treatment with the compounds reduces aberrantly high pro-inflammatory cytokine production caused by the disease (e.g., Aβ-induced increase in pro-inflammatory cytokines).

In an aspect, the invention provides a method for ameliorating progression of a disease or obtaining a less severe stage of a disease in a subject suffering from such disease (e.g., neuroinflammatory disease, in particular a neurodegenerative disease, more particularly Alzheimer's disease) comprising administering a therapeutically effective amount of a compound of the Formula I, II, III, IV, or V, a pharmaceutically acceptable salt thereof, or a composition comprising a compound of the Formula I, II, III, IV, or V and a pharmaceutically acceptable carrier, excipient, or vehicle.

The invention relates to a method of delaying the progression of a disease (e.g. neuroinflammatory disease, in particular a neurodegenerative disease, more particularly Alzheimer's disease) comprising administering a therapeutically effective amount of a compound of the Formula I, II, III, IV, or V, a pharmaceutically acceptable salt thereof, or a composition comprising a compound of the Formula I, II, III, IV, or V and a pharmaceutically acceptable carrier, excipient, or vehicle.

The invention also relates to a method of increasing survival of a subject suffering from a disease (e.g. neuroinflammatory disease, in particular a neurodegenerative disease, more particularly Alzheimer's disease) comprising administering a therapeutically effective amount of a compound of the Formula I, II, III, IV, or V, a pharmaceutically acceptable salt thereof, or a composition comprising a compound of the Formula I, II, III, IV, or V and a pharmaceutically acceptable carrier, excipient, or vehicle.

The invention has particular applications in treating or preventing a neurodegenerative disease, in particular Alzheimer's disease. In an aspect of the invention a compound of the Formula I, II, III, IV, or V is utilized in the treatment of Alzheimer's disease. Alzheimer's disease may be treated by administering a therapeutically effective amount of a compound of the Formula I, II, III, IV, or V. Such treatment may be effective for retarding the degenerative effects of Alzheimer's disease, including specifically, but not exclusively, neuroinflammation, deterioration of the central nervous system, loss of mental facilities, loss of short term memory, and disorientation.

In another aspect, the invention provides a method for treating Alzheimer's disease by providing a composition comprising a compound of the invention in an amount sufficient to reverse or inhibit neuroinflammation, activation of signaling pathways involved in inflammation (e.g., neuroinflammation), cell signaling molecule production, activation of glia or glial activation pathways and responses, proinflammatory cytokines or chemokines (e.g., interleukin (IL) or tumor necrosis factor (TNF), oxidative stress-related responses such as nitric oxide synthase production and nitric oxide accumulation, acute phase proteins, components of the complement cascade, protein kinase activity (e.g., death associated protein kinase activity), neuronal cell damage, and/or neuronal cell death for a prolonged period following administration.

In a further aspect, the invention provides a method for treating Alzheimer's disease in a patient in need thereof which includes administering to the individual a composition that provides a compound of the invention in a dose sufficient to reverse or inhibit neuroinflammation, activation of signaling pathways involved in inflammation (e.g., neuroinflammation), cell signaling molecule production, activation of glia or glial activation pathways and responses, proinflammatory cytokines or chemokines (e.g., interleukin (IL) or tumor necrosis factor (TNF), oxidative stress-related responses such as nitric oxide synthase production and nitric oxide accumulation, acute phase proteins, components of the complement cascade, protein kinase activity (e.g., death associated protein kinase activity), neuronal cell damage, and/or neuronal cell death for a prolonged period following administration.

The invention in an embodiment provides a method for treating Alzheimer's disease, the method comprising administering to a mammal in need thereof a composition comprising a compound of the invention in an amount sufficient to reduce cognitive decline for a prolonged period following administration, thereby treating the Alzheimer's disease.

In as aspect, the invention relates to a method of treatment comprising administering a therapeutically effective amount of one or more compound of the Formula I, II, III, IV, or V, a pharmaceutically acceptable salt thereof, or a composition comprising a compound of the Formula I, II, III, IV, or V and a pharmaceutically acceptable carrier, excipient, or vehicle, which upon administration to a subject with symptoms of a neurodegenerative disease, in particular Alzheimer's disease, produces one or more therapeutic effect, in particular a beneficial effect, more particularly a sustained beneficial effect. In an embodiment, a beneficial effect is evidenced by a decrease or inhibition of one or more of the following: inflammation (e.g. neuroinflammation), activation of signaling pathways involved in inflammation (e.g., neuroinflammation), cell signaling molecule production, activation of glia or glial activation pathways and responses, proinflammatory cytokines or chemokines (e.g., interleukin (IL) or tumor necrosis factor (TNF), oxidative stress-related responses such as nitric oxide synthase production and nitric oxide accumulation, acute phase proteins, components of the complement cascade, protein kinase activity (e.g., death associated protein kinase activity), cell damage (e.g., neuronal cell damage), and/or cell death (e.g., neuronal cell death).

In an embodiment, where the disease is Alzheimer's disease, beneficial effects of a compound or composition or treatment of the invention can manifest as one, two, three, four, five, six, seven, eight, or all of the following, in particular five or more, more particularly 7 or more of the following:

a) A reduction in protein kinase activity (e.g. DAPK), in particular at least about a 0.05%, 0.1%. 0.5%, 1%, 2%, 5%, 10%, 15%, 20%, 30%, 33%, 35%, 40%, 45%, 50%, 60%, 70%, 80%, 90%, 95%, or 99% decrease in protein kinase activity.
b) A reduction in glial activation response, in particular, at least about a 0.05%, 0.1%, 0.5%, 1%, 2%, 5%, 10%, 15%, 20%, 30%, 33%, 35%, 40%, 45%, 50%, 60%, 70%, 80%, 90%, 95%, or 99% reduction in glial activation.
c) A reduction in glial activity in the brain, relative to the levels determined in the absence of a compound of the Formula I, II, III, IV, or V in subjects with symptoms of Alzheimer's disease. In particular, the compounds induce at least about a 2%, 5%, 10%, 15%, 20%, 30%, 40%, 50%, 60%, 70%, 80%, or 90% decrease in glial activity
d) A reduction in oxidative stress-related responses (e.g., nitric oxide synthase production and/or nitric oxide accumulation), in particular at least about a 0.05%, 0.1%, 0.5%, 1%, 2%, 5%, 10%, 15%, 20%, 30%, 33%, 35%, 40%, 45%, 50%, 60%, 70%, 80%, 90%, 95%, or 99% reduction in oxidative stress-related responses such as nitric oxide synthase production and nitric oxide accumulation.
e) A reduction in cellular apoptosis and/or death associated protein kinase activity, in particular a 0.05%, 0.1%, 0.5%, 1%, 2%, 5%, 10%, 15%, 20%, 30%, 33%, 35%, 40%, 45%, 50%, 60%, 70%, 80%, 90%, 95%, or 99% reduction in cellular apoptosis and/or death associated protein kinase activity.
f) A reduction in proinflammatory cytokine responses in particular a 0.05%, 0.1%, 0.5%, 1%, 2%, 5%, 10%, 15%, 20%, 30%, 33%, 35%, 40%, 45%, 50%, 60%, 70%, 80%, 90%, 95%, or 99% reduction in proinflammatory cytokine responses.
g) A reduction in interleukin-1$\beta$ and/or tumor necrosis factor$\alpha$ production in particular a 0.05%, 0.1%, 0.5%, 1%, 2%, 5%, 10%, 15%, 20%, 30%, 33%, 35%, 40%, 45%, 50%, 60%, 70%, 80%, 90%, 95%, or 99% reduction in interleukin-1$\beta$ and/or tumor necrosis factor$\alpha$ production.
h) A slowing of the rate of disease progression in a subject with Alzheimer's disease.
i) Increase in survival in a subject with symptoms of Alzheimer's disease.

In particular aspects of the invention beneficial effects of compounds, compositions or treatments of the invention can manifest as (a) and (b); (a), (b) and (c); (a) through (d); (a) through (e); (a) through (f); (a) through (g); (a) through (h); or (a) through (i).

Compounds, pharmaceutical compositions and methods of the invention can be selected that have sustained beneficial effects. In an embodiment, a pharmaceutical composition with statistically significant sustained beneficial effects is provided comprising a therapeutically effective amount of a compound of the invention.

The invention provides a method for treating mild cognitive impairment (MCI) comprising administering a therapeutically effective amount of a compound of the formula I, II, III, IV, or V, a pharmaceutically acceptable salt thereof, or a composition comprising a compound of the Formula I, II, III, IV, or V and a pharmaceutically acceptable carrier, excipient, or vehicle.

In an embodiment, the invention provides a method of reversing or inhibiting neuroinflammation, activation of signaling pathways involved in inflammation (e.g., neuroinflammation), cell signaling molecule production, activation of glia or glial activation pathways and responses, proinflammatory cytokines or chemokines (e.g., interleukin (IL) or tumor necrosis factor (TNF), oxidative stress-related responses such as nitric oxide synthase production and nitric oxide accumulation, acute phase proteins, components of the complement cascade, protein kinase activity (e.g., death associated protein kinase activity), neuronal cell damage, and/or neuronal cell death, after the onset of cognitive deficits and Alzheimer's disease neuropathology in a subject comprising administering to the subject a therapeutically effective amount of a compound of the Formula I, II, III, IV, or V, a pharmaceutically acceptable salt thereof, or a composition comprising a compound of the Formula I, II, III, IV, or V and a pharmaceutically acceptable carrier, excipient, or vehicle.

The invention provides a method of preventing a disease disclosed herein in a subject with a genetic predisposition to such disease by administering an effective amount of a compound of the Formula I, II, III, IV, or V, or a pharmaceutically acceptable salt thereof, or a composition comprising a compound of the Formula I, II, III, IV, or V and a pharmaceutically acceptable carrier, excipient, or vehicle.

The invention provides a method of improving memory of a healthy subject or the memory of a subject with age impaired memory by administering an effective amount of a compound of the Formula I, II, III, IV, or V, or a pharmaceutically acceptable salt thereof, or a composition, comprising a compound of the Formula I, II, III, IV, or V and a pharmaceutically acceptable carrier, excipient, or vehicle.

The further provides a method for improving memory, especially short-term memory and other mental dysfunction associated with the aging process comprising administering an effective amount of a compound of the Formula I, II, III, IV, or V, or a pharmaceutically acceptable salt thereof or a composition comprising a compound of the Formula I, II, III, IV, or V and a pharmaceutically acceptable carrier, excipient, or vehicle.

In an embodiment, a method is provided for treating a mammal in need of improved memory, wherein the mammal has no diagnosed disease, disorder, infirmity or ailment known to impair or otherwise diminish memory, comprising the step of administering to the mammal an effective memory-improving amount of a compound of the Formula I, II, III, IV, or V, a pharmaceutically acceptable salt thereof, or a composition comprising a compound of the Formula I, II, III, IV, or V and a pharmaceutically acceptable carrier, excipient, or vehicle.

In an aspect, the invention relates to a method of improving the lifespan of a subject suffering from Alzheimer's disease comprising administering a therapeutically effective amount of a compound of the Formula I, II, III, IV, or V, a pharmaceutically acceptable salt thereof, or a composition comprising a compound, of the Formula I, II, III, IV, or V and a pharmaceutically acceptable carrier, excipient, or vehicle.

In some aspects, greater efficacy and potency of a treatment of the invention may improve the therapeutic ratio of treatment, reducing untoward side effects and toxicity. Selected methods of the invention may also improve longstanding disease even when treatment is begun long after the appearance of symptoms.

The compositions and methods described herein are indicated as therapeutic agents or methods either alone or in conjunction with other therapeutic agents or other forms of treatment. They may be combined or formulated with one or more therapies or agents used to treat a condition described herein. Compositions of the invention may be administered concurrently, separately, or sequentially with other therapeutic agents or therapies. Therefore, the compounds of the Formula I, II, III, IV, and/or V may be co-administered with one or more additional therapeutic agents including without limitation beta-secretase inhibitors, alpha-secretase inhibitors, and epsilon-secretase inhibitors, agents that are used for the treatment of complications resulting from or associated with a disease, or general medications that treat or prevent side effects.

The invention also contemplates the use of a composition comprising at least one compound of the invention for the preparation of a medicament in treating a disease disclosed herein. In an embodiment, the invention relates to the use of a therapeutically effective amount of at least one compound of the invention for preparation of a medicament for providing therapeutic effects, in particular beneficial effects, more particularly sustained beneficial effects, in treating a disorder or disease. In a still further embodiment the invention provides the use of a compound of the invention for the preparation of a medicament for prolonged or sustained treatment of a disease.

Administration

Compounds and compositions of the present invention can be administered by any means that produce contact of the active agent(s) with the agent's sites of action in the body of a subject or patient to produce a therapeutic effect, in particular a beneficial effect, in particular a sustained beneficial effect. The active ingredients can be administered simultaneously or sequentially and in any order at different points in time to provide the desired beneficial effects. A compound and composition of the invention can be formulated for sustained release, for delivery locally or systemically. It lies within the capability of a skilled physician or veterinarian to select a form and route of administration that optimizes the effects of the compositions and treatments of the present invention to provide therapeutic effects, in particular beneficial effects, more particularly sustained beneficial effects.

The compositions may be administered in oral dosage forms such as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular forms, all utilizing dosage forms well known to those of ordinary skill in the pharmaceutical arts. The compositions of the invention may be administered by intranasal route via topical use of suitable intranasal vehicles, or via a transdermal route, for example using conventional transdermal skin patches. A dosage protocol for administration using a transdermal delivery system may be continuous rather than intermittent throughout the dosage regimen. A sustained release formulation can also be used for the therapeutic agents.

An amount of a therapeutic of the invention which will be effective in the treatment of a particular disorder or disease to provide effects, in particular beneficial effects, more particularly sustained beneficial effects, will depend on the nature of the condition or disorder, and can be determined by standard clinical techniques. The precise dose to be employed in the formulation will also depend on the route of administration, and the seriousness of the disease, and should be decided according to the judgement of the practitioner and each patient's circumstances.

Thus, the dosage regimen of the invention will vary depending upon known factors such as the pharmacodynamic characteristics of the agents and their mode and route of administration; the species, age, sex, health, medical condition, and weight of the patient, the nature and extent of the symptoms, the kind of concurrent treatment, the frequency of treatment, the route of administration, the renal and hepatic function of the patient, and the desired effect.

Suitable dosage ranges for administration are particularly selected to provide therapeutic effects, in particular beneficial effects, more particularly sustained beneficial effects. A dosage range is generally effective for triggering the desired biological responses. The dosage ranges are generally about 0.5 mg to about 2 g per kg, about 1 mg to about 1 g per kg, about 1 mg to about 200 mg per kg, about 1 mg to about 100 mg per kg, about 1 mg to about 50 mg per kg, about 10 mg to about 100 mg per kg, or about 30 mg to 70 mg per kg of the weight of a subject.

A composition or treatment of the invention may comprise a unit dosage of at least one compound of the invention to provide beneficial effects. A "unit dosage" or "dosage unit" refers to a unitary i.e., a single dose which is capable of being administered to a patient, and which may be readily handled and packed, remaining as a physically and chemically stable unit dose comprising either the active agents as such or a mixture with one or more solid or liquid pharmaceutical excipients, carriers, or vehicles.

A subject may be treated with a compound of the Formula I, II, III, IV, or V or composition or formulation thereof on substantially any desired schedule. A composition of the invention may be administered one or more times per day, in particular 1 or 2 times per day, once per week, once a month or continuously. However, a subject may be treated less frequently, such as every other day or once a week, or more frequently. A compound, composition or formulation of the invention may be administered to a subject for about or at least about 1 week, 2 weeks to 4 weeks, 2 weeks to 6 weeks, 2 weeks to 8 weeks, 2 weeks to 10 weeks, 2 weeks to 12 weeks, 2 weeks to 14 weeks, 2 weeks to 16 weeks, 2 weeks to 6 months, 2 weeks to 12 months, 2 weeks to 18 months, or 2 weeks to 24 months, periodically or continuously.

The invention will be described in greater detail by way of specific examples. The following examples are offered for illustrative purposes, and are not intended to limit the invention in any manner.

EXAMPLES

Example 1

General Materials and Methods

Synthetic Chemistry. All reagents and solvents were used as purchased without further purification. Syntheses were done using variations of established methods and in-parallel synthetic schemes. Briefly, diversification of position 3 of the pyridazine ring was done by reaction of a common halogenated pyridazine precursor. For the compounds used in this report, a mixture of 0.01 mol of substituted chloropyridazine, 0.05 mol of substituted piperazine and 0.01 mol of ammonium hydrochloride in 30 mL of 1-BuOH was stirred at 130° C. for 48 h. The solvent was removed under reduced pressure. The residue was then extracted with ethyl acetate, washed with water and brine, and dried over anhydrous NaiSO-i. Removal of solvent was followed by recrystallization from 95% ethanol.

Animation of 3-chloro-6-phenylpyridazine by 2-(piperazin-1-yl)pyrimidine (FIG. 1 2) easily led to 2-(4-(6-phenylpyridazin-3-yl)piperazin-1-yl)pyrimidine (MW01-3-183WH): Light yellow crystals, yield. 96.4%; HPLC: 97.4% purity; HRMS calculated 318.1587. found 318.1579; 1HNMR (CDCl3): 5 8.356 (d, J=4.5, 2H), 8.011 (d, J=7.5, 11 2H), 7.692 (d, 3=9.5, 1H), 7.468 (t, 5 J=6.0, 2H), 7.417 (d, J=7.5, 1H), 7.047 (d, J=9.5, 1H), 6.546 (t, J=4.5, 1H), 4.013 (t, J=5.0, 4H), 3.826 (t, J=5.0, 4H).

Reactions were monitored by analytical HPLC (Rainin Instruments System Woburn, Mass.), done on a reverse phase column CIS (25 cm×4.6 mm, 5 um, Supelco, Bellefonte, Pa.) with two different UV wavelengths (X=260 nm and X=220 nm or 300 nm). Eluents were (A): 0.1% (v/v) TFA in water and (B) 80% (v/v) acetonitrile/water containing 0.08% TFA. A linear gradient from 100/0 to 0/100 A/B over 34 min at 1 mL/min was used. 1H-NMR spectra were obtained using Varian INOVA (500 MHz) spectrometer. High resolution mass spectra were obtained on a VG70-250SE mass spectrometer.

Cell Culture Assays.

BV-2 mouse microglial cells (5×103 cells/well in a 48-well plate) were cultured and treated for 16 hrs with the standard glial activating stimulus lipopolysaccharide (LPS, from *Salmonella typhimurium;* 100 ng/ml final concentration) in the presence or absence of aminopyridazine compounds, as described previously [4, 17]. EL-1/3 and TNFa levels in cell lysates were determined by electro-chemiluminescent detection in a Meso-Scale Discovery (MSD) kit, as per the manufacturer's instructions.

In vivo Assays.

Aβ-42 Infusions and treatment of C57Bl/6 mice with MW01-2-151WH were performed as previously described [5]. Briefly, oligomeric A/31-42 was infused ICV for 28 days with a micro-osmotic pump. At post-operative day 21 and continuing for 14 days thereafter, mice were injected intraperitoneally once daily with either a test compound (2.5 mg/kg per day) or solvent control (10% DMSO in saline). At post-operative day 60, mice were perfused and sacrificed, and hippocampal endpoints measured as previously described [5]. Endpoint assays included immunohistochemical detection of activated astrocytes and microglia by glial fibrillary acidic protein (GFAP) and F4/80 staining, measurement of the levels of the pro-inflammatory cytokines IL-1|S, TNFa, and S100B by ELISA, and determination of synaptic damage by analysis of the levels of postsynaptic density protein-95 (PSD-95).

Brain Uptake Assays.

MW01-2-151WH was administered to mice (25-30 g) by oral gavage using 2.5 mg/kg compound in 0.5% carboxymethylcellulose vehicle. At various times (0-60 min) after administration, mice were sacrificed, blood removed by cardiac puncture, and brains immediately harvested, weighed, quick-frozen in liquid nitrogen, and stored at −80° C. until assayed. Brain tissue was homogenized in 1.5 ml of 0.1 M perchloric acid. After centrifugation (12,000×g for 10 min), the supernatant was neutralized, with 1 M NaOH and then extracted three times with 2 ml of dichloromethane by centrifugation at 3,000×g for 5 min. The organic phases from the three successive extractions were pooled and then vaporated to dryness under reduced pressure. The dried sample was reconstituted in 100 ul of HPLC mobile phase (80% acetonitrile, 0.08% formic acid, 20% $H_2O$), and 20 μl of the reconstituted material was injected into the HPLC system. The HPLC system for detection of MWO1-2-151WH was a Luna 5 μmCIS, 250 mm×2 mm internal diameter column together with a guard column (Phenomenex, Torrance, Calif., USA), with HPLC solvent delivered at 0.2 ml/min (Dionex, model P680 pump) and absorbance monitored at 282 run (Dionex, model UVD 170U detector). Under these experimental conditions, the retention time of the test compound was 15.3 min. A standard curve of the test compound was prepared by adding increasing concentrations of the compound to brain, tissue from untreated mice, then extracting the brains and performing HPLC analysis as described above. The area under the curve increased linearly with the concentration of the compound over the range of concentrations investigated, with a correlation coefficient of 0.99. Under our experimental conditions, the compound was extracted reproducibly, with mean recoveries of 29+/−2%.

Graded dose, acute toxicity assays Vehicle (30% DMSO) or test compound (3.1, 12.5 or 50 mg/kg) in 0.5% carboxymethylcellulose was administered by oral gavage once dally for 3 days. On the 4th day, mice were anesthetized with pentobarbital, intubated and the lungs were inflated with an aircontaining syringe. The mice were perfused through the right ventricle and the lungs, liver and kidneys were then harvested and fixed in 4% paraformaldehyde for histology. Paraffin embedded hematoxylin & eosin stained sections of each organ were prepared by standard techniques. A pathologist blinded to the treatment groups performed microscopic assessment of the tissue for injury.

Results

Figure 2:
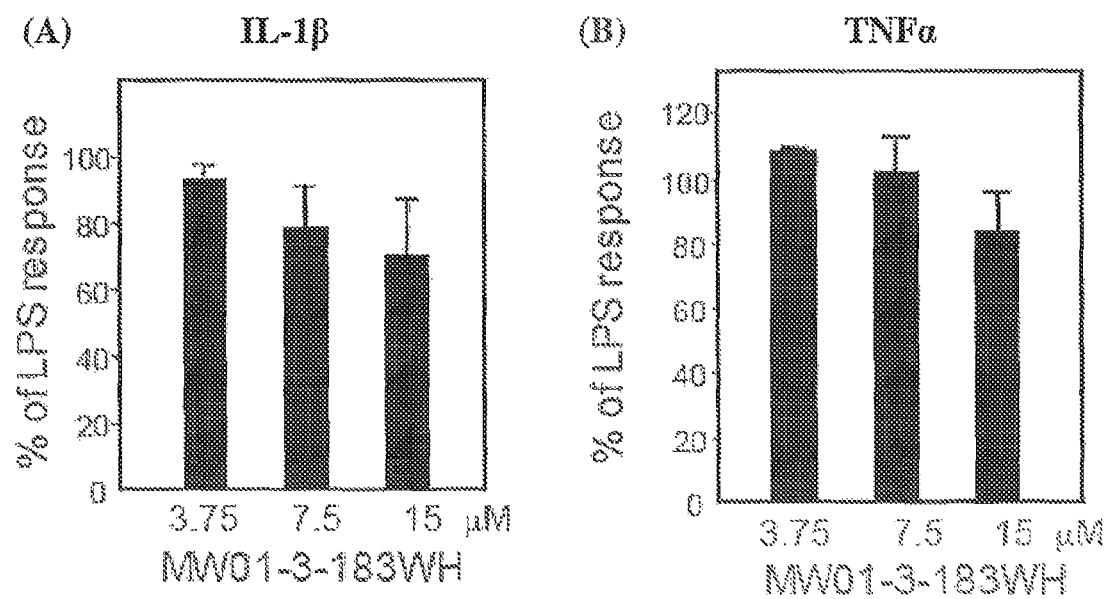
FIG. 2, parts (A) and (B), are graphs showing concentration dependent inhibition of proinflammatory cytokine production by MWO1-3-183WH in BV-2 cells FIG. 3, parts (A) thru (H), show graphs and micrographs of activity of MW01-5-188WH. (A) is a graph of IL-1β and (B) TNFα levels by the BV2 microglial cell line, (C) Accumulation of the NO metabolite, nitrite, was not inhibited; Western blots of iNOS, COX-2 or apoE production in activated glia in (D); iNOS, (E) COX-2 and (F) apoE from glia cultures. Micrographs of treatment with diluent and compound are shown in (G) and (H).

MW01-3-183WH suppressed both IL-1β and TNFα production in a concentration dependent manner (FIG. 2). As shown in FIG. 2 (parts A and B), concentration dependent inhibition of proinflammatory cytokine production by MW01-3-183WH in BV-2 cells were treated with LPS (100 ng/ml) in the absence or presence of increasing concentrations of MW01-3-183 WH for 16 hrs with levels of IL-1β and TNFα in cell lysates measured by the Meso-Scale Discovery electrochemiluminescent detection assay (See, Example 1., Materials and Methods). Data are the mean+/− SEM of triplicate determinations.

Figure 3:
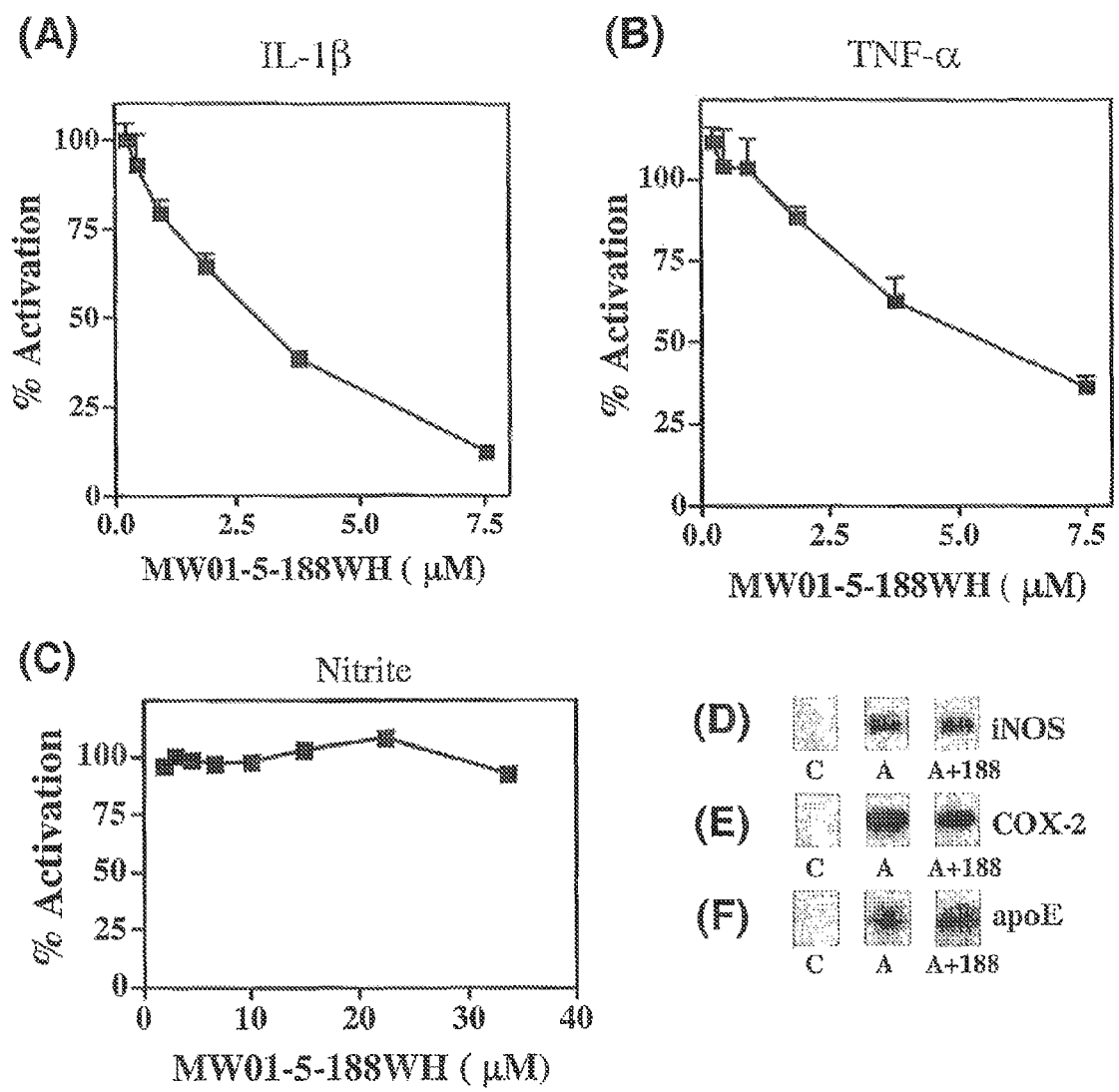
Figure 3:
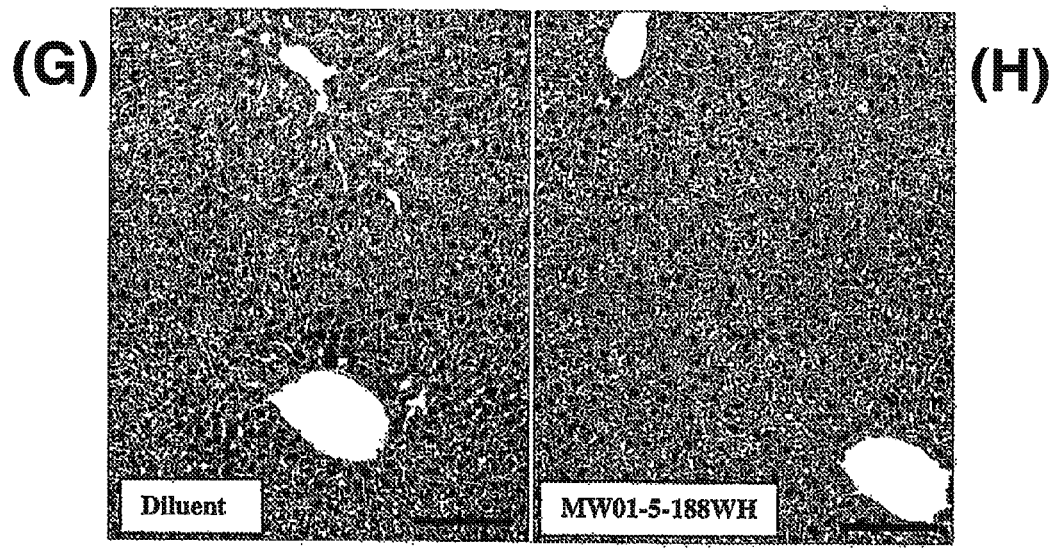
Figure 4:
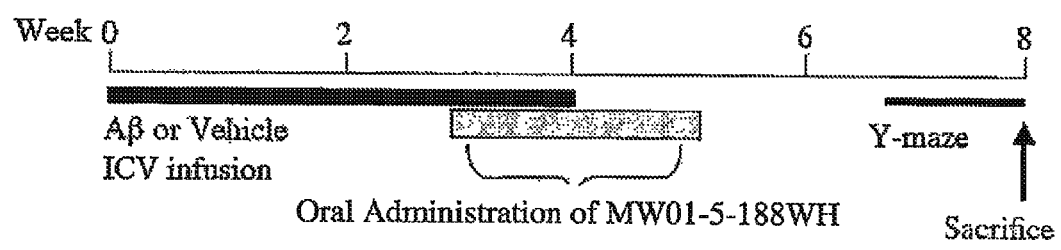
FIG. 4, parts (A) thru (H), shows graphs and micrographs of activity of MW01-5-188WH after oral administration.
Figure 4:
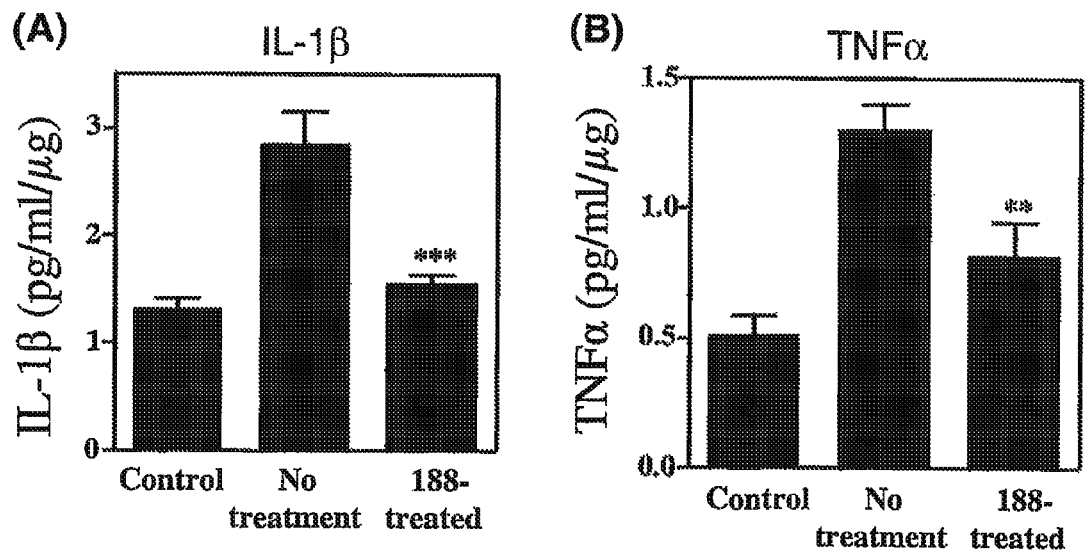
Figure 4:
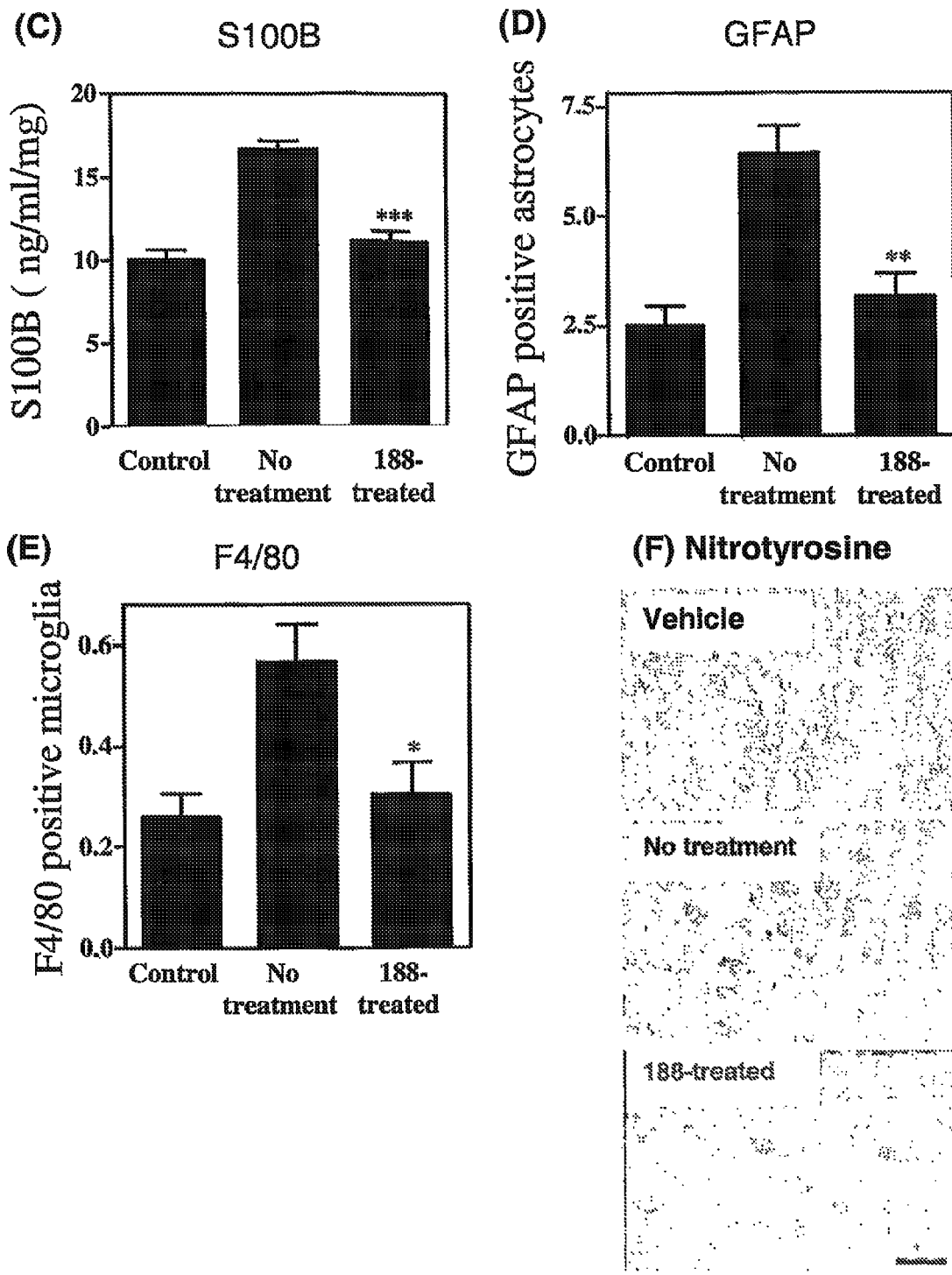
Figure 4:
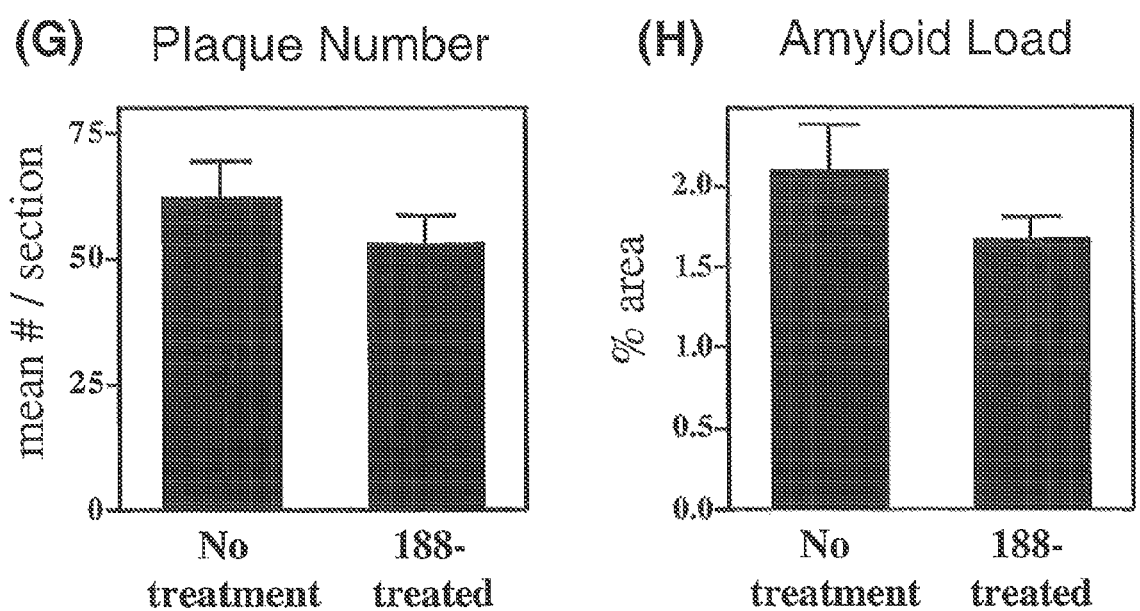
Figure 5:
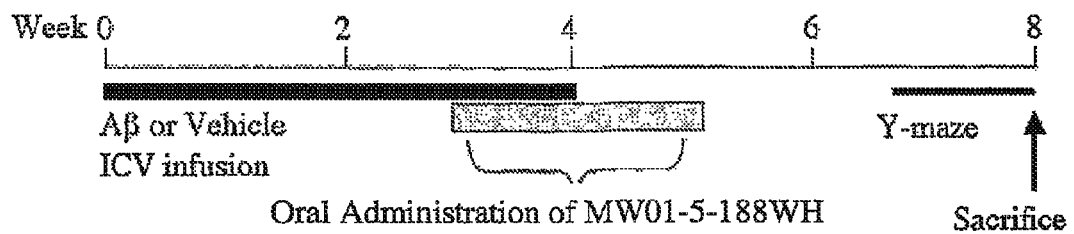
FIG. 5, parts (A) thru (C), shows graphs of results of oral administration of MW01-5-188WH.
Figure 5:
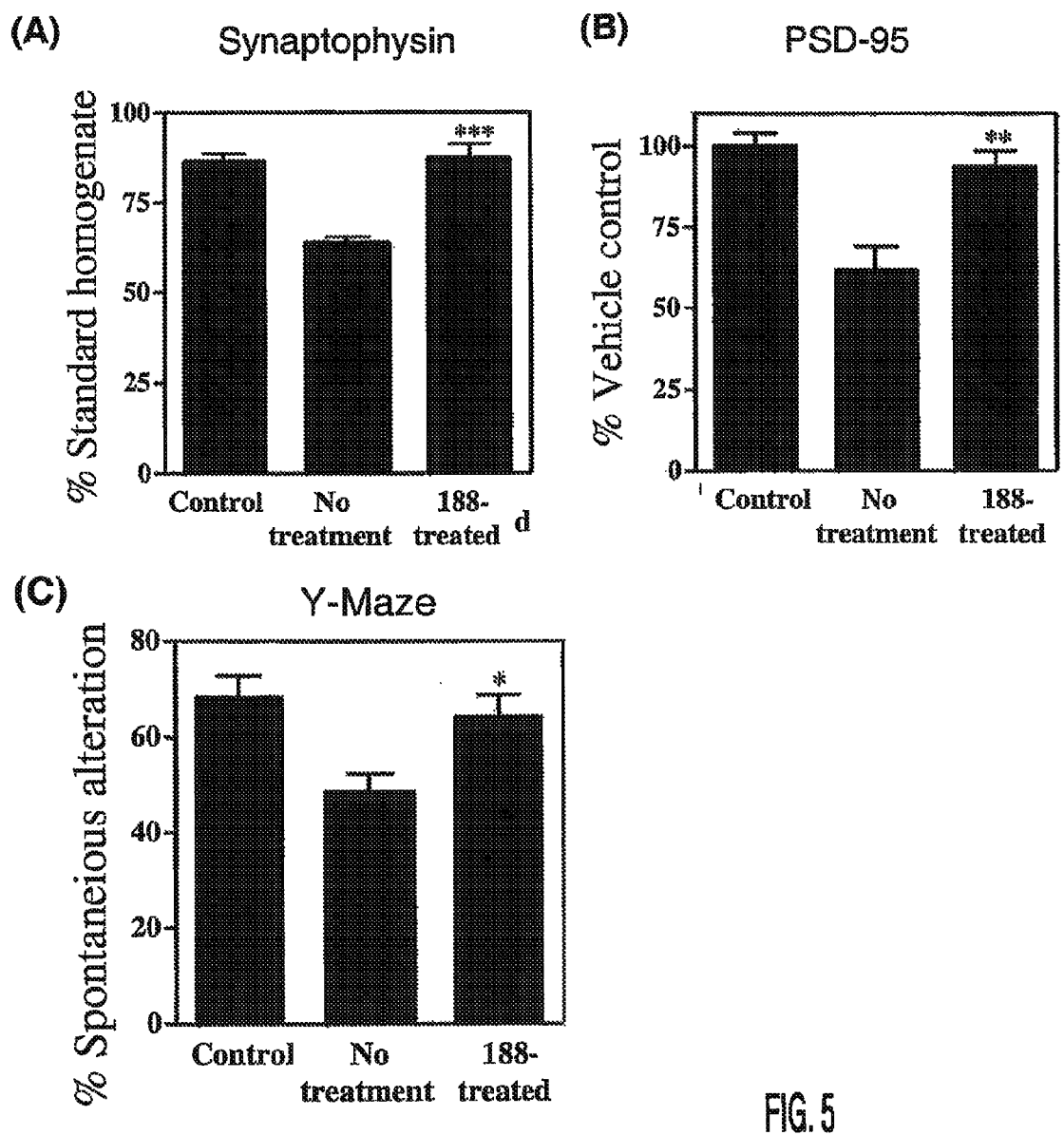

FIG. 3 illustrates that MW01-5-188WH is a concentration-dependent and selective inhibitor of proinflammatory cytokine production by activated glia and does not cause liver injury after chronic oral administration. As shown in FIG. 3, concentration-dependent inhibition by MW01-5-188WH of LPS-induced increases in (A) IL-1β and (B) TNFα levels by the BV2 microglial cell line. (C) Accumulation of the NO metabolite, nitrite, was not inhibited at concentrations up to 33 μM. MW01-5-188WH (188) does not suppress iNOS, COX-2 or apoE production in activated glia, as evidenced by the representative western blots for (D) iNOS, (E) COX-2 and (F) apoE from glia cultures. Cultures were treated with control buffer, C, or activated in the absence, A, or presence, A+188, of 7.5 μMW01-5-188WH. Daily oral administration of MW-01-5-188WH does not bring about liver injury (G). Mice were administered either diluent or MW01-5-188 WH (2.5 mg/kg/day) for 2 weeks, then liver sections were stained with haematoxylin and eosin. Bar=125 μm. FIG. 4 illustrates that oral administration of MW01-5-188WH suppresses human Aβ-induced neuroinflammation in mouse hippocampus in the absence of a detectable effect on the number of nitrotyrosine-labeled neurons, or on amyloid plaque deposition. Oral administration of MW01-5-188WH suppresses human Aβ-induced neuroinflammation in mouse hippocampus in the absence of a detectable effect on the number of nitrotyrosine-labeled neurons, or on amyloid plaque deposition. A schematic of the experimental paradigm is shown. Daily oral administration (2.5 mg/kg) of MW01-5-188WH (188-treated) for 2 weeks results in significant suppression of the human Aβ induced increase in (A) IL-1β, (B) TNFα and (C) S100B levels in hippocampal extracts (n=10 mice/group). MW01-5-188WH treatment also decreased the number of (D) GFAP-positive activated astrocytes and (E) F4/80 positive microglia in the hippocampus. (F) MW01-5-188WH treatment (188 treated) does not alter the profile of nitrotyrosine stained neurons, an indicator of oxidative stress linked injury. Representative micrographs are shown for hippocampus sections stained for nitrotyrosine-positive neurons, from vehicle-infused mice, Aβ-infused mice (no treatment), and Aβ-infused mice orally administered MW01-5-188WH (188-treated). Bars=25 μm. The number (G) of amyloid plaques or the area occupied by amyloid plaques (H) is not altered by MW01-5-188WH therapy. Quantification of amyloid burden from all mice (n=5/group) was done by determination of the amyloid load. Data are mean±SEM. Significantly different from Aβ-infused: *$p<0.05$, **$p<0.01$. FIG. 5 illustrates that oral administration of MW01-5-188WH attenuates hippocampal synaptic dysfunction and hippocampus-linked behavioral deficits. MW01-5-188WH administration significantly attenuated the loss of synaptophysin and PSD-95, and the behavioral deficit in the Ymaze. Oral administration of MW01-5-188WH attenuates hippocampal synaptic dysfunction and hippocampus-linked behavioral deficits. A schematic of the experimental paradigm is shown in FIG. 5. MW01-5-188WH administration significantly attenuated the loss of synaptophysin and PSD-95, and the behavioral deficit in the Ymaze. Levels of (A) the pre-synaptic protein synaptophysin and (B) the post-synaptic protein PSD-95 were measured in hippocampal extracts from vehicle-infused mice (control), Aβ-infused mice (no treatment), and Aβ-infused mice administered MW01-5-188WH (188-treated) at 2.5 mg/kg by oral gavage once daily for 2 weeks. (C) Spontaneous alternation of mice in the Y-maze, a hippocampus-dependent spatial learning task, was measured for 10 days during the 7th and 8th week after the start of Aβ infusion. Data are mean±SEM of n=5 or 10 per group. Significantly different from Aβ-infused (*$p<0.05$, $p<0.01$, *$p<0.001$).

MW-01-2-151SRM was found to suppress IL-1β in a concentration dependent manner. Immunoreactive levels of glial fibrillary acidic protein (GFAP), a marker of activated astrocytes were increased in Aβ-infused mice (No treatment) compared to vehicle-infused mice (Control). The Aβ infused increase in GFAP levels was suppressed by administration of MW01-2-151RSM. MW01-2-151RSM also blocked the Aβ-induced increase in the pro-inflammatory cytokines IL-1β, TNF-α, and S100B and the Aβ-induced loss of the pre-synaptic protein, synaptophysin and post-synaptic density protein PSD-95. These results are consistent with the results of the cell based assay. (See FIGS. 6 and 7.)

Example 2

Acute and Chronic Toxicity Assays

Liver toxicity is an especially important initial consideration for orally administered compounds, as the liver is the major site of initial drug metabolism and is critical to overall metabolism and homeostasis of an animal. Liver injury is also a component of idiopathic tissue injury seen in certain chronically administered drugs. Therefore, it is important to do initial assessments of liver toxicity after oral administration of compounds to mice.

Methods:

A standard approach is to test compounds in two initial in vivo toxicity assays: an acute, escalating-dose paradigm and a chronic, therapeutic dose regimen. For the escalating-dose, acute toxicity assays, mice (5 per experimental group) are administered either compound or vehicle in 0.5% carboxymethylcellulose (alternatively, castor oil or sesame oil can be used) by oral gavage once daily for 3 days. Standard compound doses are 3.1, 12.5, and 50 mg/kg; the highest dose is 20× a therapeutic dose. On the $4^{th}$ day, mice are sacrificed and the liver harvested and fixed for histology. Paraffin-embedded, hematoxylin & eosin (H&E)-stained sections of liver tissue are analyzed microscopically for injury by two individuals blinded to the treatment groups. A semi-quantitative histological scoring system from 0 (best) to 9 (worst) is applied that considers architecture features (normal to extensive fibrosis), cellular features (normal to extensive edema and widespread necrosis), and degree of inflammatory infiltrate (normal to extensive infiltrate). For each acute toxicity assay, 15 mg of compound is required.

For the therapeutic dose, chronic toxicity assays, mice (5 per experimental group) are administered either compound or vehicle in 0.5% carboxymethylcellulose by oral gavage once daily for 2 weeks at a therapeutic dose of 2.5 mg/kg/day. After two weeks of treatment, mice are sacrificed and liver toxicity analyzed as described above. For each chronic toxicity assay, 5 mg of compound is required.

Results:

MW01-5-188WH has been tested in the acute, escalating-dose assay and the chronic, therapeutic dose assay. There was no histological evidence of tissue toxicity at the lower doses but some vacuolisation was observed at the 50 mg/kg dose.

MW01-2-151SRM has been tested in the chronic, therapeutic dose assay. There was no histological evidence of tissue toxicity; no differences were seen by histology in livers from mice treated with vehicle or with compound. This compound is currently being tested in the acute, escalating dose assay.

MW01-6-189WH has been tested in the chronic, therapeutic dose assay. There was no histological evidence of tissue toxicity; no differences were seen by histology in livers from mice treated with vehicle or with compound. This compound is being tested in the acute, escalating dose assay.

Example 3 hERG Channel Inhibition Assays and Cardiac QT Interval Assays

Compounds have been screened for hERG (human ether-a-go-go) potassium ion channel binding and inhibition in order to eliminate early in the process any compounds with high potential to induce prolongation of cardiac QT interval in later studies due to off-target toxicities. The hERG channel conducts rapidly activating delayed rectifier potassium currents that critically contribute to cardiac repolarization. Mutations in the hERG channel gene and drug-induced blockade of the currents have been linked to delayed repolarization of action potentials resulting in prolonged QT interval (Finlayson et al., 2004; Recanatini et al., 2005; Roden, 2004). QT prolongation is considered a significant risk factor against cardiac safety of new drugs. Therefore, consideration of cardiac safety early in the development process by testing for hERG channel inhibition provides an efficient and predictive means to assess potential compound cardiac safety liabilities. In addition, the FDA (USA) is considering this as an approval criteria in the future and has specific recommendations at this time. The assays done to date have been by a commercial service (MDS PharmaService).

The initial assay is a radioligand binding assay that tests the ability of the test compound to compete with $^3$H-astemizole (a reference standard that binds to hERG channels with nM affinity) for binding to recombinant hERG channels stably expressed on human HEK-293 cells. This cell line was chosen because it is of human origin, has been fully characterized with regard to hERG electrophysiology and pharmacology and displays the expected characteristics of $I_{Kr}$ current as well as expected pharmacological sensitivities, and is easy to maintain in culture (Zhou et al., 1998). A single concentration (10 μM) of test compound is assayed, and % inhibition of $^3$H-astemizole binding is calculated. Generally, any compounds that show >50% inhibition are tested further in the hERG channel activity assay. This is usual for medium throughout screens but is not recommended in the FDA document and tends to give false positives, as evidenced by the results reported below.

The hERG channel activity inhibition assay provides whole cell electrophysiological data about compound effects on the hERG K$^+$ channel function. Whole cell patch clamp methodology is generally considered to be the gold-standard determination of ion channel activity, rather than simply measuring channel binding. The standard testing procedure is to use 3 to 5 concentrations of compound at log dilutions with each concentration tested in triplicate (three cells). This allows a balance between achieving a reasonably accurate IC50 measurement against a broad concentration range, and reducing cell attrition that would occur during more protracted experiment durations. After completion of compound dose-response procedures, a known hERG channel inhibitor, such as astemizole, is applied as a positive control.

Compounds which exhibit inhibition of hERG channel activity are verified as positives (the hERG channel activity assay can give false positives and false negatives) by testing in vivo for prolongation of cardiac QT interval. The QT interval studies are performed by evaluating compounds for effects on QT interval in Lead II electrocardiograms measured in anesthetized guinea pigs (Hirohashi et al., 1991), one of the species recommended in the FDA white paper. Vehicle or compound is administered orally at 15 mg/kg (dosing volume of 10 ml/kg) to groups of male guinea pigs (weighing 330-350 g), with 5 animals per group. This dose corresponds approximately to 20-fold the therapeutic dose by taking into account the body surface area of the animals. Heart rate, arterial blood pressure, and QT intervals are measured at baseline, and at 15, 30, 45, and 60 min after compound administration. Sotalol administered iv at 0.3 mg/kg serves as the positive control compound. The QT intervals are corrected for changes in heart rate using both Bazett's and Fridericia's formulae. Any increase in QT interval values over baseline values exceeding the upper 95% confidence limit of the mean changes at the corresponding time point in the vehicle-treated control group for two consecutive observation times indicates significant QT interval prolongation in the individually treated animals. This functional testing in early discovery provides a rapid and cost-effective method to better anticipate and eliminate compounds that may have adverse QT prolongation potential in humans.

Calculations of Amount of Compound Needed:
Competition binding assay: 1-2 mg
Patch clamp assay: 1-2 mg
QT interval assay: 5 mg/animal/dose=25 mg per assay at 15 mg/kg dose Because the ex vivo activity assays are subject to false positives and negatives, it is considered better to complete studies of in vivo QT interval assay following the guidelines of the PDA position paper.

Results:
Competition Inhibition Assay:
MW01-5-188WH, MW01-2-151SRM, and MW01-6-127WH were tested at 10 μM concentration.
MW01-5-188WH showed 91% inhibition at 10 μM. MW01-2-151SRM and MW01-6-127WH were negative, showing only 8% and 19% inhibition, respectively.
Patch Clamp Inhibition Assay:
MW01-2-151SRM and MW01-6-189WH were tested at three concentrations (0.1, 1, 10 μM). These compounds showed minimal inhibition, with IC$_{50}$ values of 4.81 μM for MW01-6-189WH and 9.21 μM for MW01-2-151SRM.
Cardiac QT Interval Prolongation Assay:
MW01-5-188WH and MW01-2-151SRM were administered PO at 15 mg/kg to 5 guinea pigs (330-350 g weight). QT intervals were obtained at baseline and at 15 min, 30 min, 45 min, and 60 min after compound administration. Neither compound increased cardiac QT interval above the mean+2 SD of corresponding values in the vehicle control group. There were also no significant effects on mean blood pressure or heart rate after compound administration.

Example 4

Preparation of 2-(4-(6-phenylpyridazin-3-yl)piperazin-1-yl)pyrimidine (MW01-3-183WH)

FIG. 1 depicts a synthetic scheme for the preparation of 2-(4-(6-phenylpyridazin-3-yl)piperazin-1-yl)pyrimidine (MW01-3-183WH). Reagent and condition: (a) 1-BuOH, NH$_4$Cl, and 2-(piperazin-1-yl)pyrimidine. A typical reaction mixture of comprised about 0.01 mol of 3-chloro-6-phenylpyridazine by 2-(piperazin-1-yl)pyrimidine, about 0.05 mol of 2-(piperazin-1-yl)pyrimidine and about 0.01 mol of ammonium hydrochloride was prepared in about 15 ml of 1-BuOH. The mixture was stirred at about 130° C. for about 48 h, and then the solvent was removed under reduced pressure. The remaining residue was then extracted with ethyl acetate, washed with water and brine, dried over anhydrous $Na_2SO_4$. Removal of solvent followed by recrystallization from 95% ethanol yielded light yellow crystals, yield 96.4%; HPLC: 97.4% purity: HRMS calculated 318.1587. found 318.1579; 1H NMR (CDCl3): δ 8.356 (d, J=4.5, 2H), 8.011 (d, J=7.5, 11 2H), 7.692 (d, J=9.5, 1H), 7.468 (t, J=6.0, 2H), 7.417 (d, J=7.5, 1H), 7.047 (d, J=9.5, 1H), 6.546 (t, J=4.5, 1H), 4.013 (t, J=5.0, 4H), 3.826 (t, J=5.0, 4H).

Example 5

Biological Activity, Metabolic Stability and Toxicity of 4-methyl-6-phenyl-3-(4-pyrimidin-2-ylpiperazin-1-yl)pyridazine (W01-2-151SRM)

Figure 6:
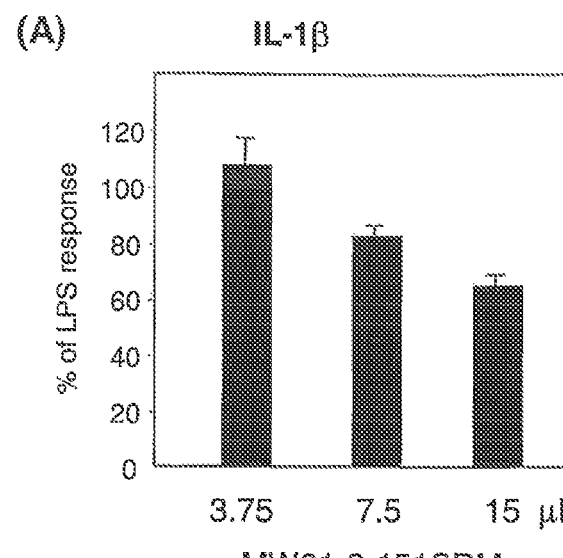
FIG. 6, parts (A) thru (D), shows graphs and immunoblots illustrating the cell-based activity of MW01-2-151SRM in BV-2 microglial cells.
Figure 6:
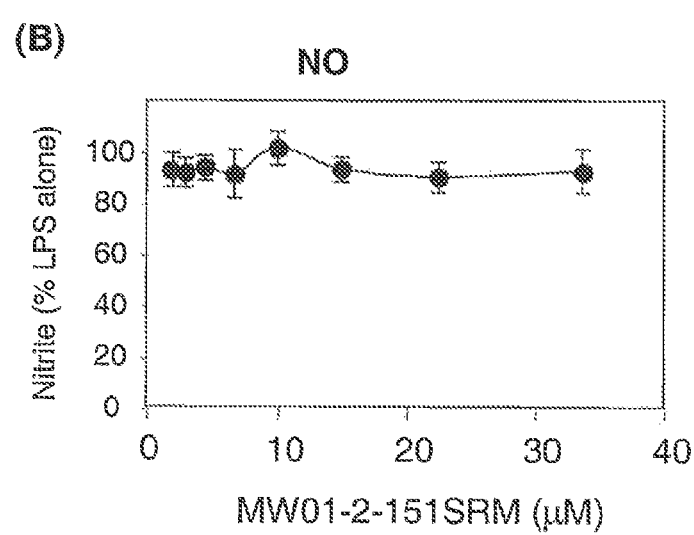
Figure 6:
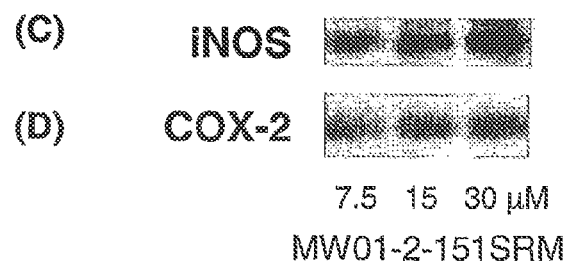
Figure 7:
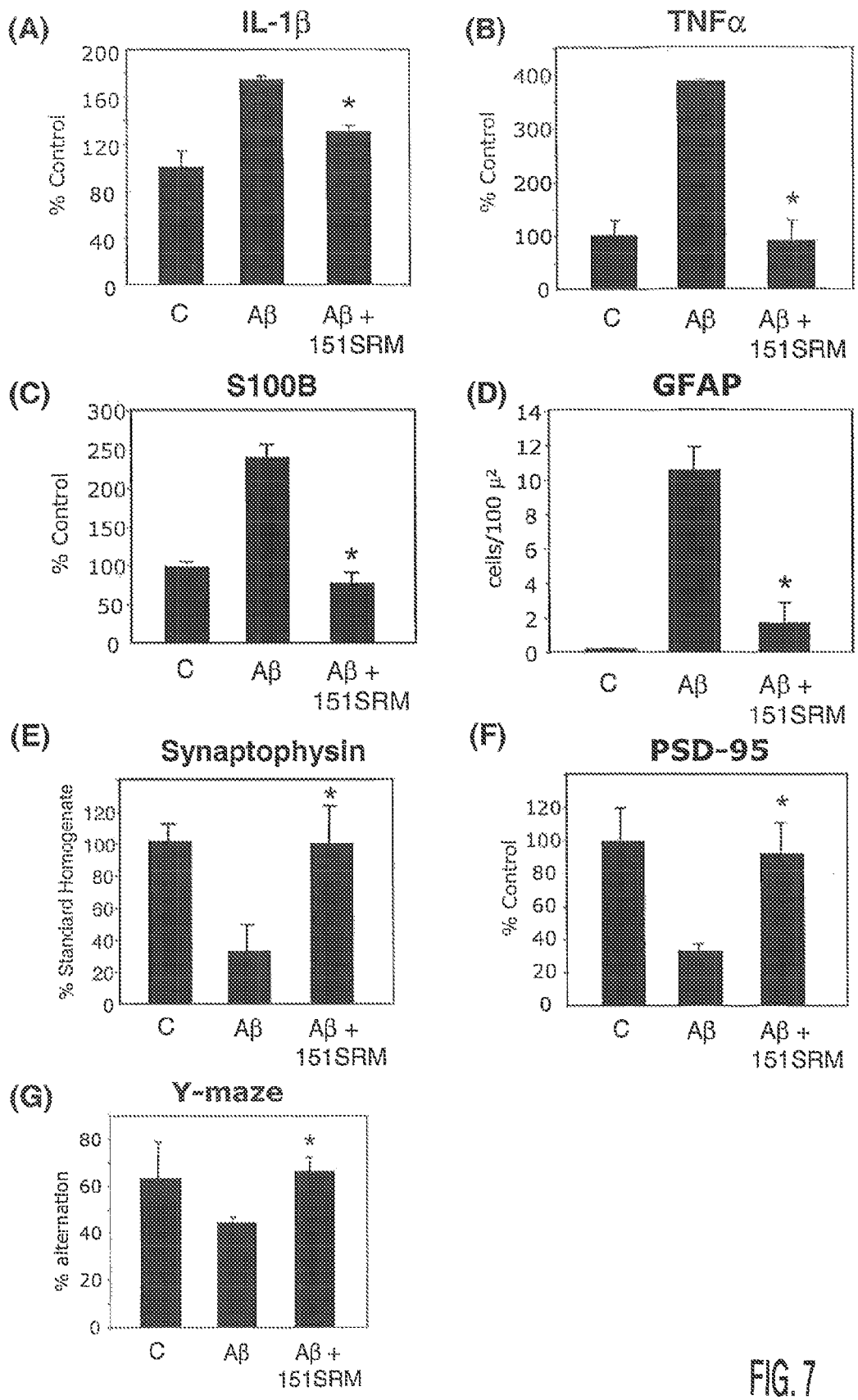
FIG. 7, parts (A) thru (G), shows graphs illustrating in vivo activity of MW01-2-151SRM in the Aβ infusion mouse model. Graphs are of MW01-2-151SRM suppression of Aβ-induced neuroinflammation and synaptic damage and activity in the Y-maze. Hippocampal sections or extracts from vehicle-infused mice (control). Aβ-infused mice injected with solvent, and Aβ-infused mice injected with MW01-2-151SRM were evaluated for neuroinflammation by measurement of the levels of the pro-inflammatory cytokines IL-1β (A), TNFα (B), and S100B (C), and the number of GFAP-positive astrocytes, (D) and the presynaptic marker, synaptophysin, (E), and evaluated for synaptic damage by analysis of the levels of the post-synaptic density protein 95 (PSD-95) (F), and Y-maze. Data are from one of two independent experiments, and are the mean+SEM for 4-5 mice per experimental group.

As shown in FIG. 6 (parts A-D) and FIG. 7 parts A-G), the biological activity of MW011-2-151SRM was investigated using the assays described herein for biological activity of the compounds. The compound was orally available, and targeted to glia responses to protect against neurodeneration, but did not suppress the same inflammatory response endpoints outside the brain. The compound was a selective suppressor of activated glia responses, especially key proinflammatory responses that have been linked to AD pathology. It also showed efficacy in the mouse model of human Aβ-induced neuroinflammation and neuronal injury as shown by the assays of FIG. 7 (parts A-G).

Figure 47:
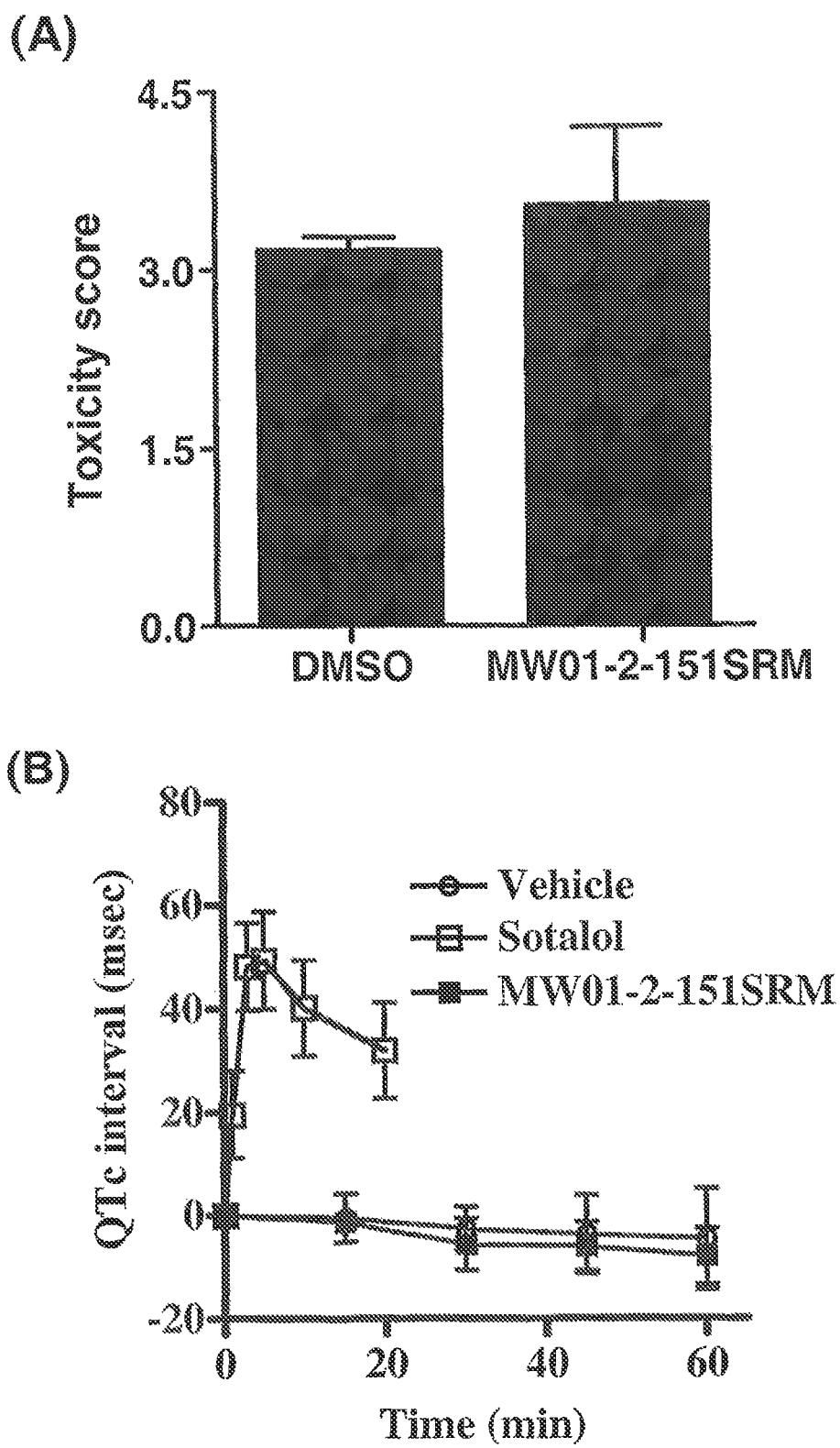
FIG. 47, parts (A) and (B), are graphs of response to MW01-2-151SRM, in a test for toxicity where DMSO in saline was the control, and QTc interval measurement. QT intervals were obtained at baseline and at 15 min, 30 min, 45 min, and 60 min after compound administration.
Figure 48:
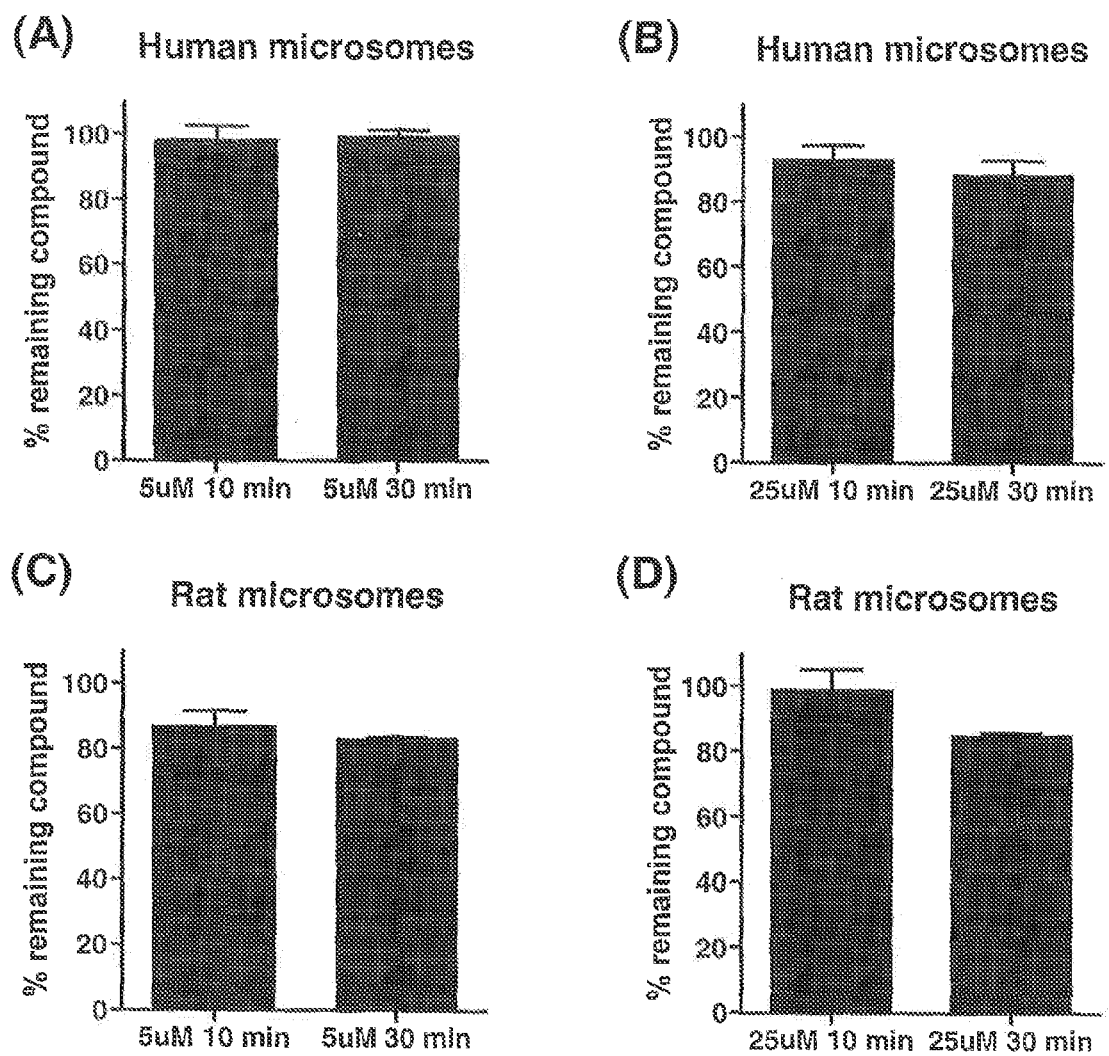
FIG. 48, parts (A) thru (F), are graphs of stability data using human (A,B) and rat (C,D) microsomes with MW01-2-151SRM in two different amounts, for two time periods. E and F show human (E) and (F) rat microsomes with MW01-2-151SRM stability for different time periods compared to minaprine.
Figure 48:
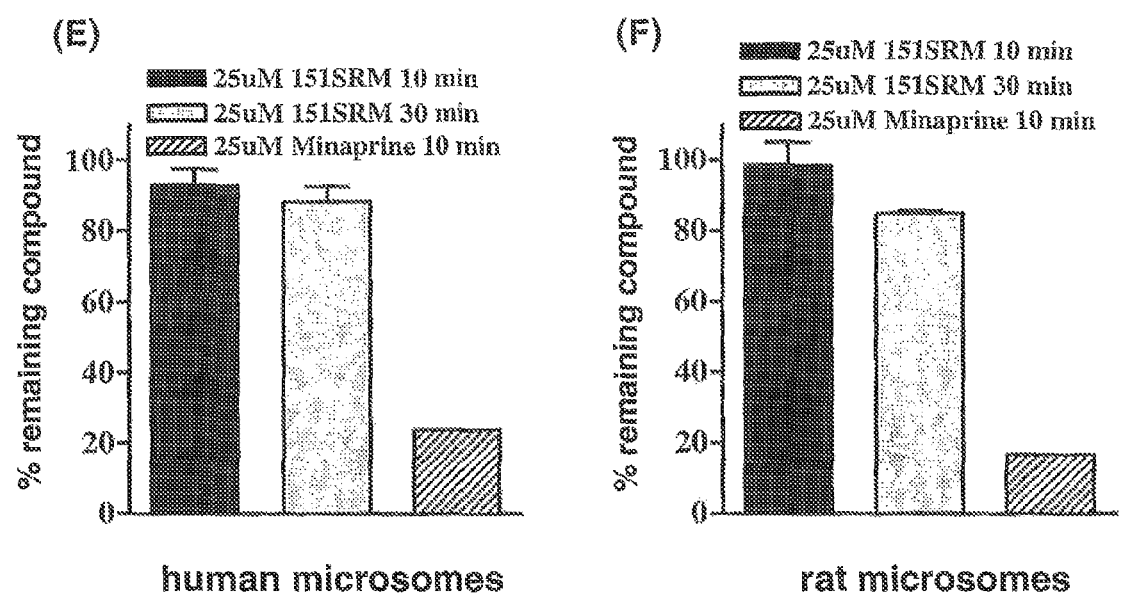
Figure 49:
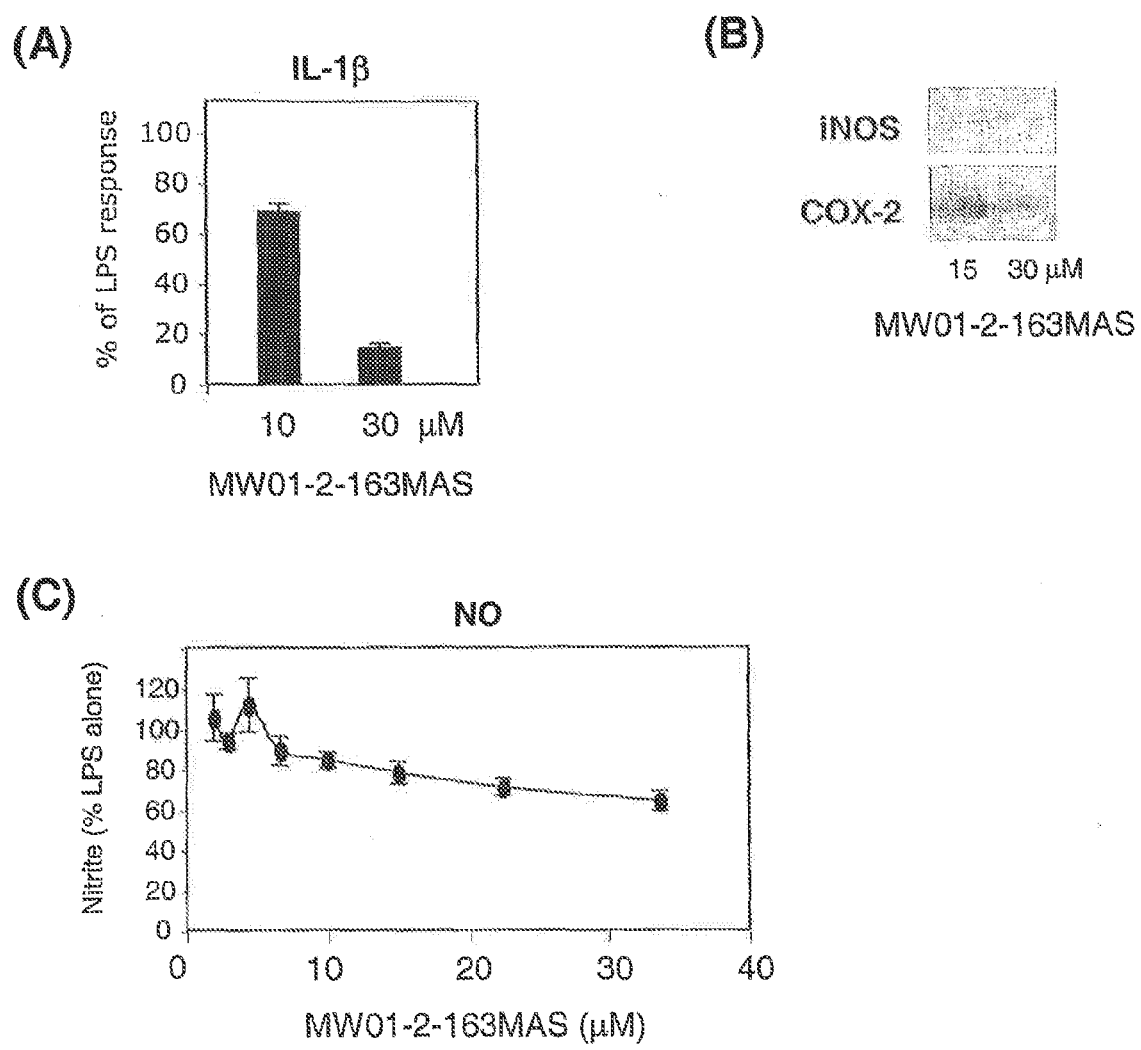
FIG. 49, parts (A) thru (C), shows graphical data of the assays used herein and immunoblots for biological activity of MW01-2-163MAS.
Figure 50:
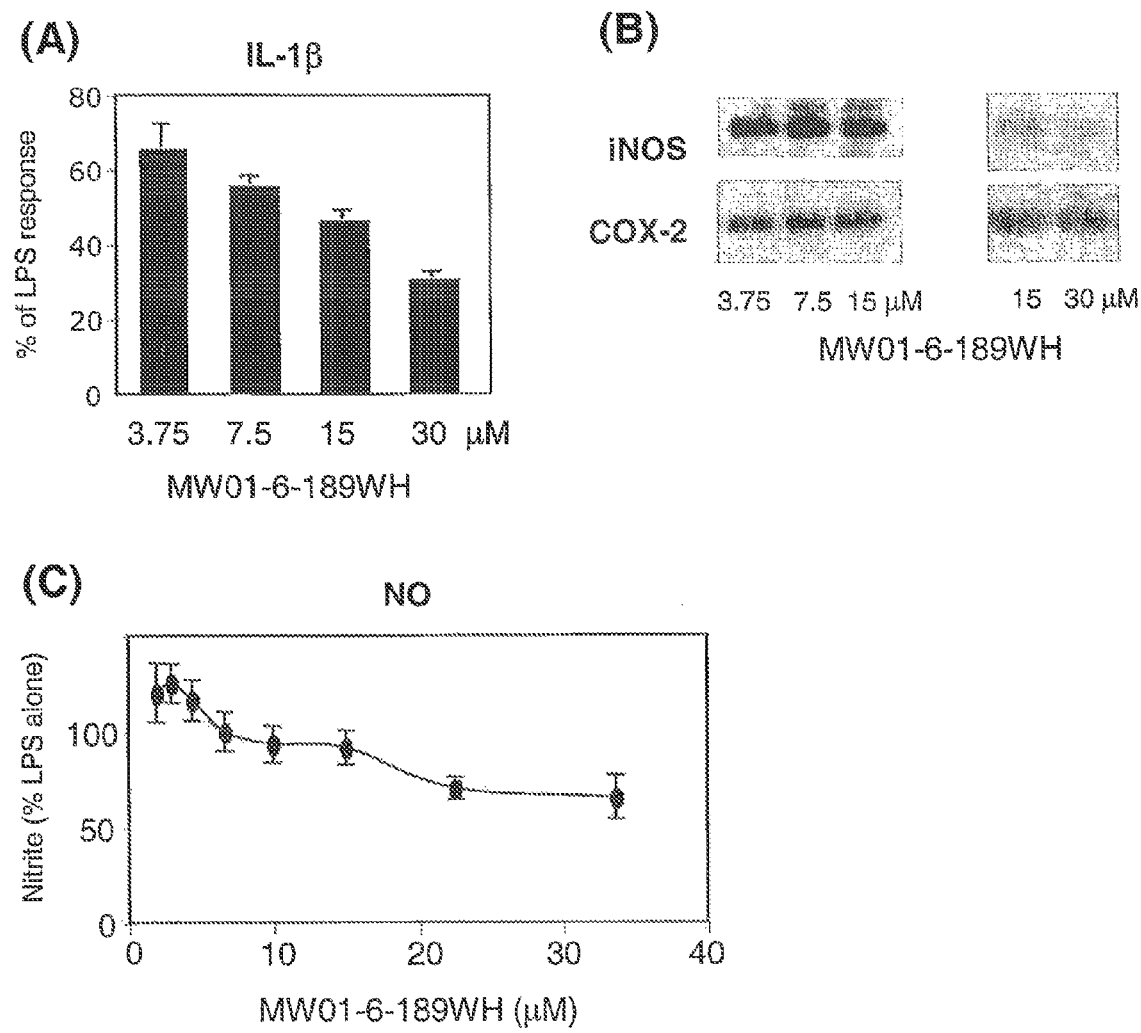
FIG. 50, parts (A) thru (C), shows graphical data of the assays used herein and immunoblots for biological activity of MW01-6-189WH.
Figure 51:
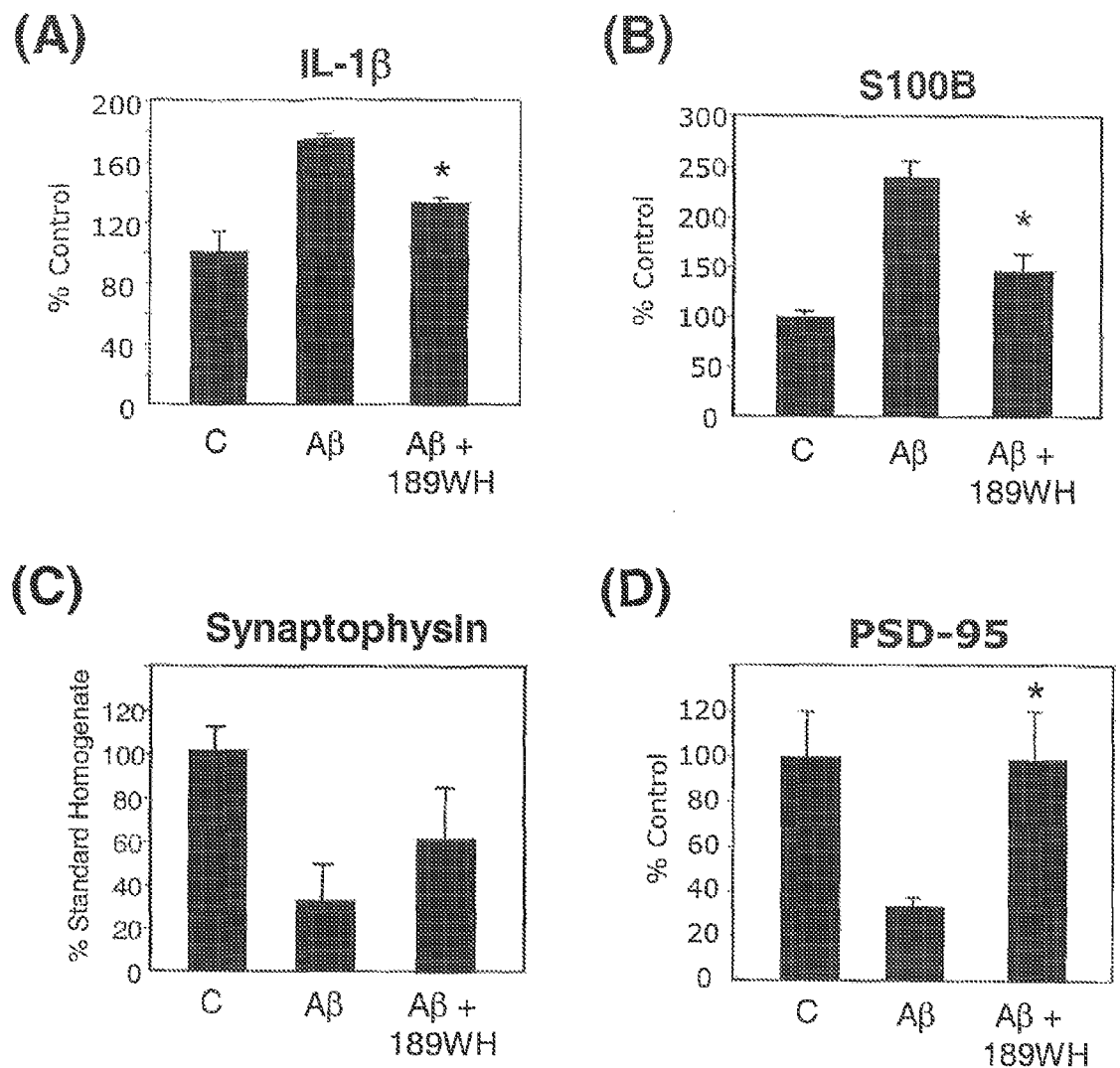
FIG. 51, parts (A) thru (D), shows graphical data of the assays used herein for MW01-6-189WH.

The stability of MW01-2-151SRM in microsomes, as shown in FIGS. 47 and 48, was demonstrated for MW01-2-151SRM. The stability of MW01-5-188WH (1 μM) in a standard incubation with rat liver microsomes (BD Biosciences) and an NADPH-regenerating system was done at 37° C. for the times shown. Reactions were stopped by acetonitrile, and the reaction mixture was centrifuged at 16 000×g for 10 min, 10 μl of the supernatant was analyzed by calibrated HPLC to quantify the percentage of the initial amount of MW01-2-151SRM remaining after the incubation. The HPLC system (Dionex Corp., Sunnyvale, Calif.) includes a Dionex P480 pump, a Phenomenex Luna. (318 column (250×2.0 mm, 5□m) with a guard column (Phenomenex, Torrance, Calif.) and a Dionex UVD340U Ultraviolet (UV) detector. The mobile phase consisted of 0.1% formic acid as reagent A and 0.08% formic acid/water in 80% acetonitrile as reagent B, at a flow rate of 0.2 ml per minute. The gradient consisted of the following linear and isocratic gradient elution changes in reagent B: isocratic at 60% from 0 to 5 min, 60% to 90% from 5 to 39 min, isocratic at 90% until 44 min. Peak quantification was done based on absorption measured at 260 nm relative to a standard curve obtained by using serial dilutions of MW01-2-151SRM.

Liver toxicity after chronic in vivo administration of MW01-2-151SRM was investigated, see FIG. 47 A. Mice were administered by oral gavage either MW01-2-151 SRM (2.5 mg/kg/day) or diluent (10% DMSO) in a 0.5% (w/v) carboxymethylcellulose suspension once dally for two weeks. Mice were anesthetized and sacrificed. Livers were removed, fixed in 4% (v/v) paraformaldehyde and paraffin-embedded for histology. To assess histological toxicity, 4 □m liver sections were stained with haematoxylin and eosin. Two independent observers blinded to the treatment groups performed microscopic assessment of the tissue for injury.

Example 6

Preparation of N-(cyclopropylmethyl)-6-phenyl-4-(pyridin-4-yl)pyridazin-3-amine (MW1-7-084WH)

Figure 8:
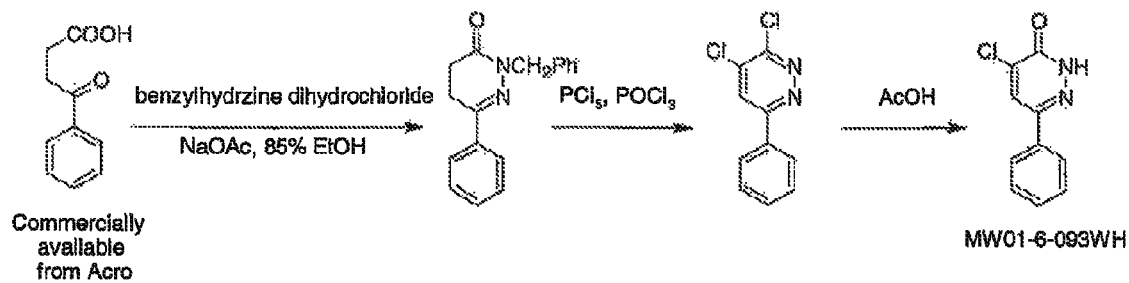
FIG. 8 is a synthetic scheme for MW01-7-084WH.
Figure 8:
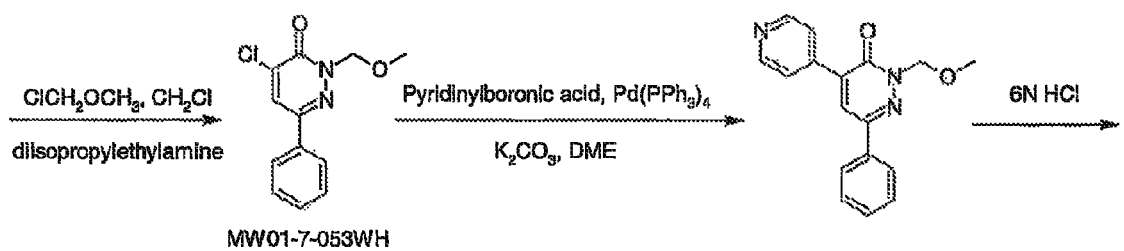
Figure 8:
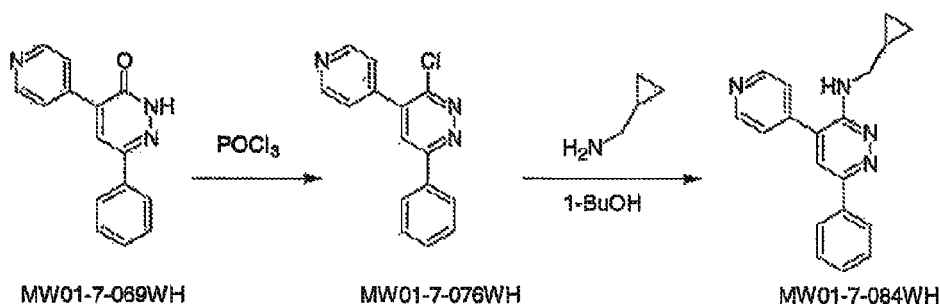

A synthetic scheme for the preparation of N-(cyclopropylmethyl)-6-phenyl-4-(pyridin-4-yl)pyridazin-3-amine (MW01-7-084WH) is depicted in FIG. 8, and synthesis was carried out as described herein.

4-chloro-6-phenylpyridazin-3(2H)-one (MW01-6-093WH)

4-chloro-6-phenylpyridazin-3(2H)-one was synthesized according to the procedure described by Coudert, P. [18].

4-chloro-2-(methoxymethyl)-6-phenylpyridazin-3(2H)-one (MW01-7-053WH)

A mixture of chloropyridazinone 1 (25.5 g, 0.12 mol), 4-N,N-dimethylaminopyridine (0.20 g) and i-Pr2NEt (26.7 g, 0.21 mol) in anhydrous $CH_2Cl_2$ (300 mL) was stirred at 0° C. (ice bath) for 30 min. Methoxymethyl chloride (25 g, 0.31 mol) was added and the mixture was stirred at 0 ¸ãC for 1 h and then allowed to warm to room temperature. The reaction was stirred at room temperature till complete. The solvent was then removed in vacuo, the residue was treated with water, washed with dilute $Na_2CO_3$ solution and extracted with EtOAc. The organic layer was dried over anhydrous $Na_2SO_4$, filtered and evaporated. The residue was then purified by re-crystallization from 95% ethanol to give 20.1 light yellow solid. Yield 66.9%.

6-phenyl-4-(pyridin-4-yl)pyridazin-3(2H)-one (MW01-7-069WH)

The protected pyridazinone MW01-7-053WH (1.0 equiv.) was mixed with arylboronic acid (1.37 equiv.), Pd(PPh3)4 (0.05 equiv.) and K2CO3 (3.1 equiv) and 200 mL of DME in a 350 ml of pressure vessel, flushed with argon for 3 min, and the mixture was then stirred and refluxed (oil bath, 120° C.) until the starting material had disappeared. After cooling, the solution was concentrated to dryness under reduced pressure, the residue was treated with water and filtered off. The filter cake was washed with water over filter funnel and then used for next step directly. The residue obtained above was dissolved in 200 ml of EtOH, 6 N HCl (200 mL) was added and the reaction mixture was refluxed (oil bath, 12.0 ¸ãC) for 6 h, then it was allowed to cool to room temperature, and concentrated to dryness under reduced pressure. The residue was neutralized with dilute NaOH solution. The suspension was then filter off, washed with water and dried over filter funnel. Recrystallization from 90% ethanol provided brown yellow solid. Yield 80.4%. ESI-MS: m/z 294.3 (M+H+)

3-chloro-6-phenyl-4-(pyridin-4-yl)pyridazine (MW01-7-076WH)

3-chloro-6-phenyl-4-(pyridin-4-yl)pyridazine (MW01-7-076WH) (66 mmol) was suspended in 75 ml phosphorus oxychloride and heated with stirring at 100° C. for 3 h. After cooling to room temperature the mixture was poured onto crushed ice. The mixture was then neutralized with NaOH solution to give white suspension. The precipitation was filtered off, washed with water, dried over filter funnel to yielding a light yellow solid. ESI-MS: m/z 268.4 (M+H+).

N-(cyclopropylmethyl)-6-phenyl-4-(pyridin-4-yl)pyridazin-3-amine (MW01-7-084WH)

A mixture of N-(cyclopropylmethyl)-6-phenyl-4-(pyridin-4-yl)pyridazin-3-amine (MW01-7-084WH) (0.5 mmol), C-Cyclopropyl-methylamine (2.0 mmol) in 3 ml of 1-BuOH was heated with stirring at 130° C. for 7 days. The solvent was removed by evaporation in vacuo, the residue was treated with water to give a suspension. The solid was then filtered off, washed with water, then 1:3, Ethyl Acetate: Petroleum ether, dried over filter funnel in vacuo yielding gray solid. ESI-MS: m/z 330.4 (M+H+).

Example 7

Preparation of 3-(4-methylpiperazin-1-yl)-6-phenyl-4-(pyridin-4-yl)pyridazine (MW01-7-085WH)

Figure 9:
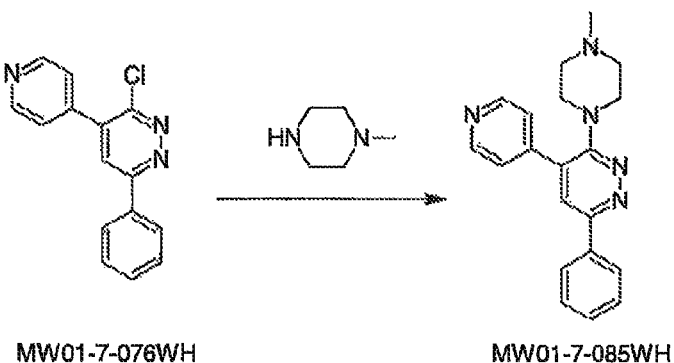
FIG. 9 is a synthetic scheme for MW01-7-085WH.

A mixture of 3-chloro-6-phenyl-4-(pyridin-4-yl)pyridazine (MW01-7-076WH) (0.5 mmol), 1-methyl-piperazine (2.0 mmol) in 3 ml of 1-BuOH was heated with stirring at 130° C. for about 7 days. The solvent was removed by evaporation in vacuo, the residue was treated with water to give a suspension. The solid was then filtered off, washed with water, then 1:3, Ethyl Acetate: Petroleum ether, dried over filter funnel in vacuo to yield a brown solid. ESI-MS: m/z 332.2 (M+H+). A synthetic reaction scheme for the preparation of 3-(4-methylpiperazin-1-yl)-6-phenyl-4-(pyridin-4-yl)pyridazine (MW01-7-085WH) is depicted in FIG. 9.

Example 8

Preparation of N-(2-morpholinoethyl)-6-phenyl-4-(pyridin-4-yl)pyridazin-3-amine (MW01-7-091WH)

Figure 10:
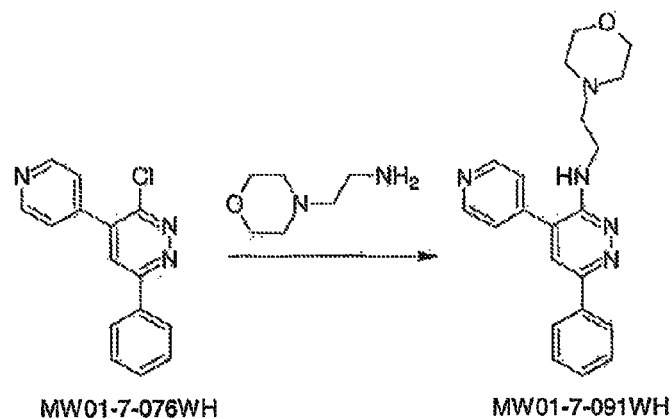
FIG. 10 is a synthetic scheme for MW01-7-091WH.

A mixture of 3-chloro-6-phenyl-4-(pyridin-4-yl)pyridazine (MW01-7-076WH) (0.5 mmol), 2-Morpholin-4-yl-ethylamine (2.0 mmol) in 3 ml of 1-BuOH was heated with stirring at 130° C. for about 7 days. The solvent was removed by evaporation in vacuo, the residue was treated with water to give a suspension. The solid was then filtered off, washed with water, then 1:3, Ethyl Acetate: Petroleum, ether, dried over filter funnel in vacuo to yield a gray solid. ESI-MS: m/z 362.2 (M+H$^1$). A synthetic reaction scheme for the preparation of 3-(4-methylpiperazin-1-yl)-N-(2-morpholinoethyl)-6-phenyl-4-(pyridin-4-yl)pyridazin-3-amine (MW01-7-091WH) is depicted in FIG. 10.

Example 9

Preparation of 5-(4-Fluorophenyl)-3-phenyl-6-(4-pyrimidin-2-ylpiperazin-1-yl)pyridazine (MW01-2-065LKM)

Figure 11:
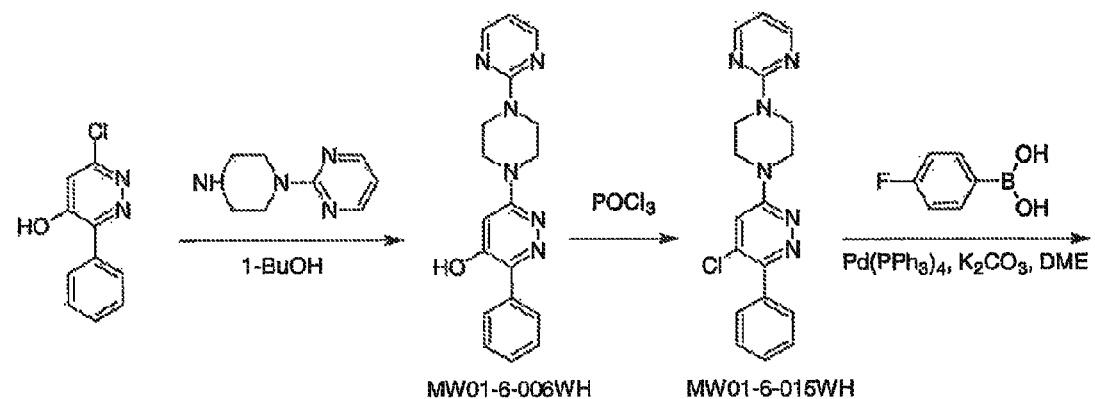
FIG. 11 is a synthetic scheme for MW01-2-065LKM.
Figure 11:
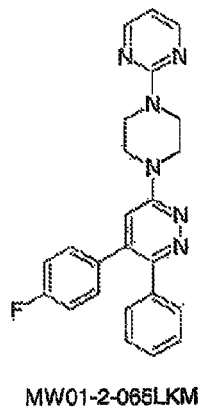

A synthetic reaction scheme for the preparation of 5-(4-Florophenyl)-3-phenyl-6-(4-pyrimidin-2-ylpiperazin-1-yl)pyridazine (MW01-2-065LKM) is depicted in FIG. 11, and synthesis was carried out as described herein.

3-phenyl-6-(4-pyrimidin-2-piperazin-1-yl)pyridazin-5-ol (MW01-6-006WH)

This compound was prepared from 3-chloro-5-hydroxy-6-phenylpyridazine (1.4 g, 6.8 mmol) in the same manner as described for MW01-6-121WH, yielding white solid (2.12 g, 6.15 mmol, 90.4%). MALDI-TOF: m/z 335.7 (M+H+). 1H NMR (DMSO): d 8.433 (t, J=2.0, J=2.4, 2H), 7.773 (d, J=3.2, 2H), 7.497 (t, J=2.0, J=3.6, 3H), 7.182 (s, 1H), 6.727 (s, 1H), 3.949 (s, 4H).

5-chloro-3-phenyl-6-(4-pyrimidin-2-ylpiperazin-1-yl)pyridazine (MW01-6-015WH)

3-chloro-5-hydroxy-6-phenylpyridazine (66 mmol) was suspended in 75 ml phosphorus oxychloride and heated with stirring at 100° C. for 3 h. After cooling to room temperature the mixture was poured onto crushed ice. The mixture was then neutralized with NaOH solution to give white suspension. The precipitation was filtered off, washed with water, dried over filter funnel to yield white solid (98.8%). ESI-MS: m/z 353.3 (M+H+). 1H NMR (CDCl3): d 8.375 (d, J=5.0, 2H), 7.776 (d, J=7.0, 2H), 7.487 (m, 3H), 7.073 (s, 1H), 6.588 (t, J=4.5, 1H), 4.046 (t, J=4.5, J=5.5, 4H), 3.849 (t, J=5.5, J=5.0, 4H).

5-(4-Florophenyl)-3-phenyl-6-(4-pyrimidin-2-ylpiperazin-1-yl)pyridazine (MW01-2-065LKM)

This compound was prepared in the same manner as described for MW01-7-069WHWH, yielding a white solid (60.4%). MALDI-TOF: m/z 413.4 (M+H+).

Example 10

Preparation of 5-(4-pyridyl)-3-phenyl-6-(4-pyrimidin-2-ylpiperazin-1-yl)pyridazine (MW01-2-069A-SRM)

Figure 12:
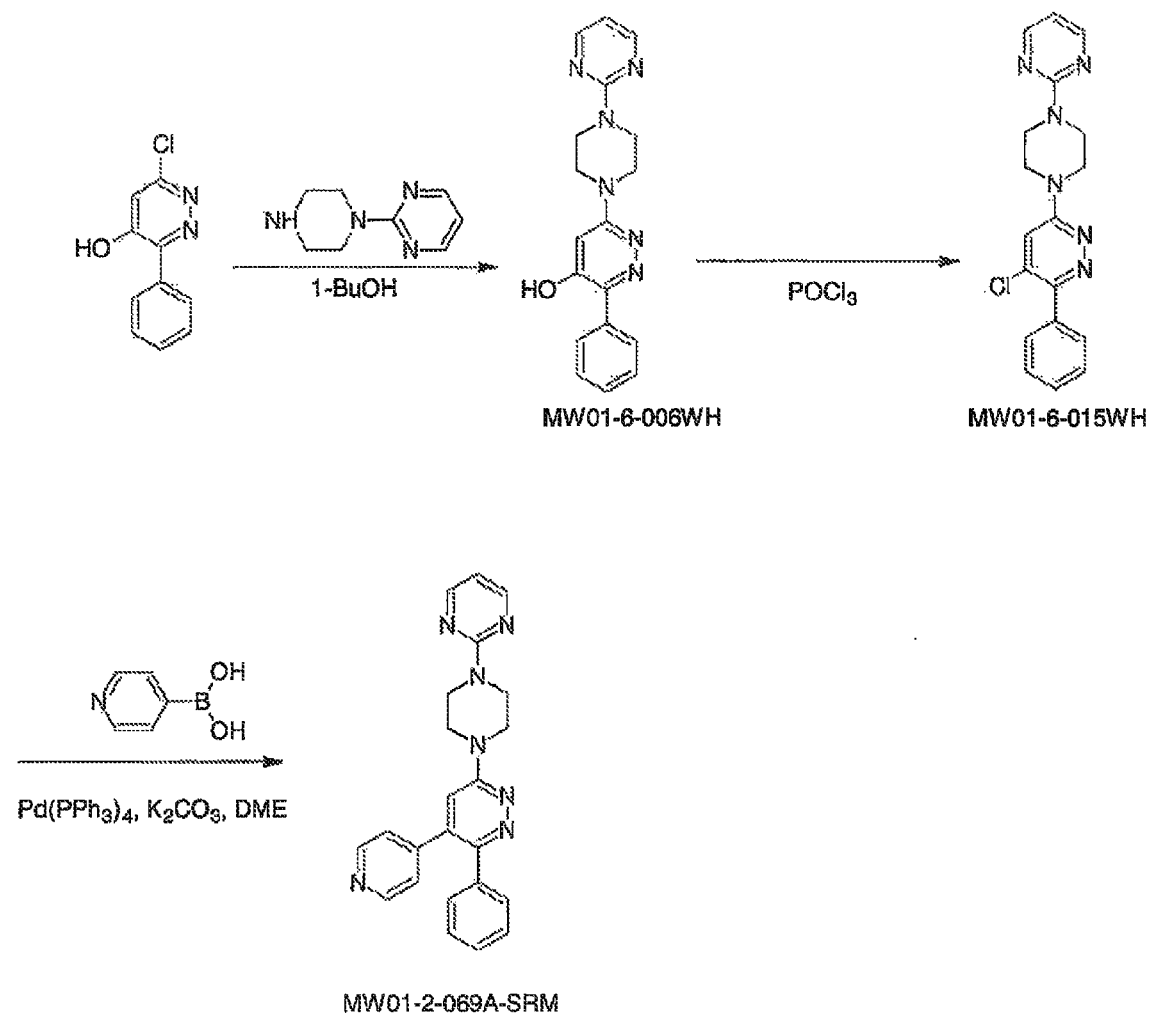
FIG. 12 is a synthetic scheme for MW01-2-069A-SRM.

A synthetic reaction scheme for the preparation of 5-(4-pyridyl)-3-phenyl-6-(4-pyrimidin-2-ylpiperazin-1-yl)pyridazine (MW01-2-069A-SRM) is depicted in FIG. 12, and synthesis was carried out as described herein. This compound was prepared in the same manner as described for MW01-2-065LKM, yielding white solid (65.4%). MALDI-TOF: m/z 396.2 (M+H+).

Example 11

Preparation of 4-methyl-6-phenyl-3-(4-pyrimidin-2-ylpiperazin-1-yl)pyridazine (MW01-2-151SRM)

Figure 13:
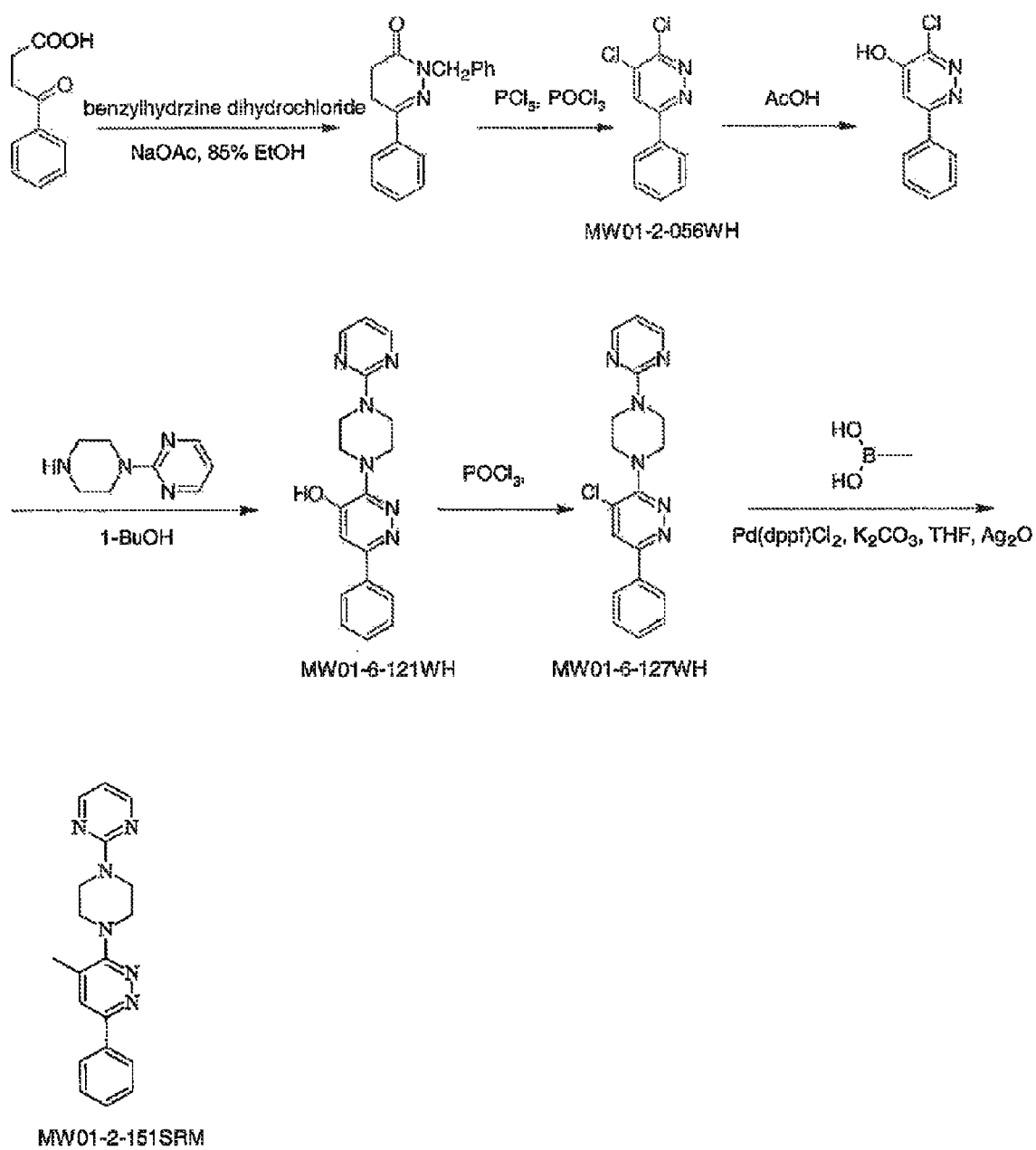
FIG. 13 is a synthetic scheme for MW01-2-151 SRM.
Figure 14:
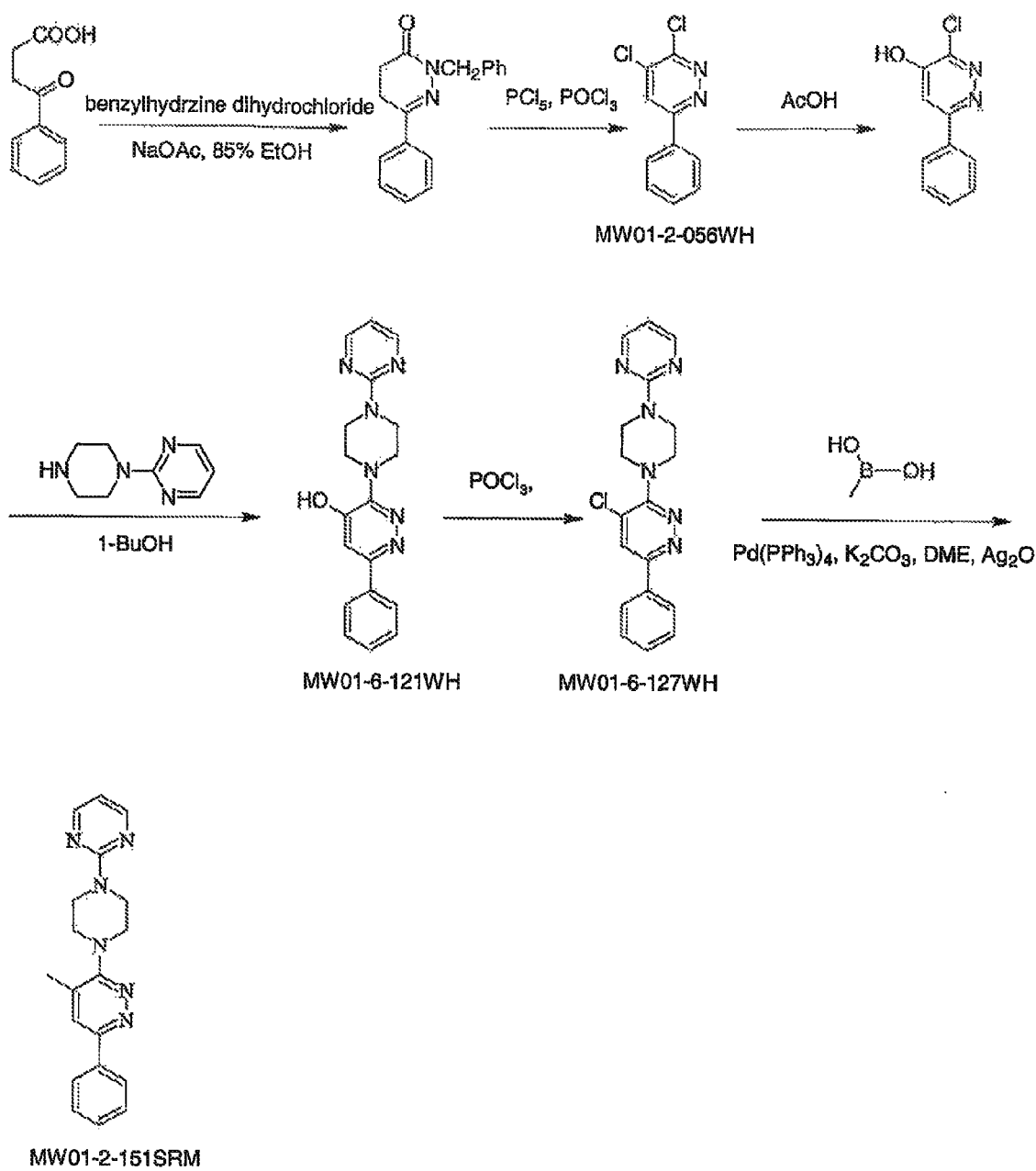
FIG. 14 is a synthetic scheme for MW01-2-151SRM.
Figure 15:
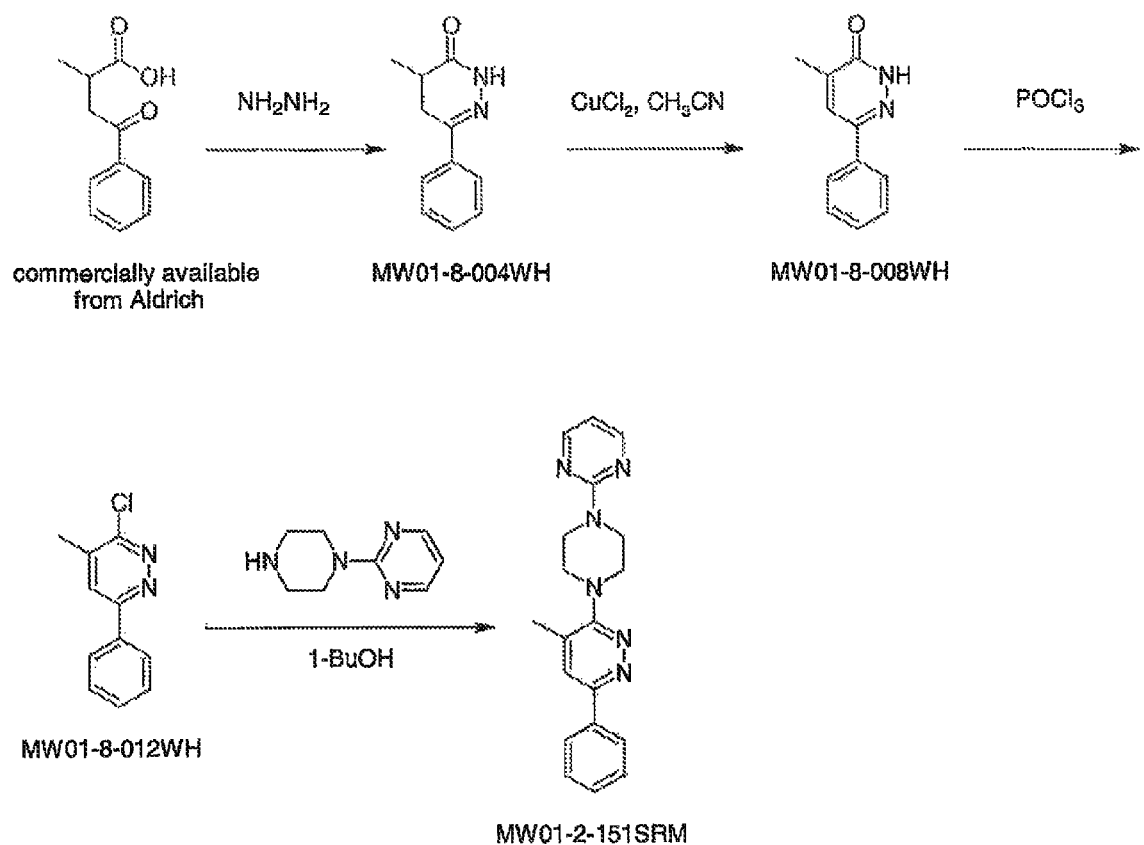
FIG. 15 is a synthetic scheme for MW01-2-151SRM.

4-methyl-6-phenyl-3-(4-pyrimidin-2-ylpiperazin-1-yl)pyridazine (MW01-2-151SRM) was prepared by several synthetic schemes as depicted in FIG. 13 (Scheme 1), FIG. 14 (Scheme 2), and FIG. 15 (Scheme 3), which were carried out as described in detail herein. The various reaction schemes (Schemes 1, 2, and 3) are generally applicable to the compounds of the present invention and are not restricted in utility only to the preparation of MW01-2-151SRM.

Scheme 1

3-chloro-6-phenylpyridazin-4-ol was synthesized according to the procedure described by Coudert, P., et al. [18].

6-phenyl-3-(4-(pyrimidin-2-yl)piperazin-1-yl)pyridazin-4-ol (MW01-7-121WH)

This compound was prepared from 3-chloro-4-hydroxy-6-phenylpyridazine (14 g, 68 mmol) in the same manner as described below, yielding white solid (22.1 g, 66 mmol, 97.3%). ESI-MS: m/z 335.2 (M+H+). 1H NMR (DMSO): 1H NMR (DMSO): d 8.406 (d, J=6.5, 2H), 7.740 (d, J=4.0, 2H), 7.558 (s, 3H), 6.686 (t, J=4.8, J=4.4, 1H), 6.841 (s, 1H), 3.881 (s, 4H), 3.620 (s, 4H), 3.776 (s, 4H).

4-chloro-6-phenyl-3-(4-pyrimidin-2-ylpiperazin-1-yl)pyridazine (MW01-6-127WH)

6-phenyl-3-(4-pyrimidin-2-ylpiperazin-1-yl)pyridazin-4-ol (22.0 g, 66 mmol) was suspended in 75 ml phosphorus oxychloride and heated with stirring at 100° C. for 3 h. After cooling to room temperature the mixture was poured onto crushed ice. The mixture was then neutralized with NaOH solution to give white suspension. The precipitation was filtered off, washed with water, dried over filter funnel to provide white solid (21.3 g, 60.3 mmol, 91.4%). ESI-MS: m/z 353.4 (M+H+). 1H NMR (CDCl3): d 8.377 (d, J=4.5, 2H), 8.036 (d, J=7.5, 2H), 7.833 (s, 1H), 7.508 (m, 3H), 6.564 (t, J=4.5, 1H), 4.073 (t, J=4.0, J=4.5, 4H), 3.672 (t, J=4.0, J=4.5, 4H).

4-methyl-6-phenyl-3-(4-pyrimidin-2-ylpiperazin-1-yl)pyridazine (MW01-2-151SRM)

Into a reaction tube were added MW01-6-127WH (1.4 g, 4.0 mmol), K2CO3 powder (1.7 g, 12.4 mmol), Pd(dppf)Cl2 (326 mg, 0.4 mmol), silver oxide (2.3 g, 10 mmol), methylboronic acid (324 mg, 5.4 mmol) and 20 ml of THF. Argon was then flushed through the tube for 3 min. The tube was then sealed tightly and heated with stirring at 80 degree for 12 h. After cooled down, the mixture was quenched with 10% NaOH solution and extracted with ethyl acetate. The organic phase was concentrated in vacuo and the residue was purified by column chromatography eluting with 1:4, Ethyl Acetate: Petroleum ether. White powder solid was obtained (0.60 g, 1.8 mmol, yield 45.2%). ESI-MS: m/z 333.4 (M+H+). 1H NMR (CDCl3): d 8.380 (d, J=5.0, 2H), 7.065 (d, J=7.0, 2H), 7.626 (s, 1H), 7.473 (m, 3H), 6.567 (t, J=4.5, J=5.0, 1H), 4.056 (t, J=5.0, 4H), 3.475 (t, J=5.0, 4H), 2.456 (s, 3H).

Scheme 2

Into a reaction tube were added MW01-6-127WH (1.4 g, 4.0 mmol), K2CO3 powder (1.7 g, 12.4 mmol), Pd(PPh3)4 (240 mg, 0.2 mmol), silver oxide (2.3 g, 10 mmol), methylboronic acid (324 mg, 5.4 mmol) and 20 ml of DME. Argon was then flushed through the tube for 3 min. The tube was then sealed tightly and heated with stirring at 120° C. for 24 h. After cooled down, the mixture was filter through acelite earth, the filtrate was then concentrated and the residue was purified by column chromatography during with 1:4, Ethyl Acetate:Petroleum ether. White powder solid was obtained (0.64 g, 1.93 mmol, yield 48.1%). ESI-MS: m/z 333.4 (M+H+). 1H NMR (CDCl3): d 8.380 (d, J=5.0, 2H), 7.065 (d, J=7.0, 2H), 7.626 (s, 1H), 7.473 (m, 3H), 6.567 (t, J=4.5, J=5.0, 1H), 4.056 (t, J=5.0, 4H), 3.475 (t, J=5.0, 4H), 2.456 (s, 3H).

Scheme 3

4,5-dihydro-4-methyl-6-phenylpyridazin-3(2H)-one (MW01-8-004WH)

7.7 g (40 mmole) of 2-methyl-4-oxo-4-phenylbutanoic acid was added to a 100 ml single-necked round bottom flask followed by 3.0 ml (60 mmole) of hydrazine monohydrate and then 20 ml of reagent grade ethanol (100%, 95% of ethanol should be fine also). The flask was fitted with a reflux condenser and the reaction mixture was heated to reflux in an oil bath at 110 C (temperature of oil bath) and stirred for 2 h. The flask was then removed from the oil bath and the reaction mixture cooled to ambient temperature. The stir bar was removed and the solvent was evaporated in vacuo in a water bath at 45° C. The residue was then treated with 50 ml of Milli-Q water and stirred, for 10 minutes to give a suspension. The precipitate was collected by filtering, washed with 100 ml of 2N NaHCO$_3$, then washed with 60 ml Milli-Q water three times, and dried over a medium frit sintered glass funnel in vacuo to give 7.15 g of white crystals (Syn. ID, WH-8-004). Yield, 95%, confirmed by ESI-MS. ESI-MS: m/z 189.2 (M+H+).

4-methyl-6-phenylpyridazine-3(2H)-one (MW01-8-008WH)

7.0 g (35 mmole) of MW01-8-004WH was placed in a 100 ml single-necked round bottom flask followed by 9.4 g (70 mmole) of anhydrous copper (II) chloride and then 30 ml of acetonitrile to give a brown yellow suspension. A reflux condenser was connected to the flask and a dry tube filled with CaCl2 was fitted to the top of the condenser. The reaction mixture was heated to reflux in an oil bath (110° C.) for 3 h. The color of the reaction suspension changed to dark yellow once the reflux started. After the completion of the reaction (monitored by HPLC), the flask was removed from the oil bath and cooled to ambient temperature. The mixture was poured on to 300 g of crushed ice and stirred vigorously for 10 minutes to give a gray precipitate and blue liquid. The precipitate was then collected by filtering (pH of the filtrate was 1.5-2.0), and washed with 100 ml of a 1N HCl solution to rid the solid of any remaining copper byproducts. This is followed by washing with 100 ml of Milli-Q water to get rid of the acid in the solid, and is monitored by checking the pH value of the filtrate. The solid was washed until the filtrate shows a pH of 7, after approximately 5 washes. The solid was dried over a medium frit sintered glass funnel in vacuo to give 6.3 g of a blue gray solid. Yield was 96.7% and confirmed by ESI-MS. ESI-MS: m/z 187.3 (M+H+).

3-chloro-4-methyl-6-phenylpyridazine (MW01-8-012WH)

6.0 g (32 mmole) of MW01-8-008WH and 30 ml (320 mmole) of phosphorus oxychloride were placed in a 100 ml single-necked round bottom flask. The flask was connected with a reflux condenser and a dry tube filled with anhydrous CaCl$_2$ was fitted to the top of the condenser. (HCl gas is formed in the reaction so a basic solution such as NaOH may be needed to absorb HCl in a large-scale synthesis). The reaction mixture was stirred in an oil bath (90° C.) for 2 h, then cooled to ambient temperature and poured onto crushed ice. (phosphorus oxychloride can be decomposed by water to give HCl and H$_3$PO$_4$). The mixture was then stirred vigorously for 10 minutes to give a white suspension. The suspension was neutralized with a 2N NaOH solution until the pH of the suspension was pH=7. The precipitate was filtered, washed three times with 100 ml of Milli-Q water and dried over a medium frit sintered glass funnel in vacuo to provide 5.9 g of a light pink powder (Syn. ID, WH-8-012). Yield was 89.4% and confirmed by ESI-MS. ESI-MS: m/z 205.4 (M+H+).

2-(4-(4-methyl-6-phenylpyridazin-3-yl)piperazin-1-yl)pyrimidine (MW01-2-151SRM)

0.82 g (4.0 mmole) of WH-8-012 was placed in a 30 ml pressure vessel followed by addition of 2.6 g (16.0 mmole) of 1-(2-pyrimidyl)piperazine and then 15 ml of 1-BuOH. The vessel was sealed tightly and placed into an oil bath, and stirred at 130 C (temperature of oil bath) for 2.5 days. The reaction mixture was then cooled to ambient temperature and transferred to a single-necked flask for evaporation under reduced pressure. Removal of solvent gave rise to a brown-red residue that was treated with 30 ml of water to give a brown sticky oil. The mixture was kept at ambient temperature overnight while the oil solidified gradually. The formed solid was then broken into small pieces with a steel spatula. The solid was collected by filtering and washed with 50 ml of Milli-Q water three times and dried over a filter funnel in vacuo to provide 1.25 g of light yellow solid (Syn. ID, WH-8-020). Yield was 94%. (Alternative separation is to use precipitation procedure instead of solidification process. Solidification is a simple and cheap operation, yet time-consuming. Precipitation is time efficient, yet more costly than the former one. So it is up to the process chemist to decide which procedure to pick for the manufacture. The precipitation process is below: The oil product was dissolved completely in 10 ml of reagent grade ethanol or acetone to form a solution. The solution was then added dropwise to 150 ml of ice water under vigorous stirring. Light yellow suspension was then formed gradually. The solid was collected by filtering, washed with Milli-Q water, dried over filter funnel in vacuo to give the desired product.) The final compound was confirmed by ESI-MS and NMR. ESI-MS: m/z 333.8 (M+H+). 1H NMR (CDCl3): d 8.380 (d, J=5.0, 2H), 7.065 (d, J=7.0, 2H), 7.626 (s, 1H), 7.473 (m, 3H), 6.567 (t, J=4.5, J=5.0, 1H), 4.056 (t, J=5.0, 4H), 3.475 (t J=5.0, 4H), 2.456 (s, 3H).

Example 12

Preparation of 4,6-diphenyl-3-(4-pyrimidin-2-ylpiperazin-1-yl)pyridazine (MW01-5-188WH)

Figure 16:
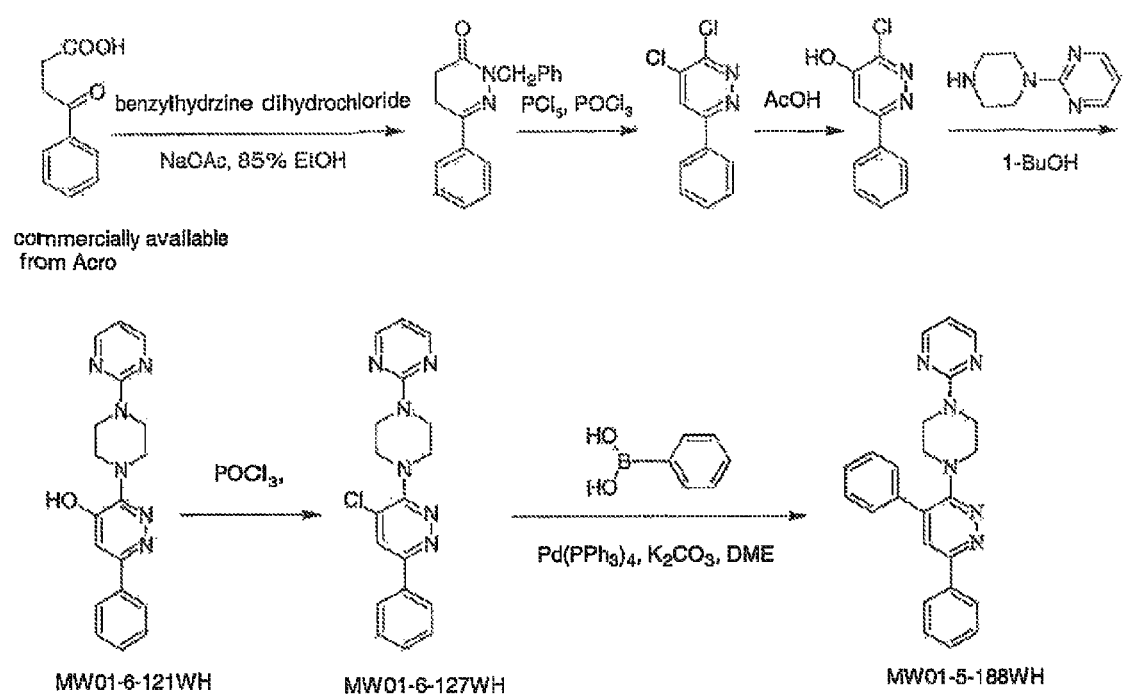
FIG. 16 is a synthetic scheme for MW01-5-188WH.
Figure 17:
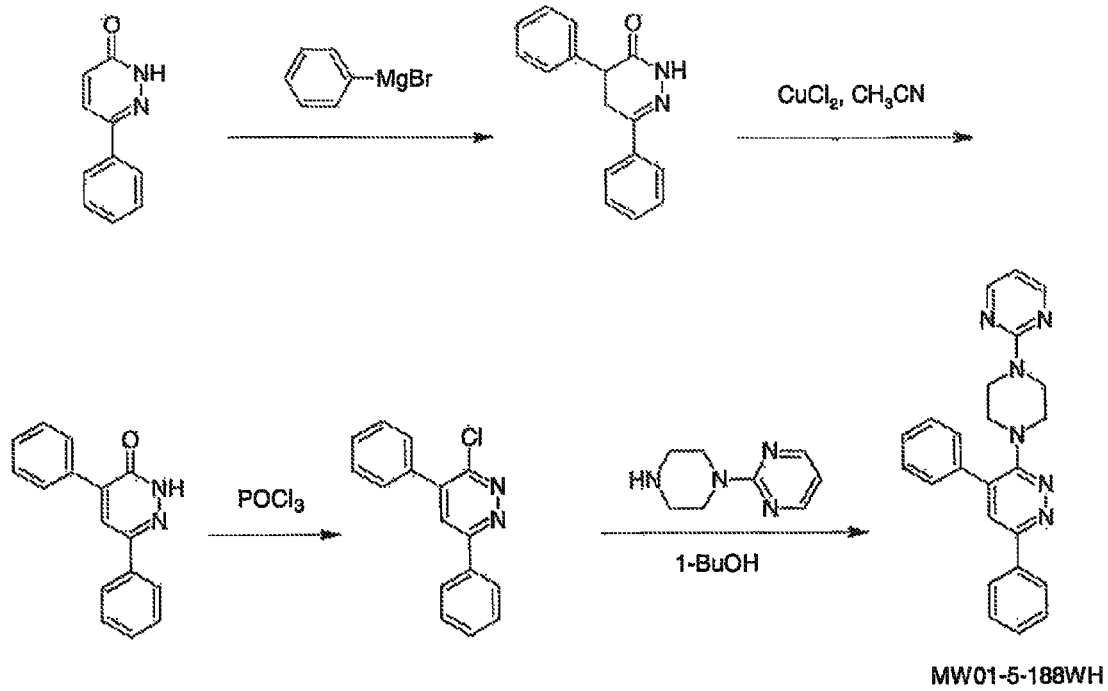
FIG. 17 is a synthetic scheme for MW01-5-188WH.
Figure 18:
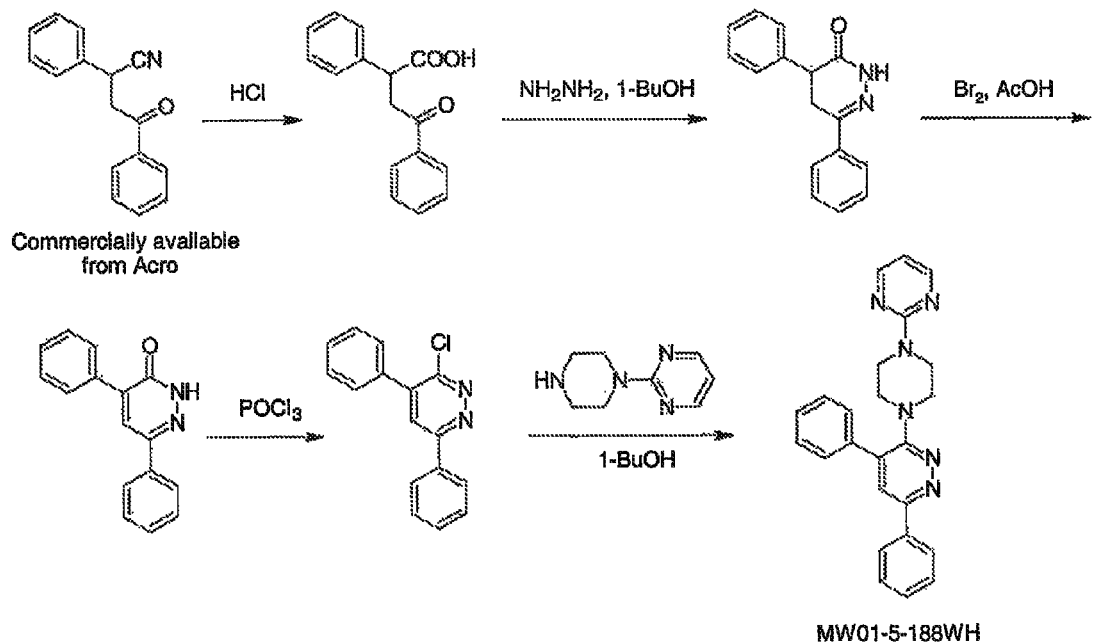
FIG. 18 is a synthetic scheme for MW01-5-188 WH.

4,6-diphenyl-3-(4-pyrimidin-2-ylpiperazin-1-yl)pyridazine (MW01-5-188WH) was prepared by several synthetic schemes as depicted in FIG. 16 (Scheme 1), FIG. 17 (Scheme 2), and FIG. 18 (Scheme 3), which were carried out as described in detail herein. The various reaction schemes (Schemes 1, 2, and 3) are generally applicable to the compounds of the present invention and are not restricted in utility only to the preparation of MW01-2-188WH.

Scheme 1

3-chloro-6-phenylpyridazin-4-ol was synthesized according to the procedure described by Coudert, P., et al. [18].

6-phenyl-3-(4-(pyrimidin-2-yl)piperazin-1-yl)pyridazin-4-ol (MW01-7-121WH)

The compound was prepared from 3-chloro-4-hydroxy-6-phenylpyridazine (14 g, 68 mmol). A mixture of 3-chloro-4,6-diphenylpyridazine (267 mg, 1.0 mmol), 1-(2-pyrimidyl)piperazine (656 mg, 4.0 mmol) in 3 ml of 1-BuOH was heated with stirring at 130° C. for 3 days. The solvent was removed by evaporation in vacuo, the residue was treated with water to give a suspension. The solid was then filtered off, washed with water, dried over filter funnel in vacuo to give light pink solid, yielding white solid (22.1 g, 66 mmol, 97.3%). ESI-MS: m/z 335.2 (M+H+). 1H NMR (DMSO): 1H NMR (DMSO): d 8.406 (d, J=6.5, 2H), 7.740 (d, J=4.0, 2H), 7.558 (s, 3H), 6.686 (t, J=4.8, J=4.4, 1H), 6.841 (s, 1H), 3.881 (s, 4H), 3.620 (s, 4H), 3.776 (s, 4H).

4-chloro-6-phenyl-3-(4-pyrimidin-2-ylpiperazin-1-yl)pyridazine (MW01-6-127WH)

6-phenyl-3-(4-pyrimidin-2-ylpiperazin-1-yl)pyridazin-4-ol (22.0 g, 66 mmol) was suspended in 75 ml phosphorus oxychloride and heated with stirring at 100° C. for 3 h. After cooling to room temperature the mixture was poured onto crushed ice. The mixture was then neutralized with NaOH solution to give white suspension. The precipitation was filtered off, washed with water, dried over filter funnel to provide white solid (21.3 g, 60.3 mmol, 91.4%). ESI-MS: m/z 353.4 (M+H+). 1H NMR (CDCl3): d 8.377 (d, J=4.5, 2H), 8.036 (d, J=7.5, 2H), 7.833 (s, 1H), 7.508 (m, 3H), 6.564 (1, J=4.5, 1H), 4.073 (t, J=4.0, J=4.5, 4H), 3.672 (t, J=4.0, J=4.5, 4H).

4,6-diphenyl-3-(4-pyrimidin-2-ylpiperazin-1-yl)pyridazine (MW01-5-188WH)

A mixture of 3-chloro-4,6-diphenylpyridazine (267 mg, 1.0 mmol), 1-(2-pyrimidyl)piperazine (656 mg, 4.0 mmol) in 3 ml of 1-BuOH was heated with stirring at 130° C. for 3 days. The solvent was removed by evaporation in vacuo, the residue was treated with water to give a suspension. The solid was then filtered off washed with water, dried over filter funnel in vacuo to give light pink solid. (320 mg, 0.81 mmol, yield 81.1%). ESI-MS: m/z 395.5 (M+H+). HRMS calcd 395.1979. found 395.1973; 1H NMR (CDCl3): d 8.329 (d, J=5.0, 2H), 8.101 (d, J=7.5, 2H), 7.734 (d, J=7.5, 2H), 7.655 (s, 1H), 7.509 (m, 6H), 6.530 (t, J=4.5, 1H), 3.836 (t, J=4.5, J=5.0, 4H), 3.394 (t, J=5.0, J=4.5, 4H).

Scheme 2

4,5-dihydro-6-phenyl-4-phenylpyridazin-3(2H)-one 135 ml (135 mmole) of a solution of phenylmagnesium bromide (1M) in THF was added to a hot suspension of 6-phenylpyridazinone compound 7.8 g (45 mmole) in dry toluene (50 ml). The mixture was refluxed for 8 h, left overnight at ambient temperature, then decomposed with a saturated solution of ammonium chloride. The organic layer was separated, and the aqueous layer was extracted with 100 ml of ethyl acetate. The solvent was removed and the residue was crystallized from ethanol. The crystals were collected by filtering and dried over a medium frit sintered glass funnel in vacuo to give 5.6 g of white crystals. Yield was 50%, confirmed by ESI-MS, ESI-MS: m/z 250.1 (M+H+).

6-phenyl-4-phenylpyridazin-3(2H)-one 4.4 g (17.5 mmole) of 6-pyridazinone obtained above was placed in a 50 ml single-necked round bottom flask followed by 4.7 g (35 mmole) of anhydrous copper (II) chloride and then 20 ml of acetonitrile to give a brown yellow suspension. A reflux condenser was connected to the flask and a dry tube filled with CaCl2 was fitted to the top of the condenser. The reaction mixture was heated to reflux in an oil bath (110 C) for 3 h. The color of the reaction suspension changed to dark yellow once the reflux started. After the completion of the reaction (monitored by HPLC), the flask was removed from the oil bath and cooled to ambient temperature. The mixture was poured on to 200 g of crushed ice and stirred vigorously for 10 minutes to give a gray precipitate and blue liquid. The precipitate was then collected by filtering (pH of the filtrate was 1.5-2.0), and washed with 50 ml of a 1N HCl solution to rid the solid of any remaining copper byproducts. This is followed by washing with 100 ml of Milli-Q water to get rid of the acid in the solid, and is monitored by checking the pH value of the filtrate. The solid was washed until the filtrate shows a pH of 7, after approximately 5 washes. The solid was dried over a medium frit sintered glass funnel in vacuo to give 3.9 g of a blue gray solid. Yield was 90%, confirmed by ESI-MS. ESI-MS: m/z 248.1 (M+H+).

3-chloro-6-phenyl-4-phenylpyridazine 2.0 g (8 mmole) of 6-phenylpyridazinone obtained above and 10 ml (54 mmole) of phosphorus oxychloride (reagent grade, Aldrich) were placed in a 50 ml single-necked round bottom flask. The flask was connected with a reflux condenser and a dry tube filled with CaCl2 was fitted to the top of the condenser. (HCl gas is formed in the reaction so a basic solution such as NaOH may be needed to absorb HCl in a large-scale synthesis). The reaction mixture was stirred in an oil bath (90 C) for 2 h, then cooled to ambient temperature and poured onto crushed ice. (phosphorus oxychloride can be decomposed by water to give HCl and $H_3PO_4$). The mixture was then stirred vigorously for 10 minutes to give a white suspension. The suspension was neutralized with a 2N NaOH solution until the pH of the suspension was pH=7. The precipitate was filtered, washed three times with 100 ml of water and dried over a medium frit sintered glass funnel in vacuo to provide 1.8 g of a light pink powder. Yield was 85%, confirmed by ESI-MS. ESI-MS: m/z 266.4 (M+H+).

2-(4-(6-phenyl-4-phenylpyridazin-3-yl)piperazin-1-yl)pyrimidine 1.1 g (4.0 mmole) of 3-chloropyridazine obtained above was placed in a 30 ml pressure vessel followed by addition of 2.6 g (16.0 mmole) of 1-(2-pyrimidyl)piperazine and then 15 ml of 1-BuOH (reagent grade). The vessel was sealed tightly and placed into an oil bath and stirred at 130° C. (temperature of oil bath) for 3 days. The reaction mixture was then cooled to ambient temperature and transferred to a single-necked flask for evaporation under reduced pressure. Removal of solvent gave rise to a brown-red residue that was treated with 30 ml of water to give a brown suspension. The solid was collected by filtering and washed with 50 mL of water three times and dried over a filter funnel in vacuo to provide 0.96 g of light yellow solid. Yield was 90%, ESI-MS: m/z 395.5 (M+H+). HRMS calcd 395.1979. found 395.1973; 1H NMR (CDCl3): d 8.329 (d, J=5.0, 2H), 8.101 (d, J=7.5, 2H), 7.734 (d, J=7.5, 2H), 7.655 (s, 1H), 7.509 (m, 6H), 6.530 (t, J=4.5, 1H), 3.836 (t, J=4.5, J=5.0, 4H), 3.394 (t, J=5.0, J=4.5, 4H).

Scheme 3

3-chloro-6-phenylpyridazin-4-ol was synthesized according to the procedure described by Coudert, P., et al. [18].

4,6-diphenyl-3-(4-pyrimidin-2-ylpiperazin-1-yl)pyridazine (MW01-5-188WH)

A mixture of 3-chloro-4,6-diphenylpyridazine (267 mg, 1.0 mmol), 1-(2-pyrimidyl)piperazine (656 mg, 4.0 mmol) in 3 ml of 1-BuOH was heated with stirring at 130 C for 3 days. The solvent was removed by evaporation in vacuo, the residue was treated with water to give a suspension. The solid was then filtered off, washed with water, dried over filter funnel in vacuo to give light pink solid. (320 mg, 0.81 mmol, yield 81.1%). ESI-MS: m/z 395.5 (M+H+). HRMS calcd 395.1979. found 395.1973; 1H NMR (CDCl3): d 8.329 (d, J=5.0, 2H), 8.101 (d, J=7.5, 2H), 7.734 (d, J=7.5, 2H), 7.655 (s, 1H), 7.509 (m, 6H), 6.530 (t, J=4.5, 1H), 3.836 (t, J=4.5, J=5.0, 4H), 3.394 (t, J=5.0, J=4.5, 4H).

Example 13

Preparation of 4-pyridyl-6-phenyl-3-(4-pyrimidin-2-ylpiperazin-1-yl)pyridazine (MW01-6-189WH)

Figure 19:
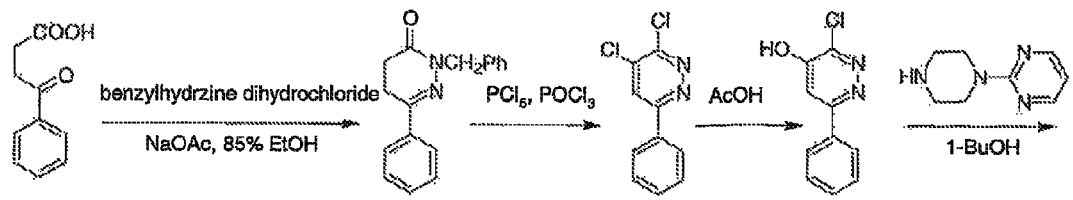
FIG. 19, parts (A) and (B), are synthetic schemes for MW01-6-189WH.
Figure 19:
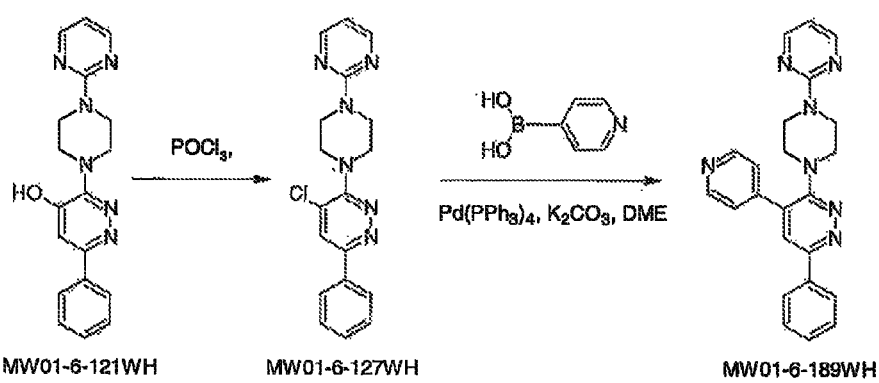
Figure 19:
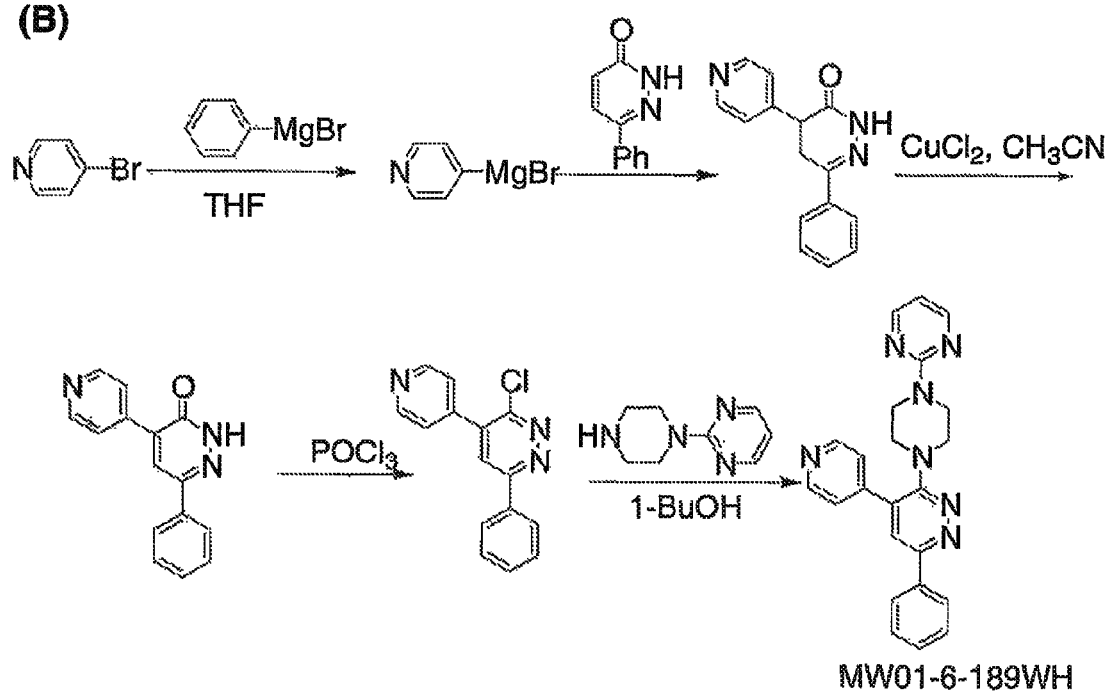

4-pyridyl-6-phenyl-3-(4-pyrimidin-2-ylpiperazin-1-yl)pyridazine (MW01-6-189WH) was prepared by two synthetic schemes as depicted in FIG. 19 (parts (A) and (B)), which were carried out as described in detail herein. The various reaction schemes (Schemes 1 and 2) are generally applicable to the compounds of the present invention and are not restricted in utility only to the preparation of MW01-2-189WH.

Scheme 1

3-chloro-6-phenylpyridazin-4-ol was synthesized according to the procedure described by Coudert, P., et al. [18].

6-phenyl-3-(4-pyrimidin-2-yl)piperazin-1-yl)pyridazin-4-ol (MW01-7-121WH)

This compound was prepared from 3-chloro-4-hydroxy-6-phenylpyridazine (14 g, 68 mmol) A mixture of 3-chloro-4,6-diphenylpyridazine (267 mg, 1.0 mmol), 1-(2-pyrimidyl)piperazine (656 mg, 4.0 mmol) in 3 ml of 1-BuOH was heated with stirring at 130° C. for 3 days. The solvent was removed by evaporation in vacuo, the residue was treated with water to give a suspension. The solid was then filtered off, washed with water, dried over filter funnel in vacuo to give light pink solid. yielding white solid (22.1 g, 66 mmol, 97.3%). ESI-MS: m/z 335.2 (M+H+). 1H NMR (DMSO): 1H NMR (DMSO): d 8.406 (d, J=6.5, 2H), 7.740 (d, J=4.0, 2H), 7.558 (s, 3H), 6.686 (t, J=4.8, J=4.4, 1H), 6.841 (s, 1H), 3.881 (s, 4H), 3.620 (s, 4H), 3.776 (s, 4H).

4-chloro-6-phenyl-3-(4-pyrimidin-2-ylpiperazin-1-yl)pyridazine (MW01-5-127WH)

6-phenyl-3-(4-pyrimidin-2-ylpiperazin-1-yl)pyridazin-4-ol 1 h (22.0 g, 66 mmol) was suspended in 75 ml phosphorus oxychloride and heated with stirring at 100 for 3 h. After cooling to room temperature the mixture was poured onto crushed ice. The mixture was then neutralized with NaOH solution to give white suspension. The precipitation was filtered off, washed with water, dried over filter funnel to provide white solid (21.3 g, 60.3 mmol, 91.4%). ESI-MS: m/z 353.4 (M+H+). 1H NMR. (CDCl3): d 8.377 (d, J=4.5, 2H), 8.036 (d, J=7.5, 2H), 7.833 (s, 1H), 7.508 (m, 3H), 6.564 (t, J=4.5, 1H), 4.073 (t, J=4.0, J=4.5, 4H), 3.672 (t, J=4.0, J=4.5, 4H).

4-pyridyl-6-phenyl-3-(4-pyrimidin-2-ylpiperazin-1-yl)pyridazine (MW01-6-189WH)

Into a reaction tube were added WH-6-127 (1.4 g, 4.0 mmol), K2CO3 powder (1.7 g, 12.4 mmol), Pd(PPh3)4 (240 mg, 0.2 mmol), 4-pyridineboronic acid (664 mg, 5.4 mmol) and 20 ml of DME. Argon was then flushed through the tube for 3 min. The tube was then sealed tightly and heated with stirring at 120 degree for 24 h. After cooled down, the mixture was filter through a celite earth, the filtrate was then concentrated and the residue was purified by column chromatography eluting with 1:4, Ethyl Acetate:Petroleum ether. Tight yellow needle crystals were obtained (0.65 g, 1.65 mmol, yield 41.2%). Confirmed by ESI-MS and NMR. ESI-MS: m/z 396.2 (M+H+). 1H NMR (CDCl3): d 8.809 (d, J=6.0, 2H), 8.335 (d, J=5.0, 2H), 8.090 (d, J=7.5, 2H), 7.750 (m, 6H), 6.543 (t, J=4.5, 1H), 3.868 (t, J=5.0, 4H), 3.404 (t, J=5.0, 4H).

Scheme 2

4,5-dihydro-6-phenyl-4-(pyridin-4-yl)pyridazin-3 (2H)-one

To a 200 ml, three-necked, round-bottomed flask equipped with a magnetic stir bar, 150 ml pressure-equalizing addition funnel, reflux condenser and a glass stopper, was added 21 g (135 mmole) of 4-bromopyridine and 70 of anhydrous THF. The system was oven-dried and flushed with argon before use. 135 ml (135 mmole) of THF solution of phenylmagnesium bromide (1M) was placed in the pressure-equalizing addition funnel. Then, the grignard solution was added drop wise over a period of 10 minutes. After the addition, the reaction was stirred for 15 minutes for completion. The solution of Grignard reagent was then obtained. A solution of 4-pyridylmagnesium bromide obtained above was added to a hot suspension of 6-phenylpyridazinone compound 7.8 g (45 mmole) in dry toluene (50 ml). The mixture was refluxed for 8 h, left overnight at ambient temperature, then decomposed with a saturated solution of ammonium chloride. The organic layer was separated, and the aqueous layer was extracted with 100 ml of ethyl acetate. The solvent was removed and the residue was crystallized from ethanol. The crystals were collected by filtering and dried over a medium frit sintered glass funnel in vacuo to give 5.6 g of white crystals. Yield was 50%, confirmed by ESI-MS. ESI-MS: m/z 252.1 (M+H+).

6-phenyl-4-(pyridin-4-yl)pyridazin-3(2H)-one 4.4 g (17.5 mmole) of 6-pyridazinone obtained above was placed in a 50 ml single-necked round bottom flask followed by 4.7 g (35 mmole) of anhydrous copper (II) chloride and then 20 ml of acetonitrile to give a brown yellow suspension. A reflux condenser was connected to the flask and a dry tube filled with CaCl2 was fitted to the top of the condenser. The reaction mixture was heated to reflux in an oil bath (110 C) for 3 h. The color of the reaction suspension changed to dark yellow once the reflux started. After the completion of the reaction (monitored by HPLC), the flask was removed from the oil bath and cooled to ambient temperature. The mixture was poured on to 200 g of crushed ice and stirred vigorously for 10 minutes to give a gray precipitate and blue liquid. The precipitate was then collected by filtering (pH of the filtrate was 1.5-2.0), and washed with 50 ml of a 1N HCl solution to rid the solid of any remaining copper byproducts. This is followed by washing with 100 ml of Milli-Q water to get rid of the acid in the solid, and is monitored by checking the pH value of the filtrate. The solid was washed until the filtrate shows a pH of 7, after approximately 5 washes. The solid was dried over a medium frit sintered glass funnel in vacuo to give 3.9 g of a blue gray solid. Yield was 90%, confirmed by ESI-MS, ESI-MS: m/z 250.1 (M+H+).

3-chloro-6-phenyl-4-(pyridin-4-yl)pyridazine 2.0 g (8 mmole) of 6-phenylpyridazinone obtained above and 10 ml (54 mmole) of phosphorus oxychloride (reagent grade, Aldrich) were placed in a 50 ml single-necked round bottom flask. The flask was connected with a reflux condenser and a dry tube filled with CaCl2 was fitted to the top of the condenser. (HCl gas is formed in the reaction so a basic solution such as NaOH may be needed to absorb HCl in a large-scale synthesis). The reaction mixture was stirred in an oil bath (90 C) for 2 h, then cooled to ambient temperature and poured onto crushed ice. (phosphorus oxychloride can be decomposed by water to give HCl and H3PO4). The mixture was then stirred vigorously for 10 minutes to give a white suspension. The suspension was neutralized with a 2N NaOH solution until the pH of the suspension was pH=7. The precipitate was filtered, washed three times with 100 ml of water and dried over a medium frit sintered glass funnel in vacuo to provide 1.8 g of a light pink powder. Yield was 85%, confirmed by ESI-MS. ESI-MS: m/z 268.4 (M+H+).

4-pyridyl-6-phenyl-3-(4-pyrimidin-2-ylpiperazin-1-yl)pyridazine (MW01-6-189WH)

1.1 g (4.0 mmole) of 3-chloropyridazine obtained above was placed in a 30 ml pressure vessel followed by addition of 2.6 g (16.0 mmole) of 1-(2-pyrimidyl)piperazine and then 15 ml of 1-BuOH (reagent grade). The vessel was sealed tightly and placed into an oil bath and stirred at 130° C. (temperature of oil bath) for 3 days. The reaction mixture was then cooled to ambient temperature and transferred to a single-necked flask for evaporation under reduced pressure. Removal of solvent gave rise to a brown-red residue that was treated with 30 ml of water to give a brown suspension. The solid was collected by filtering and washed with 50 mL of water three times and dried over a filter funnel in vacuo to provide 0.96 g of light yellow solid. Yield was 90%, confirmed by ESI-MS and NMR. ESI-MS: m/z 396.2 (M+H+). 1H NMR (CDCl3): d 8.809 (d, J=6.0, 2H), 8.335 (d, J=5.0, 211), 8.090 (d, J=7.5, 2H), 7.750 (m, 6H), 6.543 (t, J=4.5, 1H), 3.868 (t, J=5.0, 4H), 3.404 (t, J=5.0, 4H).

Example 14

Preparation of 4,6-diphenyl-3-(4-phenylpiperazin-1-yl)pyridazine (MW01-7-029WH)

Figure 20:
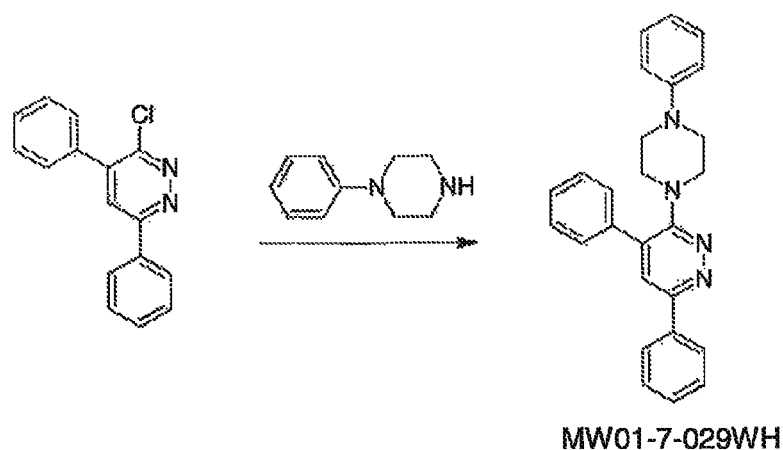
FIG. 20 is a synthetic scheme for MW01-7-029WH.

A synthetic reaction scheme for the preparation of 4,6-diphenyl-3-(4-phenylpiperazin-1-yl)pyridazine (MW01-7-029WH) is depicted in FIG. 20, and synthesis was carried out as described herein. The compound was prepared from 3-chloro-4,6-diphenylpyridazine (100 mg, 0.37 mmol) in the same manner as described for MW01-7-057WH, yielding white solid (123 mg, 0.31 mmol, 83.1%). ESI-MS: m/z 393.2 (M+H+). NMR (CDCl3): d 8.107 (d, J=8.0, 2H), 7.736 (d, J=7.5, 2H), 7.651 (s, 1H), 7.500 (m, 5H), 7.290 (t, J=8.5, J=6.5, 3H), 6.958 (d, J=7.5, 2H), 6.899 (t, J=7.0, 1H), 3.487 (s, 4H), 3.214 (s, 4H).

Example 15

Preparation of 4,6-diphenyl-3-(4-methylpiperazin-1-yl)pyridazine (MW01-7-027B-WH)

A synthetic reaction scheme for the preparation of 4,6-diphenyl-3-(4-methylpiperazin-1-yl)pyridazine (MW01-7-

Figure 21:
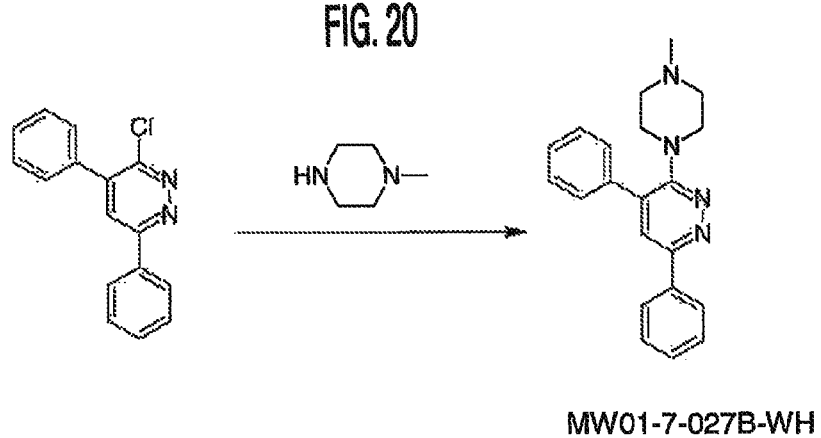
FIG. 21 is a synthetic scheme for MW01-7-027B-WH.

027B-WH) is depicted in FIG. 21, and synthesis was carried out as described herein. The compound was prepared from 3-chloro-4,6-diphenylpyridazine (100 mg, 0.37 mmol) in the same manner as described for MW01-7-057WH, yielding white solid (119 mg, 0.35 mmol, 94.5%). ESI-MS: m/z 331.1 (M+H+). NMR (CDCl3): d 8.089 (d, J=7.5, 2H), 7.643 (d, J=7.5, 2H), 7.611 (s, 1H), 7.510 (m, 6H), 3.365 (s, 3H), 2.472 (s, 4H), 2.337 (s, 4H).

Example 16

Preparation of 4,6-diphenyl-3-(4-cyclohexylpiperazin-1-yl)pyridazine (MW01-3-065SRM)

Figure 22:
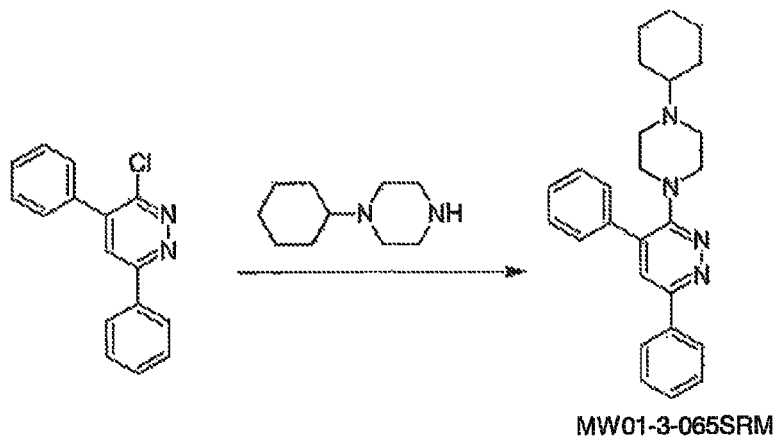
FIG. 22 is a synthetic scheme for MW01-3-065SRM.

A synthetic reaction scheme for the preparation of 4,6-diphenyl-3-(4-cyclohexylpiperazin-1-yl)pyridazine (MW01-3-065SRM) is depicted in FIG. 22, and synthesis was carried out as described herein. The compound was prepared from 3-chloro-4,6-diphenylpyridazine (300 mg, 1.1 mmol) in the same manner as described for MW01-7-057WH, yielding white solid (350 mg, 0.87 mmol, 87%). ESI-MS: m/z 399.2 (M+H+). 1H NMR (CDCl3): d 8.09 (d, J=7.5, 2H), 7.68 (d, J=7.5, 2H), 7.59 (s, 1H), 7.56-7.42 (m, 6H), 3.39 (s, 4H), 2.62 (s, 4H), 2.273 (s, 1H), 2.01-1.78 (m, 4H), 1.63 (d, J=12.5, 1H), 1.33-1.08 (m, 5H).

Example 17

Preparation of 4,6-diphenyl-3-(4-isopropylpiperazin-1-yl)pyridazine (MW01-3-066SRM)

Figure 23:
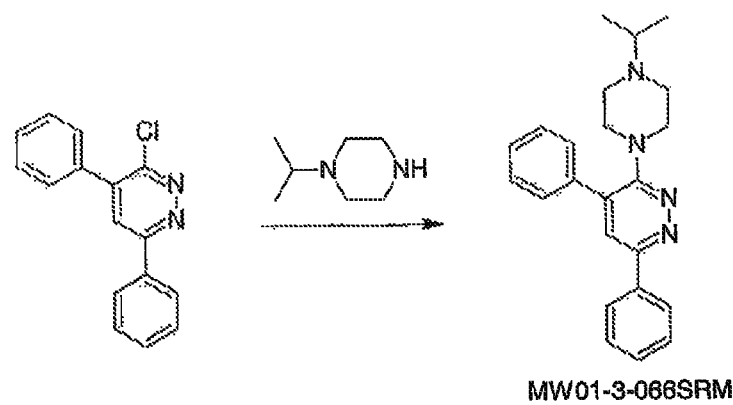
FIG. 23 is a synthetic scheme for MW01-3-066SRM.

A synthetic reaction scheme for the preparation of 4,6-diphenyl-3-(4-isopropylpiperazin-1-yl)pyridazine (MW01-3-066SRM) is depicted in FIG. 23, and synthesis was carried out as described herein. The compound was prepared from 3-chloro-4,6-diphenylpyridazine (300 mg, 1.1 mmol) in the same manner as described for MW01-7-057WH, yielding white solid (290 mg, 0.81 mmol, 72%). m/z 359.2 (M+H+), 1H NMR (CDCl3): d 8.09 (d, J=7.5, 2H), 7.69 (d, J=7.5, 2H), 7.61 (s, 1H), 7.54-7.46 (m, 6H), 3.40 (s, 4H), 2.72 (m, 1H), 2.59 (s, 4H), 1.10 (d, J=6, 6H).

Example 18

Preparation of 4,6-diphenyl-3-piperazinylpyridazine (MW01-7-133WH)

Figure 24:
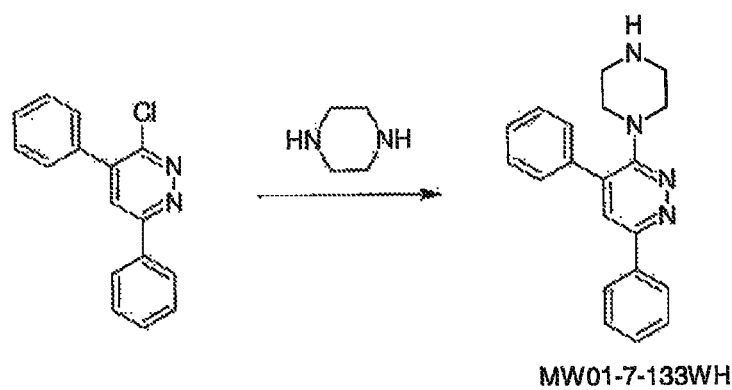
FIG. 24 is a synthetic scheme for MW01-7-133WH.

A synthetic reaction scheme for the preparation of 4,6-diphenyl-3-piperazinylpyridazine (MW01-7-133WH) is depicted in FIG. 24, and synthesis was carried out as described herein. The compound was prepared from 3-chloro-4,6-diphenylpyridazine (533 mg, 20 mmole) in the same manner as described for MW01-7-057WH, yielding light yellow solid (550 mg, 17.4 mmole, yield 86.9%). ESI-MS: m/z 317.3 (M+H+). 1H NMR (CDCl3): d 8.086 (d, J=7.5, 2M), 7.705 (d, J=7.5, 2H), 7.619 (s, 1H), 7.498 (m, 6H), 3.318 (d, J=4.0, 4H), 2.932 (d, J=4.0, 4H) 1.896 (s, 1H).

Example 19

Preparation of 2-(4-(6-phenyl-4-(piperidin-1-yl) pyridazin-3-yl)piperazin-1-yl)pyrimidine (MW01-7-107WH)

Figure 25:
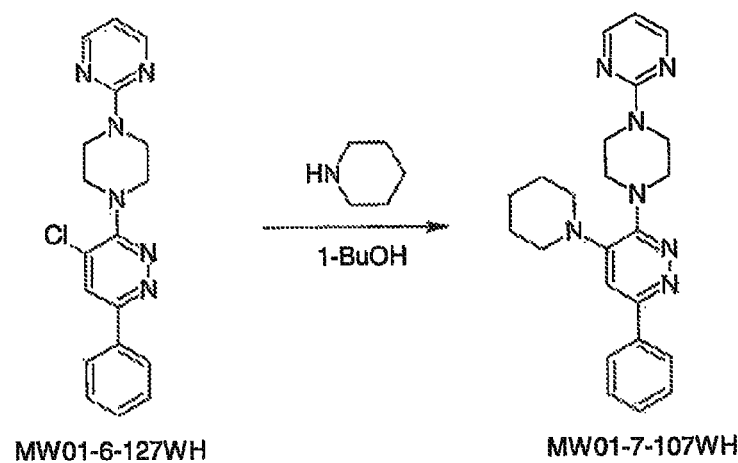
FIG. 25 is a synthetic scheme for MW01-7-107WH.

A synthetic reaction scheme for the preparation of 2-(4-(6-phenyl-4-(piperidin-1-yl)pyridazin-3-yl)piperazin-1-yl)pyrimidine (MW01-7-107WH) is depicted in FIG. 25, and synthesis was carried out as described herein. The compound was prepared from MW01-6-127WH (200 mg, 0.57 mmole) in the same manner as described for MW01-7-057WH, yielding light yellow solid (220 mg, 0.55 mmole, yield 96.3%). ESI-MS: m/z 402.5 (M+H+).

Example 20

Preparation of 6-methyl-4-phenyl-3-(4-pyrimidin-2-ylpiperazin-1-yl)pyridazine (MW01-7-057)

Figure 26:
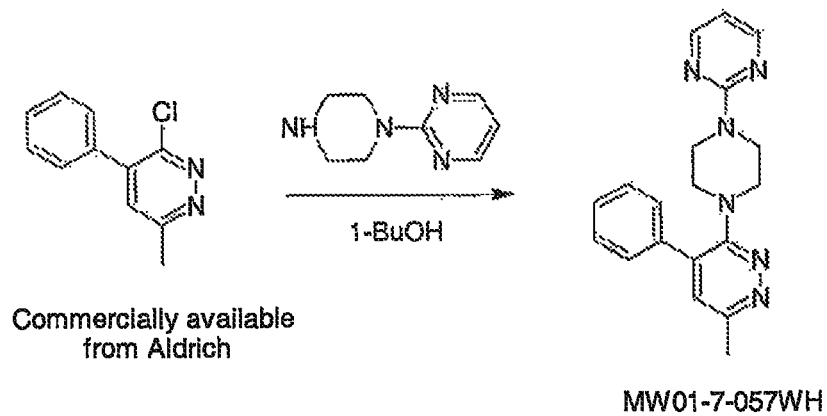
FIG. 26 is a synthetic scheme for MW01-7-057WH.

A synthetic reaction scheme for the preparation of 6-methyl-4-phenyl-3-(4-pyrimidin-2-ylpiperazin-1-yl) pyridazine (MW01-7-057) is depicted in FIG. 26, and synthesis was carried out as described herein. A mixture of 3-chloro-6-methyl-4-phenylpyridazine (100 mg, 0.5 mmol), 1-(2-pyrimidyl)piperazine (400 mg, 2.0 mmol) in 3 ml of 1-BuOH was heated with stirring at 130 C for 7 days. The solvent was removed by evaporation in vacuo, the residue was treated with water to give a suspension. The solid was then filtered off, washed with water, then 1:3, Ethyl Acetate: Petroleum ether, dried over filter tunnel in vacuo to give light yellow solid (68 mg, 0.20 mmol, yield 41.7%). Purity >95%; ESI-MS: m/z 333.1 (M+H+). 1H NMR (CDCl3): d 8.310 (d, J=5.0, 2H), 7.678 (d, J=7.5, 2H), 7.476 (m, 3H), 7.119 (s, H), 6.509 (t, J=4.5, 1H), 3.785 (t, J=4.5, J=5.0, 4H), 3.277 (t, J=4.5, J=5.0, 4H), 2.669 (s, 3H).

Example 21

Preparation of 2-(4-(5-phenyl-6-(pyridin-4-yl) pyridazin-3-yl)piperazin-1-yl)pyrimidine (MW01-2-163MAS)

Figure 27:
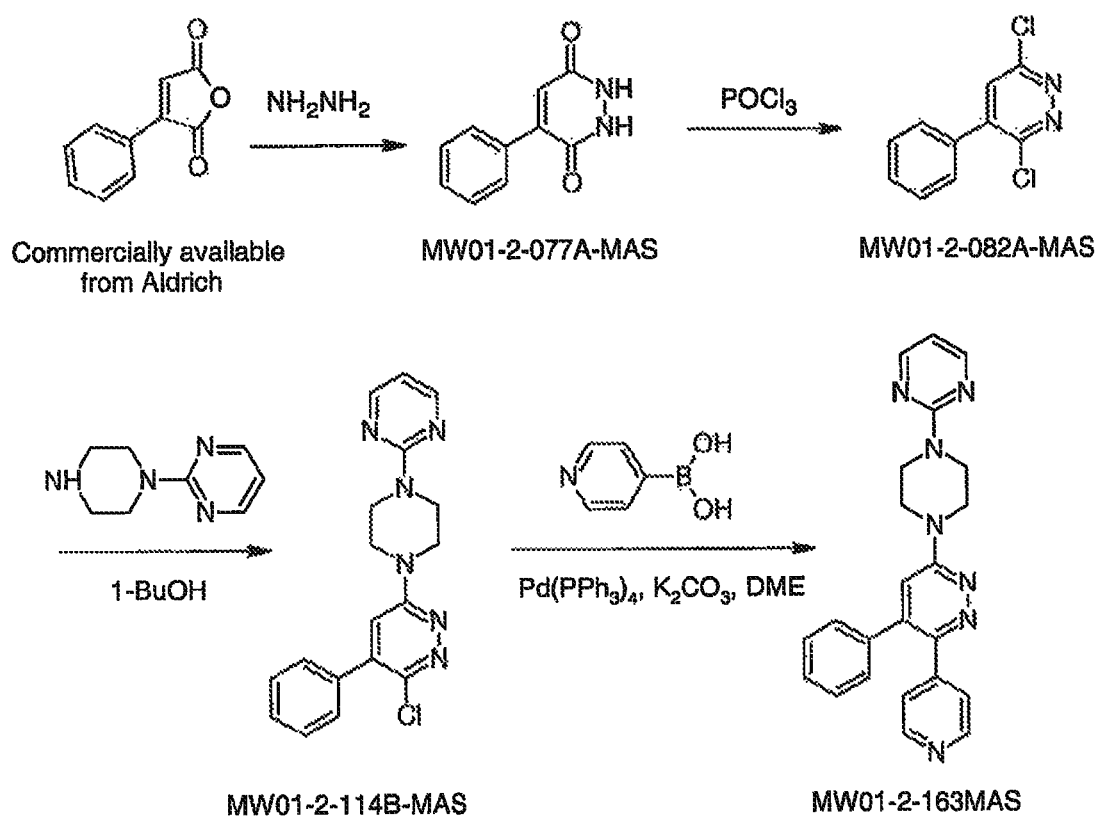
FIG. 27 is a synthetic scheme for MW01-2-163MAS.

A synthetic reaction scheme for the preparation of 2-(4-(5-phenyl-6-(pyridin-4-yl)pyridazin-3-yl)piperazin-1-yl)pyrimidine (MW01-2-163MAS) is depicted in FIG. 27, and synthesis was carried out as described herein.

1,2-dihydro-4-phenylpyridazine-3,6-dione (MW01-2-077A-MAS)

4.0 g (23 mmole) of 3-phenylfuran-2,5-dione was added to a 100 ml single-necked round bottom flask followed by 2.9 g (27.6 mmole) of hydrazine monohydrate and then 20 ml of reagent grade ethanol (95%). The flask was fitted with a reflux condenser and the reaction mixture was heated to reflux in an oil bath at 110 degree (temperature of oil bath) and stirred for 2 h. The flask was then removed from the oil bath and the reaction mixture cooled to ambient temperature. The stir bar was removed and the solvent was evaporated in vacuo in a water bath at 45 degree. The residue was then treated with 50 ml of Milli-Q water and stirred for 10 minutes to give a suspension. The precipitate was collected by filtering, washed with 100 ml of Milli-Q water, and dried over a medium frit sintered glass funnel in vacuo to give 3.9 g of white solid. Yield, 91%, confirmed by ESI-MS. ESI-MS: m/z 189.2 (M+H$^+$).

3,6-dichloro-4-phenylpyridazine (MW01-2-082A-MAS)

1.5 g (8 mmole) of 6-phenylpyridazinone obtained above and 10 ml (54 mmole) of phosphorus oxychloride (reagent grade, Aldrich) were placed in a 50 ml single-necked round bottom flask. The flask was connected with a reflux condenser and a dry tube filled with CaCl2 was fitted to the top of the condenser. (HCl gas is formed in the reaction so a basic solution such as NaOH may be needed to absorb HCl in a large-scale synthesis). The reaction mixture was stirred in an oil bath (90° C.) for 2 h, then cooled to ambient temperature and poured onto crushed ice. (phosphorus oxychloride can be decomposed by water to give HCl and H3PO4). The mixture was then stirred vigorously for 10 minutes to give a white suspension. The suspension was neutralized with a 2N NaOH solution until the pH of the suspension was pH=7. The precipitate was filtered, washed three times with 100 ml of water and dried over a medium frit sintered glass funnel in vacuo to provide 1.5 g of a white solid, Yield was 85%, confirmed by ESI-MS. ESI-MS: m/z 226.1 (M+H$^+$).

2-(4-(6-chloro-5-phenylpyridazin-3-yl)piperazin-1-yl)pyrimidine (MW01-2-114B-MAS)

A mixture of 3,6-dichloro-4-phenylpyridazine (1.35 g, 6 mmol), 1-(2-pyrimidyl)piperazine (1.2 g, 6.6 mmol) in 10 ml of 1-BuOH was heated with stirring at 80° C. for 12 h. The solvent was removed by evaporation in vacuo, the residue was treated with water to give a suspension. The solid was then filtered off, washed with water, dried over filter funnel in vacuo to give white solid (1.8 g, 5.2 mmol, yield 86.0%). ESI-MS: m/z 353.9.

2-(4-(5-phenyl-6-(pyridin-4-yl)pyridazin-3-yl)piperazin-1-yl)pyrimidine (MW01-2-163MAS)

Into a reaction tube were added MW01-2-114B-MAS (1.4 g, 4.0 mmol), K$_2$CO$_3$ powder (1.7 g, 12.4 mmol), Pd(PPh3)4 (240 mg, 0.2 mmol), 4-pyridineboronic acid (664 mg, 5.4 mmol) and 20 ml of DME. Argon was then flushed through the tube for 3 min. The tube was then sealed tightly and heated with stirring at 120° C. for 24 h. After cooled down, the mixture was filter through a celite earth, the filtrate was then concentrated and the residue was purified by column chromatography eluting with 1:4, Ethyl Acetate:Petroleum ether. Light yellow needle crystals were obtained (0.69 g, 1.74 mmol, yield 43.5%). Confirmed by ESI-MS and NMR. ESI-MS: m/z 396.2 (M+H$^+$).

Example 22

Preparation of N-(cyclopropylmethyl)-6-phenyl-4-(pyridin-4-yl)pyridazin-3-amine (MW01-7-084WH)

Figure 28:
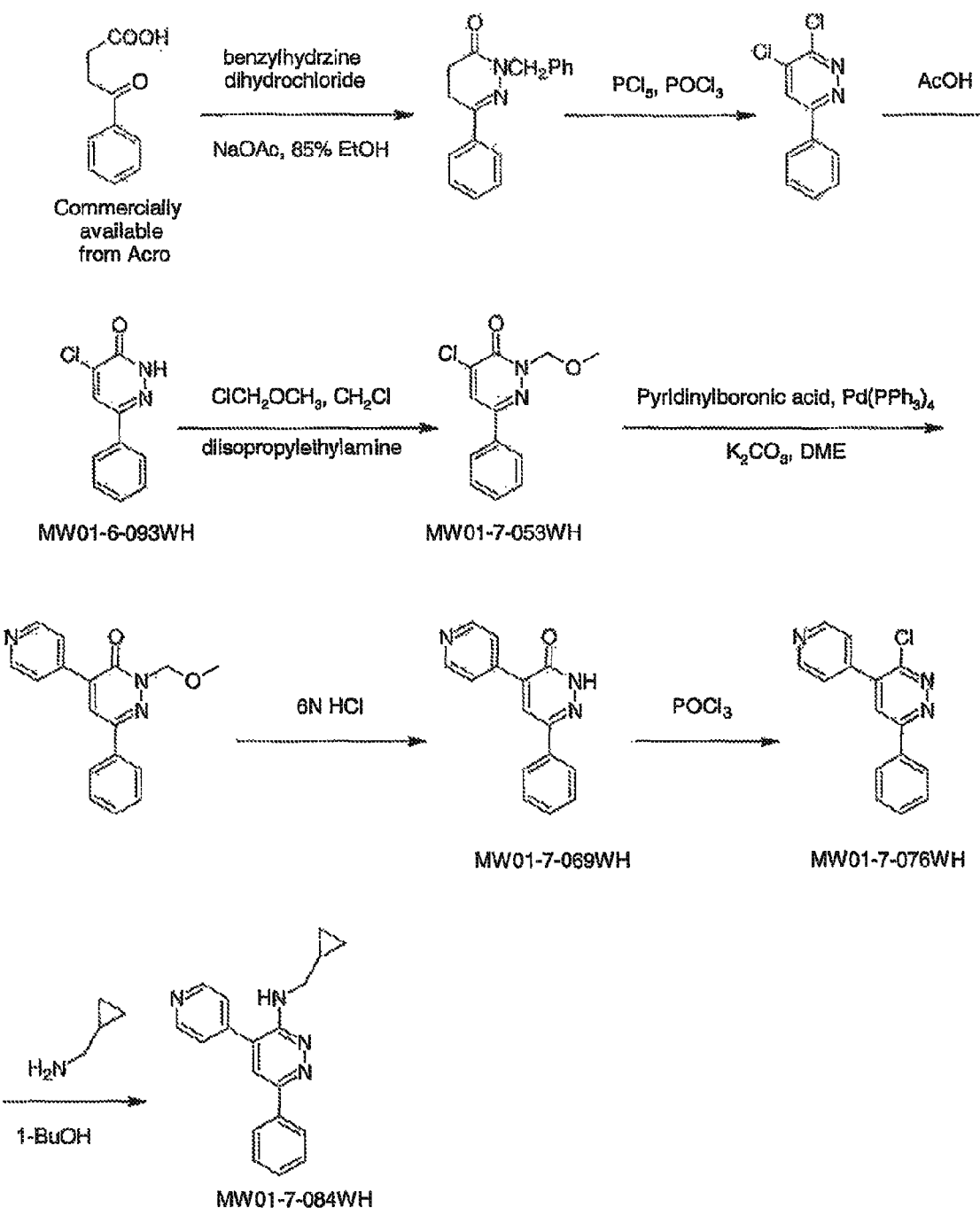
FIG. 28 is a synthetic scheme for MW01-7-084WH.
Figure 29:
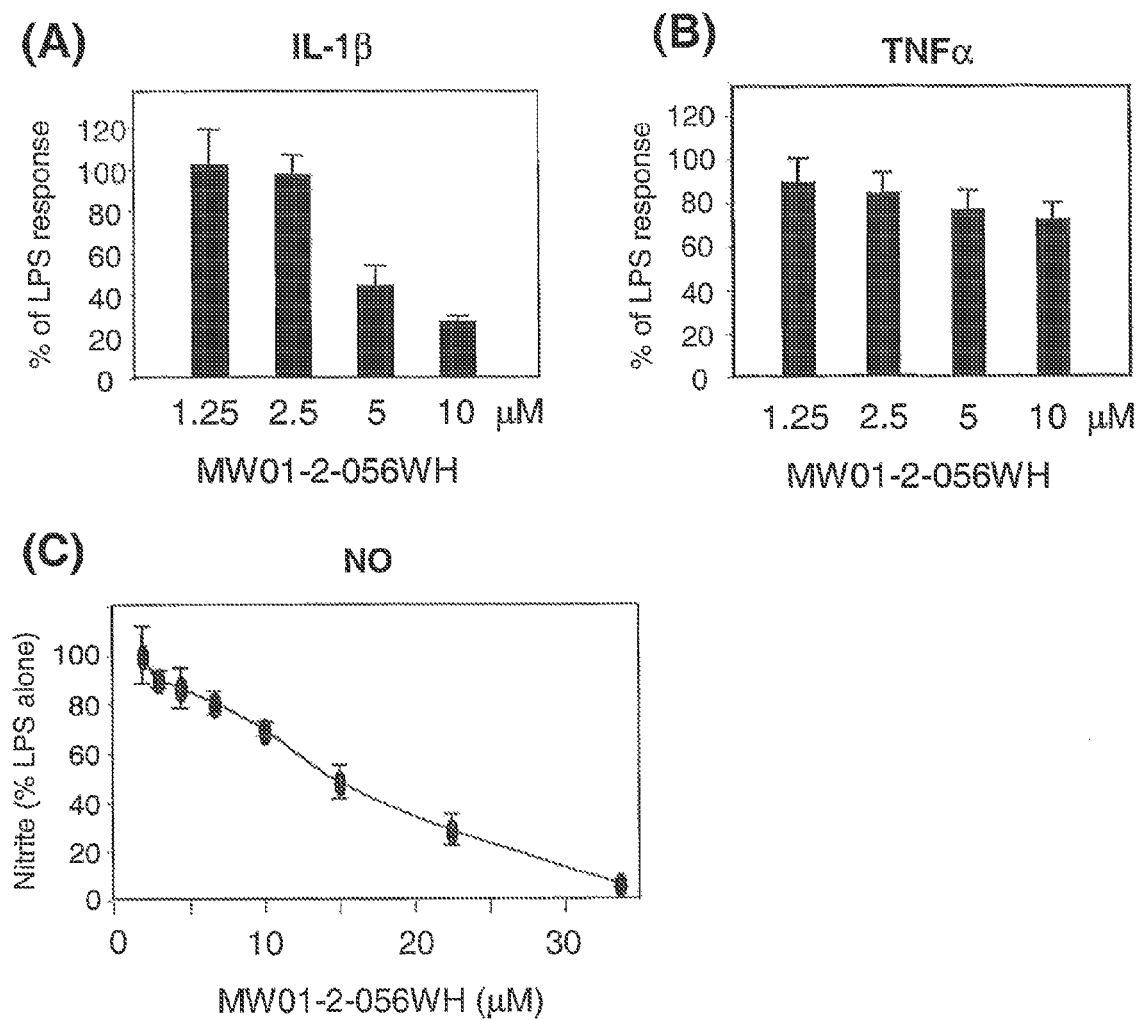
FIG. 29, parts (A) thru (C), shows graphical data of the assays used herein for MW01-2-056WH.
Figure 30:
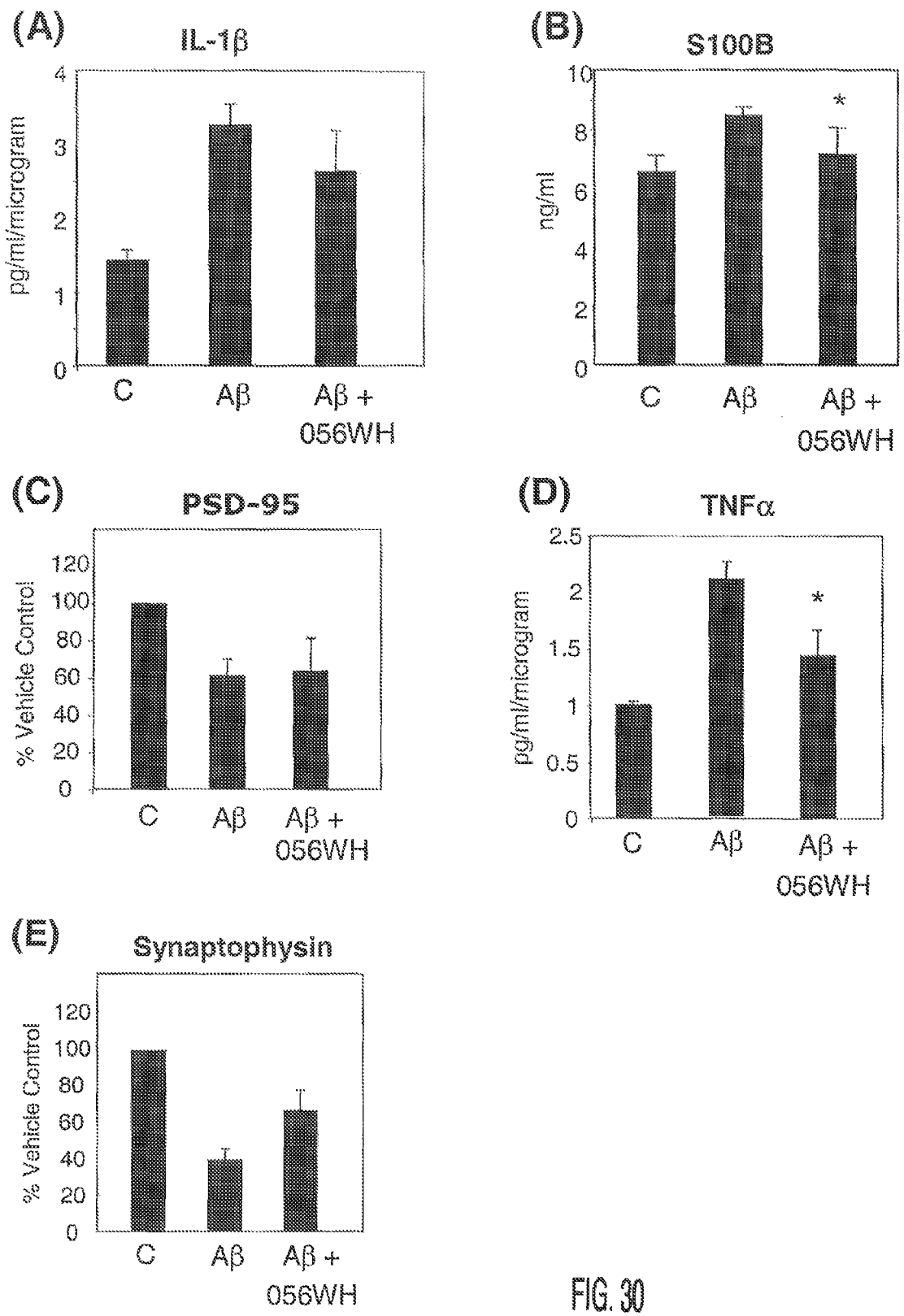
FIG. 30, parts (A) thru (E), shows graphical data of the assays used herein for MW01-2-056WH.
Figure 31:
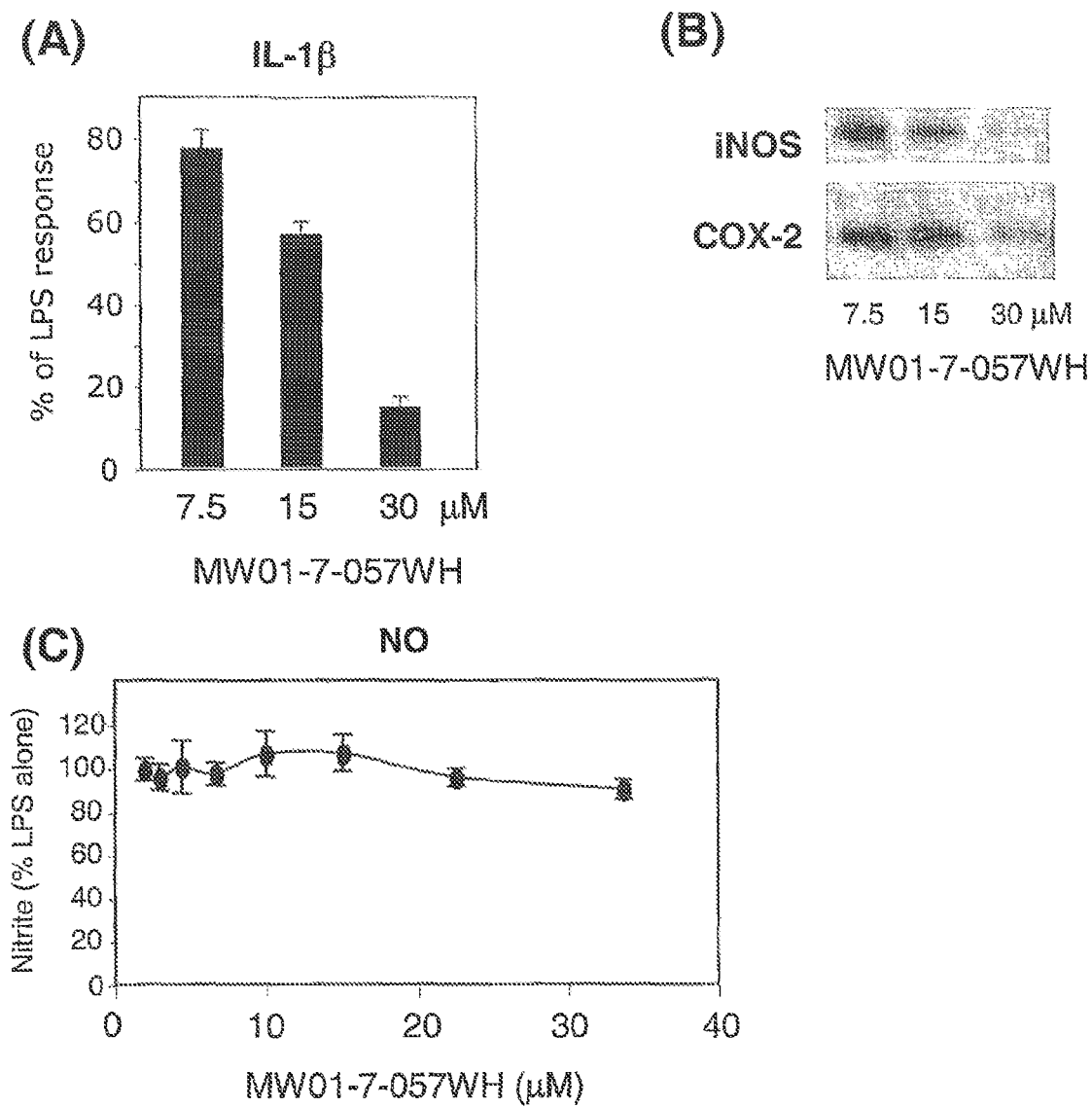
FIG. 31, parts (A) thru (C), shows graphical data of the assays used herein and immunoblots for biological activity of MW01-7-057WH.
Figure 32:
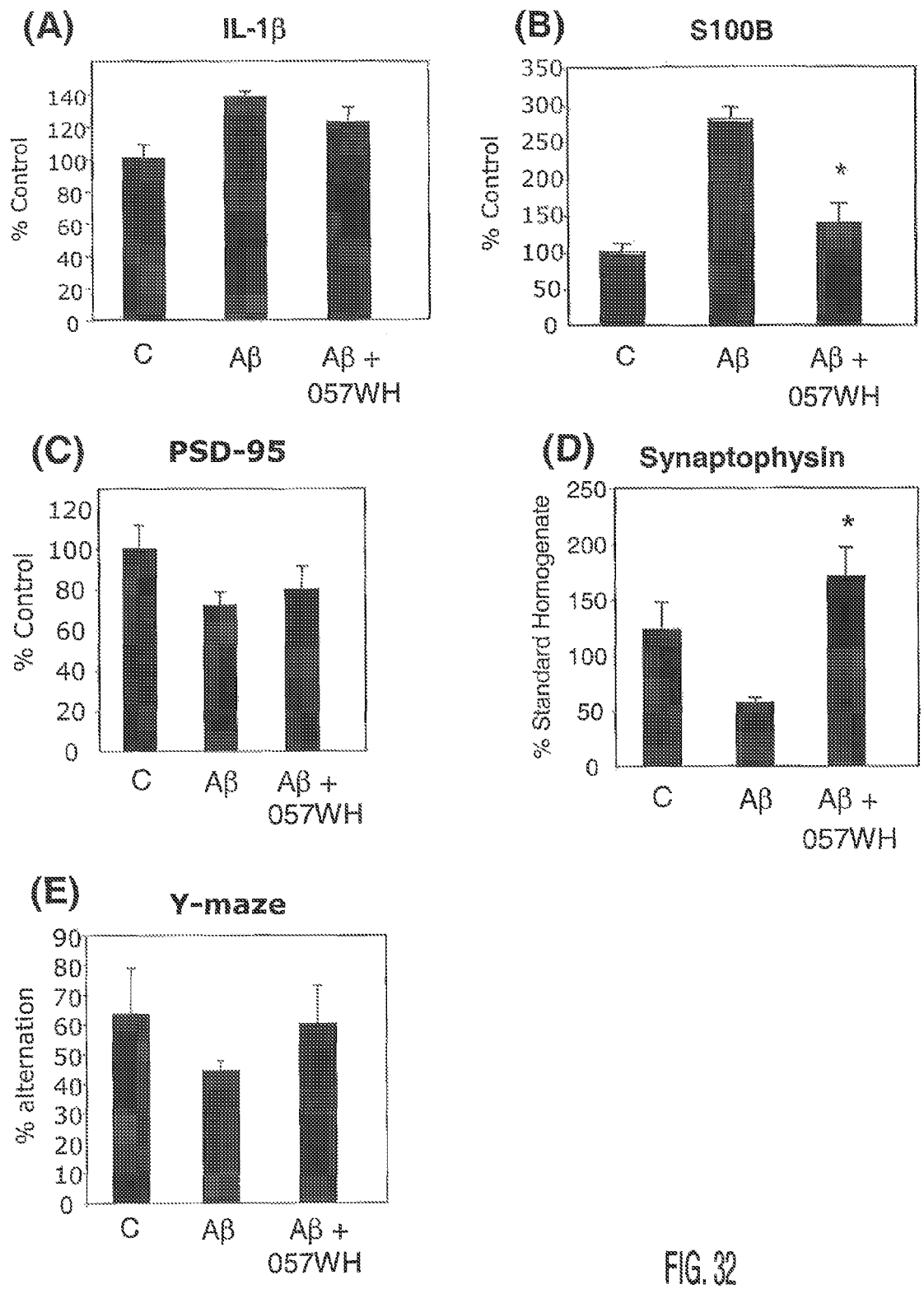
FIG. 32, parts (A) thru (E), shows graphical data of the assays used herein for MW01-7-057WH.
Figure 33:
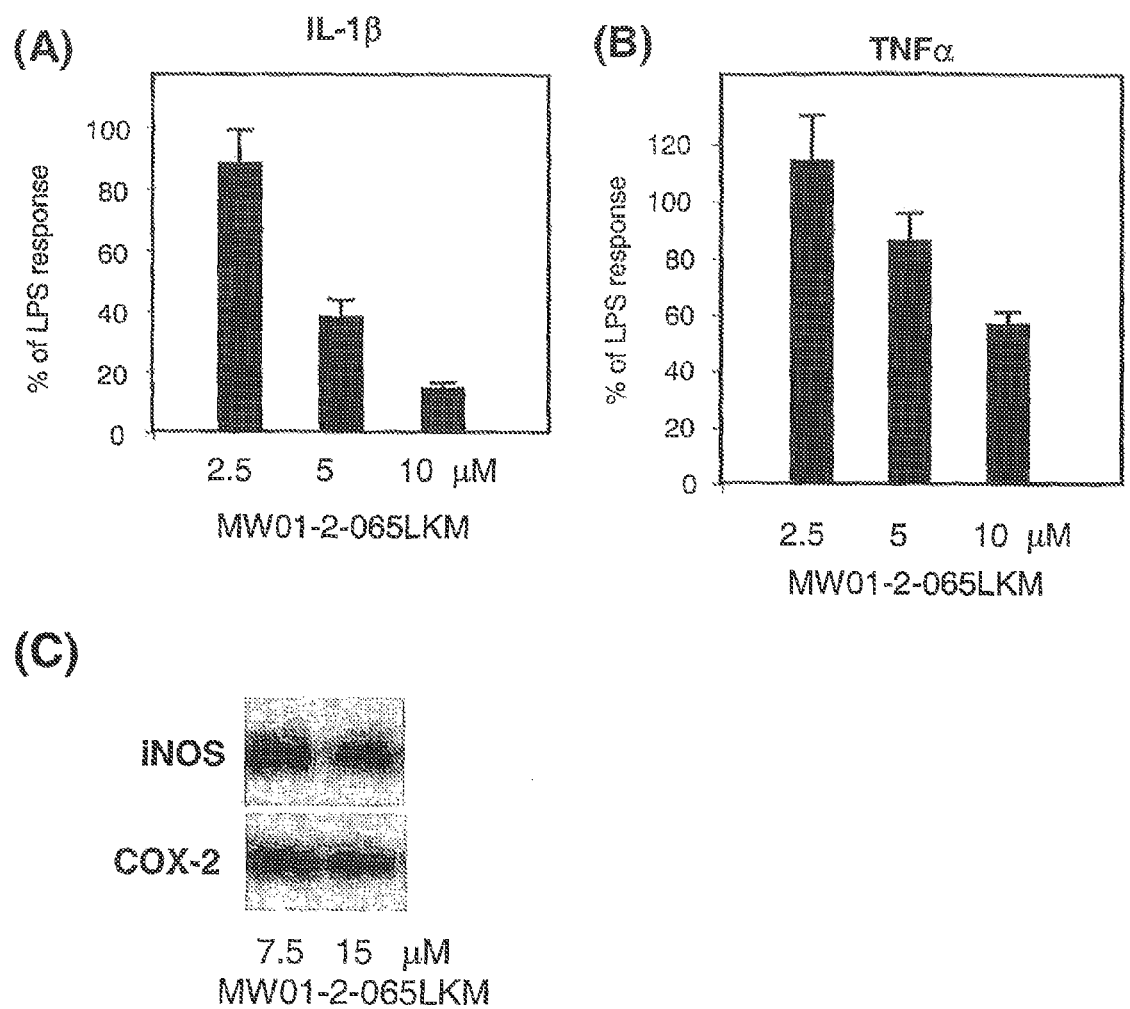
FIG. 33, parts (A) thru (C), shows graphical data of the assays used herein and immunoblots for biological activity of MW01-2-065LKM.
Figure 34:
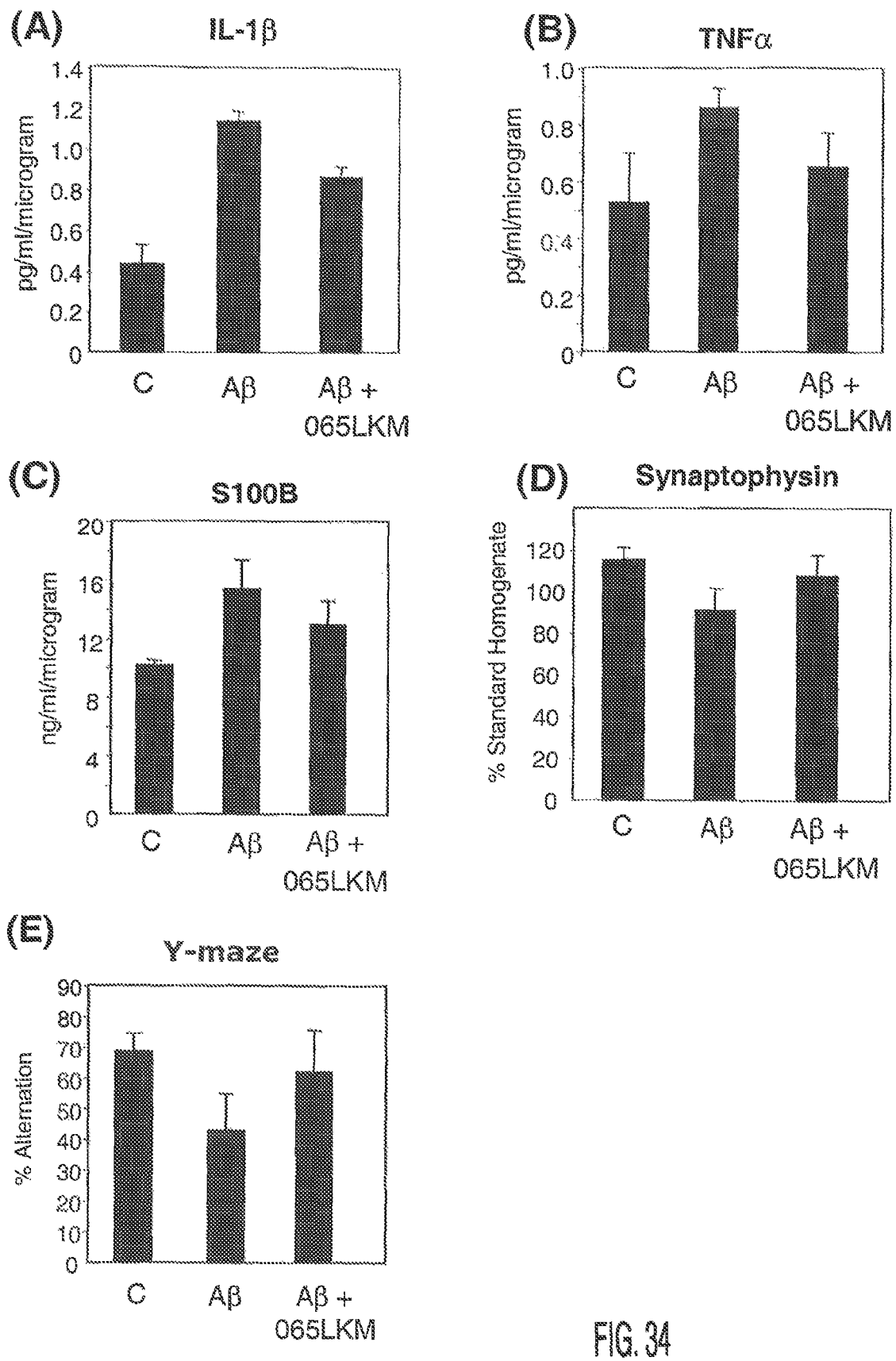
FIG. 34, parts (A) thru (E), shows graphical data of the assays used herein for MW01-2-065LKM.
Figure 35:
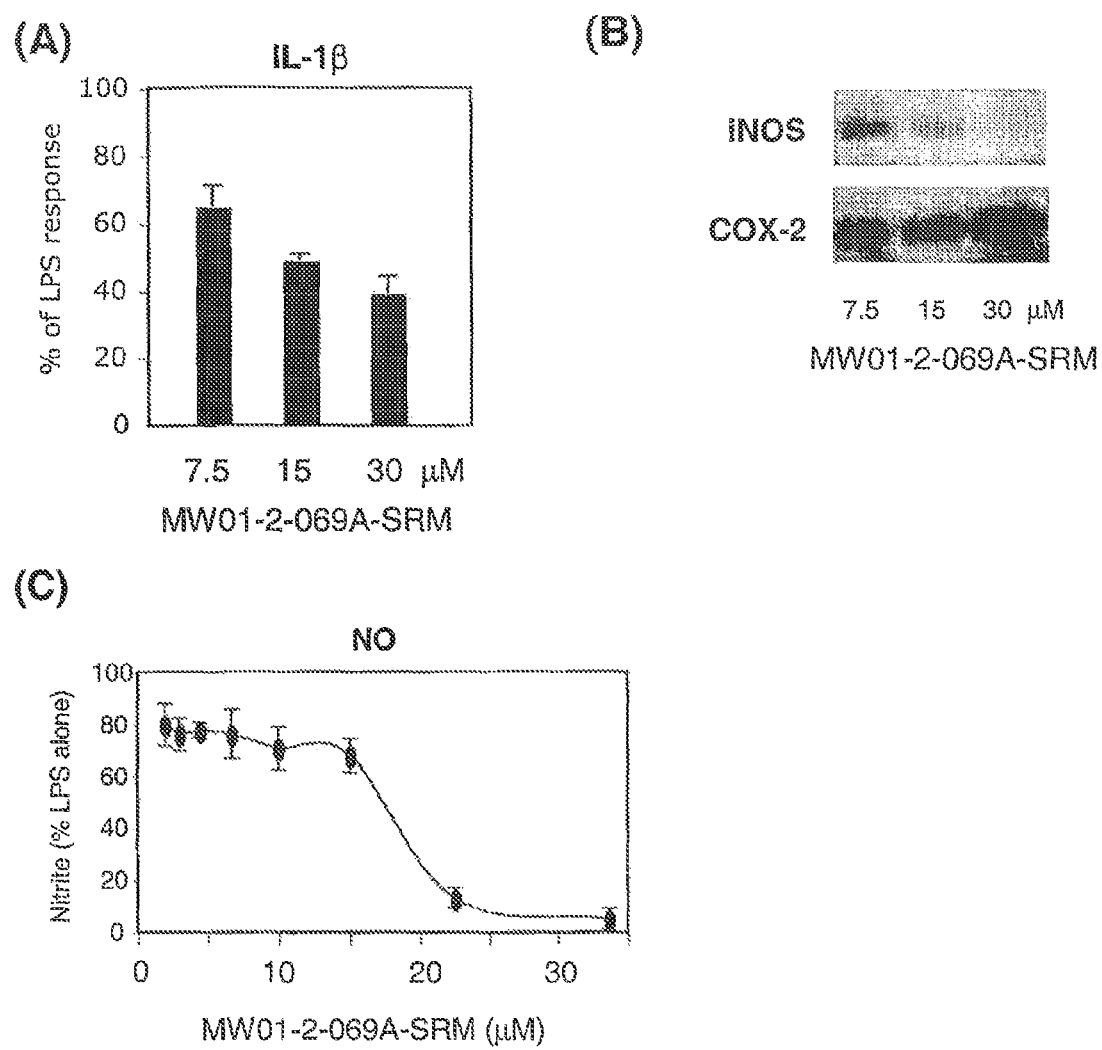
FIG. 35, parts (A) thru (C), shows graphical data of the assays used herein and immunoblots for biological activity of MW01-2-069A-SRM.
Figure 36:
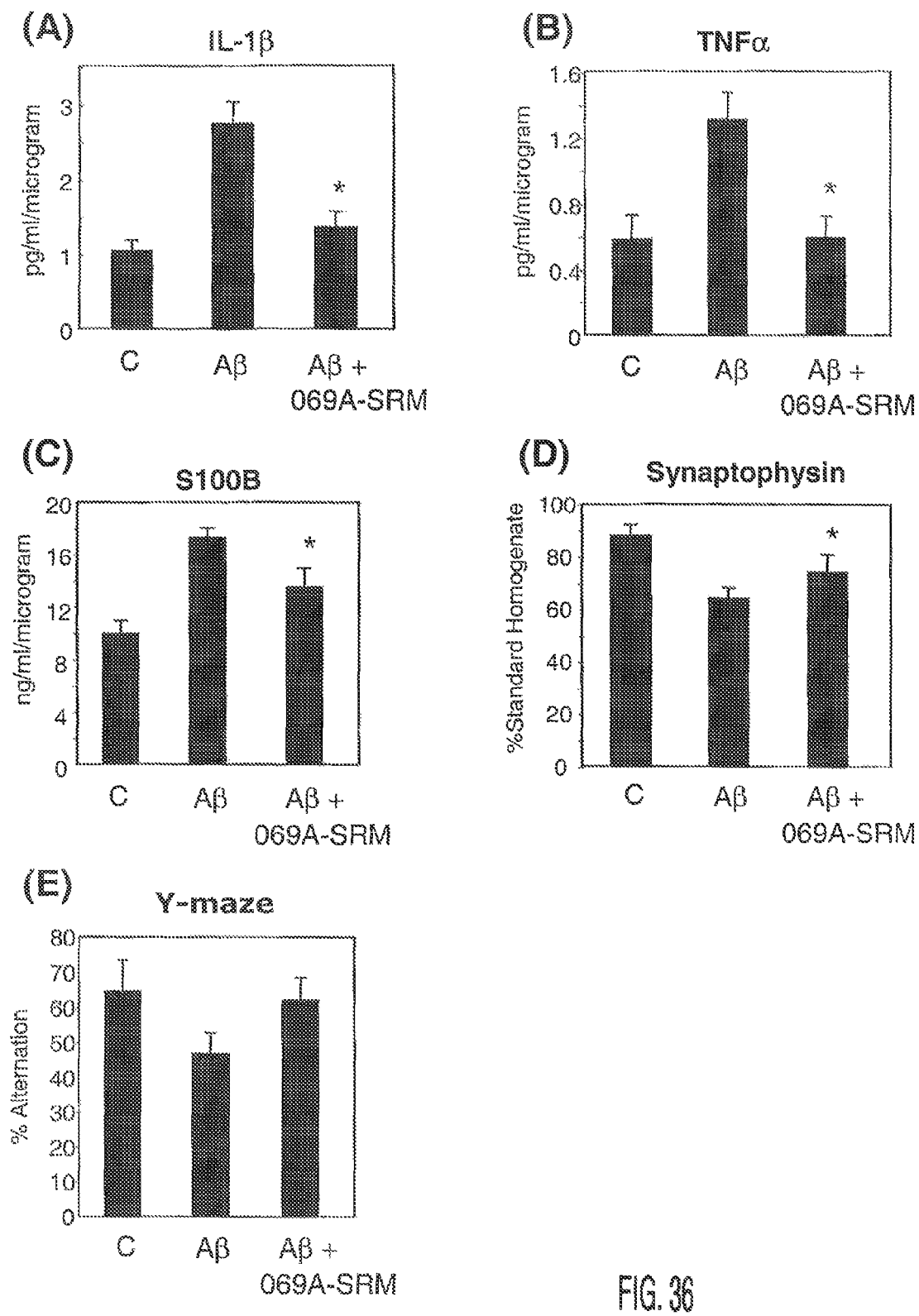
FIG. 36, parts (A) thru (E), shows graphical data of the assays used herein for MW01-2-069A-SRM.
Figure 37:
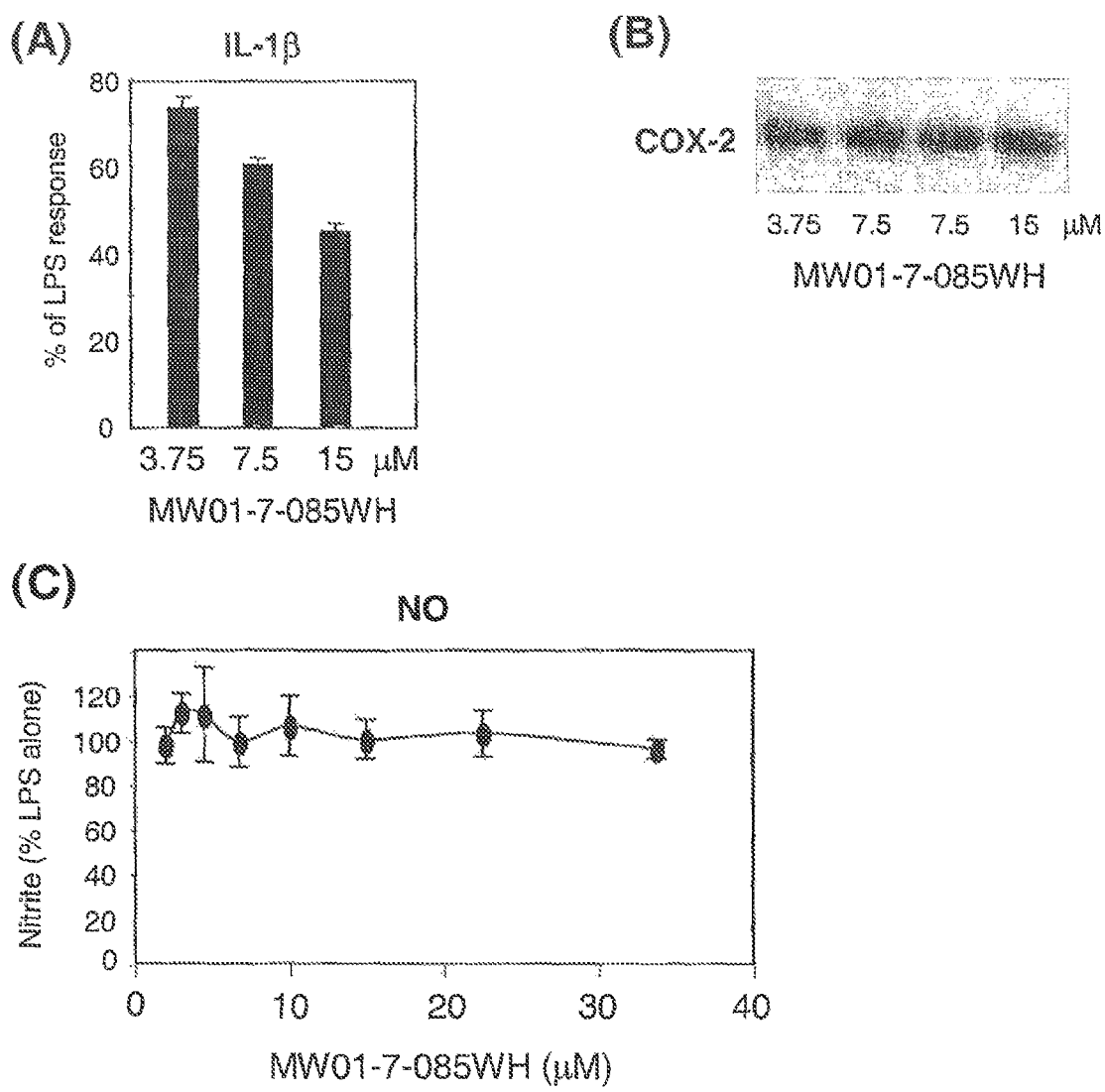
FIG. 37, parts (A) thru (C), shows graphical data of the assays used herein and immunoblots for biological activity of MW01-7-085WH.
Figure 38:
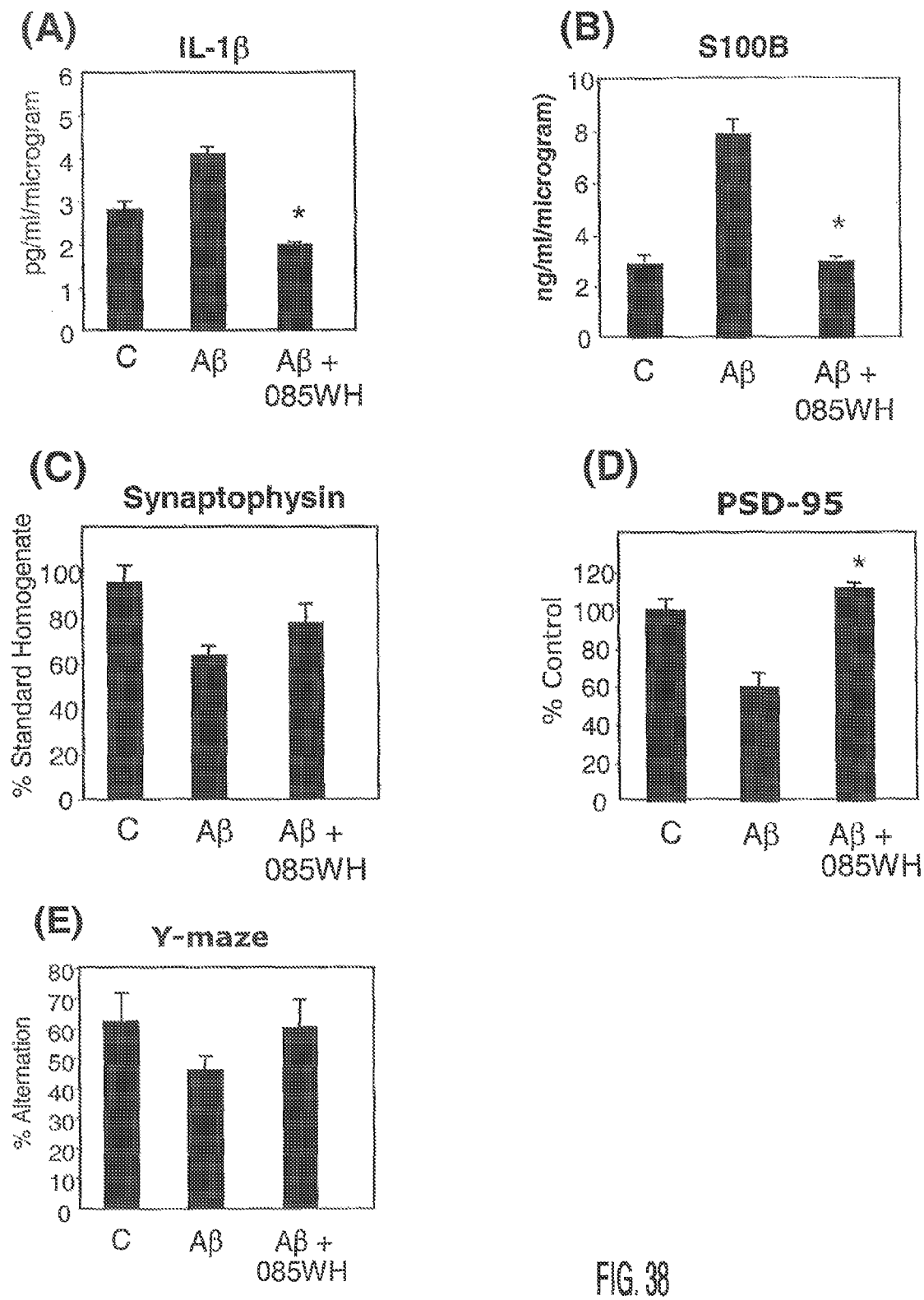
FIG. 38, parts (A) thru (E), shows graphical data of the assays used herein for MW01-7-085WH.
Figure 39:
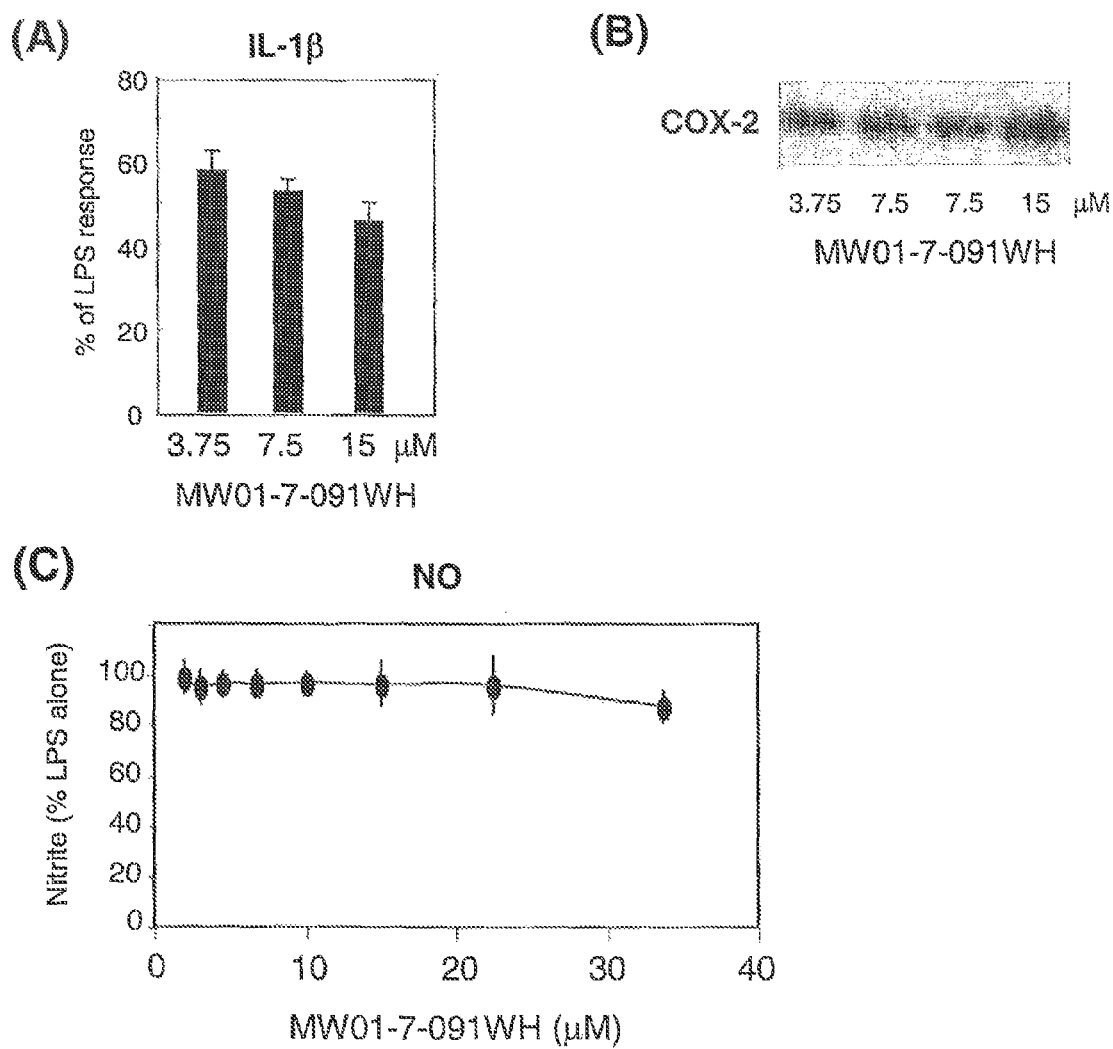
FIG. 39, parts (A) thru (C), shows graphical data of the assays used herein and immunoblots for biological activity of MW01-7-091WH.
Figure 40:
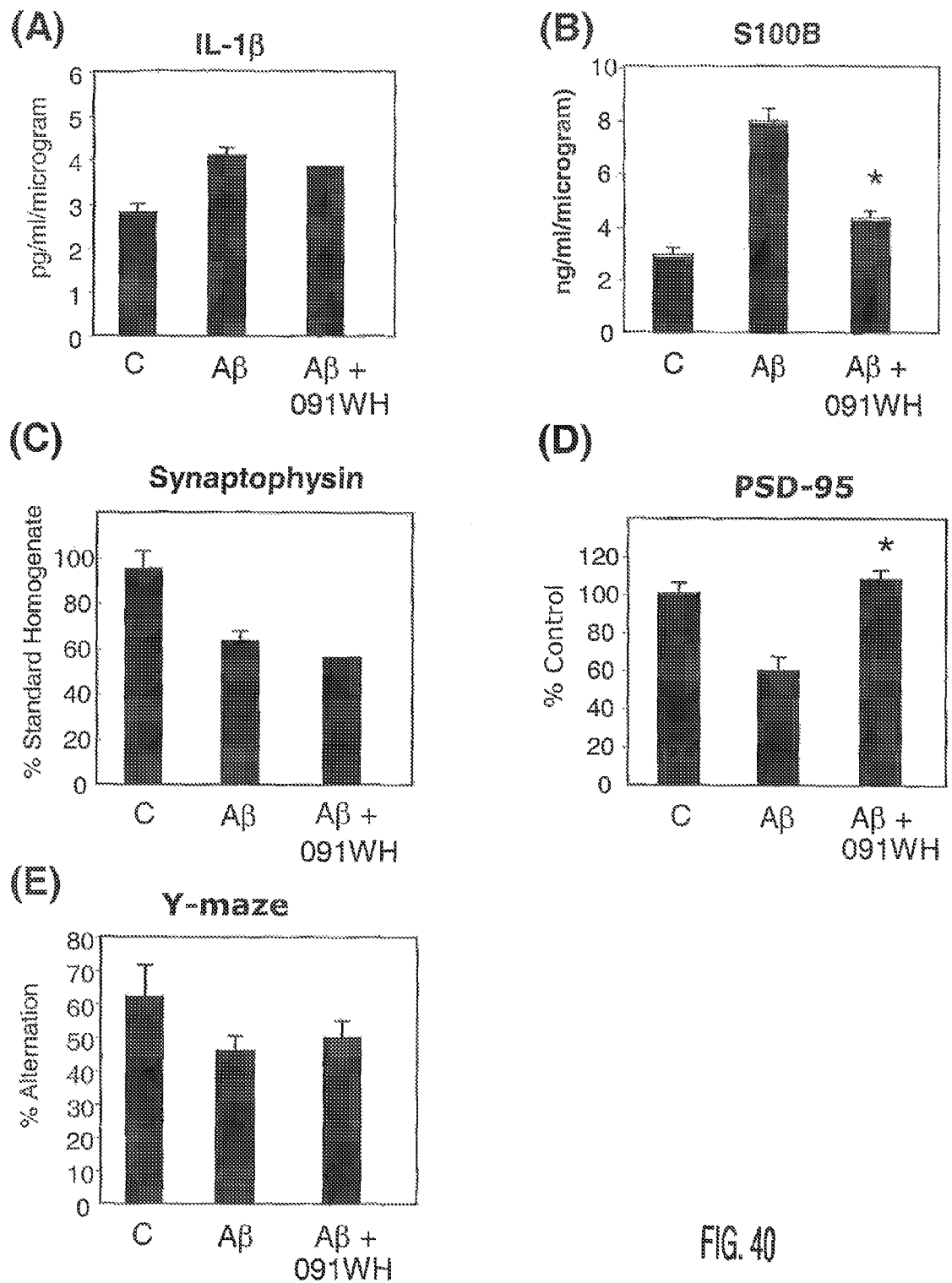
FIG. 40, parts (A) thru (E), shows graphical data of the assays used herein for MW01-7-091WH.
Figure 41:
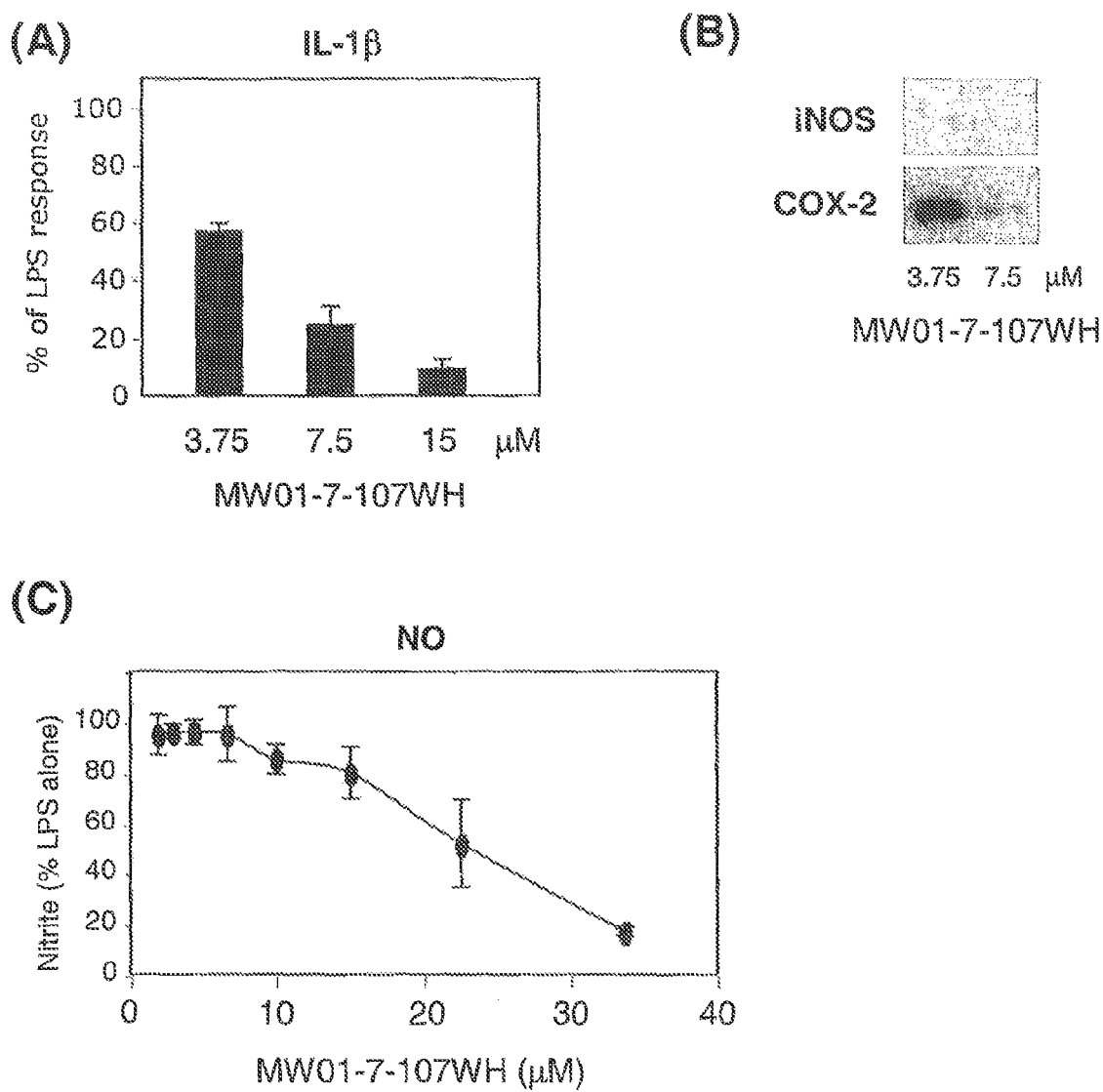
FIG. 41, parts (A) thru (C), shows graphical data of the assays used herein and immunoblots for biological activity of MW01-7-107WH.
Figure 42:
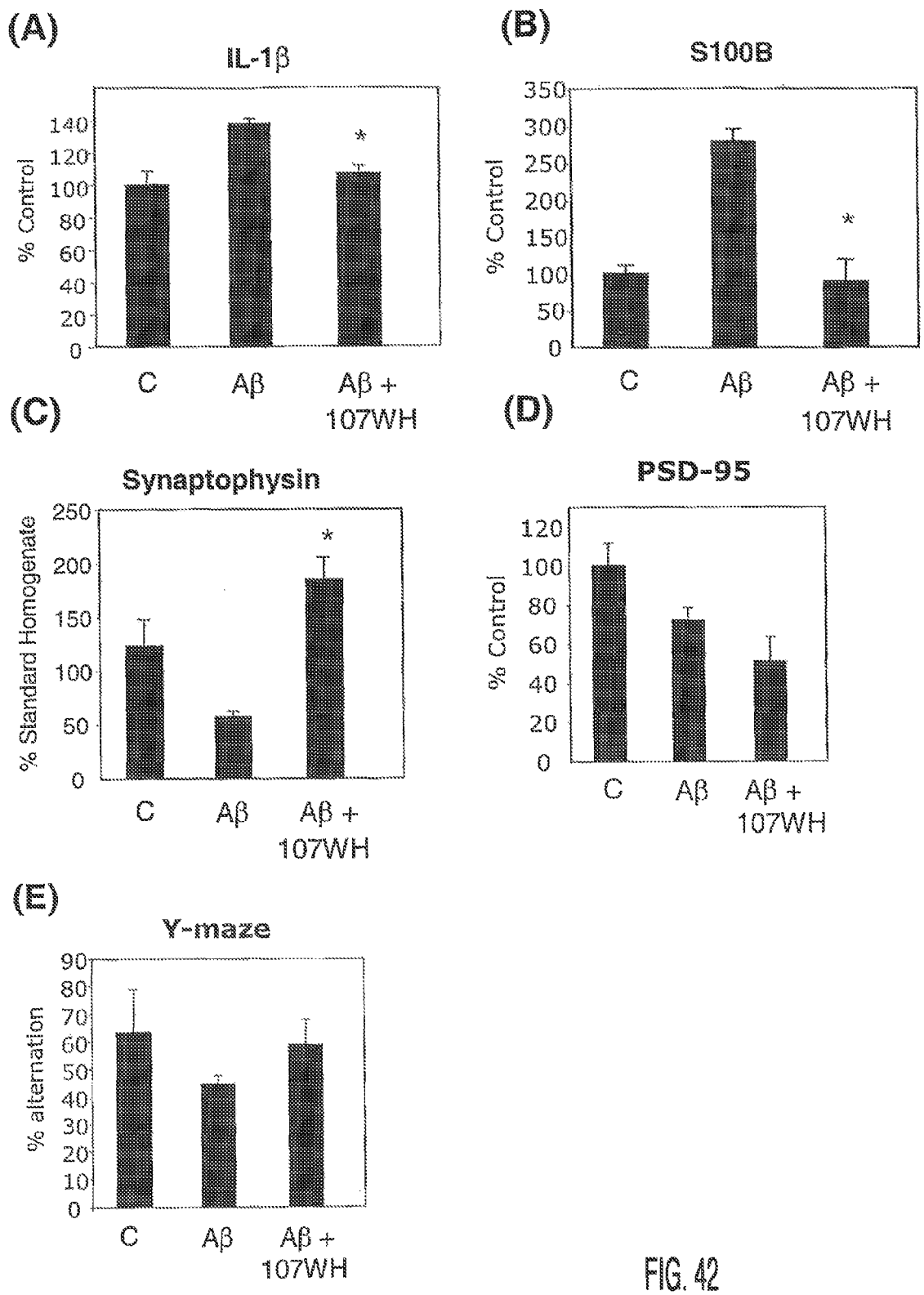
FIG. 42, parts (A) thru (E), shows graphical data of the assays used herein for MW01-7-107WH.
Figure 43:
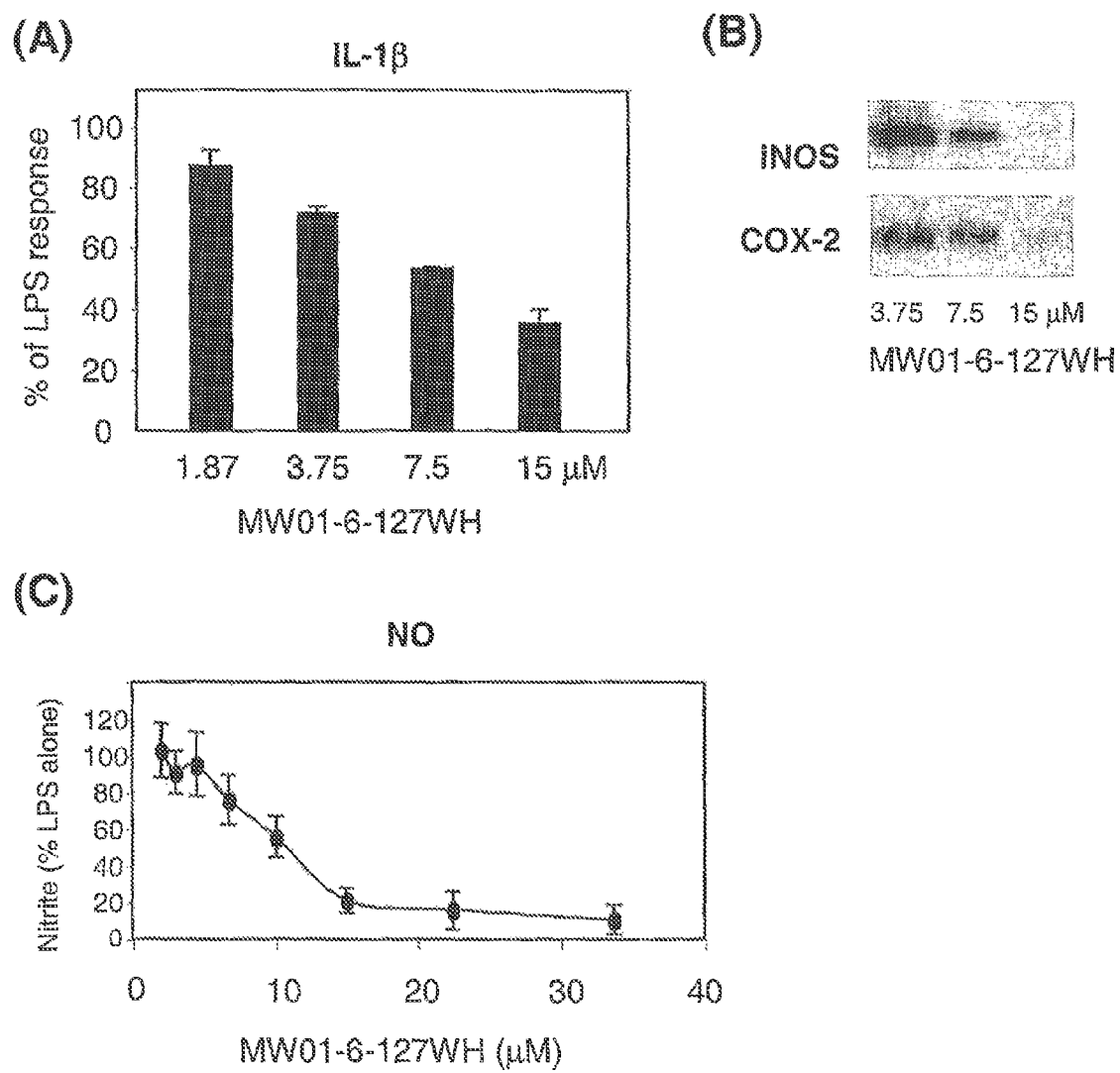
FIG. 43, parts (A) thru (C), shows graphical data of the assays used herein and immunobiots for biological activity of MW01-7-127WH.
Figure 44:
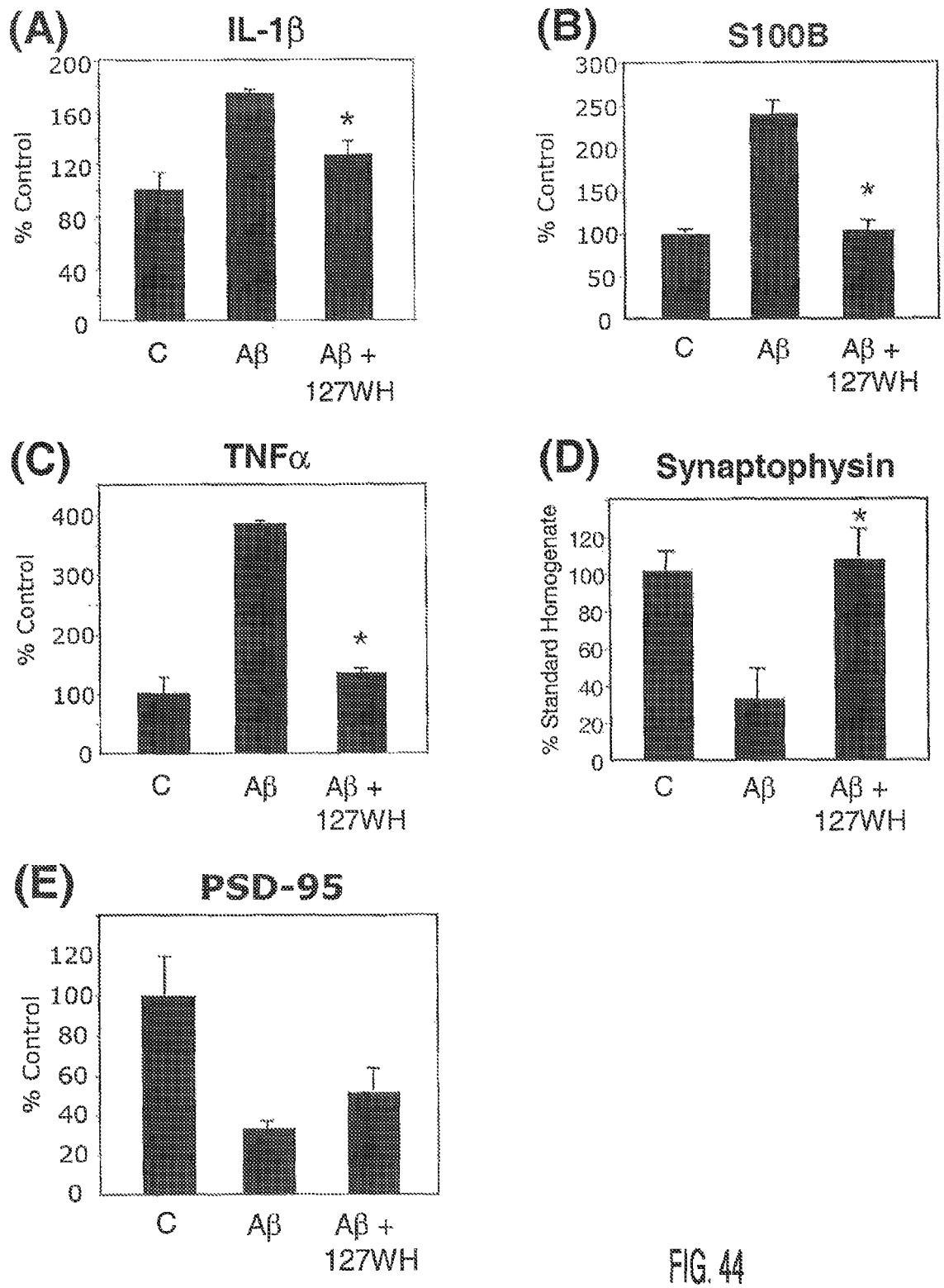
FIG. 44, parts (A) thru (E), shows graphical data of the assays used herein for MW01-7-127WH.
Figure 45:
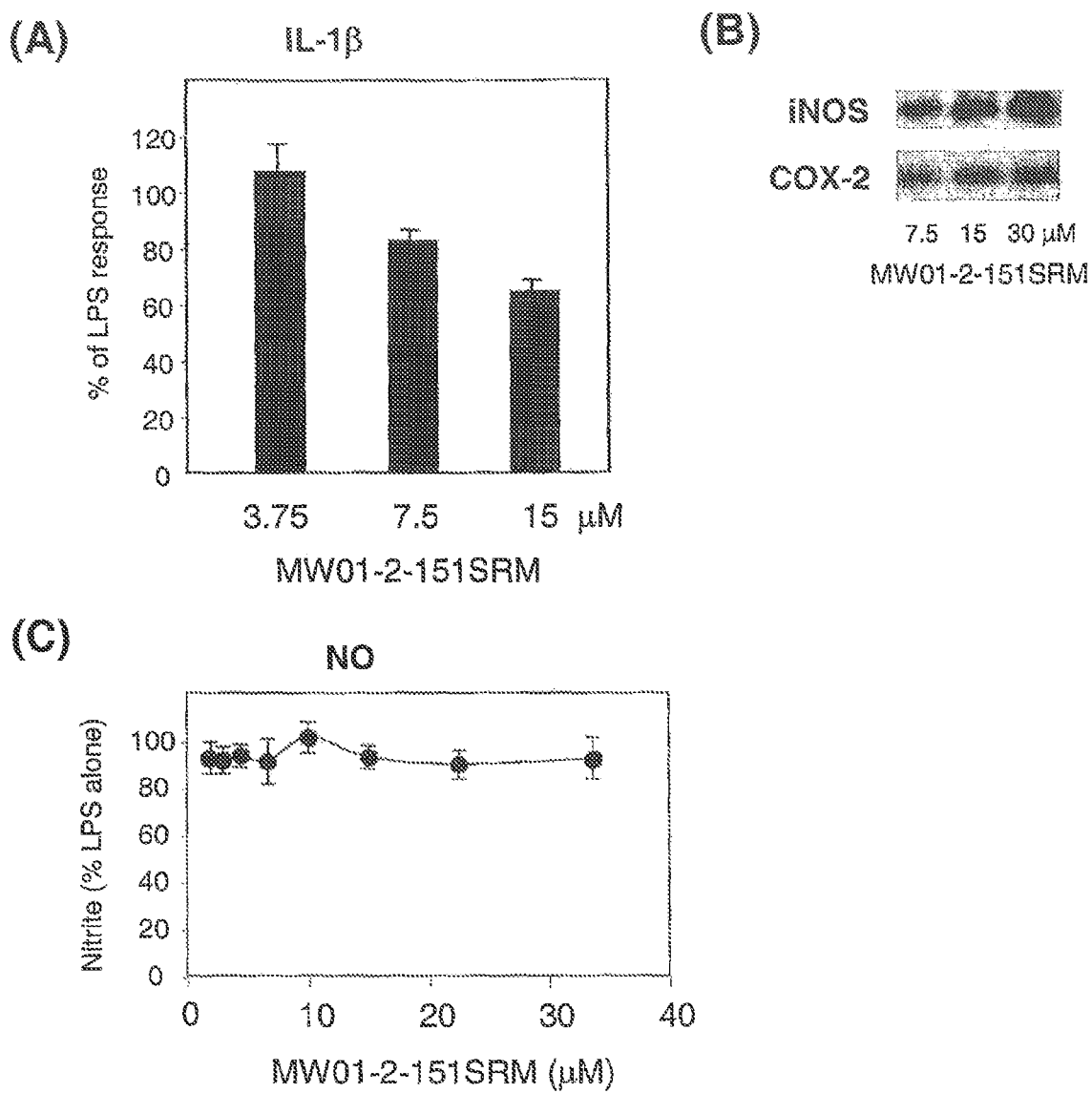
FIG. 45, parts (A) thru (C), shows graphical data of the assays used herein and immunoblots for biological activity of MW01-2-151SRM.
Figure 46:
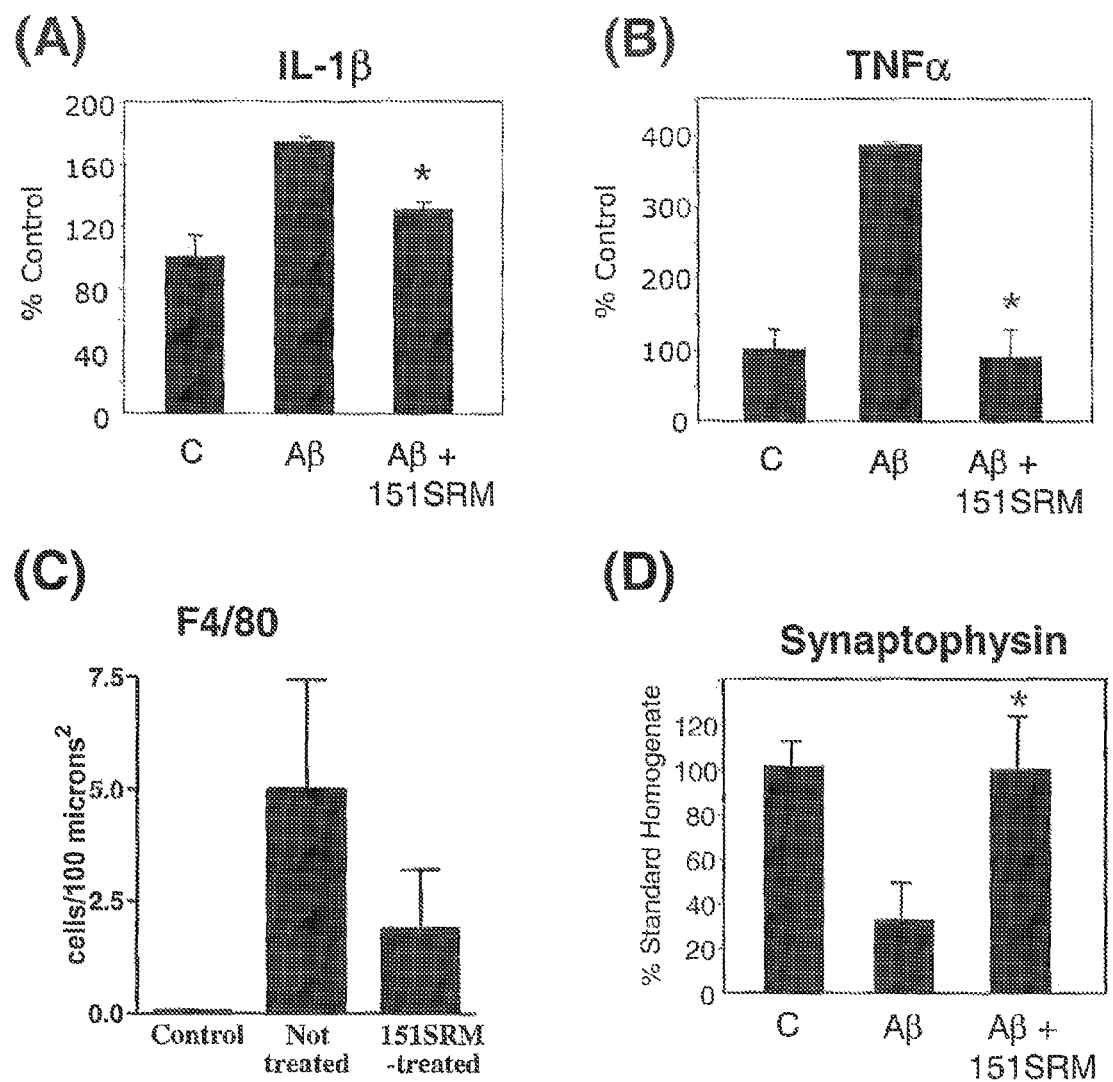
FIG. 46, parts (A) thru (H), shows graphical data of the assays used herein for MW01-2-151SRM.
Figure 46:
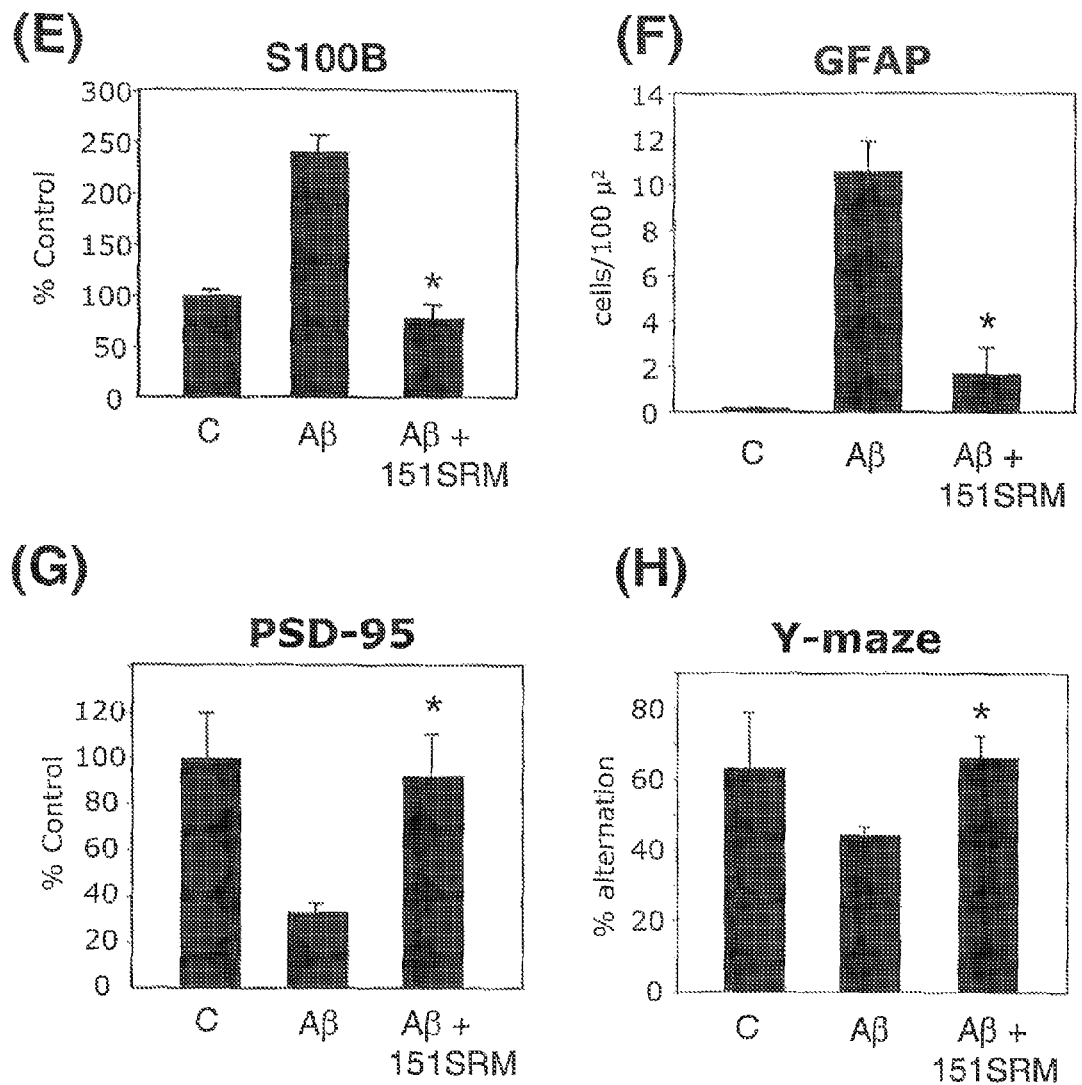

A synthetic reaction scheme for the preparation of N-(cyclopropylmethyl)-6-phenyl-4-(pyridin-4-yl)pyridazin-3-amine (MW01-7-084WH) is depicted in FIG. 28, and synthesis was carried out as described herein.

4-chloro-6-phenylpyridazin-3(2H)-one (MW01-6-093WH) was synthesized according to the procedure described by Coudert, P., et al. [18].

4-chloro-2-(methoxymethyl)-6-phenylpyridazin-3(2H)-one (MW01-7-053WH)

A mixture of chloropyridazinone 1 (25.5 g, 0.12 mol), 4-N,N-dimethylaminopyridine (0.20 g) and i-Pr2NEt (26.7 g, 0.21 mol) in anhydrous CH2Cl2 (300 mL) was stirred at 0 ¸аC (ice bath) for 30 min. Methoxymethyl chloride (25 g, 0.31 mol) was added and the mixture was stirred at 0° C. for 1 h and then allowed to warm to r. t. The reaction was stirred at r.t. till it complete. The solvent was then removed in vacuo, the residue was treated with water, washed with dilute Na$_2$CO$_3$ solution and extracted with EtOAc. The organic layer was dried over anhydrous Na$_2$SO$_4$, filtered and evaporated. The residue was then purified by recrystallization from 95% ethanol to give 20.1 light yellow solid. Yield 66.9%.

6-phenyl-4-(pyridin-4-yl)pyridazin-3(2H)-one (MW01-7-069WH)

The protected pyridazinone MW01-7-053WH (1.0 equiv.) was mixed with arylboronic acid (1.37 equiv.), Pd(PPh3)4 (0.05 equiv.) and K2CO3 (3.1 equiv) and 200 mL of DME in a 350 ml of pressure vessel, flushed with argon for 3 min, and the mixture was then stirred and refluxed (oil bath, 120° C.) until the starting material had disappeared. After cooling, the solution was concentrated to dryness under reduced pressure, the residue was treated with water and filtered off. The filler cake was washed with water over filter funnel and then used for next step directly. The residue obtained above was dissolved in 200 ml of EtOH, 6 N HCl (200 mL) was added and the reaction mixture was refluxed (oil bath, 120° C.) for 6 h, then it was allowed to cool to room temperature, and concentrated to dryness under reduced pressure. The residue was neutralized with dilute NaOH solution. The suspension was then filter off, washed with water and dried over filter funnel. Recrystallization from 90% ethanol provided brown yellow solid. Yield 80.4%. ESI-MS: m/z 294.3 (M+H$^+$)

3-chloro-6-phenyl-4-(pyridin-4-yl)pyridazine (MW01-7-076WH)

This compound was prepared from MW01-7-069WH in the same manner as described for MW01-6-127WH, yielding light yellow solid. ESI-MS: m/z 268.4 (M+H$^+$).

N-(cyclopropylmethyl)-6-phenyl-4-(pyridin-4-yl)pyridazin-3-amine (MW01-7-084WH)

This compound was prepared from MW01-7-076WH in the same manner as described for MW01-7-057WH, yielding gray solid. ESI-MS: m/z 330.4 (M+H$^+$).

The present invention is not to be limited in scope by the specific embodiments described herein, since such embodiments are intended, as but single illustrations of one aspect of the invention and any functionally equivalent embodiments are within the scope of this invention. Indeed, various modifications of the invention in addition to those shown and described herein will become apparent to those skilled in the art from the foregoing description and accompanying drawings. Such modifications are intended to fall within the scope of the appended claims.

All publications, patents and patent applications referred to herein are incorporated by reference in their entirety to the same extent as if each individual publication, patent or patent application was specifically and individually indicated to be incorporated by reference in its entirety. All publications, patents and patent applications mentioned herein are incorporated herein by reference for the purpose of describing and disclosing the methods etc. which are reported therein which might be used in connection with the invention. Nothing herein is to be construed as an admission that the invention is not entitled to antedate such disclosure by virtue of prior invention.

TABLE 1

| Compound Number | Compound Structure | Synthetic Code |
|---|---|---|
| 1 | 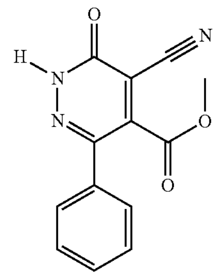 [SMILES: COC(=O)c1c(-c2ccccc2)n[nH]c(=O)c1C#N] | MW01-ES1 |
| 4 | 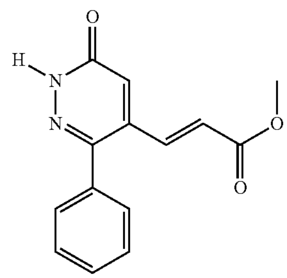 [SMILES: COC(=O)/C=C/c1cc(=O)[nH]nc1-c1ccccc1] | MW01-ES112 |
| 10 | 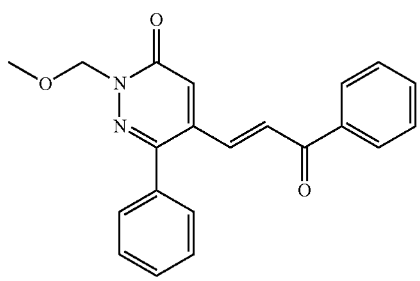 [SMILES: COCn1nc(-c2ccccc2)c(/C=C/C(=O)c2ccccc2)cc1=O] | MW01-ES159 |
| 11 | 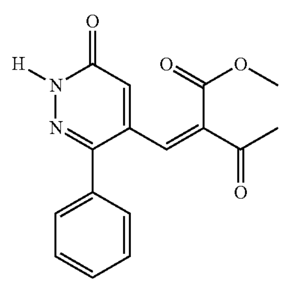 [SMILES: COC(=O)/C(=C\c1cc(=O)[nH]nc1-c1ccccc1)C(C)=O] | MW01-ES21 |
| 12 | 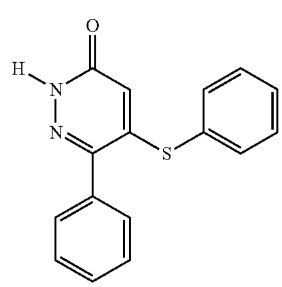 [SMILES: O=c1cc(Sc2ccccc2)c(-c2ccccc2)n[nH]1] | MW01-ES31 |

TABLE 1-continued

| Compound Number | Compound Structure | Synthetic Code |
|---|---|---|
| 13 | 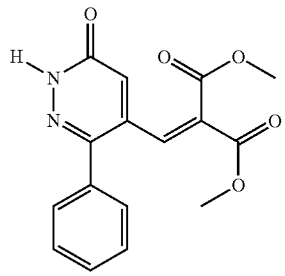 [SMILES: COC(=O)C(=Cc1cc(=O)[nH]nc1-c1ccccc1)C(=O)OC] | MW01-ES60 |
| 14 | 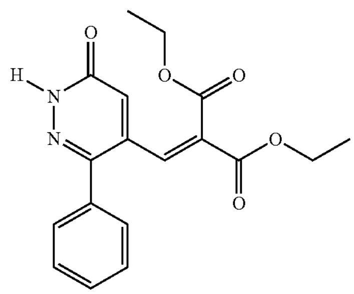 [SMILES: CCOC(=O)C(=Cc1cc(=O)[nH]nc1-c1ccccc1)C(=O)OCC] | MW01-ES61 |
| 16 | 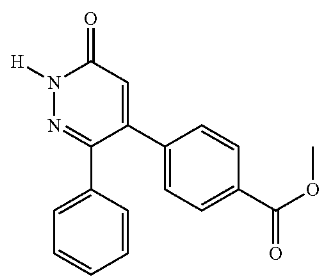 [SMILES: COC(=O)c1ccc(-c2cc(=O)[nH]nc2-c2ccccc2)cc1] | MW01-ES75 |
| 17 | 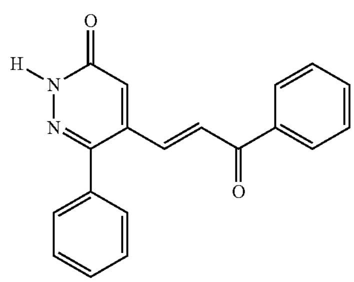 [SMILES: O=C(/C=C/c1cc(=O)[nH]nc1-c1ccccc1)c1ccccc1] | MW01-ES81 |
| 18 | 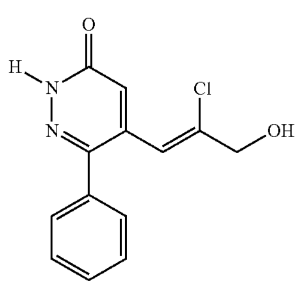 [SMILES: O=c1cc(/C=C(\Cl)CO)c(-c2ccccc2)n[nH]1] | MW01-ES91 |
| 20 | 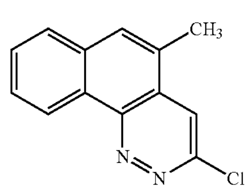 [SMILES: Cc1cc2ccccc2c2nnc(Cl)cc12] | MW01-1-04-L-D04 |

TABLE 1-continued

| Compound Number | Compound Structure | Synthetic Code |
|---|---|---|
| 23 | 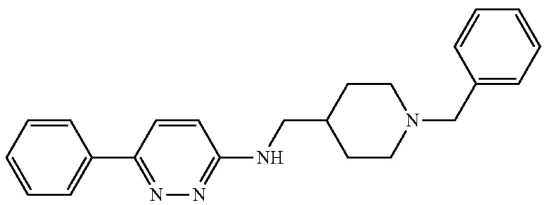 [SMILES: c1ccc(CN2CCC(CNc3ccc(-c4ccccc4)nn3)CC2)cc1] | MW01-15-L-H07 |
| 24 | 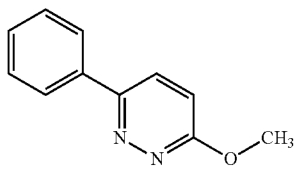 | MW01-1-16-L-F05 |
| 25 | 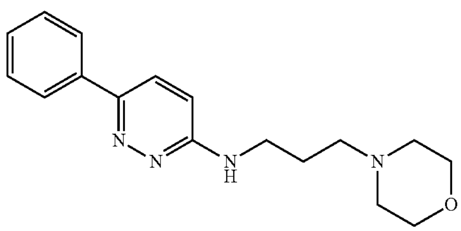 [SMILES: c1ccc(-c2ccc(NCCCN3CCOCC3)nn2)cc1] | MW01-1-18-L-B09 |
| 31 | 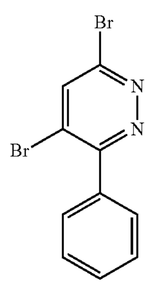 [SMILES: Brc1cc(Br)c(-c2ccccc2)nn1] | MW01-1-035LKM |
| 40 | 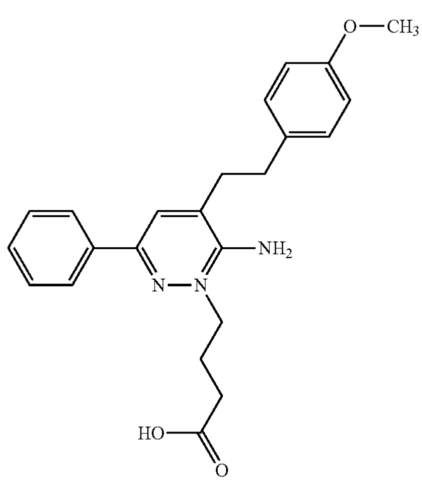 | MW01-1-09-L-G07 |

TABLE 1-continued

| Compound Number | Compound Structure | Synthetic Code |
|---|---|---|
| 41 | ethyl 3-((2-morpholinoethyl)amino)-6-phenylpyridazine-4-carboxylate | MW01-2-03-L-C02 |
| 43 | 3-hydrazinyl-5,6-diphenylpyridazine | MW01-1-15-L-E09 |
| 44 | 3-hydrazinyl-4-methyl-6-phenylpyridazine | MW01-1-16-L-B11 |
| 47 | 6-(4-chlorophenyl)pyridazin-3-amine | MW01-4-198B-Z |
| 48 | 6-(3,4-dimethoxyphenyl)pyridazin-3-amine | MW01-5-144A-Z |
| 49 | 4-methyl-6-phenylpyridazin-3-amine | MW01-4-198C-Z |
| 50 | 5-(4-chlorophenyl)-6-phenylpyridazin-3-amine | MW01-5-144C-Z |
| 51 | 5-(4-methoxyphenyl)-6-phenylpyridazin-3-amine | MW01-5-144D-Z |

TABLE 1-continued

| Compound Number | Compound Structure | Synthetic Code |
|---|---|---|
| 52 | (6-phenyl-4-(2-phenylethyl)pyridazin-3-amine) | MW01-5-145A-Z |
| 54 | (4-methyl-6-phenylpyridazin-3-amine) | MW01-5-189Z |
| 55 | (6-methylpyridazin-3-amine) | MW01-5-202B-Z |
| 61 | (2-((6-phenylpyridazin-3-yl)amino)ethanol) | MW01-1-01-L-D06 |
| 65 | (3-hydrazinyl-6-phenylpyridazine) | MW01-1-01-L-E10 |
| 66 | (3-(methylthio)-6-phenylpyridazin-1-ium iodide) | MW01-1-02-L-E08 |

TABLE 1-continued
| Compound Number | Compound Structure | Synthetic Code |
|---|---|---|
| 70 | 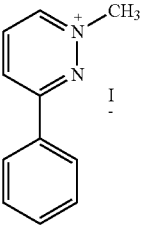 | MW01-1-03-L-D03 |
| 71 | 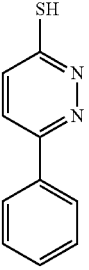 [SMILES: Sc1ccc(-c2ccccc2)nn1] | MW01-1-03-L-F03 |
| 73 | 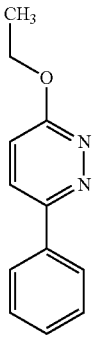 | MW01-1-03-L-G10 |
| 74 | 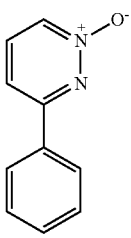 | MW01-1-03-L-H06 |
| 75 | 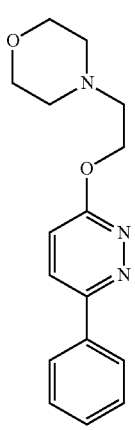 [SMILES: c1ccc(-c2ccc(OCCN3CCOCC3)nn2)cc1] | MW01-1-04-L-C03 |

TABLE 1-continued
| Compound Number | Compound Structure | Synthetic Code |
|---|---|---|
| 76 | 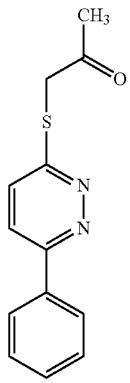 [SMILES: CC(=O)CSc1ccc(-c2ccccc2)nn1] | MW01-1-07-L-H04 |
| 88 | 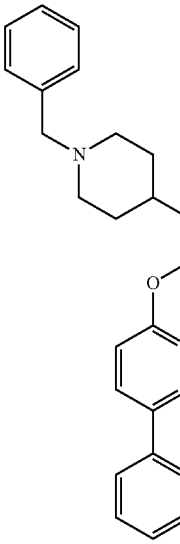 | MW01-1-100-L-A04 |
| 89 | 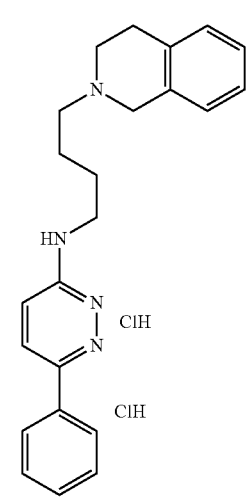 [SMILES: c1ccc(-c2ccc(NCCCCN3CCc4ccccc4C3)nn2)cc1 ; Cl ; Cl] | MW01-1-100-L-A05 |

TABLE 1-continued
| Compound Number | Compound Structure | Synthetic Code |
|---|---|---|
| 90 | 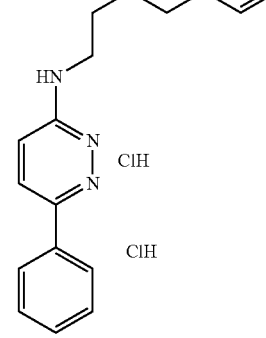 | MW01-1-100-L-A08 |
| 91 | 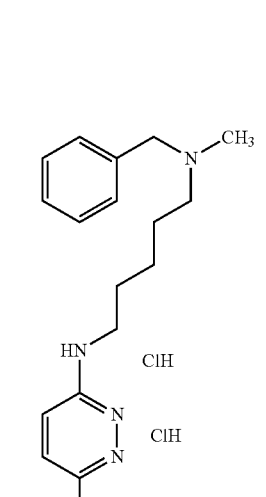 | MW01-1-100-L-A09 |
| 92 | 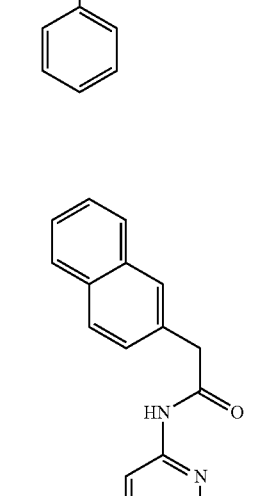 | MW01-1-11-L-E08 |

TABLE 1-continued
| Compound Number | Compound Structure | Synthetic Code |
|---|---|---|
| 94 | 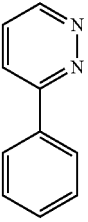 [SMILES: c1ccc(-c2cccnn2)cc1] | MW01-1-15-L-G09 |
| 97 | 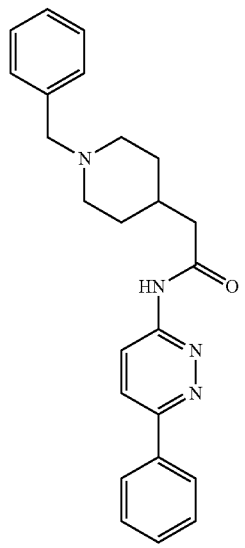 [SMILES: O=C(CC1CCN(Cc2ccccc2)CC1)Nc1ccc(-c2ccccc2)nn1] | MW01-1-16-L-G03 |
| 106 | 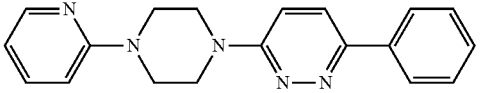 [SMILES: c1ccc(-c2ccc(N3CCN(c4ccccn4)CC3)nn2)cc1] | MW01-9-039Z |
| 107 | 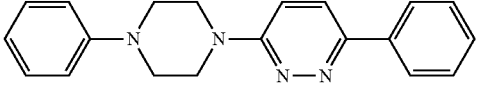 [SMILES: c1ccc(-c2ccc(N3CCN(c4ccccc4)CC3)nn2)cc1] | MW01-9-040Z |
| 108 | 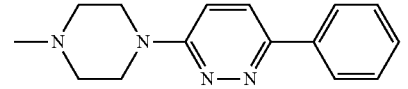 [SMILES: CN1CCN(c2ccc(-c3ccccc3)nn2)CC1] | MW01-9-041Z |
| 109 | 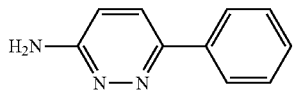 | MW01-9-104A-Z |
| 110 | 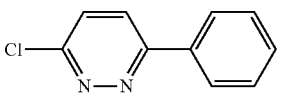 [SMILES: Clc1ccc(-c2ccccc2)nn1] | MW01-9-105A-Z |
| 111 | 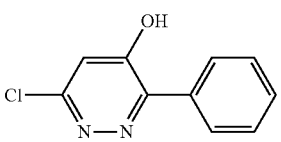 [SMILES: Oc1cc(Cl)nnc1-c1ccccc1] | MW01-9-110A-Z |
| 112 | 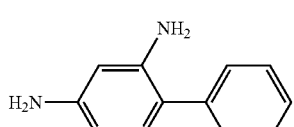 | MW01-9-133A-Z |

TABLE 1-continued
| Compound Number | Compound Structure | Synthetic Code |
|---|---|---|
| 113 | 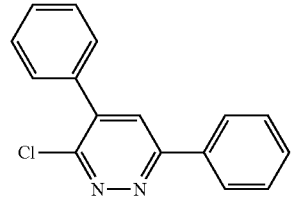 [SMILES: Clc1nnc(-c2ccccc2)cc1-c1ccccc1] | MW01-9-149A-Z |
| 114 | 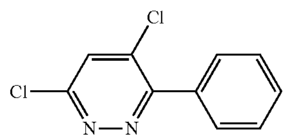 [SMILES: Clc1cc(Cl)c(-c2ccccc2)nn1] | MW01-9-159A-Z |
| 115 | 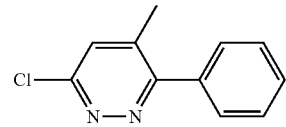 | MW01-9-171Z |
| 116 | 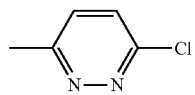 | MW01-9-172Z |
| 118 | 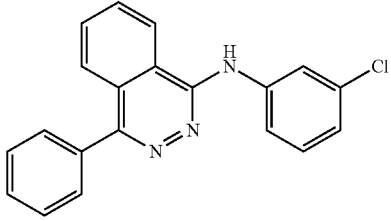 [SMILES: Clc1cccc(Nc2nnc(-c3ccccc3)c3ccccc23)c1] | MW01-9-204Z |
| 120 | 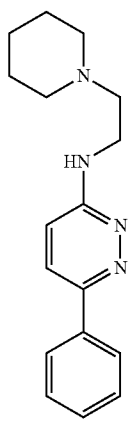 | MW01-1-16-L-G08 |

TABLE 1-continued
| Compound Number | Compound Structure | Synthetic Code |
|---|---|---|
| 122 | 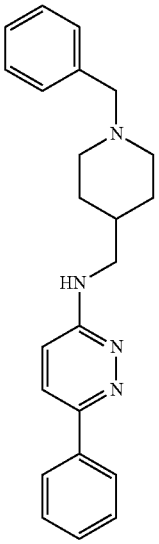 [SMILES: c1ccc(CN2CCC(CNc3ccc(-c4ccccc4)nn3)CC2)cc1] | MW01-17-L-G05 |
| 123 | 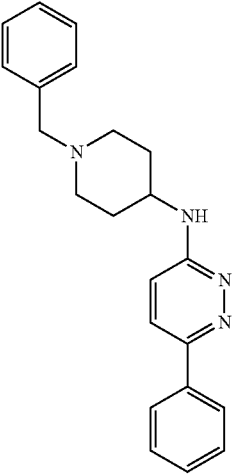 [SMILES: c1ccc(CN2CCC(Nc3ccc(-c4ccccc4)nn3)CC2)cc1] | MW01-1-17-L-G11 |
| 125 | 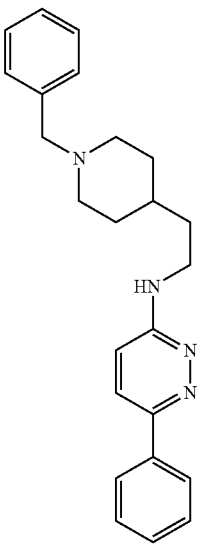 [SMILES: c1ccc(CN2CCC(CCNc3ccc(-c4ccccc4)nn3)CC2)cc1] | MW01-1-17-L-H03 |

TABLE 1-continued

| Compound Number | Compound Structure | Synthetic Code |
| --- | --- | --- |
| 127 | 1-benzyl-4-(2-((6-phenylpyridazin-3-yl)amino)ethyl)piperazine | MW01-1-17-L-H11 |
| 130 | 1-(4-benzylpiperazin-1-yl)-2-((6-phenylpyridazin-3-yl)amino)ethan-1-one | MW01-1-18-L-A08 |
| 137 | 4-(3-chloro-6-phenylpyridazin-4-yl)morpholine | MW01-2-020SRM |
| 143 | 3,4-dichloro-6-phenylpyridazine | MW01-2-056WH |

TABLE 1-continued

| Compound Number | Compound Structure | Synthetic Code |
|---|---|---|
| 149 | 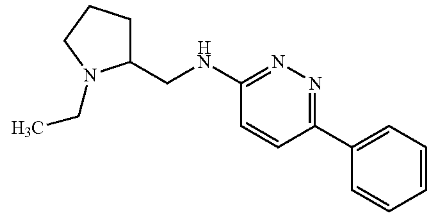 [SMILES: CCN1CCCC1CNc1ccc(-c2ccccc2)nn1] | MW01-1-18-L-A11 |
| 150 | 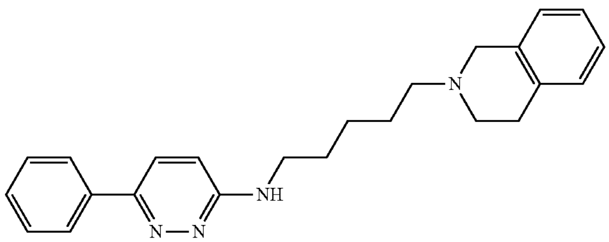 [SMILES: c1ccc(-c2ccc(NCCCCCN3CCc4ccccc4C3)nn2)cc1] | MW01-1-18-L-B03 |
| 151 | 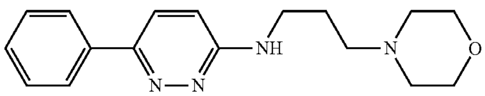 [SMILES: c1ccc(-c2ccc(NCCCN3CCOCC3)nn2)cc1] | MW01-1-18-L-B09 |
| 158 | 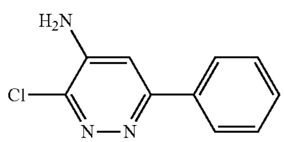 [SMILES: Nc1cc(-c2ccccc2)nnc1Cl] | MW01-3-033WH |
| 159 | 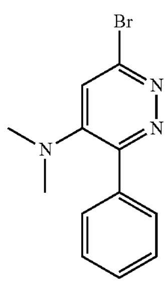 [SMILES: CN(C)c1cc(Br)nnc1-c1ccccc1] | MW01-3-009WH |
| 173 | 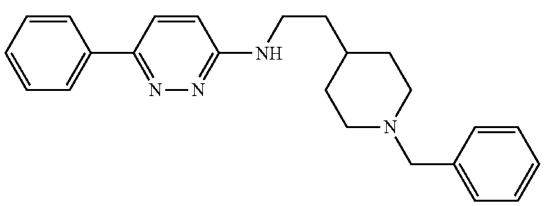 [SMILES: c1ccc(CN2CCC(CCNc3ccc(-c4ccccc4)nn3)CC2)cc1] | MW01-2-03-L-D02 |
| 175 | 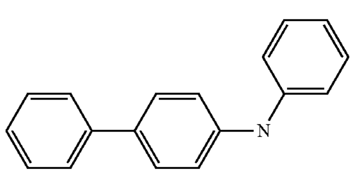 [SMILES: c1ccc(Nc2ccc(-c3ccccc3)cc2)cc1] | MW01-2-06-L-F04 |
| 175A | 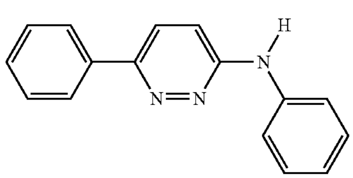 [SMILES: c1ccc(Nc2ccc(-c3ccccc3)nn2)cc1] | ????? |

TABLE 1-continued

| Compound Number | Compound Structure | Synthetic Code |
|---|---|---|
| 179 | 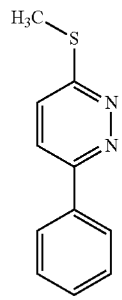 | MW01-2-33-L-B02 |
| 180 | 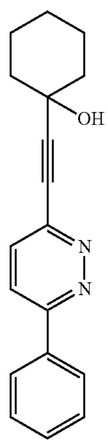 [SMILES: OC1(C#Cc2ccc(-c3ccccc3)nn2)CCCCC1] | MW01-3-01-L-G07 |
| 183 | 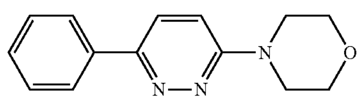 | MW01-5-160WH |
| 184 | 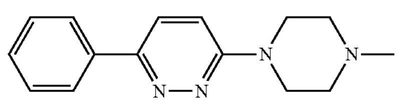 | MW01-5-161WH |
| 189 | 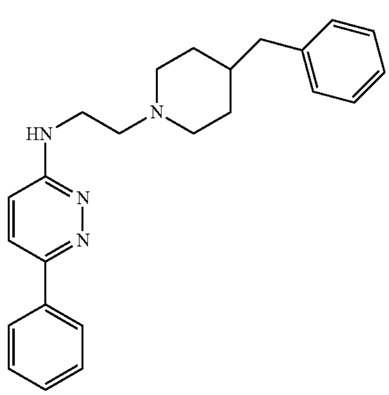 [SMILES: c1ccc(CC2CCN(CCNc3ccc(-c4ccccc4)nn3)CC2)cc1] | MW01-6-041WH |

TABLE 1-continued

| Compound Number | Compound Structure | Synthetic Code |
|---|---|---|
| 190 | 6-phenyl-N-(2-aminoethyl)pyridazin-3-amine | MW01-6-044WH |
| 192 | 6-methyl-N-(2-aminoethyl)pyridazin-3-amine | MW01-6-050WH |
| 197 | 2-((4,6-diphenylpyridazin-3-yl)amino)ethanol | MW01-1-01-L-A10 |
| 198 | N-(2-methoxyethyl)-4,6-diphenylpyridazin-3-amine | MW01-1-01-L-B03 |

TABLE 1-continued
| Compound Number | Compound Structure | Synthetic Code |
|---|---|---|
| 199 | 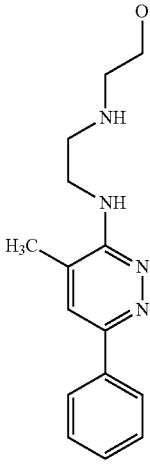 | MW01-1-01-L-B09 |
| 201 | 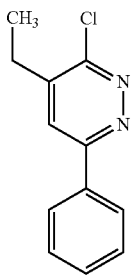 | MW01-1-01-L-E03 |
| 202 | 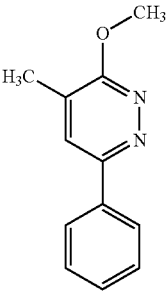 | MW01-1-01-L-E04 |
| 205 | 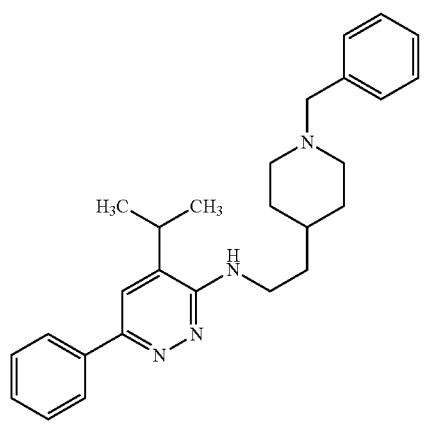 [SMILES: CC(C)c1cc(-c2ccccc2)nnc1NCCC1CCN(Cc2ccccc2)CC1] | MW01-1-18-L-B07 |

TABLE 1-continued
| Compound Number | Compound Structure | Synthetic Code |
|---|---|---|
| 208 | 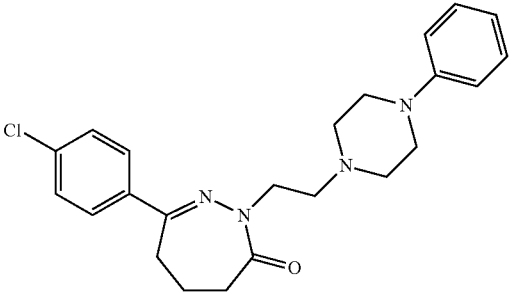 [SMILES: O=C1CCCC(c2ccc(Cl)cc2)=NN1CCN1CCN(c2ccccc2)CC1] | MW01-1-03-L-G03 |
| 210 | 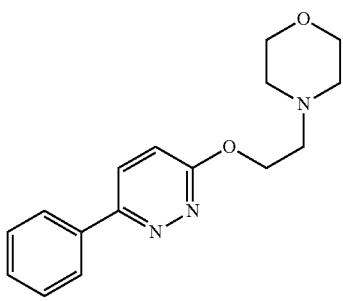 [SMILES: c1ccc(-c2ccc(OCCN3CCOCC3)nn2)cc1] | MW01-1-04-L-C03 |
| 217 | 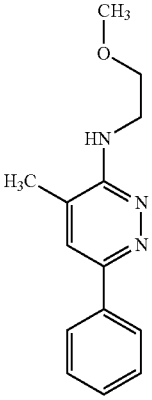 [SMILES: COCCNc1nnc(-c2ccccc2)cc1C] | MW01-1-02-L-E03 |
| 218 | 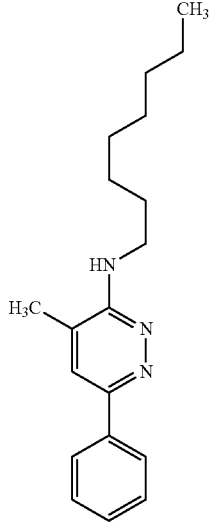 [SMILES: CCCCCCCCNc1nnc(-c2ccccc2)cc1C] | MW01-1-02-L-E06 |

TABLE 1-continued

| Compound Number | Compound Structure | Synthetic Code |
|---|---|---|
| 221 | 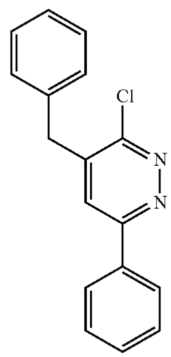 [SMILES: Clc1nnc(-c2ccccc2)cc1Cc1ccccc1] | MW01-1-02-L-F02 |
| 223 | 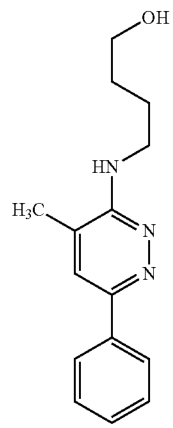 | MW01-1-02-L-F08 |
| 225 | 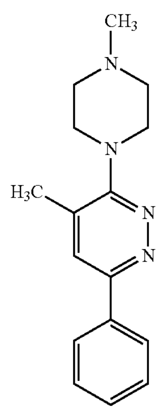 | MW01-1-02-L-G05 |
| 226 | 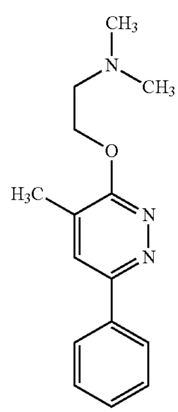 | MW01-1-02-L-G06 |

TABLE 1-continued

| Compound Number | Compound Structure | Synthetic Code |
|---|---|---|
| 227 | (3-((2-methoxyethyl)amino)-4,6-diphenylpyridazine) | MW01-1-03-L-A02 |
| 229 | (3-chloro-4-methyl-6-phenylpyridazine) | MW01-1-03-L-B09 |
| 230 | (3-((2-hydroxyethyl)amino)-4-methyl-6-phenylpyridazine) | MW01-1-03-L-B10 |
| 231 | (3-bromo-4-methyl-6-phenylpyridazine) | MW01-1-03-L-C03 |

TABLE 1-continued

| Compound Number | Compound Structure | Synthetic Code |
|---|---|---|
| 233 | 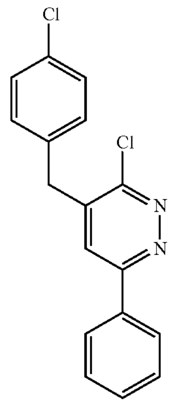 [SMILES: Clc1ccc(Cc2cc(-c3ccccc3)nnc2Cl)cc1] | MW01-1-03-L-C08 |
| 235 | 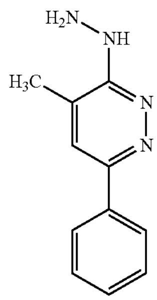 | MW01-1-03-L-E08 |
| 236 | 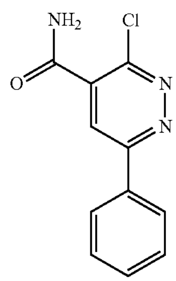 [SMILES: NC(=O)c1cc(-c2ccccc2)nnc1Cl] | MW01-1-03-L-E09 |
| 240 | 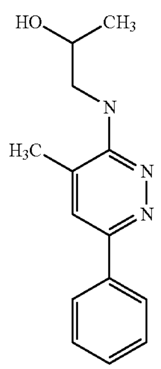 [SMILES: Cc1cc(-c2ccccc2)nnc1NCC(C)O] | MW01-1-04-L-A06 |
| 242 | 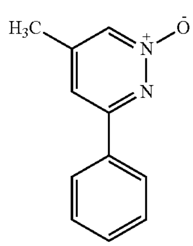 | MW01-1-04-L-D10 |

TABLE 1-continued
| Compound Number | Compound Structure | Synthetic Code |
|---|---|---|
| 250 | 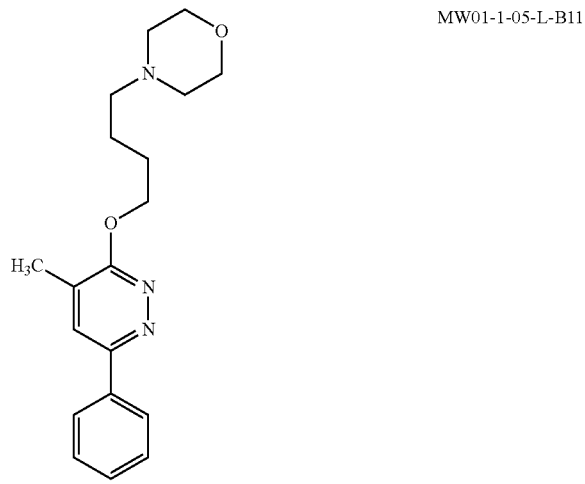 | MW01-1-05-L-B11 |
| 251 | 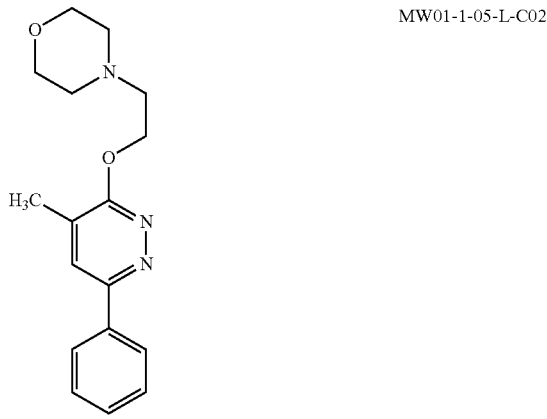 | MW01-1-05-L-C02 |
| 254 | 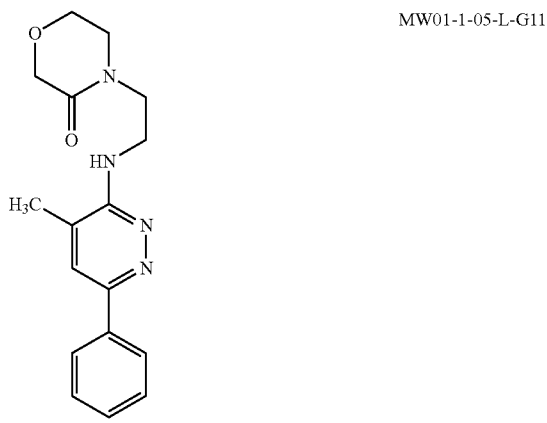 | MW01-1-05-L-G11 |

TABLE 1-continued

| Compound Number | Compound Structure | Synthetic Code |
|---|---|---|
| 255 | 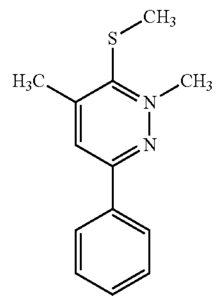 | MW01-1-05-L-H05 |
| 266 | 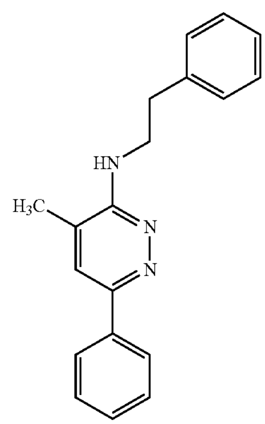 [SMILES: Cc1cc(-c2ccccc2)nnc1NCCc1ccccc1] | MW01-1-08-L-D09 |
| 268 | 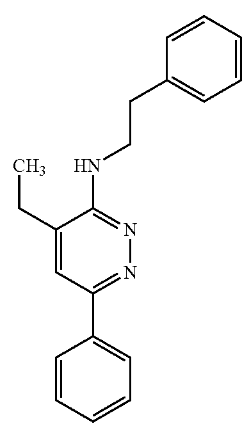 [SMILES: CCc1cc(-c2ccccc2)nnc1NCCc1ccccc1] | MW01-1-09-L-C06 |
| 270 | 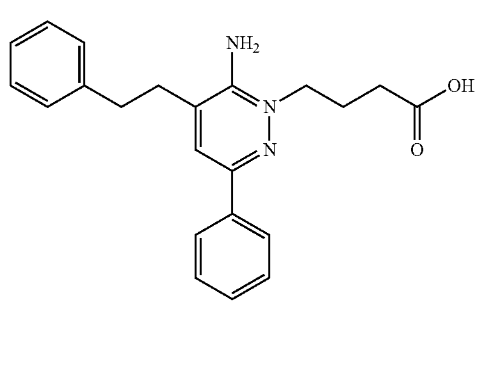 | MW01-1-09-L-G05 |

TABLE 1-continued

| Compound Number | Compound Structure | Synthetic Code |
|---|---|---|
| 271 | 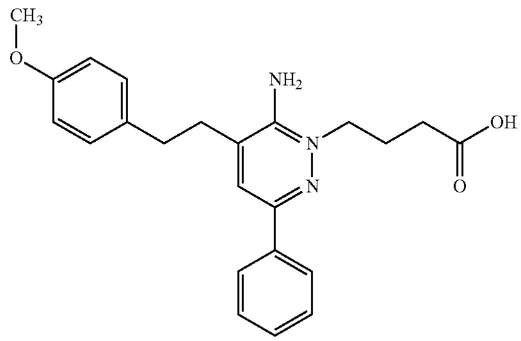 | MW01-1-09-L-G07 |
| 272 | 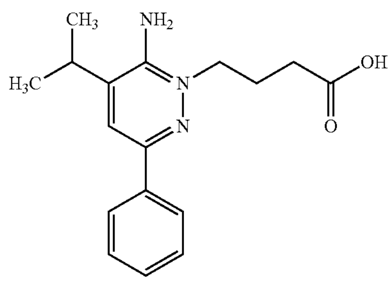 | MW01-1-09-L-G09 |
| 274 | 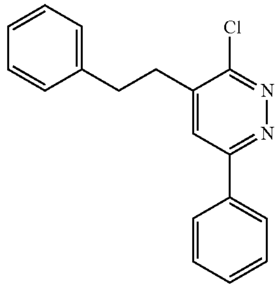 [SMILES: Clc1nnc(-c2ccccc2)cc1CCc1ccccc1] | MW01-1-09-L-H07 |
| 275 | 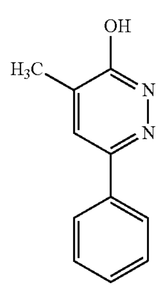 | MW01-1-15-L-A04 |
| 276 | 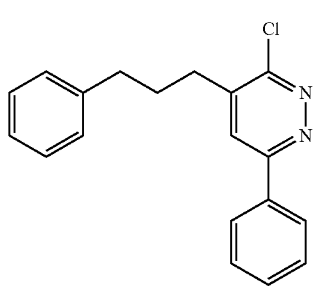 [SMILES: Clc1nnc(-c2ccccc2)cc1CCCc1ccccc1] | MW01-1-15-L-B02 |

TABLE 1-continued

| Compound Number | Compound Structure | Synthetic Code |
|---|---|---|
| 278 | 3-chloro-4-isobutyl-6-phenylpyridazine | MW01-1-15-L-B10 |
| 280 | 4-butyl-6-phenylpyridazin-3-ol | MW01-1-15-L-C04 |
| 282 | 3-chloro-4-isopropyl-6-phenylpyridazine | MW01-1-15-L-D03 |
| 284 | 4-methyl-6-phenylpyridazine | MW01-1-15-L-G10 |
| 292 | 4-methyl-3-(3-morpholinopropoxy)-6-phenylpyridazine | MW01-1-17-L-A09 |

TABLE 1-continued

| Compound Number | Compound Structure | Synthetic Code |
|---|---|---|
| 293 | 4-methyl-6-phenyl-N-(2-morpholinoethyl)pyridazin-3-amine | MW01-1-17-L-A11 |
| 294 | 2-((4-methyl-6-phenylpyridazin-3-yl)amino)ethanol | MW01-1-17-L-B02 |
| 295 | N1-(4-methyl-6-phenylpyridazin-3-yl)-N2-methylethane-1,2-diamine | MW01-1-17-L-B10 |
| 296 | N1-(4-methyl-6-phenylpyridazin-3-yl)-N2,N2-dipropylethane-1,2-diamine | MW01-1-17-L-E11 |
| 297 | 4-methyl-6-phenyl-N-(2-(piperidin-1-yl)ethyl)pyridazin-3-amine | MW01-1-17-L-F03 |
| 298 | 4-(2-((4-methyl-6-phenylpyridazin-3-yl)amino)ethyl)morpholin-3-one | MW01-1-17-L-H05 |

TABLE 1-continued
| Compound Number | Compound Structure | Synthetic Code |
|---|---|---|
| 299 | 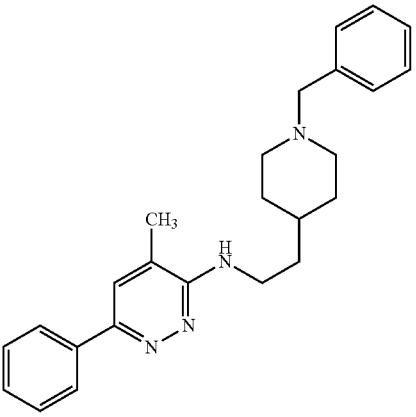 [SMILES: Cc1cc(-c2ccccc2)nnc1NCCC1CCN(Cc2ccccc2)CC1] | MW01-1-18-L-A09 |
| 308 | 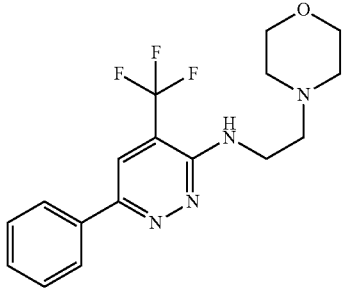 [SMILES: FC(F)(F)c1cc(-c2ccccc2)nnc1NCCN1CCOCC1] | MW01-2-03-L-B08 |
| 310 | 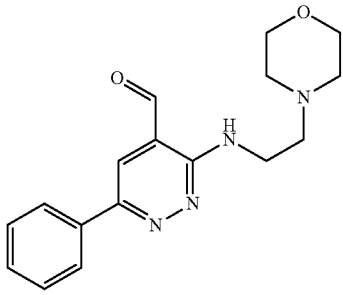 [SMILES: O=Cc1cc(-c2ccccc2)nnc1NCCN1CCOCC1] | MW01-2-03-L-C05 |
| 313 | 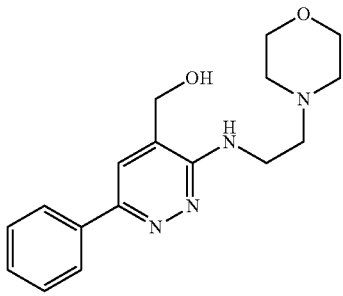 [SMILES: OCc1cc(-c2ccccc2)nnc1NCCN1CCOCC1] | MW01-2-03-L-G07 |

TABLE 1-continued

| Compound Number | Compound Structure | Synthetic Code |
|---|---|---|
| 318 | 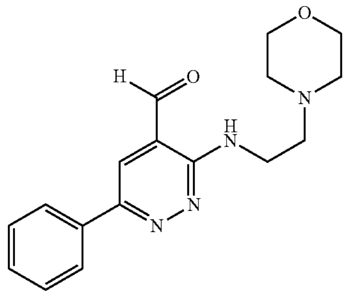 [SMILES: O=Cc1cc(-c2ccccc2)nnc1NCCN1CCOCC1] | MW01-2-101-L-H08 |
| 319 | 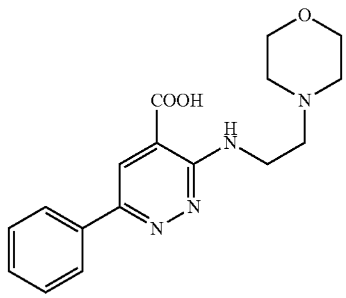 [SMILES: O=C(O)c1cc(-c2ccccc2)nnc1NCCN1CCOCC1] | MW01-2-10-L-E05 |
| 320 | 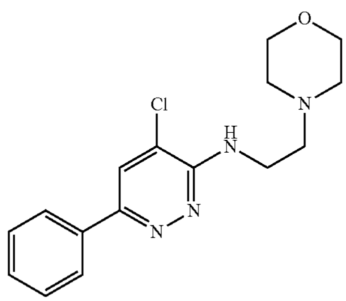 [SMILES: Clc1cc(-c2ccccc2)nnc1NCCN1CCOCC1] | MW01-2-10-L-E06 |
| 321 | 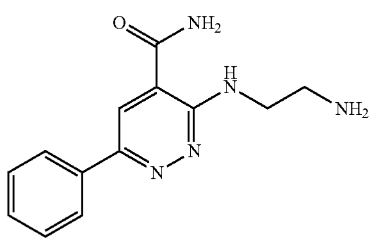 [SMILES: NCCNc1nnc(-c2ccccc2)cc1C(N)=O] | MW01-2-20-L-B02 |
| 323 | 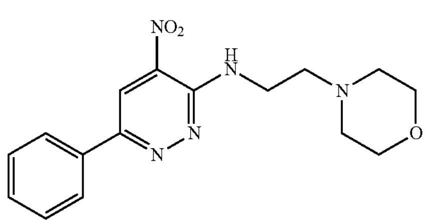 [SMILES: O=[N+]([O-])c1cc(-c2ccccc2)nnc1NCCN1CCOCC1] | MW01-2-20-L-D05 |

TABLE 1-continued
| Compound Number | Compound Structure | Synthetic Code |
|---|---|---|
| 324 | 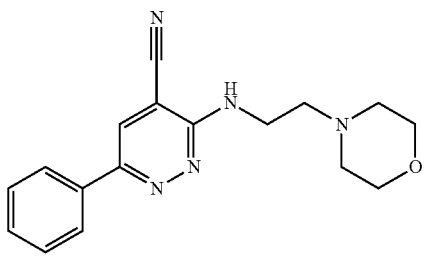 [SMILES: N#Cc1cc(-c2ccccc2)nnc1NCCN1CCOCC1] | MW01-2-20-L-E09 |
| 326 | 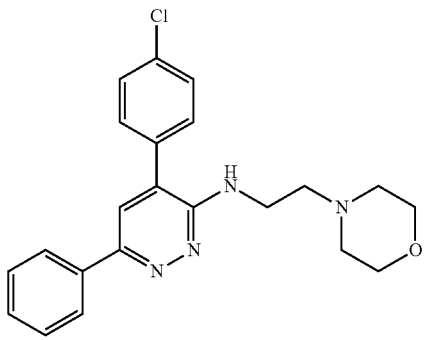 [SMILES: Clc1ccc(-c2cc(-c3ccccc3)nnc2NCCN2CCOCC2)cc1] | MW01-2-25-L-H06 |
| 328 | 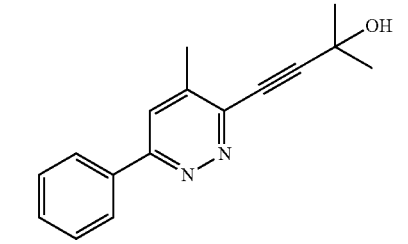 [SMILES: Cc1cc(-c2ccccc2)nnc1C#CC(C)(C)O] | MW01-3-01-L-G03 |
| 329 | 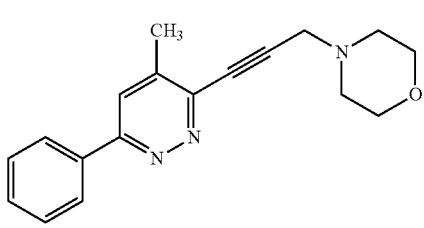 [SMILES: Cc1cc(-c2ccccc2)nnc1C#CCN1CCOCC1] | MW01-3-01-L-G04 |
| 331 | 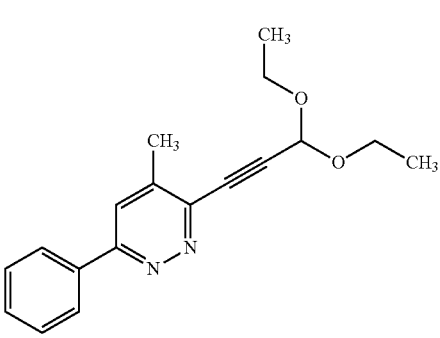 [SMILES: CCOC(C#Cc1nnc(-c2ccccc2)cc1C)OCC] | MW01-3-01-L-G08 |

TABLE 1-continued
| Compound Number | Compound Structure | Synthetic Code |
|---|---|---|
| 332 | 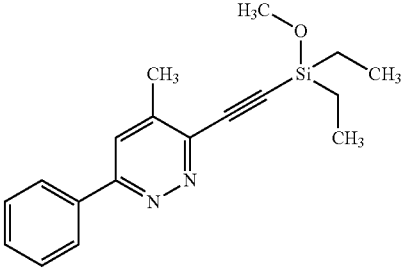 [SMILES: CC[Si](C#Cc1nnc(-c2ccccc2)cc1C)(CC)OC] | MW01-3-01-L-G09 |
| 335 | 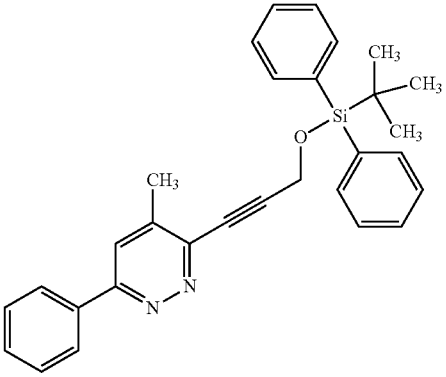 [SMILES: Cc1cc(-c2ccccc2)nnc1C#CCO[Si](c1ccccc1)(c1ccccc1)C(C)(C)C] | MW01-3-06-L-E09 |
| 337 | 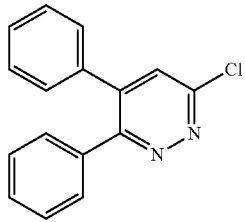 [SMILES: Clc1cc(-c2ccccc2)c(-c2ccccc2)nn1] | MW01-1-07-L-G07 |
| 339 | 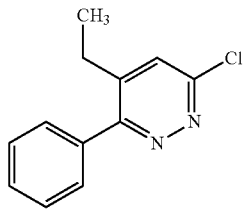 | MW01-1-15-L-C11 |
| 340 | 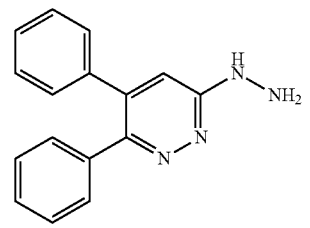 [SMILES: NNc1cc(-c2ccccc2)c(-c2ccccc2)nn1] | MW01-1-15-L-E09 |
| 341 | 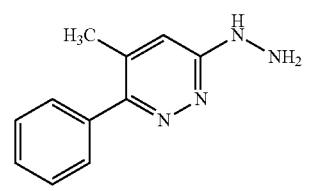 | MW01-1-16-L-B11 |

TABLE 1-continued

| Compound Number | Compound Structure | Synthetic Code |
|---|---|---|
| 346 | 5-ethyl-N-(2-(diethylamino)ethyl)-6-phenylpyridazin-3-amine | MW01-1-17-L-F10 |
| 347 | 5-ethyl-N-(2-morpholinoethyl)-6-phenylpyridazin-3-amine | MW01-1-17-L-F11 |
| 350 | 5-methyl-N-(hexahydro-1H-pyrrolizin-7a-ylmethyl)-6-phenylpyridazin-3-amine | MW01-2-20-L-B11 |
| 352 | methyl 5-methyl-6-phenylpyridazine-3-carboxylate | MW01-3-01-L-F09 |
| 359 | 3-chloro-6-(2,4-dichlorophenyl)pyridazine-4-carbonitrile | MW01-1-03-L-E05 |

TABLE 1-continued

| Compound Number | Compound Structure | Synthetic Code |
|---|---|---|
| 360 | 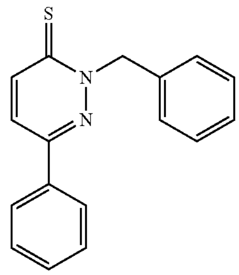 [SMILES: S=c1ccc(-c2ccccc2)nn1Cc1ccccc1] | MW01-1-03-L-A08 |
| 361 | 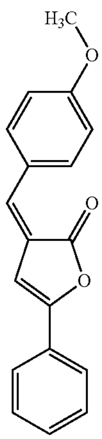 [SMILES: COc1ccc(/C=C2/C=C(c3ccccc3)OC2=O)cc1] | MW01-1-03-L-H08 |
| 362 | 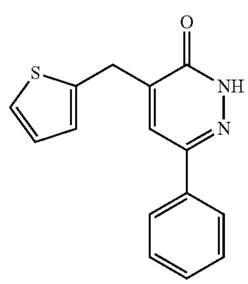 [SMILES: O=c1[nH]nc(-c2ccccc2)cc1Cc1cccs1] | MW01-1-01-L-H04 |
| 363 | 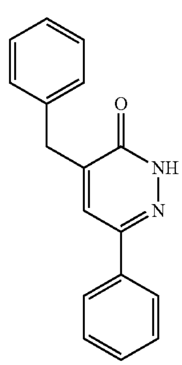 [SMILES: O=c1[nH]nc(-c2ccccc2)cc1Cc1ccccc1] | MW01-1-01-L-H06 |

TABLE 1-continued

| Compound Number | Compound Structure | Synthetic Code |
|---|---|---|
| 366 | 4-methyl-6-(4-chlorophenyl)pyridazine-3(2H)-thione | MW01-1-03-L-E07 |
| 367 | 2-((4-nitrobenzyl)thio)-4,5-dihydro-1H-imidazole | MW01-1-05-L-E05 |
| 368 | 4-methyl-6-(naphthalen-1-yl)pyridazin-3(2H)-one | MW01-1-03-L-B03 |
| 371 | 2-methyl-4-(4-nitrophenyl)thiazole | MW01-1-05-L-E07 |
| 372 | 4-methyl-6-(4-chlorophenyl)pyridazin-3(2H)-one | MW01-1-03-L-A03 |

TABLE 1-continued

| Compound Number | Compound Structure | Synthetic Code |
|---|---|---|
| 373 | 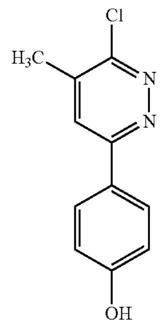 | MW01-1-03-L-E03 |
| 374 | 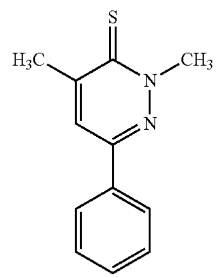 | MW01-1-01-L-H10 |
| 375 | 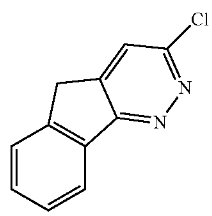 [SMILES: Clc1cc2c(nn1)-c1ccccc1C2] | MW01-1-04-L-H08 |
| 376 | 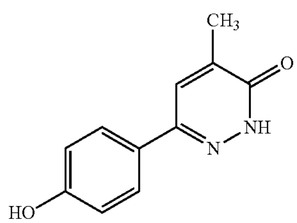 | MW01-1-01-L-G10 |
| 377 | 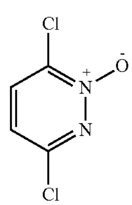 | MW01-1-03-L-G11 |
| 380 | 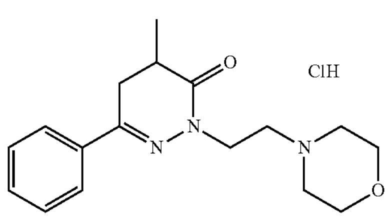 [SMILES: CC1CC(c2ccccc2)=NN(CCN2CCOCC2)C1=O ; Cl] | MW01-1-04-L-B07 |

TABLE 1-continued

| Compound Number | Compound Structure | Synthetic Code |
|---|---|---|
| 381 | (4-methyl-6-(4-bromophenyl)-2-(2-morpholinoethyl)pyridazin-3(2H)-one · HCl) | MW01-1-04-L-C09 |
| 382 | (7-phenyl-2-(2-(4-phenylpiperazin-1-yl)ethyl)-2,3,4,5-tetrahydro-1H-1,2-diazepin-3-one · oxalic acid) | MW01-1-10-L-G05 |

TABLE 2

| Compound Number | Compound Structure | Synthetic Code |
|---|---|---|
| 22 | (N'-(6-phenylpyridazin-3-yl)-N,N-dimethylformamidine) | MW01-1-15-L-E08 |
| 26 | (2,7-diphenylpyrazolo[1,2-a]pyridazin-3-ol type structure) | MW01-2-02-L-H09 |
| 29 | (3,4-bis(4-(pyrimidin-2-yl)piperazin-1-yl)-6-phenylpyridazine) | MW01-1-030A-LKM |

TABLE 2-continued

| Compound Number | Compound Structure | Synthetic Code |
|---|---|---|
| 30 | 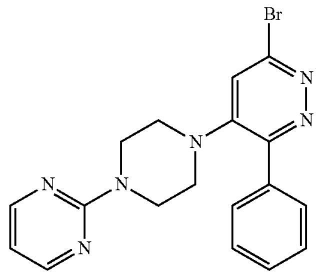 [SMILES: Brc1cc(N2CCN(c3ncccn3)CC2)c(-c2ccccc2)nn1] | MW01-1-030B-LKM |
| 32 | 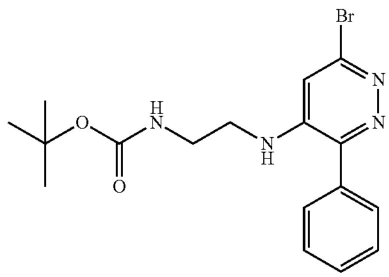 [SMILES: CC(C)(C)OC(=O)NCCNc1cc(Br)nnc1-c1ccccc1] | MW01-1-048AB-LKM |
| 33 | 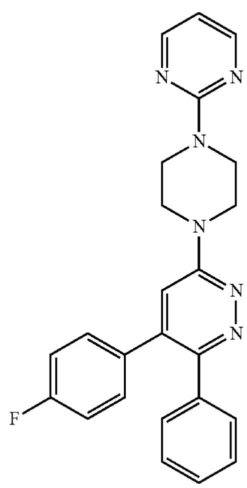 [SMILES: Fc1ccc(-c2cc(N3CCN(c4ncccn4)CC3)nnc2-c2ccccc2)cc1] | MW01-2-065LKM |
| 34 | 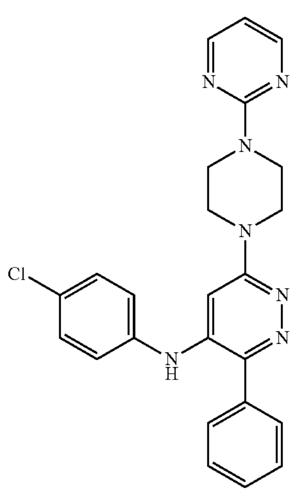 [SMILES: Clc1ccc(Nc2cc(N3CCN(c4ncccn4)CC3)nnc2-c2ccccc2)cc1] | MW01-2-127LKM |

TABLE 2-continued

| Compound Number | Compound Structure | Synthetic Code |
|---|---|---|
| 35 | 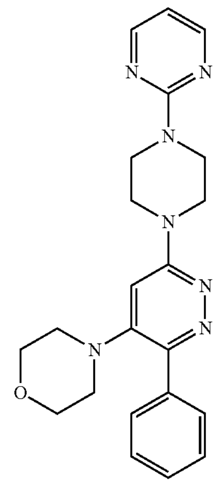 [SMILES: c1ccc(-c2nnc(N3CCN(c4ncccn4)CC3)cc2N2CCOCC2)cc1] | MW01-2-134LKM |
| 36 | 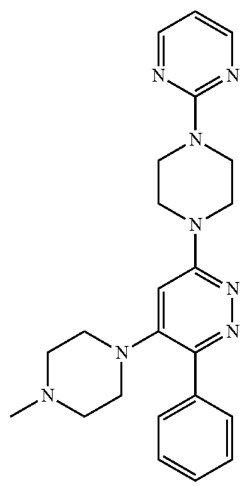 [SMILES: CN1CCN(c2cc(N3CCN(c4ncccn4)CC3)nnc2-c2ccccc2)CC1] | MW01-2-146LKM |
| 37 | 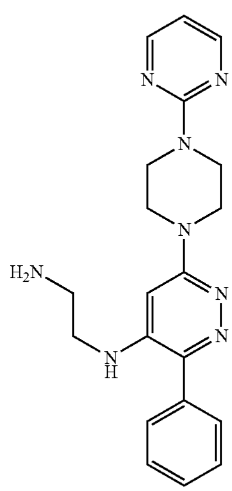 [SMILES: NCCNc1cc(N2CCN(c3ncccn3)CC2)nnc1-c1ccccc1] | MW01-2-147LKM |
| 38 | 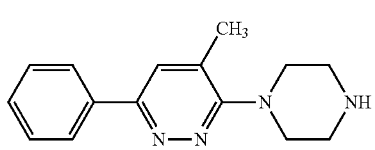 [SMILES: Cc1cc(-c2ccccc2)nnc1N1CCNCC1] | MW01-1-02-L-B11 |

TABLE 2-continued
| Compound Number | Compound Structure | Synthetic Code |
|---|---|---|
| 39 | 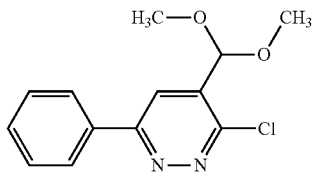 [SMILES: COC(OC)c1cc(-c2ccccc2)nnc1Cl] | MW01-1-04-L-F10 |
| 42 | 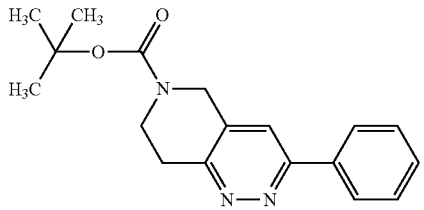 [SMILES: CC(C)(C)OC(=O)N1CCc2nnc(-c3ccccc3)cc2C1] | MW01-2-33-L-A11 |
| 45 | 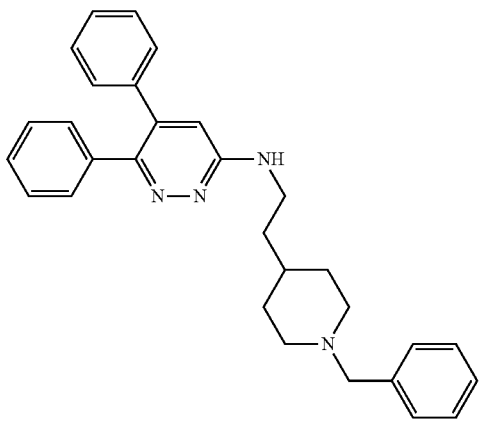 [SMILES: c1ccc(CN2CCC(CCNc3cc(-c4ccccc4)c(-c4ccccc4)nn3)CC2)cc1] | MW01-1-17-L-E06 |
| 46 | 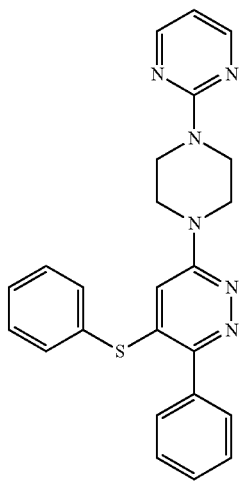 [SMILES: c1ccc(Sc2cc(N3CCN(c4ncccn4)CC3)nnc2-c2ccccc2)cc1] | MW01-1-045MAS |

TABLE 2-continued

| Compound Number | Compound Structure | Synthetic Code |
|---|---|---|
| 53 | 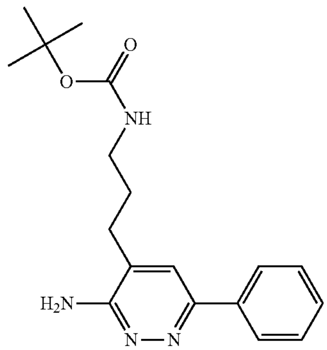 [SMILES: CC(C)(C)OC(=O)NCCCc1cc(-c2ccccc2)nnc1N] | MW01-5-145B-Z |
| 56 | 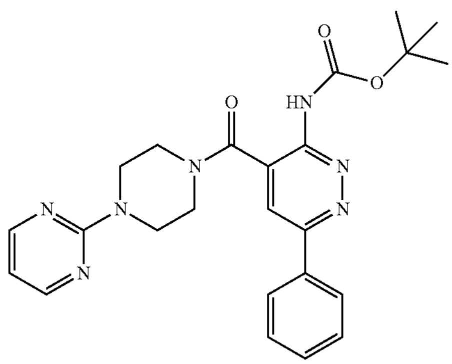 [SMILES: CC(C)(C)OC(=O)Nc1nnc(-c2ccccc2)cc1C(=O)N1CCN(c2ncccn2)CC1] | MW01-7-127AB-Z |
| 60 | 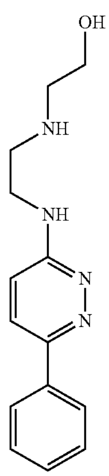 | MW01-1-01-L-B04 |
| 62 | 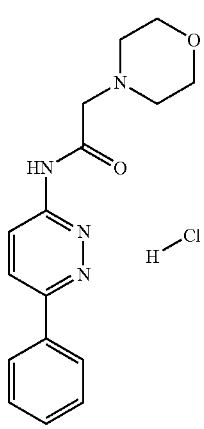 [SMILES: O=C(CN1CCOCC1)Nc1ccc(-c2ccccc2)nn1 ; Cl] | MW01-1-01-L-D10 |

TABLE 2-continued
| Compound Number | Compound Structure | Synthetic Code |
|---|---|---|
| 63 | 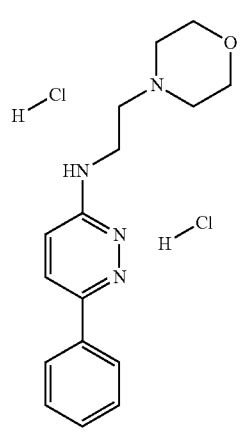 | MW01-1-01-L-E02 |
| 64 | 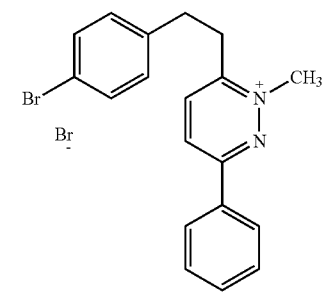 | MW01-1-01-L-E08 |
| 67 | 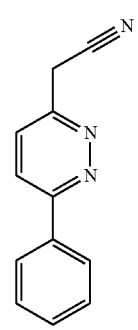 [SMILES: N#CCc1ccc(-c2ccccc2)nn1] | MW01-1-02-L-H10 |
| 68 | 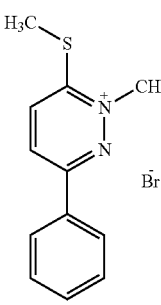 | MW01-1-03-L-A05 |

TABLE 2-continued
| Compound Number | Compound Structure | Synthetic Code |
|---|---|---|
| 69 | 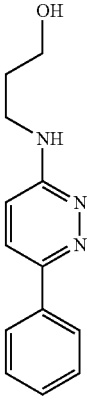 | MW01-1-03-L-B08 |
| 72 | 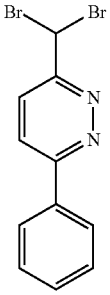 | MW01-1-03-L-G09 |
| 87 | 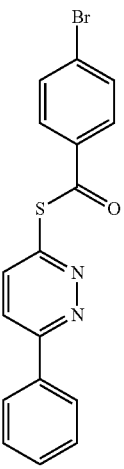 [SMILES: O=C(Sc1ccc(-c2ccccc2)nn1)c1ccc(Br)cc1] | MW01-1-08-L-E11 |

TABLE 2-continued
| Compound Number | Compound Structure | Synthetic Code |
|---|---|---|
| 93 | 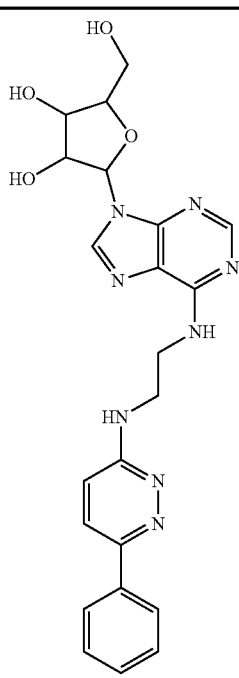 | MW01-1-13-L-G06 |
| 95 | 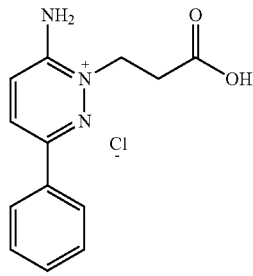 | MW01-1-16-L-D09 |
| 96 | 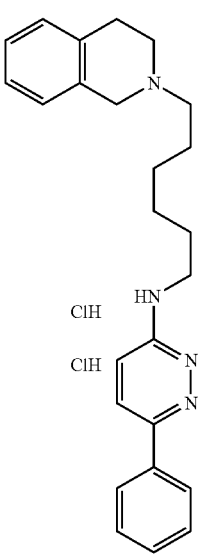 [SMILES: c1ccc(-c2ccc(NCCCCCCN3CCc4ccccc4C3)nn2)cc1 ; Cl ; Cl] | MW01-1-16-L-E02 |
| 105 | 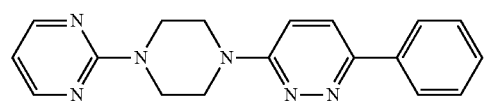 | MW01-9-038Z |

TABLE 2-continued
| Compound Number | Compound Structure | Synthetic Code |
|---|---|---|
| 121 | 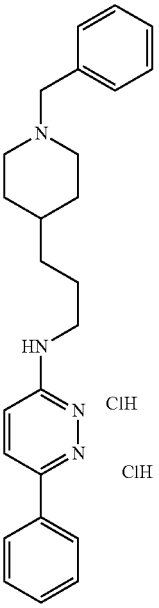 [SMILES: c1ccc(CN2CCC(CCCNc3ccc(-c4ccccc4)nn3)CC2)cc1 ; Cl ; Cl] | MW01-1-17-L-G04 |
| 124 | 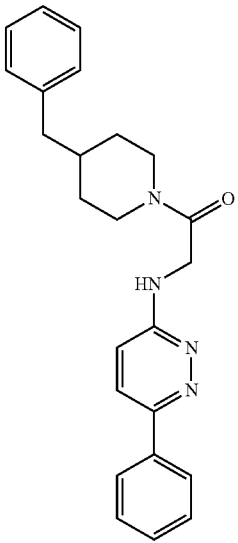 [SMILES: O=C(CNc1ccc(-c2ccccc2)nn1)N1CCC(Cc2ccccc2)CC1] | MW01-1-17-L-H02 |
| 126 | 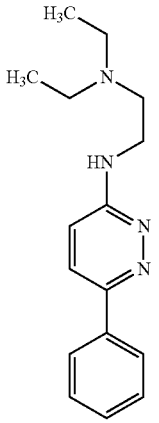 [SMILES: CCN(CC)CCNc1ccc(-c2ccccc2)nn1] | MW01-1-17-L-H07 |

TABLE 2-continued
| Compound Number | Compound Structure | Synthetic Code |
|---|---|---|
| 128 | 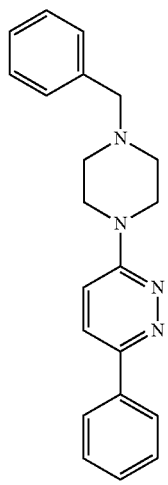 | MW01-1-18-L-A02 |
| 129 | 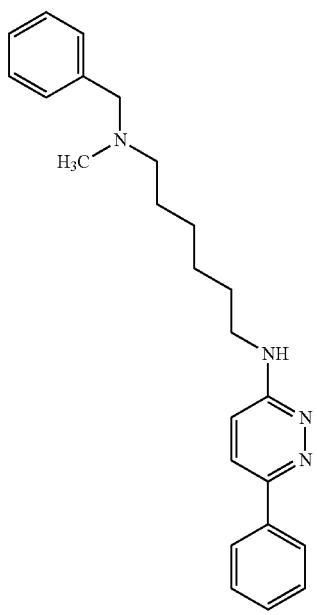 [SMILES: CN(CCCCCCNc1ccc(-c2ccccc2)nn1)Cc1ccccc1] | MW01-1-18-L-A03 |
| 136 | 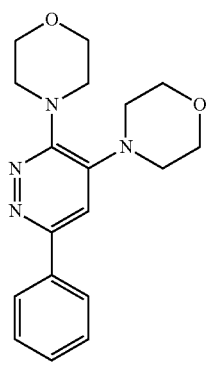 [SMILES: c1ccc(-c2cc(N3CCOCC3)c(N3CCOCC3)nn2)cc1] | MW01-2-018SRM |

TABLE 2-continued

| Compound Number | Compound Structure | Synthetic Code |
|---|---|---|
| 138 | 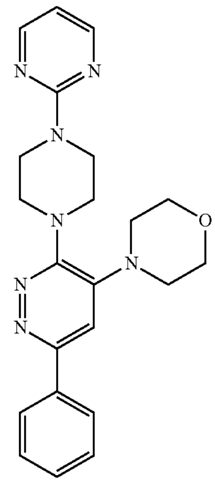 [SMILES: c1ccc(-c2cc(N3CCOCC3)c(N3CCN(c4ncccn4)CC3)nn2)cc1] | MW01-2-023SRM |
| 147 | 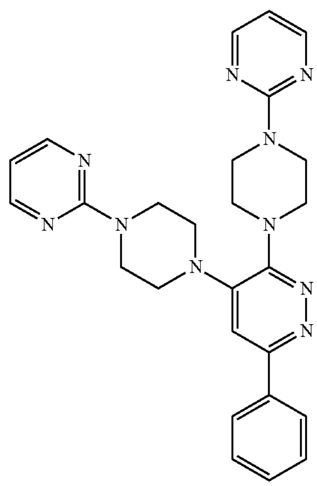 [SMILES: c1ccc(-c2cc(N3CCN(c4ncccn4)CC3)c(N3CCN(c4ncccn4)CC3)nn2)cc1] | MW01-2-177A-WH |
| 148 | 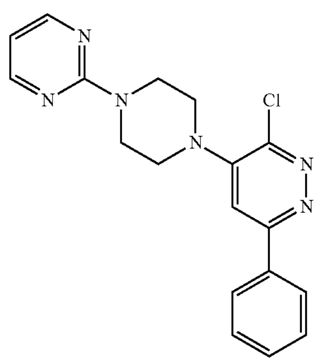 [SMILES: Clc1nnc(-c2ccccc2)cc1N1CCN(c2ncccn2)CC1] | MW01-2-177B-WH |
| 153 | 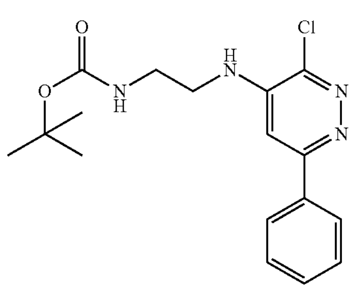 [SMILES: CC(C)(C)OC(=O)NCCNc1cc(-c2ccccc2)nnc1Cl] | MW01-2-184WH |

TABLE 2-continued
| Compound Number | Compound Structure | Synthetic Code |
|---|---|---|
| 155 | 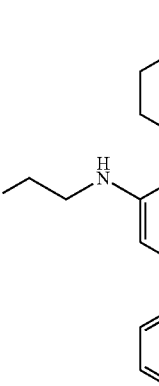 | MW01-2-191A-WH |
| 156 | 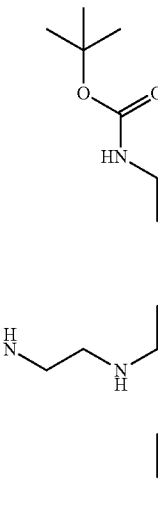 | MW01-2-193B-WH |
| 157 | 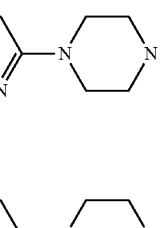 | MW01-3-003WH |
| 160 | 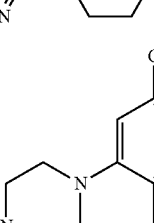 | MW01-3-019A-WH |
| 161 | 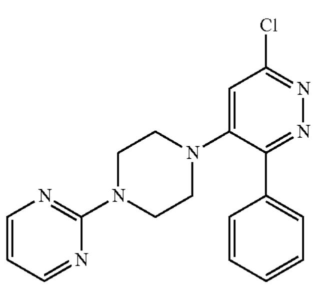 [SMILES: Clc1cc(N2CCN(c3ncccn3)CC2)c(-c2ccccc2)nn1] | MW01-3-060A-WH |

TABLE 2-continued
| Compound Number | Compound Structure | Synthetic Code |
|---|---|---|
| 162 | 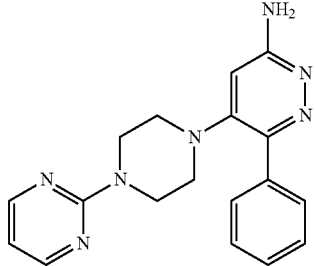 [SMILES: Nc1cc(N2CCN(c3ncccn3)CC2)c(-c2ccccc2)nn1] | MW01-3-072WH |
| 163 | 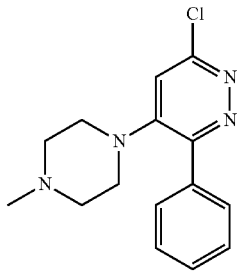 [SMILES: CN1CCN(c2cc(Cl)nnc2-c2ccccc2)CC1] | MW01-3-117WH |
| 164 | 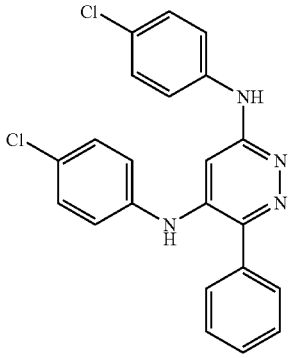 [SMILES: Clc1ccc(Nc2cc(Nc3ccc(Cl)cc3)c(-c3ccccc3)nn2)cc1] | MW01-3-118WH |
| 166 | 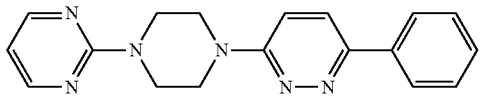 | MW01-3-183WH |
| 171 | 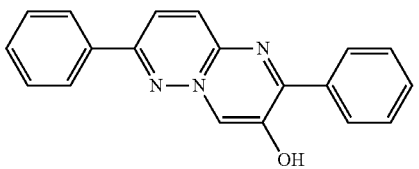 | MW01-2-03-L-G03 |
| 172 | 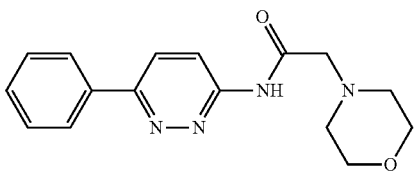 [SMILES: O=C(CN1CCOCC1)Nc1ccc(-c2ccccc2)nn1] | MW01-2-03-L-C04 |

TABLE 2-continued

| Compound Number | Compound Structure | Synthetic Code |
|---|---|---|
| 174 | 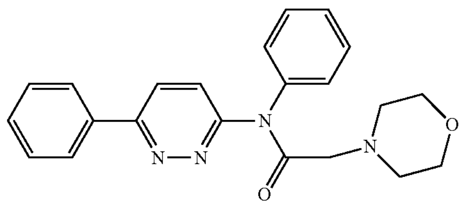 [SMILES: O=C(CN1CCOCC1)N(c1ccccc1)c1ccc(-c2ccccc2)nn1] | MW01-2-03-L-G03 |
| 176 | 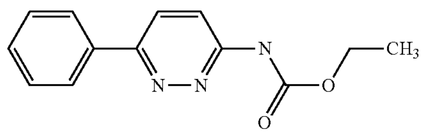 [SMILES: CCOC(=O)Nc1ccc(-c2ccccc2)nn1] | MW01-2-102-L-C11 |
| 177 | 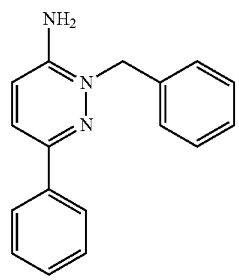 | MW01-2-21-L-F04 |
| 178 | 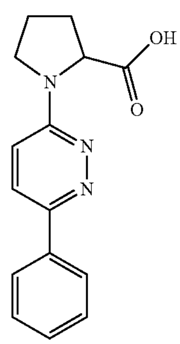 [SMILES: O=C(O)C1CCCN1c1ccc(-c2ccccc2)nn1] | MW01-2-24-L-G09 |
| 181A | 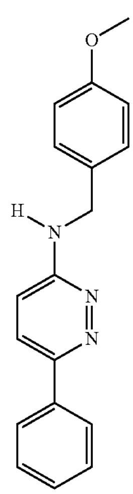 [SMILES: COc1ccc(CNc2ccc(-c3ccccc3)nn2)cc1] | |

TABLE 2-continued

| Compound Number | Compound Structure | Synthetic Code |
|---|---|---|
| 186 | 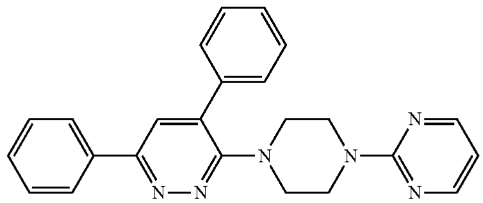 [SMILES: c1ccc(-c2cc(-c3ccccc3)c(N3CCN(c4ncccn4)CC3)nn2)cc1] | MW01-5-188WH |
| 188 | 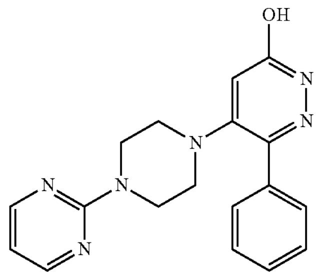 [SMILES: Oc1cc(N2CCN(c3ncccn3)CC2)c(-c2ccccc2)nn1] | MW01-6-003WH |
| 191 | 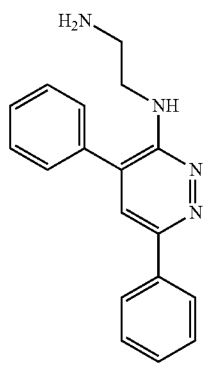 [SMILES: NCCNc1nnc(-c2ccccc2)cc1-c1ccccc1] | MW01-6-046WH |
| 200 | 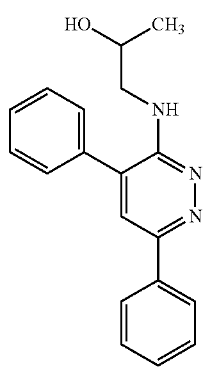 [SMILES: CC(O)CNc1nnc(-c2ccccc2)cc1-c1ccccc1] | MW01-1-01-L-C06 |
| 203 | 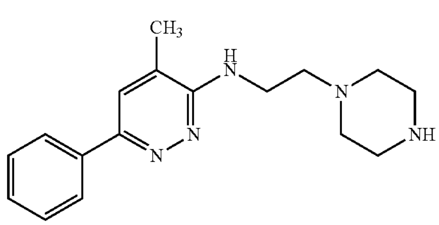 [SMILES: Cc1cc(-c2ccccc2)nnc1NCCN1CCNCC1] | MW01-2-03-L-D09 |

TABLE 2-continued
| Compound Number | Compound Structure | Synthetic Code |
|---|---|---|
| 204 | 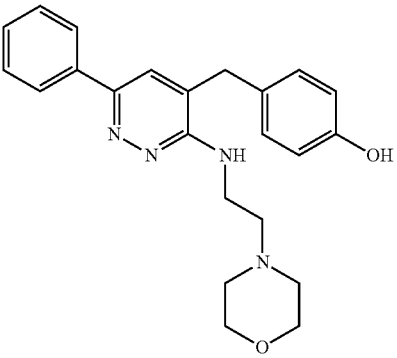 [SMILES: Oc1ccc(Cc2cc(-c3ccccc3)nnc2NCCN2CCOCC2)cc1] | MW01-1-01-L-B02 |
| 206 | 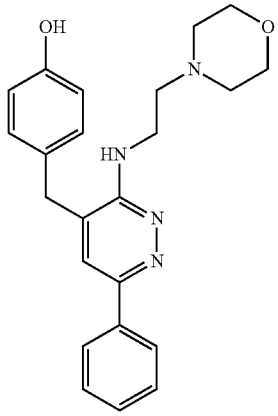 [SMILES: Oc1ccc(Cc2cc(-c3ccccc3)nnc2NCCN2CCOCC2)cc1] | MW01-2-03-L-D09 |
| 207 | 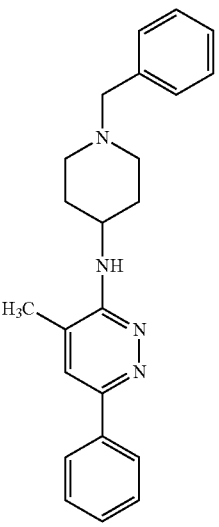 [SMILES: Cc1cc(-c2ccccc2)nnc1NC1CCN(Cc2ccccc2)CC1] | MW01-2-03-L-G04 |
| 209 | 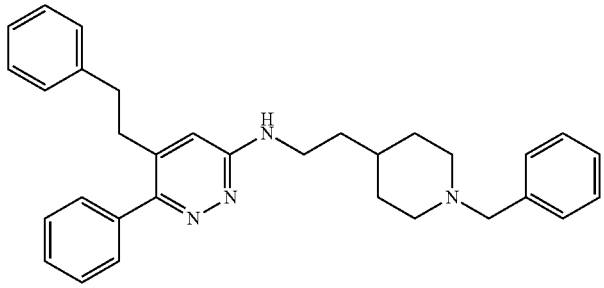 [SMILES: c1ccc(CCc2cc(NCCC3CCN(Cc4ccccc4)CC3)nnc2-c2ccccc2)cc1] | MW01-1-17-L-E05 |

TABLE 2-continued

| Compound Number | Compound Structure | Synthetic Code |
|---|---|---|
| 211 | 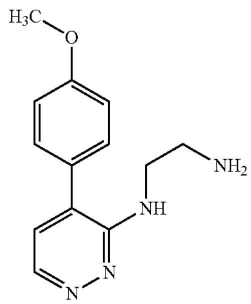 [SMILES: COc1ccc(-c2ccnnc2NCCN)cc1] | MW01-1-04-L-C03 |
| 212 | 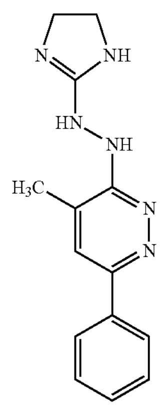 [SMILES: Cc1cc(-c2ccccc2)nnc1NNC1=NCCN1] | MW01-1-01-L-E11 |
| 213 | 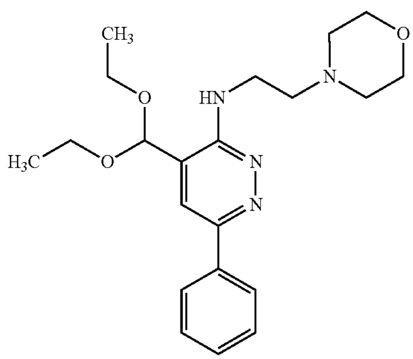 [SMILES: CCOC(OCC)c1cc(-c2ccccc2)nnc1NCCN1CCOCC1] | MW01-1-01-L-F02 |
| 214 | 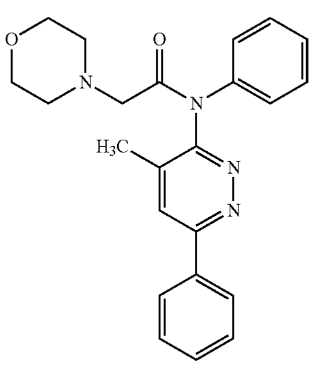 [SMILES: Cc1cc(-c2ccccc2)nnc1N(C(=O)CN1CCOCC1)c1ccccc1] | MW01-1-01-L-F03 |

TABLE 2-continued

| Compound Number | Compound Structure | Synthetic Code |
|---|---|---|
| 215 | 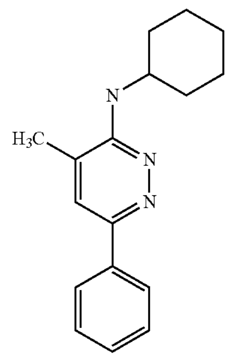 [SMILES: Cc1cc(-c2ccccc2)nnc1NC1CCCCC1] | MW01-1-01-L-G08 |
| 216 | 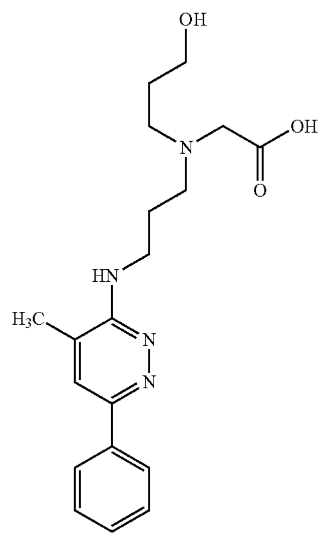 [SMILES: Cc1cc(-c2ccccc2)nnc1NCCCN(CCCO)CC(=O)O] | MW01-1-02-L-D11 |
| 219 | 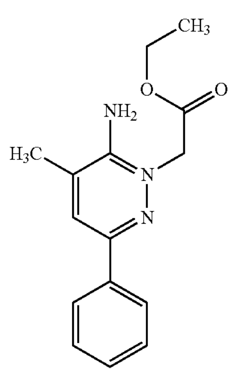 | MW01-1-02-L-E04 |
| 220 | 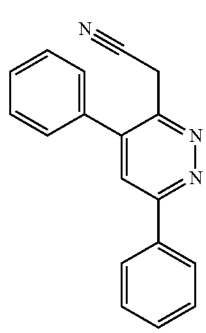 [SMILES: N#CCc1nnc(-c2ccccc2)cc1-c1ccccc1] | MW01-1-02-L-E11 |

TABLE 2-continued

| Compound Number | Compound Structure | Synthetic Code |
|---|---|---|
| 222 | 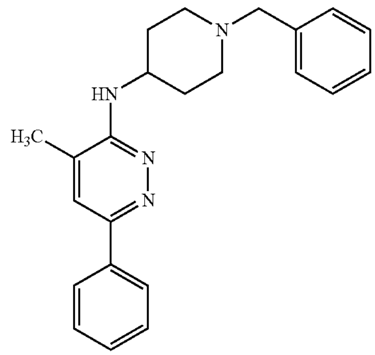 [SMILES: Cc1cc(-c2ccccc2)nnc1NC1CCN(Cc2ccccc2)CC1] | MW01-1-02-L-F04 |
| 224 | 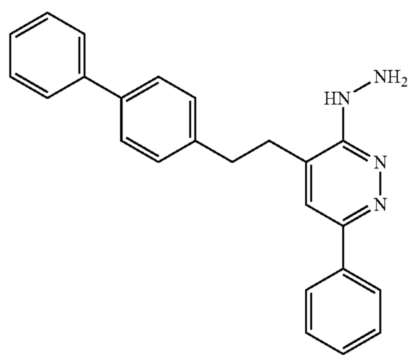 [SMILES: NNc1nnc(-c2ccccc2)cc1CCc1ccc(-c2ccccc2)cc1] | MW01-1-02-L-F09 |
| 228 | 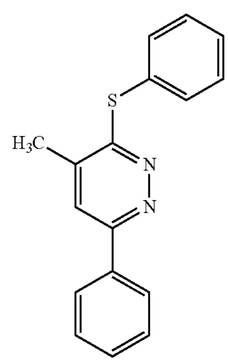 [SMILES: Cc1cc(-c2ccccc2)nnc1Sc1ccccc1] | MW01-1-03-L-A04 |
| 232 | 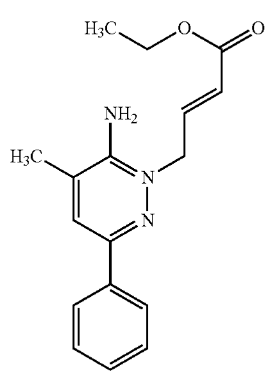 | MW01-1-03-L-C04 |

TABLE 2-continued
| Compound Number | Compound Structure | Synthetic Code |
|---|---|---|
| 234 | 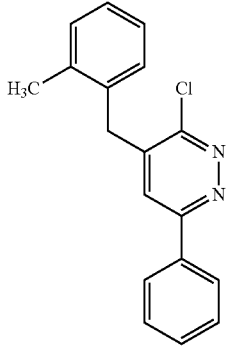 [SMILES: Cc1ccccc1Cc1cc(-c2ccccc2)nnc1Cl] | MW01-1-03-L-E04 |
| 237 | 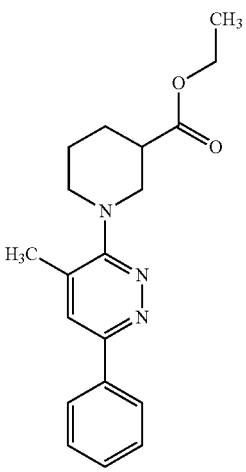 [SMILES: CCOC(=O)C1CCCN(c2nnc(-c3ccccc3)cc2C)C1] | MW01-1-03-L-E10 |
| 238 | 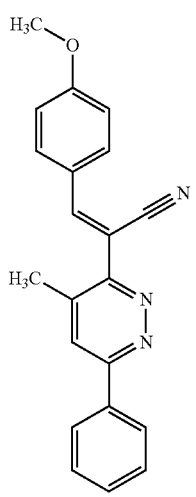 [SMILES: COc1ccc(/C=C(\C#N)c2nnc(-c3ccccc3)cc2C)cc1] | MW01-1-03-L-G02 |

TABLE 2-continued
| Compound Number | Compound Structure | Synthetic Code |
|---|---|---|
| 239 | 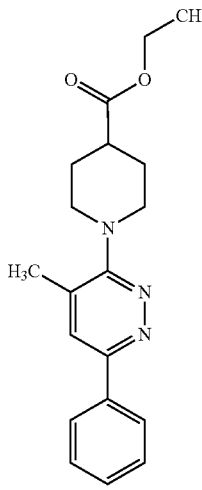 | MW01-1-03-L-H04 |
| 241 | 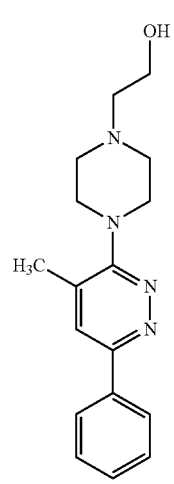 [SMILES: Cc1cc(-c2ccccc2)nnc1N1CCN(CCO)CC1] | MW01-1-04-L-D08 |
| 243 | 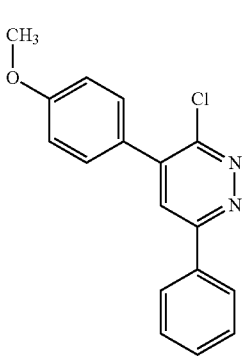 [SMILES: COc1ccc(-c2cc(-c3ccccc3)nnc2Cl)cc1] | MW01-1-04-L-E03 |

TABLE 2-continued

| Compound Number | Compound Structure | Synthetic Code |
|---|---|---|
| 244 | 3-(cyanomethyl)-4-methyl-6-phenylpyridazine | MW01-1-04-L-E04 |
| 245 | 1-(4-methyl-6-phenylpyridazin-3-yl)piperidine-4-carboxylic acid | MW01-1-04-L-E09 |
| 246 | ethyl 5-((4-methyl-6-phenylpyridazin-3-yl)amino)pentanoate | MW01-1-04-L-F06 |
| 247 | 3-chloro-4-(dibromomethyl)-6-phenylpyridazine | MW01-1-04-L-G06 |

TABLE 2-continued
| Compound Number | Compound Structure | Synthetic Code |
|---|---|---|
| 248 | 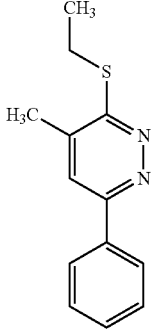 | MW01-1-04-L-H06 |
| 249 | 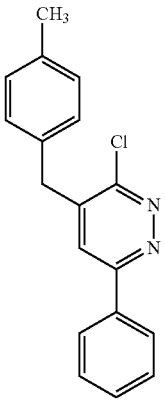 [SMILES: Cc1ccc(Cc2cc(-c3ccccc3)nnc2Cl)cc1] | MW01-1-04-L-H07 |
| 252 | 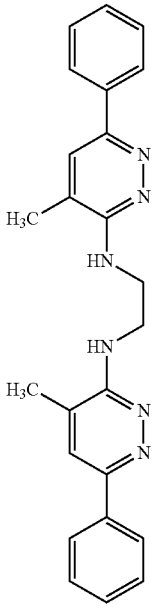 | MW01-1-05-L-F05 |

TABLE 2-continued
| Compound Number | Compound Structure | Synthetic Code |
|---|---|---|
| 253 | 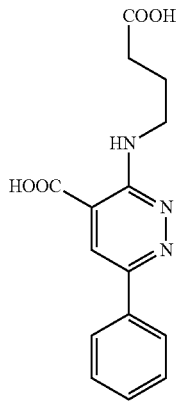 [SMILES: O=C(O)CCCNc1nnc(-c2ccccc2)cc1C(=O)O] | MW01-1-05-L-G10 |
| 256 | 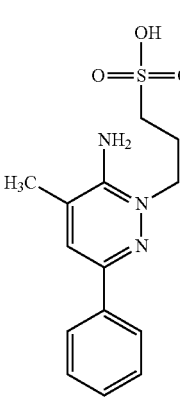 | MW01-1-05-L-H07 |
| 257 | 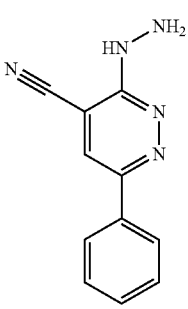 [SMILES: N#Cc1cc(-c2ccccc2)nnc1NN] | MW01-1-05-L-H09 |
| 258 | 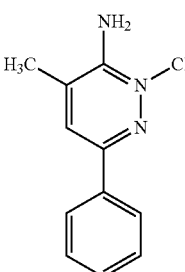 | MW01-1-05-L-H11 |

TABLE 2-continued

| Compound Number | Compound Structure | Synthetic Code |
|---|---|---|
| 259 | 3-methyl-6-phenyl-4-(pyrrolidin-1-yl)pyridazine | MW01-1-07-L-E07 |
| 260 | 3-((4-chlorophenyl)thio)-4-methyl-6-phenylpyridazine | MW01-1-07-L-G09 |
| 261 | 3-((4-chlorophenyl)sulfonyl)-4-methyl-6-phenylpyridazine | MW01-1-07-L-H03 |
| 262 | ethyl 1-(4-methyl-6-phenylpyridazin-3-yl)pyrrolidine-2-carboxylate | MW01-1-07-L-H05 |

TABLE 2-continued

| Compound Number | Compound Structure | Synthetic Code |
|---|---|---|
| 263 | 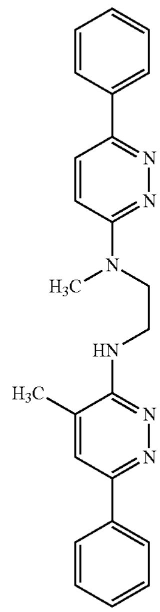 [SMILES: Cc1cc(-c2ccccc2)nnc1NCCN(C)c1ccc(-c2ccccc2)nn1] | MW01-1-07-L-H06 |
| 264 | 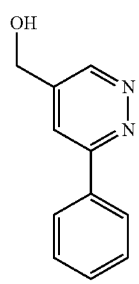 [SMILES: OCc1cnnc(-c2ccccc2)c1] | MW01-1-08-L-C07 |
| 265 | 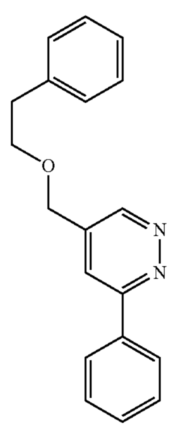 [SMILES: c1ccc(CCOCc2cnnc(-c3ccccc3)c2)cc1] | MW01-1-08-L-C09 |

TABLE 2-continued
| Compound Number | Compound Structure | Synthetic Code |
|---|---|---|
| 267 | 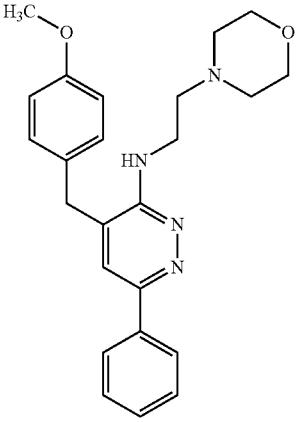 [SMILES: COc1ccc(Cc2cc(-c3ccccc3)nnc2NCCN2CCOCC2)cc1] | MW01-1-08-L-E04 |
| 269 | 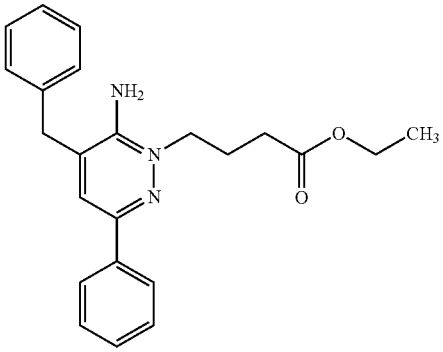 | MW01-1-09-L-G04 |
| 273 | 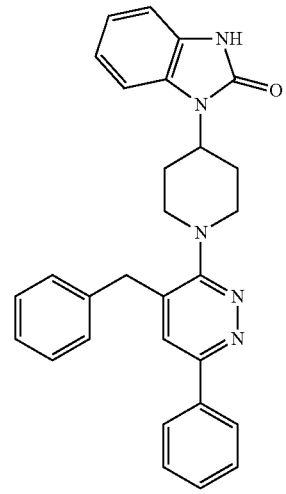 [SMILES: O=c1[nH]c2ccccc2n1C1CCN(c2nnc(-c3ccccc3)cc2Cc2ccccc2)CC1] | MW01-1-09-L-G11 |
| 277 | 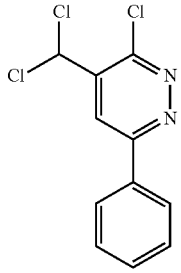 [SMILES: Clc1nnc(-c2ccccc2)cc1C(Cl)Cl] | MW01-1-15-L-B07 |

TABLE 2-continued
| Compound Number | Compound Structure | Synthetic Code |
|---|---|---|
| 279 | 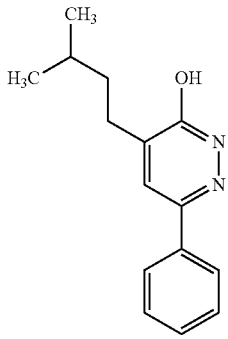 [SMILES: CC(C)CCc1cc(-c2ccccc2)nnc1O] | MW01-1-15-L-B11 |
| 281 | 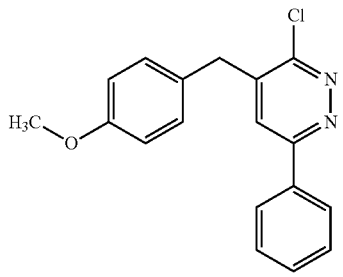 [SMILES: COc1ccc(Cc2cc(-c3ccccc3)nnc2Cl)cc1] | MW01-1-15-L-D02 |
| 282 | 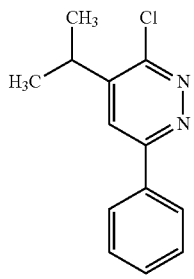 [SMILES: CC(C)c1cc(-c2ccccc2)nnc1Cl] | MW01-1-15-L-D03 |
| 283 | 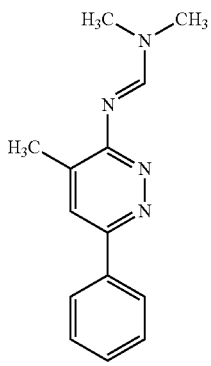 | MW01-1-15-L-E10 |
| 285 | 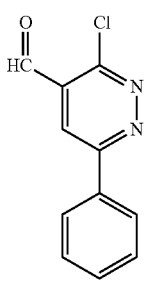 | MW01-1-15-L-H09 |

TABLE 2-continued

| Compound Number | Compound Structure | Synthetic Code |
|---|---|---|
| 286 | 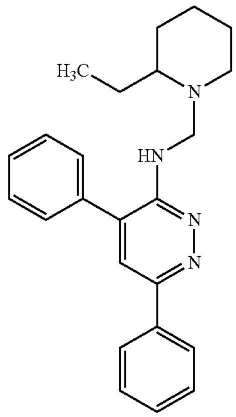 [SMILES: CCC1CCCCN1CNc1nnc(-c2ccccc2)cc1-c1ccccc1] | MW01-1-16-L-E05 |
| 287 | 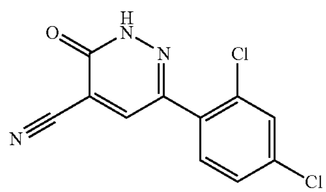 [SMILES: N#Cc1cc(-c2ccc(Cl)cc2Cl)n[nH]c1=O] | MW01-1-01-L-F11 |
| 288 | 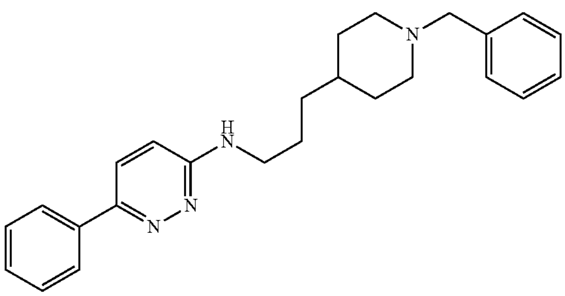 [SMILES: c1ccc(CN2CCC(CCCNc3ccc(-c4ccccc4)nn3)CC2)cc1] | MW01-1-17-L-B05 |
| 290 | 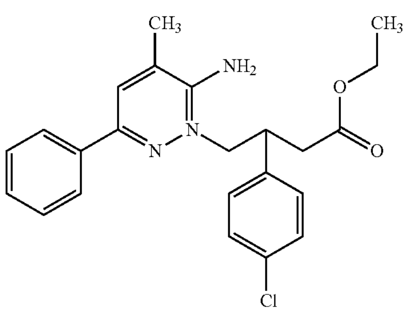 | MW01-1-16-L-E08 |
| 291 | 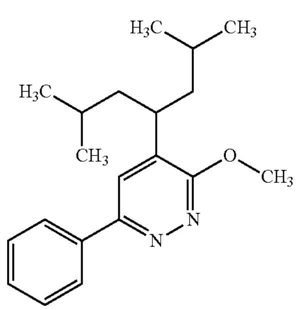 [SMILES: COc1nnc(-c2ccccc2)cc1C(CC(C)C)CC(C)C] | MW01-1-16-L-G07 |

TABLE 2-continued

| Compound Number | Compound Structure | Synthetic Code |
|---|---|---|
| 297 | 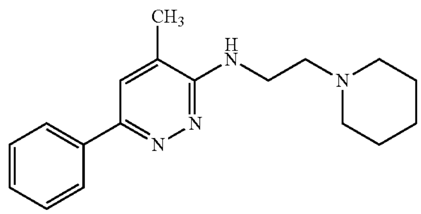 [SMILES: Cc1cc(-c2ccccc2)nnc1NCCN1CCCCC1] | MW01-1-17-L-F03 |
| 300 | 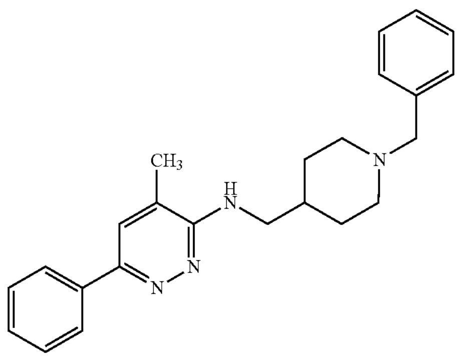 [SMILES: Cc1cc(-c2ccccc2)nnc1NCC1CCN(Cc2ccccc2)CC1] | MW01-1-18-L-B04 |
| 301 | 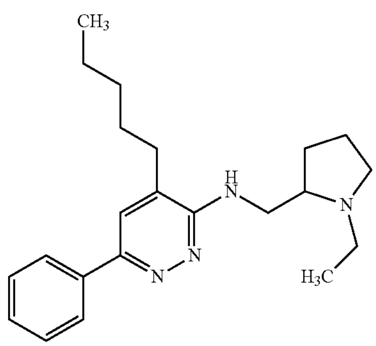 [SMILES: CCCCCc1cc(-c2ccccc2)nnc1NCC1CCCN1CC] | MW01-1-18-L-B10 |
| 302 | 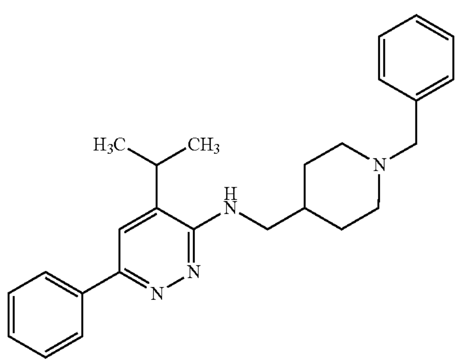 [SMILES: CC(C)c1cc(-c2ccccc2)nnc1NCC1CCN(Cc2ccccc2)CC1] | MW01-1-18-L-B11 |
| 303 | 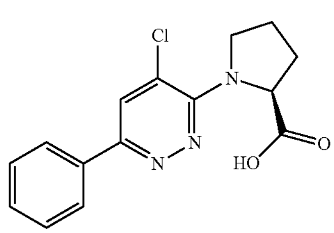 [SMILES: O=C(O)[C@@H]1CCCN1c1nnc(-c2ccccc2)cc1Cl] | MW01-1-18-L-C05 |

TABLE 2-continued

| Compound Number | Compound Structure | Synthetic Code |
|---|---|---|
| 304 | 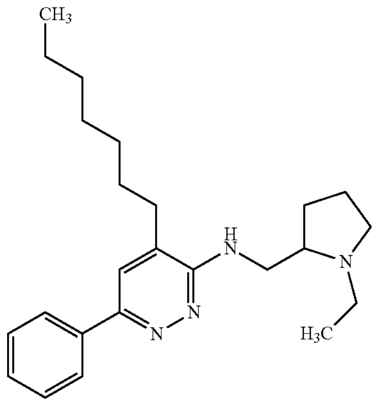 [SMILES: CCCCCCCc1cc(-c2ccccc2)nnc1NCC1CCCN1CC] | MW01-1-18-L-C06 |
| 305 | 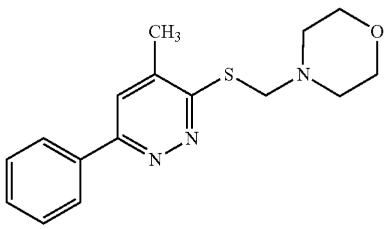 [SMILES: Cc1cc(-c2ccccc2)nnc1SCN1CCOCC1] | MW01-1-18-L-C08 |
| 306 | 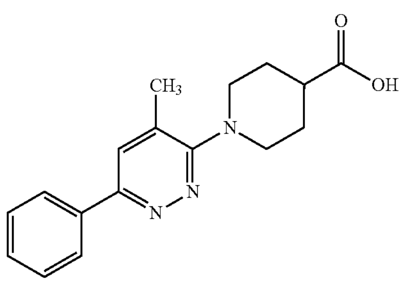 [SMILES: Cc1cc(-c2ccccc2)nnc1N1CCC(C(=O)O)CC1] | MW01-1-18-L-C10 |
| 307 | 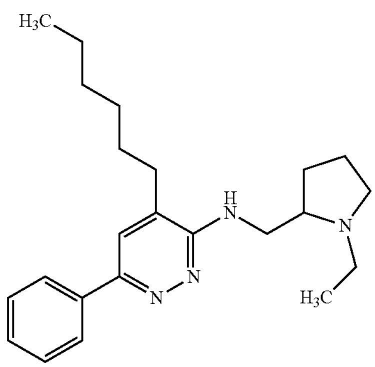 [SMILES: CCCCCCc1cc(-c2ccccc2)nnc1NCC1CCCN1CC] | MW01-1-18-L-D04 |
| 309 | 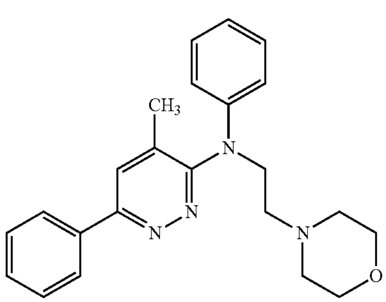 [SMILES: Cc1cc(-c2ccccc2)nnc1N(CCN1CCOCC1)c1ccccc1] | MW01-2-03-L-C03 |

TABLE 2-continued
| Compound Number | Compound Structure | Synthetic Code |
|---|---|---|
| 311 | 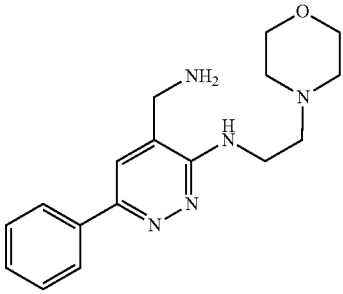 [SMILES: NCc1cc(-c2ccccc2)nnc1NCCN1CCOCC1] | MW01-2-03-L-D07 |
| 312 | 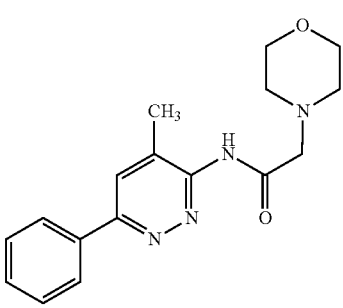 [SMILES: Cc1cc(-c2ccccc2)nnc1NC(=O)CN1CCOCC1] | MW01-2-03-L-D08 |
| 314 | 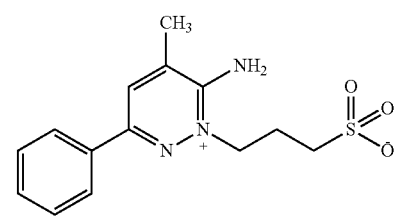 | MW01-2-03-L-G10 |
| 315 | 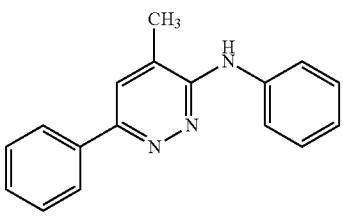 [SMILES: Cc1cc(-c2ccccc2)nnc1Nc1ccccc1] | MW01-2-06-L-F06 |
| 316 | 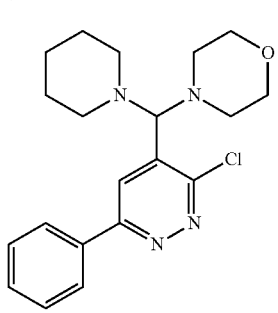 [SMILES: Clc1nnc(-c2ccccc2)cc1C(N1CCCCC1)N1CCOCC1] | MW01-2-09-L-B08 |
| 317 | 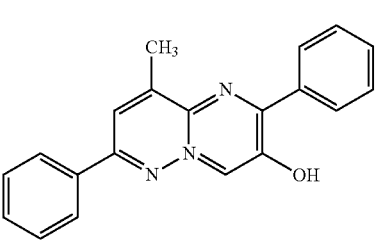 | MW01-2-09-L-E10 |

TABLE 2-continued

| Compound Number | Compound Structure | Synthetic Code |
|---|---|---|
| 322 | 3-[(2-aminoethyl)amino]-6-phenylpyridazine-4-carbonitrile | MW01-2-20-L-B10 |
| 325 | 3,4-diethoxy-6-phenylpyridazine | MW01-2-24-L-A05 |
| 327 | 4-methyl-3-(oct-1-yn-1-yl)-6-phenylpyridazine | MW01-3-01-L-G02 |
| 330 | 4-methyl-6-phenyl-3-((trimethylsilyl)ethynyl)pyridazine | MW01-3-01-L-G05 |
| 333 | 3-amino-4-methyl-6-phenyl-1-(3-phosphonopropyl)pyridazinium | MW01-3-06-L-B07 |
| 334 | 3-amino-4-methyl-6-phenyl-1-(3-phosphonopropyl)pyridazinium | MW01-3-06-L-B08 |

TABLE 2-continued

| Compound Number | Compound Structure | Synthetic Code |
|---|---|---|
| 336 | 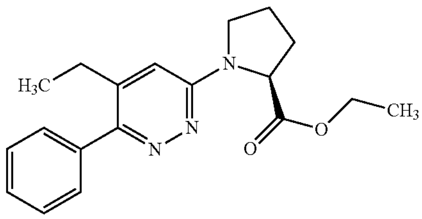 [SMILES: CCOC(=O)[C@@H]1CCCN1c1cc(CC)c(-c2ccccc2)nn1] | MW01-1-07-L-G07 |
| 338 | 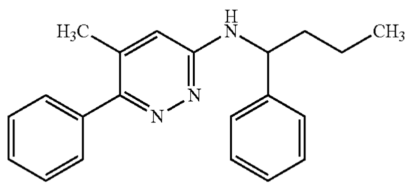 [SMILES: CCCC(Nc1cc(C)c(-c2ccccc2)nn1)c1ccccc1] | MW01-1-08-L-D03 |
| 342 | 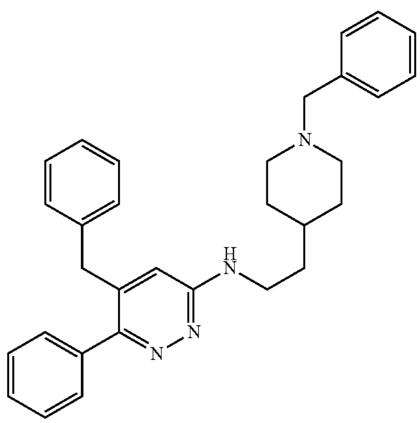 [SMILES: c1ccc(Cc2cc(NCCC3CCN(Cc4ccccc4)CC3)nnc2-c2ccccc2)cc1] | MW01-1-16-L-E09 |
| 343 | 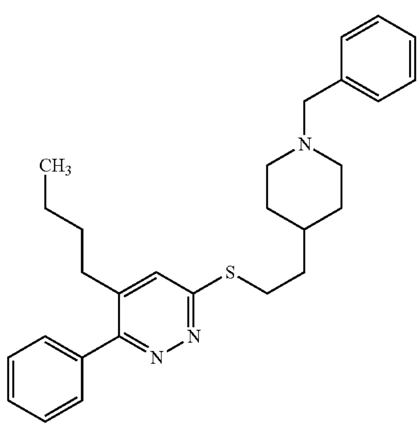 [SMILES: CCCCc1cc(SCCC2CCN(Cc3ccccc3)CC2)nnc1-c1ccccc1] | MW01-1-17-L-C09 |

| Compound Number | Compound Structure | Synthetic Code |
|---|---|---|
| 344 | 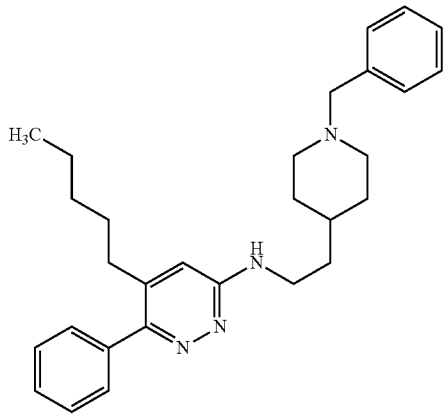 [SMILES: CCCCCc1cc(NCCC2CCN(Cc3ccccc3)CC2)nnc1-c1ccccc1] | MW01-1-17-L-E07 |
| 345 | 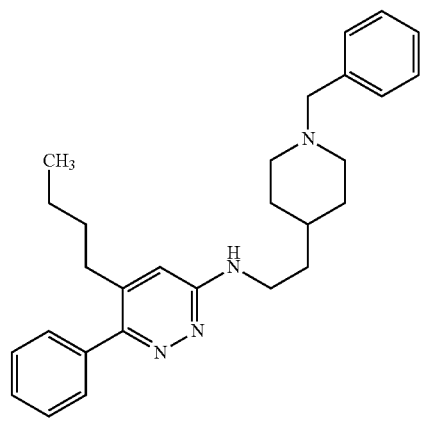 [SMILES: CCCCc1cc(NCCC2CCN(Cc3ccccc3)CC2)nnc1-c1ccccc1] | MW01-1-17-L-E08 |
| 348 | 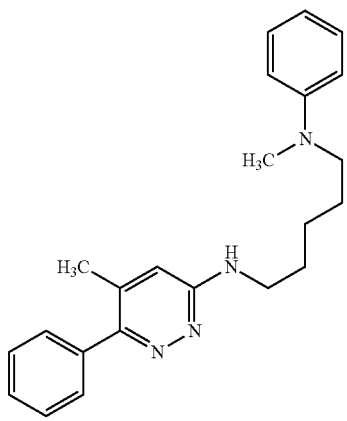 [SMILES: Cc1cc(NCCCCCN(C)c2ccccc2)nnc1-c1ccccc1] | MW01-1-18-L-A04 |

TABLE 2-continued
| Compound Number | Compound Structure | Synthetic Code |
|---|---|---|
| 349 | 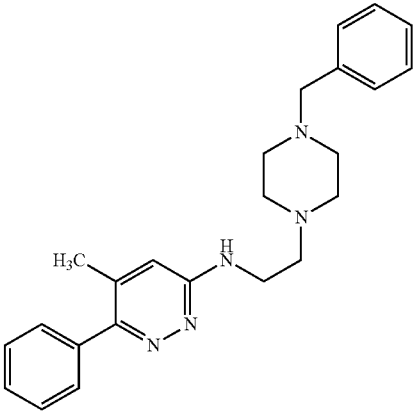 [SMILES: Cc1cc(NCCN2CCN(Cc3ccccc3)CC2)nnc1-c1ccccc1] | MW01-1-18-L-B05 |
| 351 | 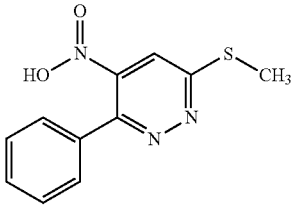 | MW01-2-33-L-A10 |
| 356 | 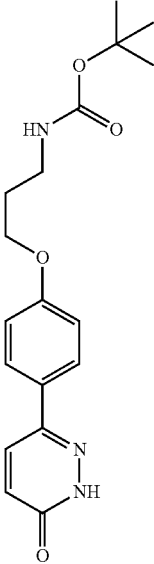 [SMILES: CC(C)(C)OC(=O)NCCCOc1ccc(-c2ccc(=O)[nH]n2)cc1] | MW01-1-01-L-E06 |
| 357 | 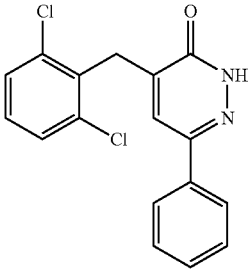 [SMILES: O=c1[nH]nc(-c2ccccc2)cc1Cc1c(Cl)cccc1Cl] | MW01-1-01-L-H09 |

TABLE 2-continued
| Compound Number | Compound Structure | Synthetic Code |
|---|---|---|
| 358 | 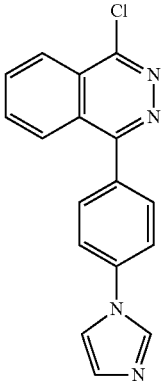 [SMILES: Clc1nnc(-c2ccc(-n3ccnc3)cc2)c2ccccc12] | MW01-1-05-L-D07 |
| 365 | 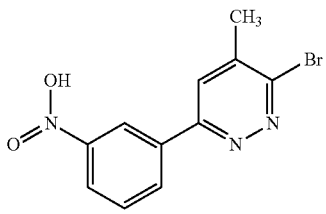 | MW01-1-03-L-D04 |
| 369 | 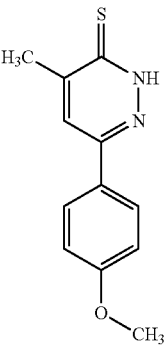 | MW01-1-04-L-G02 |
| 379 | 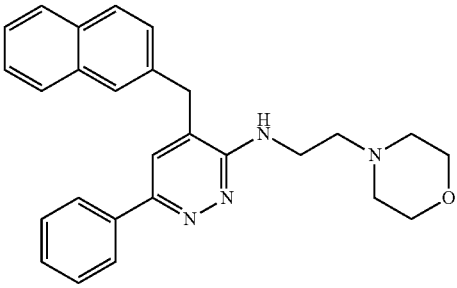 [SMILES: c1ccc(-c2cc(Cc3ccc4ccccc4c3)c(NCCN3CCOCC3)nn2)cc1] | MW01-2-24-L-E07 |
|  | 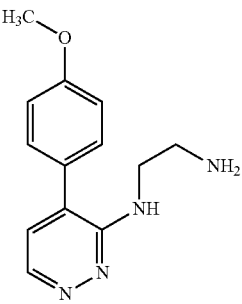 | MW01-01-01-L-B07 |

TABLE 2-continued
| Compound Number | Compound Structure | Synthetic Code |
|---|---|---|
| | 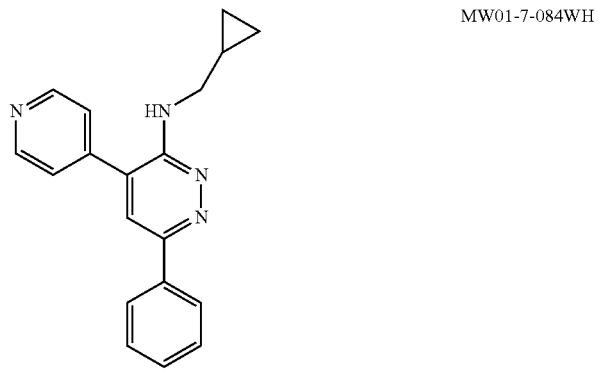 | MW01-7-084WH |
| | 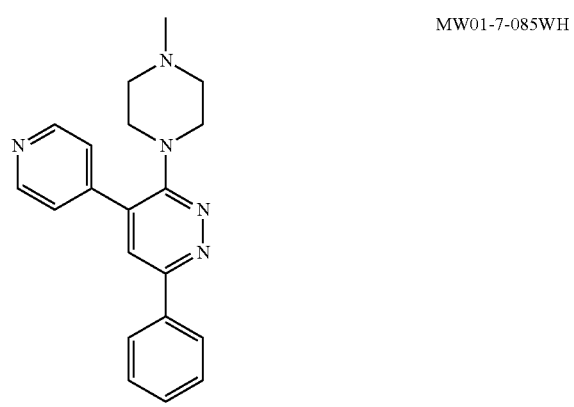 | MW01-7-085WH |
| | 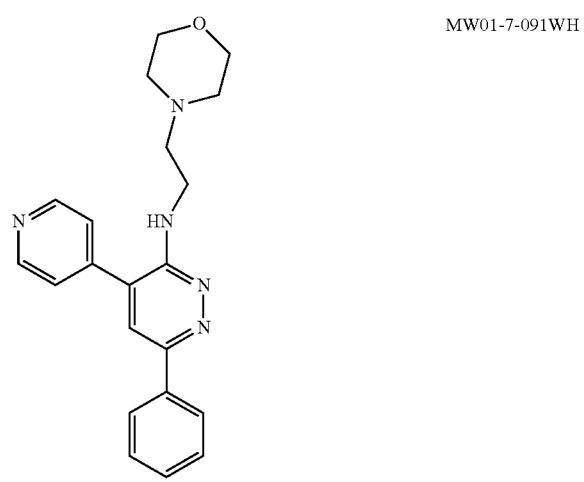 | MW01-7-091WH |

TABLE 2-continued
| Compound Number | Compound Structure | Synthetic Code |
|---|---|---|
| | 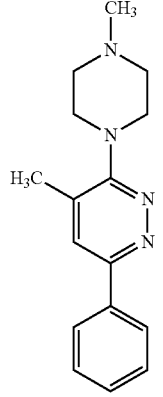 | MW01-10-12-L-G05 |
| | 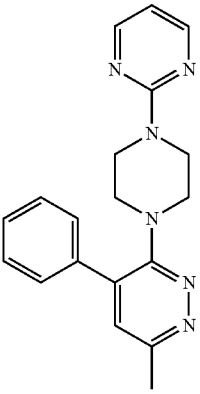 [SMILES: Cc1cc(-c2ccccc2)c(N2CCN(c3ncccn3)CC2)nn1] | MW01-7-057WH |
TABLE 3
Compounds of the Formula II
2-(4-(6-phenylpyridazin-3-yl)piperazine-1-yl) pyrimidine and Derivatives
| Compound Number | Compound Structure | Synthetic Code |
|---|---|---|
| | 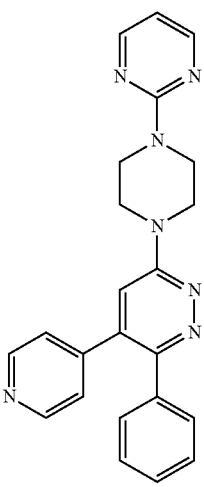 [SMILES: c1ccc(-c2nnc(N3CCN(c4ncccn4)CC3)cc2-c2ccncc2)cc1] | MWo1-2-5 069A-SRM 10 |

TABLE 3-continued
Compounds of the Formula II
2-(4-(6-phenylpyridazin-3-yl)piperazine-1-yl) pyrimidine and Derivatives
| Compound Number | Compound Structure | Synthetic Code |
|---|---|---|
| | 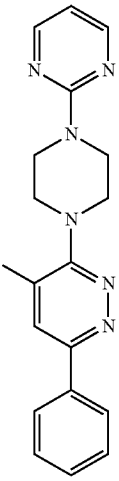 | MW01-6-127WH |
| | 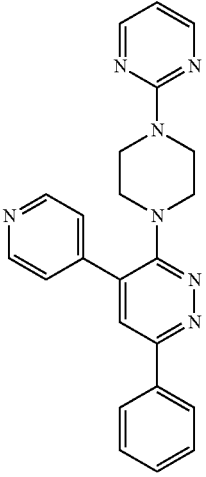 [SMILES: c1ccc(-c2cc(-c3ccncc3)c(N3CCN(c4ncccn4)CC3)nn2)cc1] | MW01-6-189WH |
| | 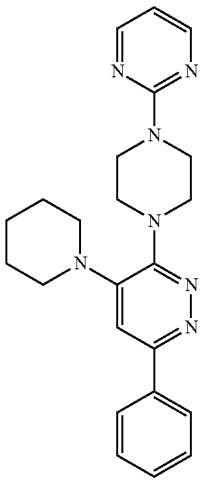 [SMILES: c1ccc(-c2cc(N3CCCCC3)c(N3CCN(c4ncccn4)CC3)nn2)cc1] | MW01-7-107WH |

TABLE 3-continued

Compounds of the Formula II
2-(4-(6-phenylpyridazin-3-yl)piperazine-1-yl) pyrimidine and Derivatives

| Compound Number | Compound Structure | Synthetic Code |
|---|---|---|
| | | MW01-2-151SRM |
| | | MW01-2-069A-SRM |

TABLE 3-continued

Compounds of the Formula II
2-(4-(6-phenylpyridazin-3-yl)piperazine-1-yl) pyrimidine and Derivatives

| Compound Number | Compound Structure | Synthetic Code |
|---|---|---|
| 29 | 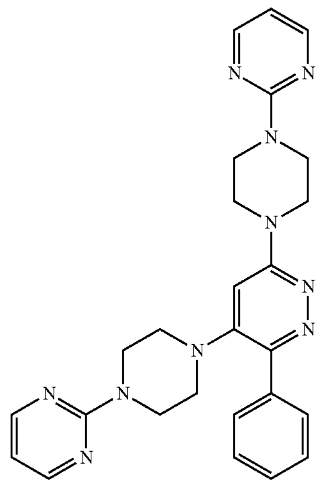 [SMILES: c1ccc(-c2nnc(N3CCN(c4ncccn4)CC3)cc2N2CCN(c3ncccn3)CC2)cc1] | MW01-1-030A-LKM |
| 33 | 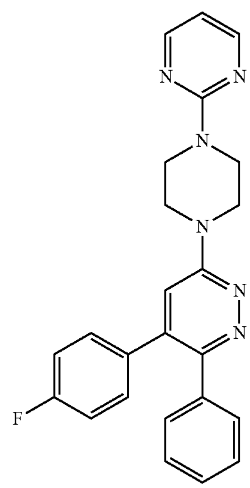 [SMILES: Fc1ccc(-c2cc(N3CCN(c4ncccn4)CC3)nnc2-c2ccccc2)cc1] | MW01-2-065-LKM |
| 34 | 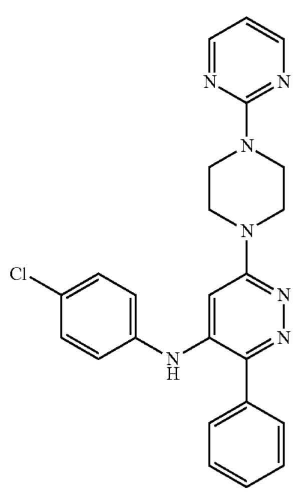 [SMILES: Clc1ccc(Nc2cc(N3CCN(c4ncccn4)CC3)nnc2-c2ccccc2)cc1] | MW01-2-127LKM |

TABLE 3-continued

Compounds of the Formula II
2-(4-(6-phenylpyridazin-3-yl)piperazine-1-yl) pyrimidine and Derivatives

| Compound Number | Compound Structure | Synthetic Code |
|---|---|---|
| 35 | 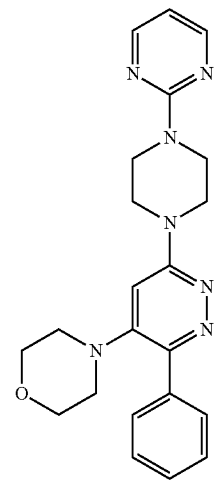 [SMILES: c1ccc(-c2nnc(N3CCN(c4ncccn4)CC3)cc2N2CCOCC2)cc1] | MW01-2-134LKM |
| 36 | 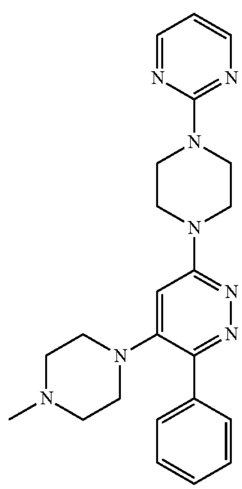 [SMILES: CN1CCN(c2cc(N3CCN(c4ncccn4)CC3)nnc2-c2ccccc2)CC1] | MW01-2-146LKM |
| 37 | 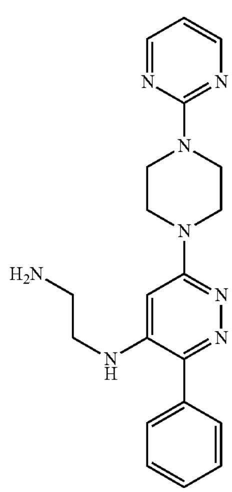 [SMILES: NCCNc1cc(N2CCN(c3ncccn3)CC2)nnc1-c1ccccc1] | MW01-2-147LKM |

TABLE 3-continued
Compounds of the Formula II
2-(4-(6-phenylpyridazin-3-yl)piperazine-1-yl) pyrimidine and Derivatives
| Compound Number | Compound Structure | Synthetic Code |
|---|---|---|
| 46 | 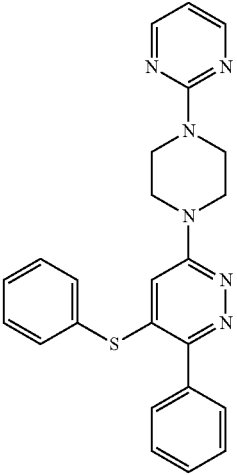 | MW01-1-045MAS |
| 105 | 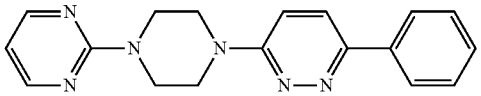 | MW01-9-038Z |
| 138 | 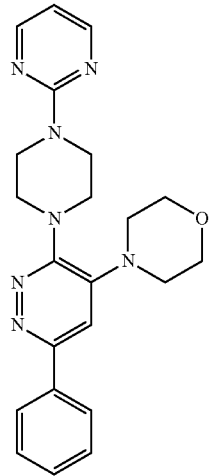 [SMILES: c1ccc(-c2cc(N3CCOCC3)c(N3CCN(c4ncccn4)CC3)nn2)cc1] | MW01-2-023SRM |

TABLE 3-continued
Compounds of the Formula II
2-(4-(6-phenylpyridazin-3-yl)piperazine-1-yl) pyrimidine and Derivatives
| Compound Number | Compound Structure | Synthetic Code |
|---|---|---|
| 147 | 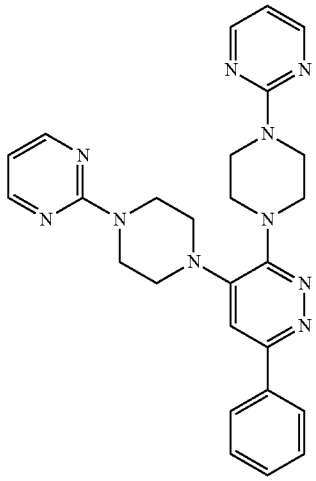 [SMILES: c1ccc(-c2cc(N3CCN(c4ncccn4)CC3)c(N3CCN(c4ncccn4)CC3)nn2)cc1] | MW01-2-177A-WH |
| 155 | 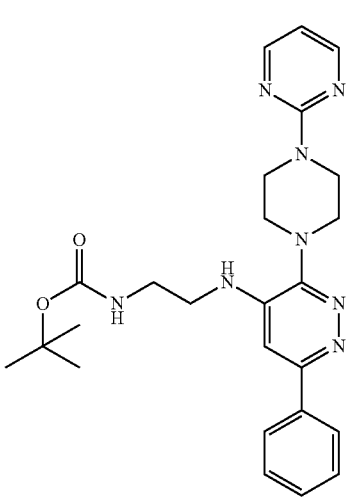 [SMILES: CC(C)(C)OC(=O)NCCNc1cc(-c2ccccc2)nnc1N1CCN(c2ncccn2)CC1] | MW01-2-191A-WH |

TABLE 3-continued

Compounds of the Formula II
2-(4-(6-phenylpyridazin-3-yl)piperazine-1-yl) pyrimidine and Derivatives

| Compound Number | Compound Structure | Synthetic Code |
|---|---|---|
| 252 | 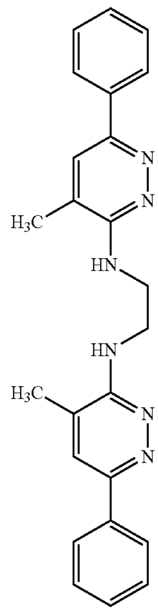 [SMILES: Cc1cc(-c2ccccc2)nnc1NCCNc1nnc(-c2ccccc2)cc1C] | MW01-1-05-L-F05 |
| 157 | 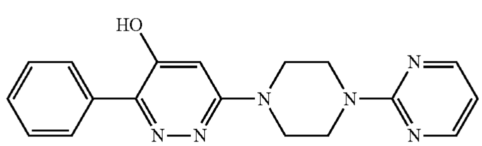 [SMILES: Oc1cc(N2CCN(c3ncccn3)CC2)nnc1-c1ccccc1] | MW01-3-003WH |
| 160 | 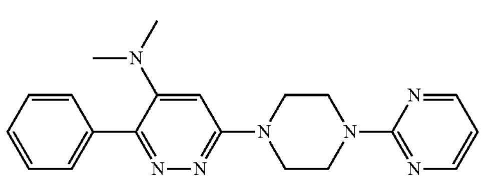 [SMILES: CN(C)c1cc(N2CCN(c3ncccn3)CC2)nnc1-c1ccccc1] | MW01-3-019A-WH |

TABLE 3-continued

Compounds of the Formula II
2-(4-(6-phenylpyridazin-3-yl)piperazine-1-yl) pyrimidine and Derivatives

| Compound Number | Compound Structure | Synthetic Code |
|---|---|---|
| 186 | 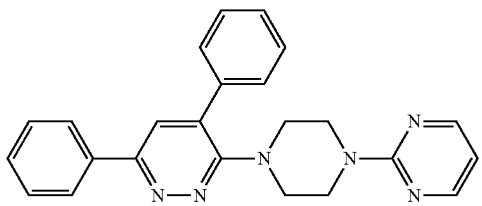 [SMILES: c1ccc(-c2cc(-c3ccccc3)c(N3CCN(c4ncccn4)CC3)nn2)cc1] | MW01-5-188WH |
| 263 | 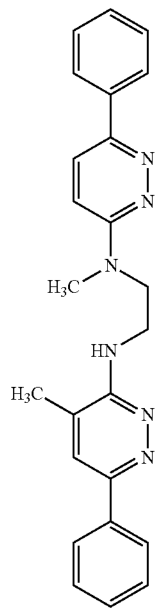 [SMILES: Cc1cc(-c2ccccc2)nnc1NCCN(C)c1ccc(-c2ccccc2)nn1] | MW01-1-07-L-H06 |

TABLE 4

| Compound | Final Code | Concentration Dependent Activity in Cell Culture Assays |
|---|---|---|
| | MW01-01-02-L-G05 | |

TABLE 4-continued
| Compound | Final Code | Concentration Dependent Activity in Cell Culture Assays |
|---|---|---|
| 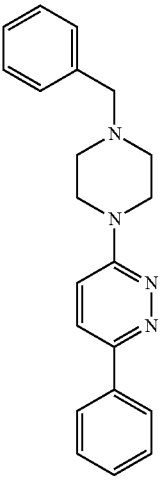 [SMILES: c1ccc(CN2CCN(c3ccc(-c4ccccc4)nn3)CC2)cc1] | MW01-01-03-L-E10 | |
| 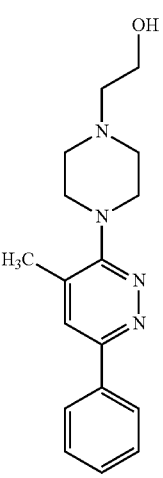 | MW01-01-04-L-D08 | |
| 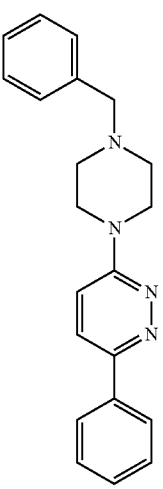 [SMILES: c1ccc(CN2CCN(c3ccc(-c4ccccc4)nn3)CC2)cc1] | MW01-01-18-L-A02 | |

TABLE 4-continued
| Compound | Final Code | Concentration Dependent Activity in Cell Culture Assays |
|---|---|---|
| 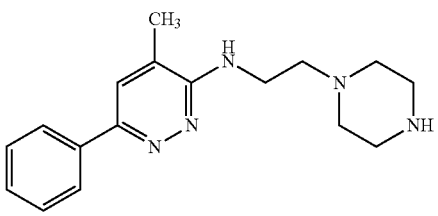 [SMILES: Cc1cc(-c2ccccc2)nnc1NCCN1CCNCC1] | MW01-01-18-L-C02 | |
| 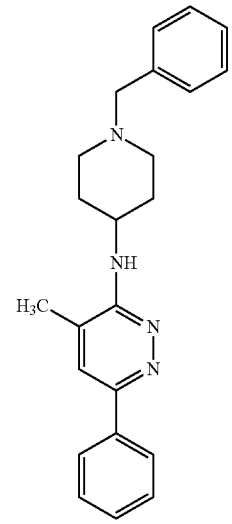 | MW01-02-03-L-G04 | |
| 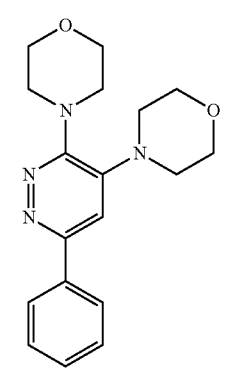 | MW01-2-018SRM | |

TABLE 4-continued
| Compound | Final Code | Concentration Dependent Activity in Cell Culture Assays |
|---|---|---|
| 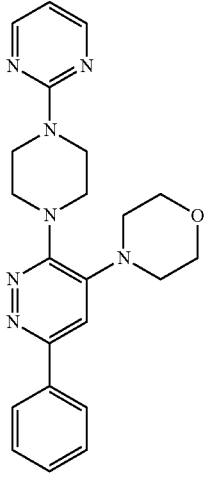 [SMILES: c1ccc(-c2cc(N3CCOCC3)c(N3CCN(c4ncccn4)CC3)nn2)cc1] | MW01-2-023SRM | |
| 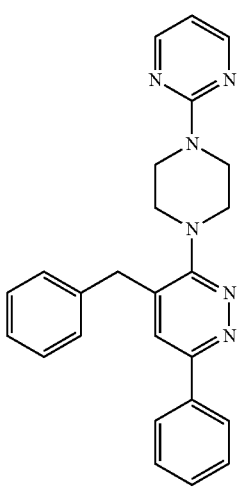 [SMILES: c1ccc(Cc2cc(-c3ccccc3)nnc2N2CCN(c3ncccn3)CC2)cc1] | MW01-2-141SRM | |
| 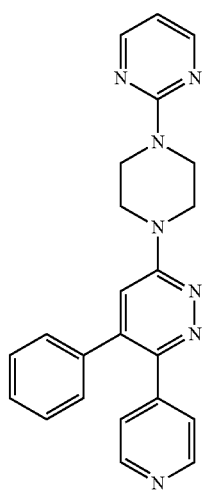 [SMILES: c1ccc(-c2cc(N3CCN(c4ncccn4)CC3)nnc2-c2ccncc2)cc1] | MW01-2-163MAS | |

TABLE 4-continued

| Compound | Final Code | Concentration Dependent Activity in Cell Culture Assays |
|---|---|---|
| | MW01-2-177A-WH | |
| | MW01-2-191A-WH | |
| | MW01-3-024SRM | |

TABLE 4-continued

| Compound | Final Code | Concentration Dependent Activity in Cell Culture Assays |
|---|---|---|
| [structure] | MW01-3-027SRM | |
| [structure] | MW01-3-057SRM | |
| [structure] | MW01-3-065SRM | |
| [structure] | MW01-3-066SRM | |
| [structure] | MW01-3-183WH | |

TABLE 4-continued

| Compound | Final Code | Concentration Dependent Activity in Cell Culture Assays |
|---|---|---|
| (structure) | MW01-4-179LKM | |
| (structure) | MW01-4-188LKM | |
| (structure) | MW01-7-027B-WH | |

TABLE 4-continued

| Compound | Final Code | Concentration Dependent Activity in Cell Culture Assays |
|---|---|---|
| *(structure)* | MW01-7-029WH | |
| *(structure)* | MW01-7-031WH | |
| *(structure)* | MW01-7-100WH | |

TABLE 4-continued

| Compound | Final Code | Concentration Dependent Activity in Cell Culture Assays |
|---|---|---|
| | MW01-7-102WH | |
| | MW01-7-133WH | |
| | MW01-9-039MZ | |
| | MW01-9-040MZ | |
| | MW01-2102LPI | |

TABLE 4-continued
| Compound | Final Code | Concentration Dependent Activity in Cell Culture Assays |
|---|---|---|
| 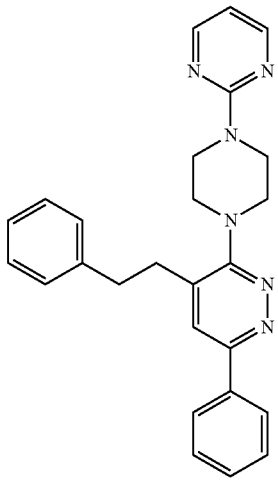 [SMILES: c1ccc(CCc2cc(-c3ccccc3)nnc2N2CCN(c3ncccn3)CC2)cc1] | MW01-2103LPI | |
TABLE 5
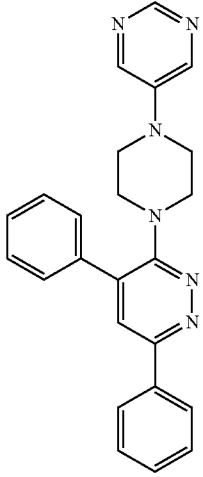 [SMILES: c1ccc(-c2cc(-c3ccccc3)c(N3CCN(c4cncnc4)CC3)nn2)cc1]
Structure 5
Structure 6
TABLE 5-continued
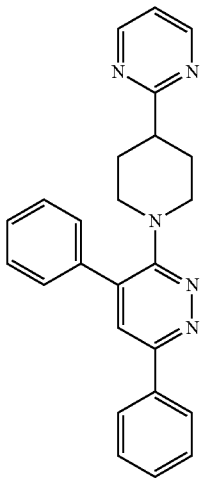 [SMILES: c1ccc(-c2cc(-c3ccccc3)c(N3CCC(c4ncccn4)CC3)nn2)cc1]
Structure 9
Structure 10

TABLE 5-continued

Structure 14

Structure 21

Structure 15

Structure 7

Structure 19

Structure 8

TABLE 5-continued
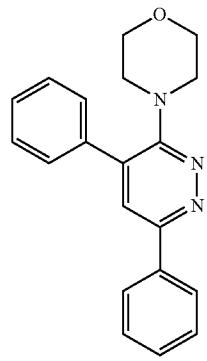 [SMILES: c1ccc(-c2cc(-c3ccccc3)c(N3CCOCC3)nn2)cc1]
Structure 12
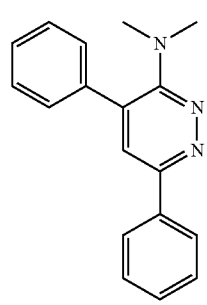 [SMILES: CN(C)c1nnc(-c2ccccc2)cc1-c1ccccc1]
Structure 13
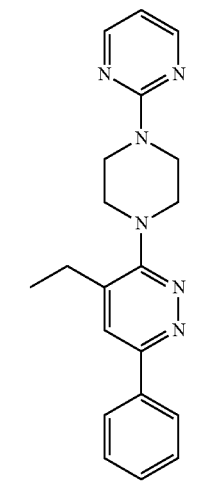 [SMILES: CCc1cc(-c2ccccc2)nnc1N1CCN(c2ncccn2)CC1]
Structure 17
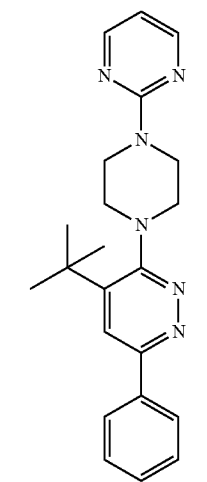 [SMILES: CC(C)(C)c1cc(-c2ccccc2)nnc1N1CCN(c2ncccn2)CC1]
Structure 18
TABLE 5-continued
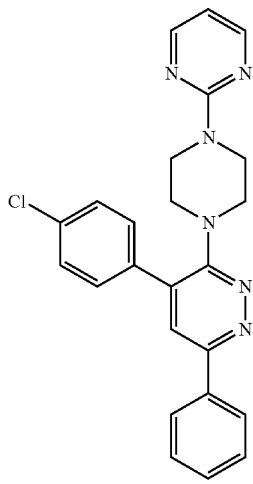 [SMILES: Clc1ccc(-c2cc(-c3ccccc3)nnc2N2CCN(c3ncccn3)CC2)cc1]
Structure 22
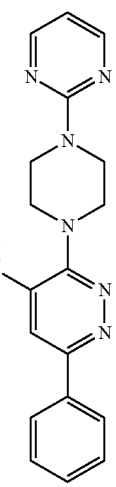
Structure 23
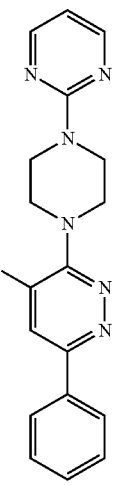
Structure 24

TABLE 5-continued
Structure 25
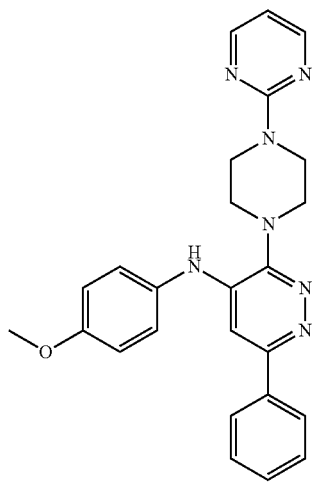 [SMILES: COc1ccc(Nc2cc(-c3ccccc3)nnc2N2CCN(c3ncccn3)CC2)cc1]
Structure 50
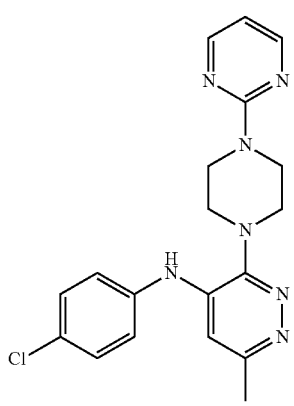 [SMILES: Cc1cc(Nc2ccc(Cl)cc2)c(N2CCN(c3ncccn3)CC2)nn1]
Structure 32
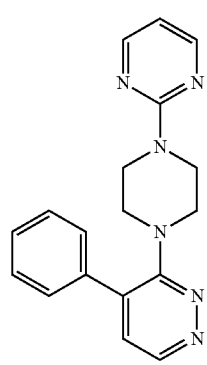 [SMILES: c1ccc(-c2ccnnc2N2CCN(c3ncccn3)CC2)cc1]
TABLE 5-continued
Structure 33
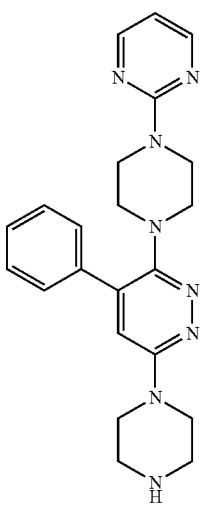 [SMILES: c1ccc(-c2cc(N3CCNCC3)nnc2N2CCN(c3ncccn3)CC2)cc1]
Structure 36
Structure 38
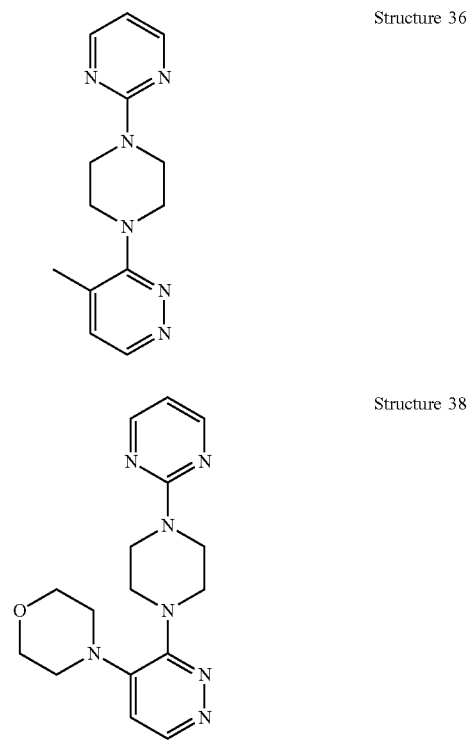
Structure 42
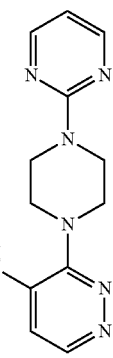

TABLE 5-continued
Structure 26
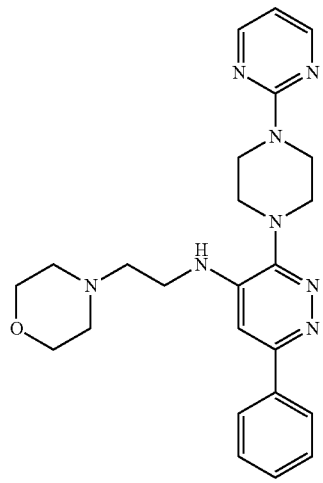 [SMILES: c1ccc(-c2cc(NCCN3CCOCC3)c(N3CCN(c4ncccn4)CC3)nn2)cc1]
Structure 27
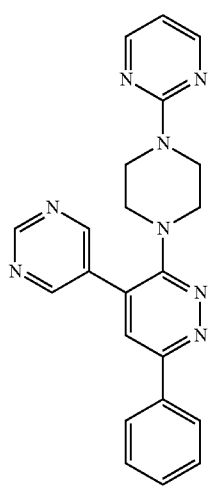 [SMILES: c1ccc(-c2cc(-c3cncnc3)c(N3CCN(c4ncccn4)CC3)nn2)cc1]
Structure 34
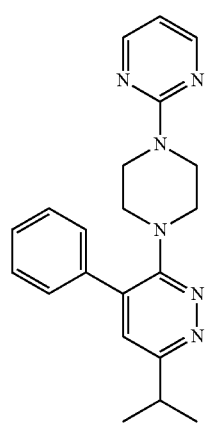 [SMILES: CC(C)c1cc(-c2ccccc2)c(N2CCN(c3ncccn3)CC2)nn1]
TABLE 5-continued
Structure 35
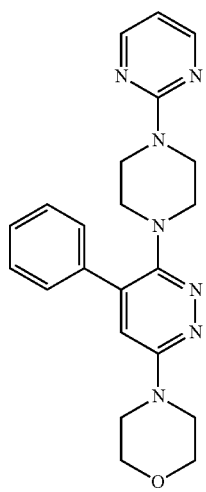 [SMILES: c1ccc(-c2cc(N3CCOCC3)nnc2N2CCN(c3ncccn3)CC2)cc1]
Structure 39
Structure 40
Structure 43

TABLE 5-continued
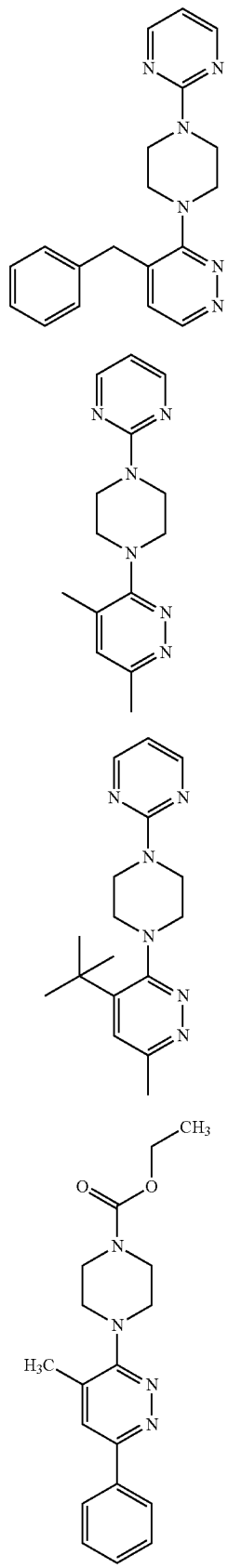
Structure 44
Structure 46
Structure 47
Structure 181
TABLE 5-continued
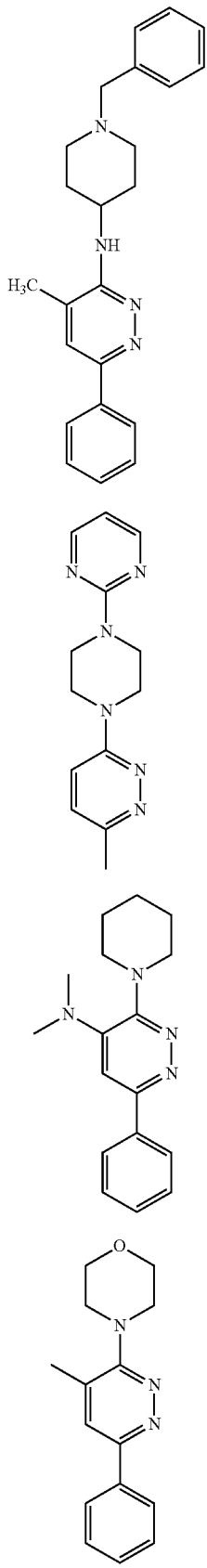
Structure 188
Structure 63
Structure 31
Structure 60

TABLE 5-continued
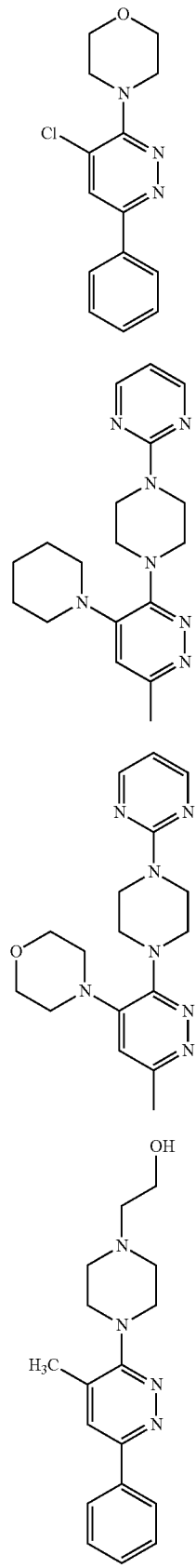
Structure 61
Structure 48
Structure 49
Structure 377
TABLE 5-continued
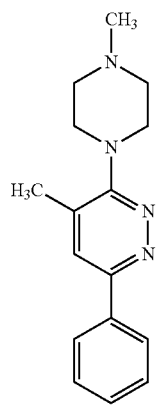 [SMILES: Cc1cc(-c2ccccc2)nnc1N1CCN(C)CC1]
Structure 378
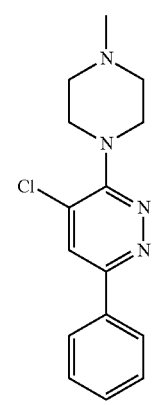
Structure 58
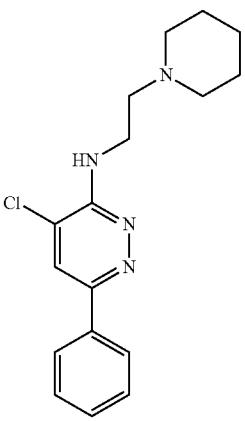 [SMILES: Clc1cc(-c2ccccc2)nnc1NCCN1CCCCC1]
Structure 59

TABLE 5-continued
Structure 62
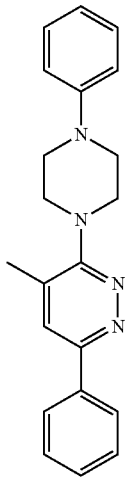
Structure 63
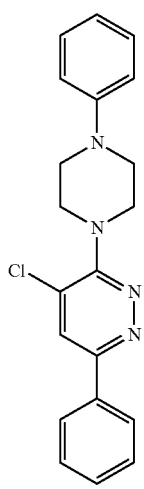
Structure 64
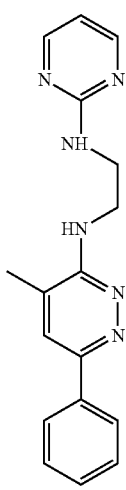
TABLE 5-continued
Structure 65
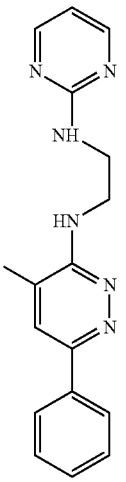
Structure 68
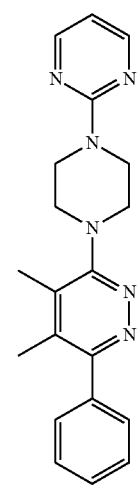 [SMILES: Cc1c(-c2ccccc2)nnc(N2CCN(c3ncccn3)CC2)c1C]
Structure 69
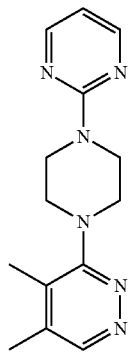 [SMILES: Cc1cnnc(N2CCN(c3ncccn3)CC2)c1C]

TABLE 5-continued
Structure 75
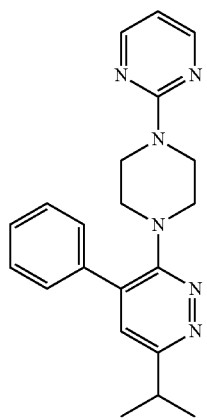 [SMILES: CC(C)c1cc(-c2ccccc2)c(N2CCN(c3ncccn3)CC2)nn1]
Structure 76
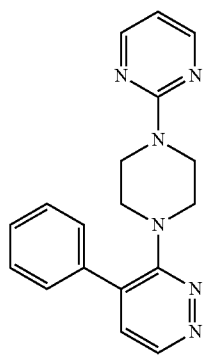 [SMILES: c1ccc(-c2ccnnc2N2CCN(c3ncccn3)CC2)cc1]
Structure 79
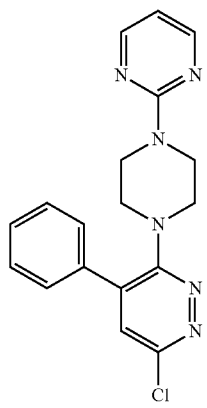 [SMILES: Clc1cc(-c2ccccc2)c(N2CCN(c3ncccn3)CC2)nn1]
TABLE 5-continued
Structure 80
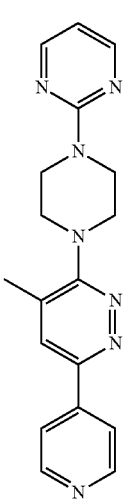 [SMILES: Cc1cc(-c2ccncc2)nnc1N1CCN(c2ncccn2)CC1]
Structure 66
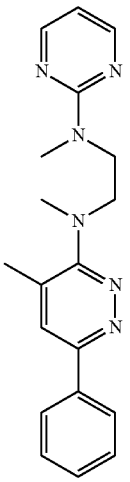 [SMILES: Cc1cc(-c2ccccc2)nnc1N(C)CCN(C)c1ncccn1]
Structure 67
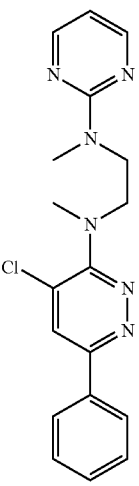

TABLE 5-continued
Structure 70
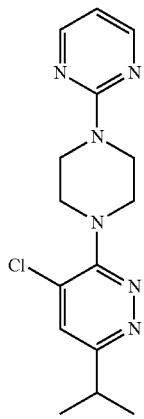
Structure 71
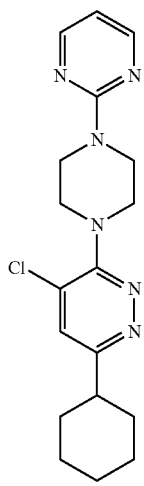
Structure 77
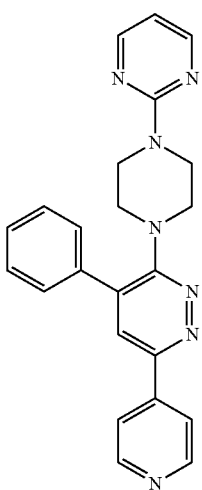 [SMILES: c1ccc(-c2cc(-c3ccncc3)nnc2N2CCN(c3ncccn3)CC2)cc1]
TABLE 5-continued
Structure 78
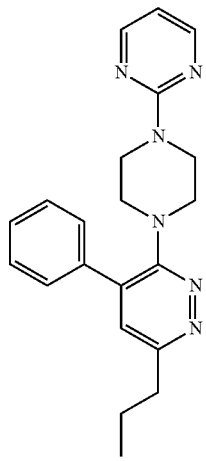 [SMILES: CCCc1cc(-c2ccccc2)c(N2CCN(c3ncccn3)CC2)nn1]
Structure 81
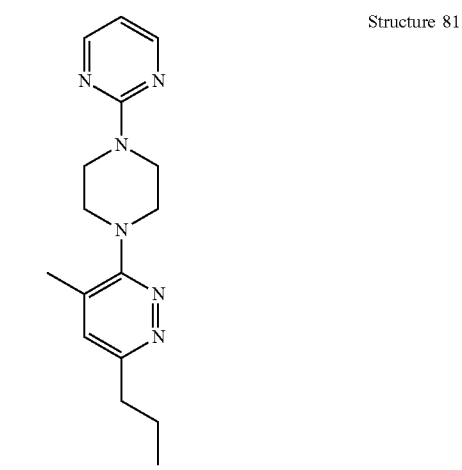
Structure 82
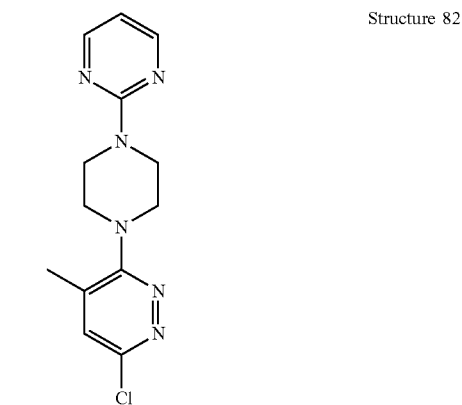

TABLE 5-continued
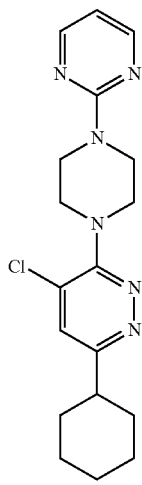
Structure 83
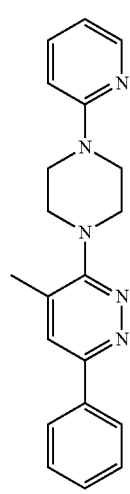
Structure 84
Structure 87
TABLE 5-continued
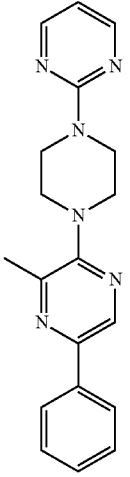 [SMILES: Cc1nc(-c2ccccc2)cnc1N1CCN(c2ncccn2)CC1]
Structure 142
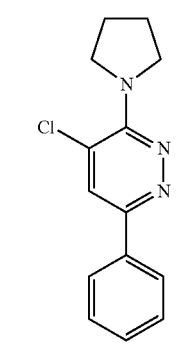
Structure 91
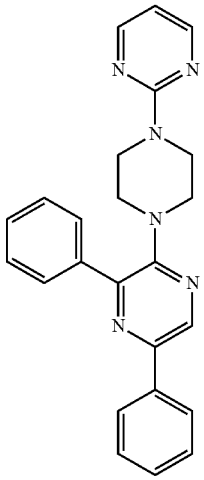 [SMILES: c1ccc(-c2cnc(N3CCN(c4ncccn4)CC3)c(-c3ccccc3)n2)cc1]
Structure 143
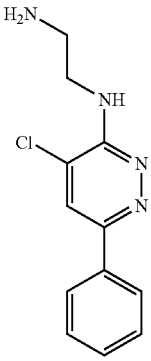 [SMILES: NCCNc1nnc(-c2ccccc2)cc1Cl]
Structure 97

TABLE 5-continued
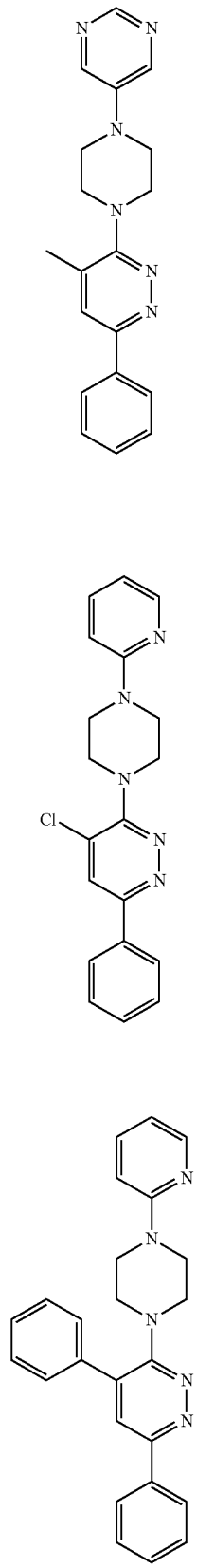
Structure 485
Structure 85
Structure 86
TABLE 5-continued
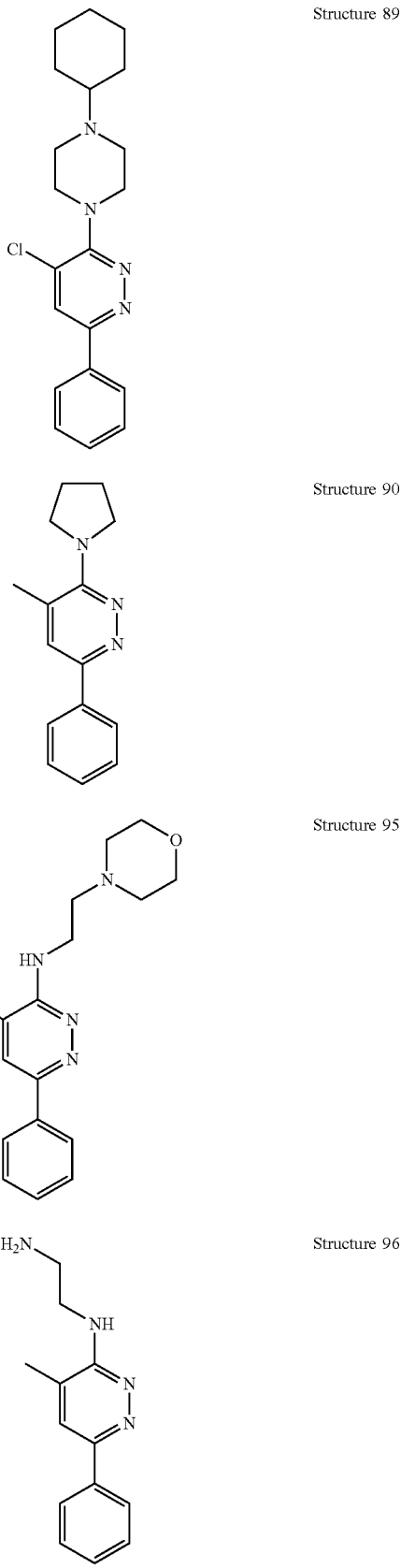
Structure 89
Structure 90
Structure 95
Structure 96

TABLE 5-continued
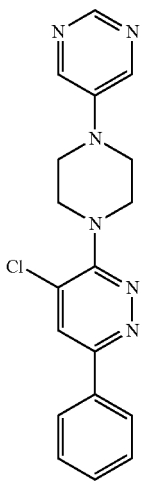
Structure 99
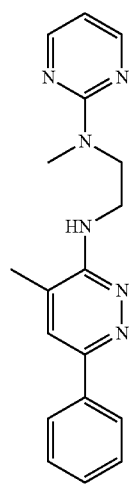 [SMILES: Cc1cc(-c2ccccc2)nnc1NCCN(C)c1ncccn1]
Structure 100
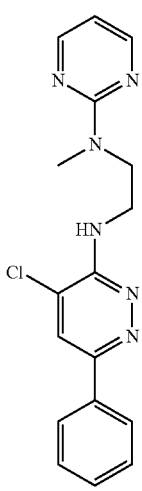
Structure 101
TABLE 5-continued
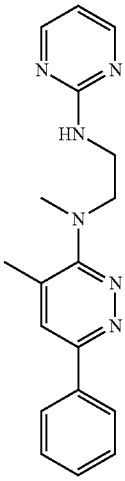 [SMILES: Cc1cc(-c2ccccc2)nnc1N(C)CCNc1ncccn1]
Structure 102
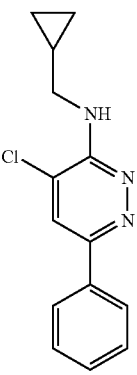
Structure 105
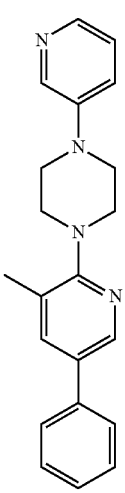 [SMILES: Cc1cc(-c2ccccc2)cnc1N1CCN(c2cccnc2)CC1]
Structure 106

TABLE 5-continued
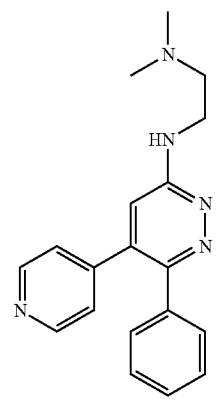 [SMILES: CN(C)CCNc1cc(-c2ccncc2)c(-c2ccccc2)nn1]
Structure 109
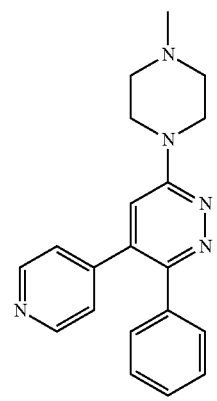 [SMILES: CN1CCN(c2cc(-c3ccncc3)c(-c3ccccc3)nn2)CC1]
Structure 110
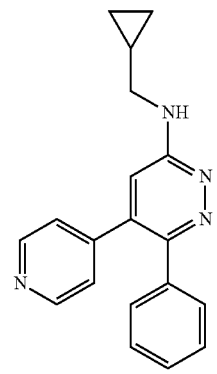 [SMILES: c1ccc(-c2nnc(NCC3CC3)cc2-c2ccncc2)cc1]
Structure 113
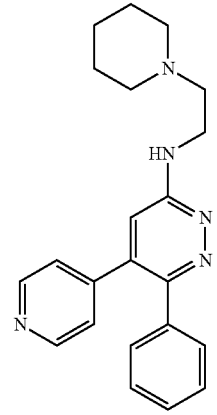 [SMILES: c1ccc(-c2nnc(NCCN3CCCCC3)cc2-c2ccncc2)cc1]
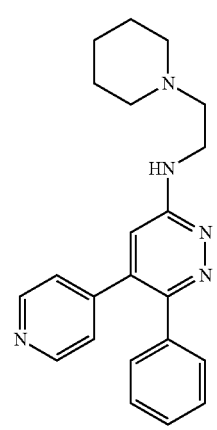
Structure 114
TABLE 5-continued
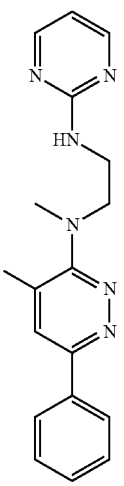
Structure 103
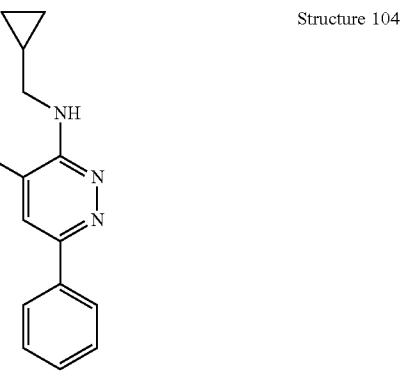
Structure 104
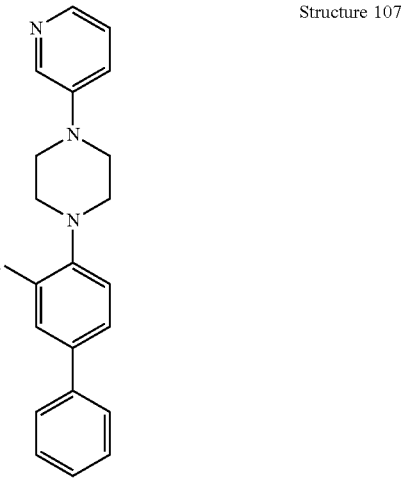
Structure 107

TABLE 5-continued
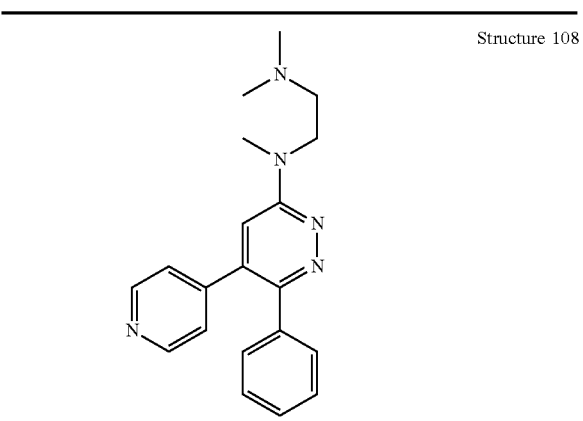
Structure 108
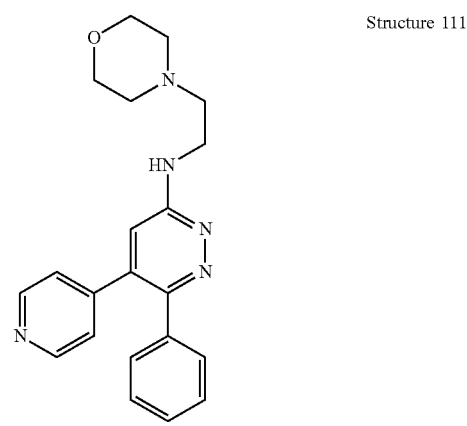
Structure 111
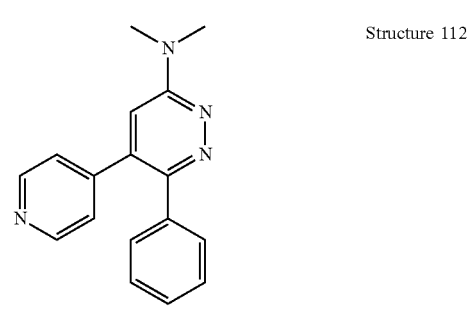
Structure 112
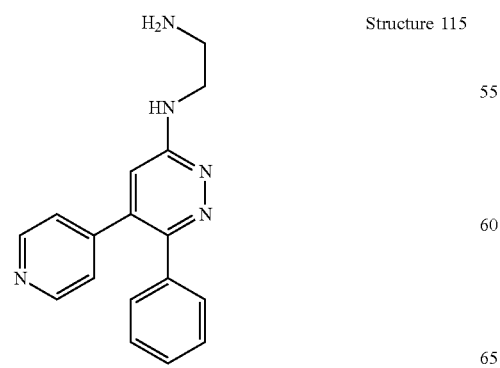
Structure 115
TABLE 5-continued
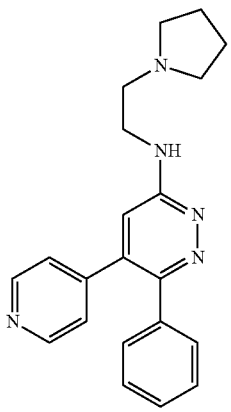 [SMILES: c1ccc(-c2nnc(NCCN3CCCC3)cc2-c2ccncc2)cc1]
Structure 116
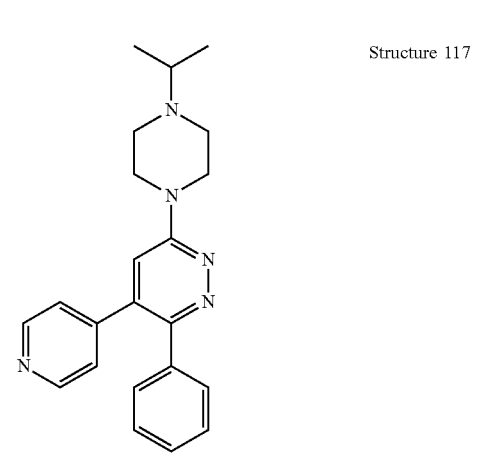
Structure 117
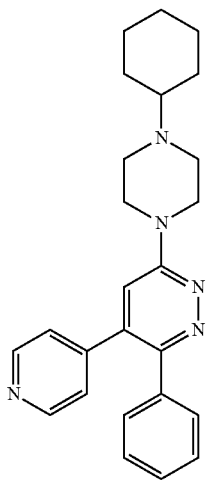 [SMILES: c1ccc(-c2nnc(N3CCN(C4CCCCC4)CC3)cc2-c2ccncc2)cc1]
Structure 118

TABLE 5-continued
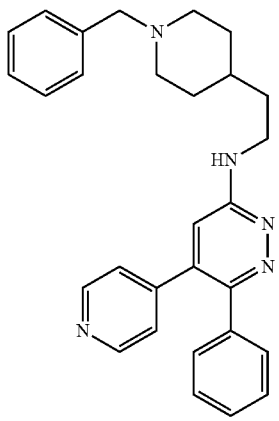 [SMILES: c1ccc(CN2CCC(CCNc3cc(-c4ccncc4)c(-c4ccccc4)nn3)CC2)cc1]
Structure 121
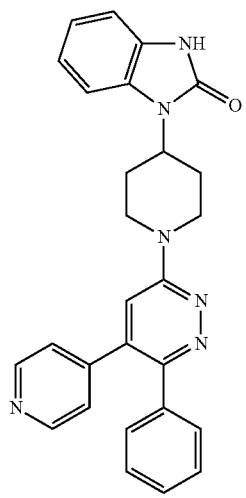 [SMILES: O=c1[nH]c2ccccc2n1C1CCN(c2cc(-c3ccncc3)c(-c3ccccc3)nn2)CC1]
Structure 122
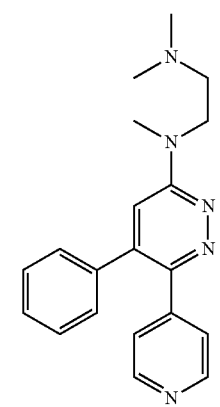 [SMILES: CN(C)CCN(C)c1cc(-c2ccccc2)c(-c2ccncc2)nn1]
Structure 125
TABLE 5-continued
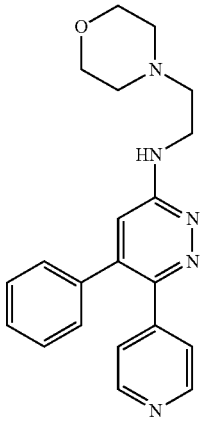 [SMILES: c1ccc(-c2cc(NCCN3CCOCC3)nnc2-c2ccncc2)cc1]
Structure 126
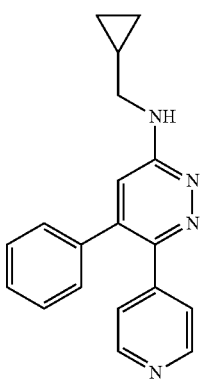 [SMILES: c1ccc(-c2cc(NCC3CC3)nnc2-c2ccncc2)cc1]
Structure 129
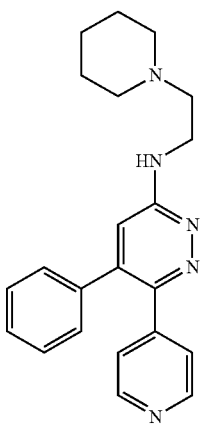 [SMILES: c1ccc(-c2cc(NCCN3CCCCC3)nnc2-c2ccncc2)cc1]
Structure 130

TABLE 5-continued
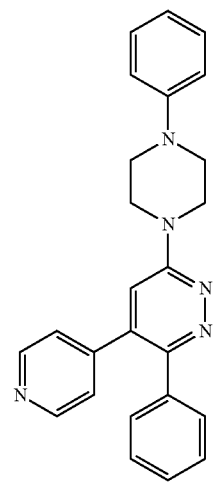 [SMILES: c1ccc(-c2nnc(N3CCN(c4ccccc4)CC3)cc2-c2ccncc2)cc1]
Structure 119
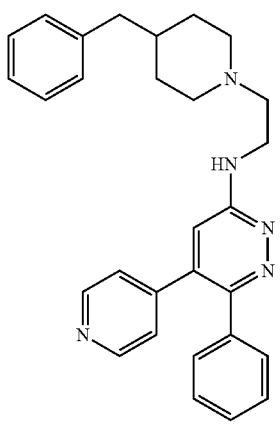 [SMILES: c1ccc(CC2CCN(CCNc3cc(-c4ccncc4)c(-c4ccccc4)nn3)CC2)cc1]
Structure 120
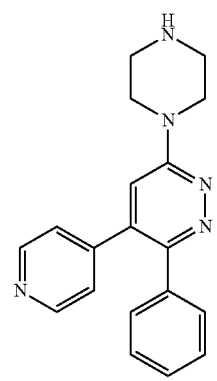 [SMILES: c1ccc(-c2nnc(N3CCNCC3)cc2-c2ccncc2)cc1]
Structure 123
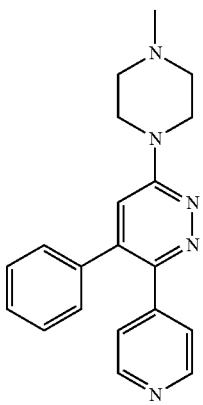 [SMILES: CN1CCN(c2cc(-c3ccccc3)c(-c3ccncc3)nn2)CC1]
Structure 124
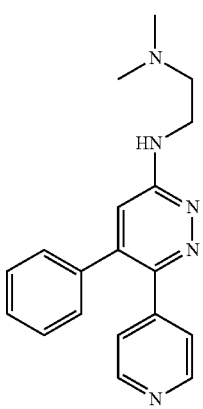 [SMILES: CN(C)CCNc1cc(-c2ccccc2)c(-c2ccncc2)nn1]
Structure 127
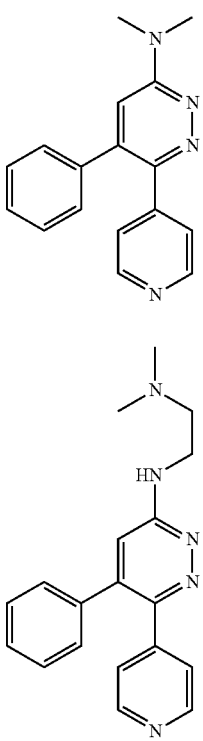
Structure 128
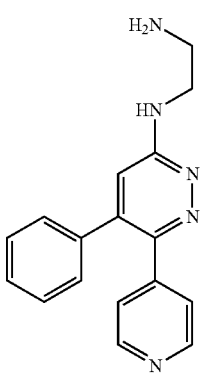 [SMILES: NCCNc1cc(-c2ccccc2)c(-c2ccncc2)nn1]
Structure 131

TABLE 5-continued
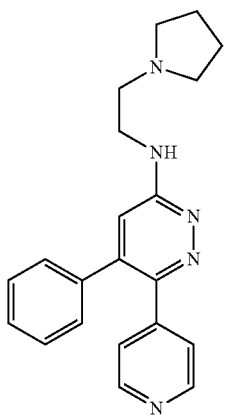 [SMILES: c1ccc(-c2cc(NCCN3CCCC3)nnc2-c2ccncc2)cc1]
Structure 132
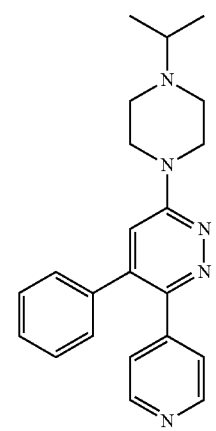 [SMILES: CC(C)N1CCN(c2cc(-c3ccccc3)c(-c3ccncc3)nn2)CC1]
Structure 133
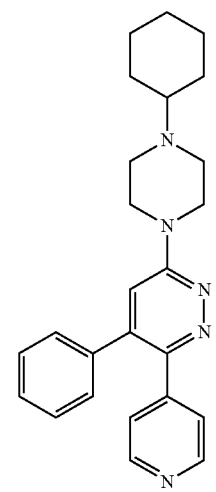 [SMILES: c1ccc(-c2cc(N3CCN(C4CCCCC4)CC3)nnc2-c2ccncc2)cc1]
Structure 134
TABLE 5-continued
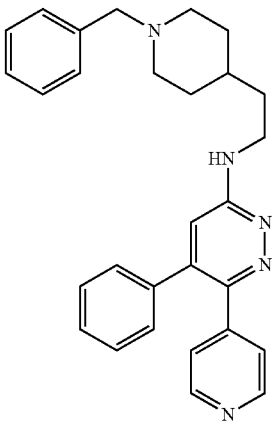 [SMILES: c1ccc(CN2CCC(CCNc3cc(-c4ccccc4)c(-c4ccncc4)nn3)CC2)cc1]
Structure 137
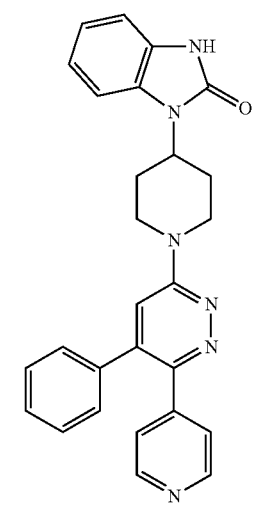 [SMILES: O=c1[nH]c2ccccc2n1C1CCN(c2cc(-c3ccccc3)c(-c3ccncc3)nn2)CC1]
Structure 138
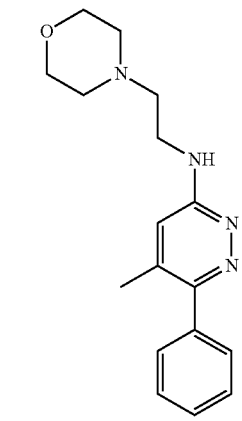 [SMILES: Cc1cc(NCCN2CCOCC2)nnc1-c1ccccc1]
Structure 141

TABLE 5-continued

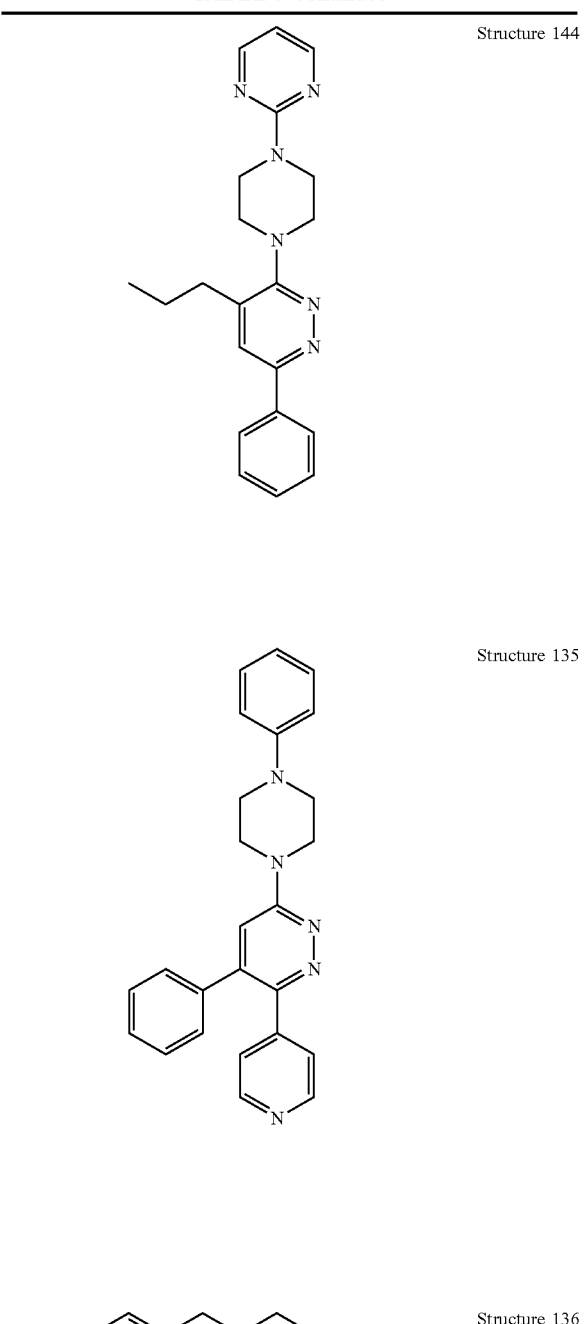

Structure 144

Structure 135

Structure 136

TABLE 5-continued

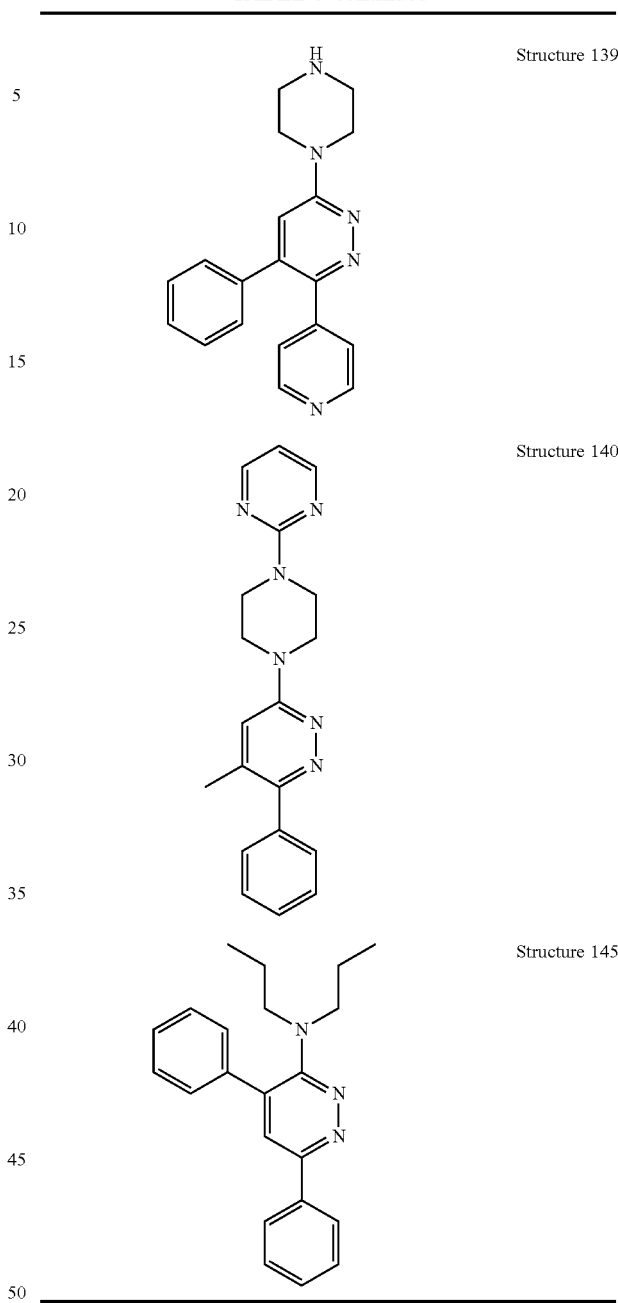

Structure 139

Structure 140

Structure 145

REFERENCES

[1] Akiyama H, Barger S, Barnum S, Bradt B, Bauer J, Cole G M, et al. Inflammation and Alzheimer's disease. Neurobiol Aging 21: 383-421 (2000).

[2] Mirzoeva S, Sawkar A, Zasadzki M, Quo L, Velentza A V, Dunlap V, et al, discovery of a 3-amino-6-phenyl-pyridazine derivative as a new synthetic anti-neuroinflammatory compound. J Med Chem 45: 563-566 (2002).

[3] Watterson D M, Haiech J and Van Eldik L J. Discovery of new chemical classes of synthetic ligands that suppress neuroinflammatory responses. J Mol Neurosci 19: 89-94 (2002).

[4] Watterson D M, Velentza A V, Zasadzki M, Craft J M, Haiech J and Van Eldik L J. Discovery of a new class of synthetic protein kinase inhibitors that suppress selective aspects of glial activation and protect against [J-amylold induced injury. A foundation for future medicinal chemistry efforts focused on targeting Alzheimer's disease progression. J Mol Neurosci 20: 411-424 (2003).

[5] Craft J M, Watterson D M, Frautschy S A and Van Eldik L J, Aminopyridazines inhibit β-amyloid induced glial activation and neuronal damage in vivo. Neurobiol. Aging 25: 1283-1292 (2004),

[6] Craft J M, Van Eldik L J, Zasadzki M, Hu W, Watterson D M. Aminopyridazines attenuate hippocampus dependent behavioral deficits induced by human (J-amyloid in a murine model of neuroinflammation, J Mol Neurosci 24: 115-122 (2004).

[7] Griffin W S T, Sheng J G, Royston M C, Gentleman S M, McKenzie I E, Graham D I, et al. Glial-neuronal interactions in Alzheimer's disease: the potential role of a "cytokine cycle" in disease progression. Brain Pathol 8: 65-72 (1998).

[8] Wermuth C G. Search for new lead compounds: The example of the chemical and pharmacological dissection of aminopyridazines. J Heterocyclic Chem 35: 1091-1100 (1998).

[9] Frautschy S A, Yang F, Calderon L and Cole G M Rodent models of Alzheimer's disease: rat A β infusion approaches to amyloid deposits. Neurobiol Aging 17: 311-21 1996).

[10] Veber D F, Johnson S R, Cheng H Y, Smith B R, Ward K W and Kopple K D Molecular 30 properties that influence the oral bioavailability of drug candidates. J Med Chem 45; 2615-2623 (2002).

[11] Vieth M, Siegel M G, Higgs R E, Watson I A, Robertson D H, Savin K A, et al (2004) Characteristic physical properties and structural fragments of marketed oral drugs. J Med Chem 47: 224-232 (2004).

[12] Cignarella G, Barlocco D, Pinna G, Loriga M, Curzu M M, Tofanetti O, et al. Synthesis and biological evaluation of substituted benzo[A]cinnolinones and 3H-benzo[6,7]cyclohepta[1,2-c]pyridazinones: higher homologues of the antihypertensive and antithrombotic 5H-indeno[1,2-c]pyridazinones. J Med Chem 32: 2277-2282 (1989).

[13] Costantino L, Rastelli G, Vescovini K, Cignarella G, Vianello P, Corso A D, et al. Synthesis, activity, and molecular modeling of a new series of tricyclic pyridazinones as selective aldose reductase inhibitors. J Med Chem 39: 4396-4405 (1996).

[14] Sotelo E and Ravina E. Efficient aromatization of 4,5-dihydro-3-(2H)-pyridazinones substituted at 5 position by using anhydrous copper (II) chloride. Synthetic Communications 30; 1-7 (2000),

[15] Wermuth C O, Bourguignon J J, Schlewer G, Gies J P, Schoenfelder A, Meiikian A, et al. Synthesis and structure-activity relationships of a series of aminopyridazine derivatives of y-aminobutyric acid acting as selective GABAj, antagonists. J Med Chem 30: 239-249 (1987).

[16] Wermuth C G, Schlewer G, Bourguignon J J, Maghioros G, Bouchet M J, Moire C, et al. (1989) 3-amiaopyridazine derivatives with atypical antidepressant, serotonergic, and dopaminergic activities. J Med Chem 32: 528-537 (1989).

[17] Mirzoeva S, Koppal T, Petrova T V, Lukas T J, Watterson D M and Van Eldik L J Screening in a cell-based assay for inhibitors of microglial nitric oxide production reveals calmodulin-regulated protein kinases as potential drug discovery targets. Brain Res 844: 126-134 (1999).

[18] Coudert, P.; Couquelet, J.; Tronche, P. A new synthetic route to 4,6-diarylpyridazinones and some of their derivatives. Journal of Heterocyclic Chemistry. 1988, 25 (3), 799-802.

What is claimed is:
1. A compound of Formula Ib:

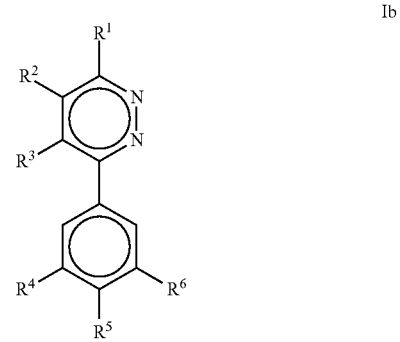

wherein:
$R^1$ is a substituted amino group;
$R^2$ is cycloalkyl, cycloalkenyl, aryl, aryloxy, arylalkoxy, aroyl, heteroaryl, heterocyclic, acyl, acyloxy, sulfonyl, sulfinyl, sulfenyl, amino, imino, azido, thiol, thioalkyl, thioalkoxy, thioaryl, nitro, ureido, cyano, halo, silyl, silyloxy, silylalkyl, silylthio, carboxyl, carbonyl, carbamoyl, or carboxamide,
wherein heteroaryl is a fully unsaturated heteroatom-containing ring-shaped aromatic radical having one, two or three rings attached in a pendant manner or fused, having 5 or 6 members in each ring and having at least one heteroatom selected from carbon, nitrogen, sulfur and oxygen, and heterocyclic is a saturated or partially saturated heteroatom-containing ring-shaped radical having one, two or three rings attached in a pendant manner or fused, having 3 to 6 members in each ring and having at least one heteroatom selected from carbon, nitrogen, sulfur and oxygen, and each of heteroaryl and heterocyclic is optionally substituted by halogen, hydroxy, thio, nitro, amino, ketone, aldehyde, ester, amide, alkyl, aryl, or cycloalkyl,
$R^3$ is hydrogen, and
$R^4$, $R^5$ and $R^6$ are independently hydrogen, alkyl, alkoxy, halo or nitro;
or a pharmaceutically acceptable salt thereof.

2. A compound according to claim 1, wherein the compound is:

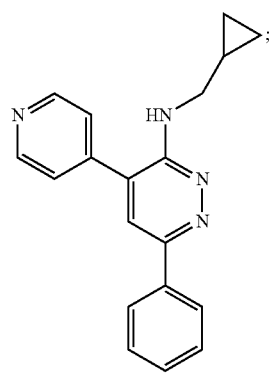 [SMILES: c1ccc(-c2cc(-c3ccncc3)c(NCC3CC3)nn2)cc1]

or a pharmaceutically acceptable salt thereof.

3. A compound according to claim 1, wherein the substituted amino group for $R^1$ has the formula —NR21R22, where R21 and R22 are any combination of hydrogen, hydroxyl, alkyl, cycloalkyl, alkoxy, alkenyl, alkynyl, aryl, carbonyl, carboxyl, amino, silyl, heteroaryl or heterocyclic, each of which are optionally substituted, provided that R21 and R22 are not both hydrogen.

4. A compound according to claim 1, wherein the substituted amino group for $R^1$ is methylamino, ethylamino, dimethylamino, 2-propylamino, butylamino, isobutylamino, cyclopropylamino, benzylamino, allylamino, hydroxylamino, cyclohexylamino, piperidinyl, hydrazinyl, diphenylmethylamino, tritylamino, trimethylsilylamino or dimethyl-tert.-butylsilylamino, each of which are optionally substituted.

5. A compound according to claim 1, wherein $R^2$ is pyrrolyl, pyrrolinyl, imidazolyl, pyrazolyl, 2-pyridyl, 3-pyridyl, 4-pyridyl, pyridinyl, pyrimidinyl, pyrazinyl, pyridazinyl, triazolyl or tetrazolyl.

6. A compound according to claim 1, wherein the compound is one of the following two compounds:

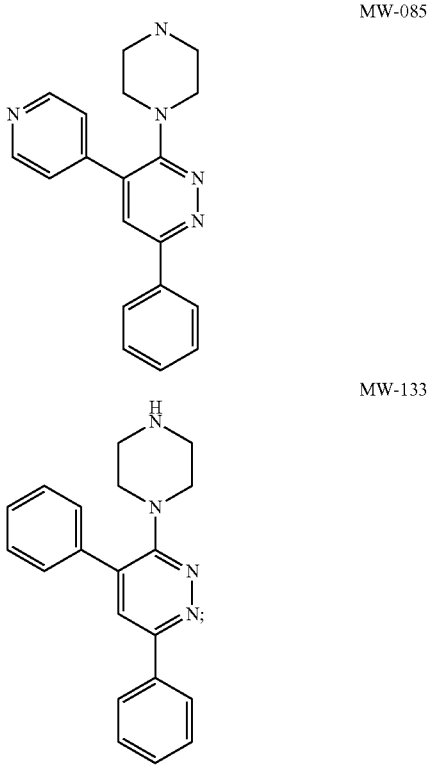

or a pharmaceutically acceptable salt thereof.

7. A compound according to claim 1, wherein $R^2$ is pyridinyl.

8. A method for reducing neuroinflammation to treat a disease or condition which presents neuroinflammation in a subject, comprising administering to the subject a compound of claim 1.

9. A method for reducing neuroinflammation to treat a disease or condition which presents neuroinflammation in a subject, comprising administering to the subject a compound of claim 2.

10. The method of claim 8, wherein progression of said disease or condition is ameliorated or progresses to a less severe stage.

11. The method of claim 8, wherein said compound reduces neuroinflammation associated with any one of traumatic brain injury, intracerebral hemorrhage, or Alzheimer's disease.

12. The method of claim 8, wherein said compound decreases neuroinflammation by acting on one or more of cell signaling molecule production, activation of glia or glial activation pathways and responses, proinflammatory cytokines or chemokines, oxidative stress-related responses, acute phase proteins, components of the complement cascade, protein kinase activity, cell damage and cell death signal transduction pathways.

13. The method of claim 8, wherein said disease includes mild cognitive impairment (MCI).

14. The method of claim 8, further comprising: administering a pharmaceutically acceptable carrier, excipient, or vehicle to said subject and wherein kinase activity, glial activation, neuronal cell damage, and/or neuronal cell death is reduced or inhibited.

15. The method of claim 8, wherein the progression of said disease is delayed.

16. The method of claim 8, wherein the disease or condition treated is Alzheimer's disease, intracerebral hemorrhage or traumatic brain injury, which disease or condition presents neuroinflammation.

17. The method of claim 8, wherein the compound inhibits pro-inflammatory cytokines or chemokines.

18. The method of claim 8, wherein the compound inhibits IL-1β, TNF-α and/or S100β.

19. The method of claim 9, wherein the disease or condition treated is Alzheimer's disease, intracerebral hemorrhage or traumatic brain injury, which disease or condition presents neuroinflammation and/or wherein the compound reduces neuroinflammation associated with any one of traumatic brain injury, intracerebral hemorrhage, or Alzheimer's disease.

20. A method for reducing neuroinflammation to treat a disease or condition which presents neuroinflammation in a subject, comprising administering to the subject a compound of claim 6.

21. The method of claim 20, wherein the disease or condition treated is Alzheimer's disease, intracerebral hemorrhage or traumatic brain injury, which disease or condition presents neuroinflammation and/or wherein the compound reduces neuroinflammation associated with any one of traumatic brain injury, intracerebral hemorrhage, or Alzheimer's disease.

* * * * *